(12) United States Patent
Wu et al.

(10) Patent No.: US 8,268,858 B2
(45) Date of Patent: Sep. 18, 2012

(54) COMPOUNDS AND METHODS FOR KINASE MODULATION, AND INDICATIONS THEREFOR

(75) Inventors: Guoxian Wu, Palo Alto, CA (US); Wayne Spevak, Berkeley, CA (US); Songyuan Shi, Fremont, CA (US); Hanna Cho, Oakland, CA (US); Prabha N. Ibrahim, Mountain View, CA (US); Chao Zhang, Moraga, CA (US); Shenghua Shi, San Diego, CA (US); Yong Zhou, San Francisco, CA (US); Dean Artis, Kensington, CA (US); Jiazhong Zhang, Foster City, CA (US)

(73) Assignee: Plexxikon Inc., Berkeley, CA (US)

( * ) Notice: Subject to any disclaimer, the term of this patent is extended or adjusted under 35 U.S.C. 154(b) by 1306 days.

(21) Appl. No.: 11/961,901

(22) Filed: Dec. 20, 2007

(65) Prior Publication Data

US 2008/0188514 A1 Aug. 7, 2008

Related U.S. Application Data

(60) Provisional application No. 60/876,744, filed on Dec. 21, 2006.

(51) Int. Cl.
*A61K 31/437* (2006.01)
*C07D 471/04* (2006.01)
(52) U.S. Cl. .................. 514/300; 546/113
(58) Field of Classification Search .............. 514/300; 546/113
See application file for complete search history.

(56) References Cited

U.S. PATENT DOCUMENTS

| | | | |
|---|---|---|---|
| 2,234,705 A | 3/1941 | Normington et al. |
| 2,413,258 A | 12/1946 | Soday et al. |
| 4,150,949 A | 4/1979 | Smith |
| 4,568,649 A | 2/1986 | Bertoglio-Matte |
| 4,626,513 A | 12/1986 | Burton et al. |
| 4,634,701 A | 1/1987 | De Vincentiis |
| 4,714,693 A | 12/1987 | Targos |
| 4,727,395 A | 2/1988 | Oda et al. |
| 5,120,782 A | 6/1992 | Hubsch et al. |
| 5,143,854 A | 9/1992 | Pirrung et al. |
| 5,338,849 A | 8/1994 | Festal et al. |
| 5,426,039 A | 6/1995 | Wallace et al. |
| 5,432,177 A | 7/1995 | Baker et al. |
| 5,434,049 A | 7/1995 | Okano et al. |
| 5,449,614 A | 9/1995 | Danos et al. |
| 5,474,935 A | 12/1995 | Chatterjee et al. |
| 5,486,525 A | 1/1996 | Summers et al. |
| 5,556,752 A | 9/1996 | Lockhart et al. |
| 5,576,319 A | 11/1996 | Baker et al. |
| 5,580,859 A | 12/1996 | Felgner et al. |
| 5,631,236 A | 5/1997 | Woo et al. |
| 5,632,957 A | 5/1997 | Heller et al. |
| 5,658,775 A | 8/1997 | Gilboa |
| 5,681,959 A | 10/1997 | Bishop et al. |
| 5,700,637 A | 12/1997 | Southern |
| 5,700,809 A | 12/1997 | Leeson et al. |
| 5,712,285 A | 1/1998 | Curtis et al. |
| 5,721,118 A | 2/1998 | Scheffler |
| 5,744,305 A | 4/1998 | Fodor et al. |
| 5,747,276 A | 5/1998 | Hoch et al. |
| 5,763,198 A | 6/1998 | Hirth et al. |
| 5,770,456 A | 6/1998 | Holmes |
| 5,800,992 A | 9/1998 | Fodor et al. |
| 5,807,522 A | 9/1998 | Brown et al. |
| 5,830,645 A | 11/1998 | Pinkel et al. |
| 5,840,485 A | 11/1998 | Lebl et al. |
| 5,856,174 A | 1/1999 | Lipshutz et al. |
| 5,877,007 A | 3/1999 | Housey |
| 5,959,098 A | 9/1999 | Goldberg et al. |
| 5,965,452 A | 10/1999 | Kovacs |
| 6,013,440 A | 1/2000 | Lipshutz et al. |
| 6,022,963 A | 2/2000 | McGall et al. |
| 6,025,155 A | 2/2000 | Hadlaczky et al. |
| 6,045,996 A | 4/2000 | Cronin et al. |
| 6,048,695 A | 4/2000 | Bradley et al. |
| 6,054,270 A | 4/2000 | Southern |
| 6,090,912 A | 7/2000 | Lebl et al. |
| 6,096,718 A | 8/2000 | Weitzman et al. |
| 6,107,478 A | 8/2000 | Pedersen et al. |
| 6,110,456 A | 8/2000 | During |
| 6,110,458 A | 8/2000 | Freeman et al. |
| 6,113,913 A | 9/2000 | Brough et al. |
| 6,117,681 A | 9/2000 | Salmons et al. |
| 6,161,776 A | 12/2000 | Byles |
| 6,178,384 B1 | 1/2001 | Kolossvary |
| 6,235,769 B1 | 5/2001 | Clary |

(Continued)

FOREIGN PATENT DOCUMENTS

CL 1595-2006 6/2006

(Continued)

OTHER PUBLICATIONS

Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Bell, Fluorescence: Solution Studies,(1981), Spectroscopy in Biochemistry, vol. I, pp. 155-194, CRC Press.
Fivash et al., BIAcore for macromolecular interaction; (1998) BIAcore for macromolecular interaction, Current Opinion in Biotechnology. 9:97-101.
Jarugula et al., Nonlinear Pharmacokinetics of 5-Fluorouracil in Rats. 1997, J Pharm Sci 86(6):756-757.
Leuner et al., Improving drug solubility for oral delivery using solid dispersions. European Journal of Pharma. and Biopharma., 50:47-60, 2000.
Matsumoto and Zografi, Physical properties of solid molecular dispersions of indomethacin with poly(vinylpyrrolindone) and poly(vinylpyrrolidone-co-vinyl-acetate) in relation to indomethacin crystallization. Pharmaceutical Research, 16:11, 1722-1728, 1999.
Notice of Allowance dated Jun. 6, 2008 for U.S. Appl. No. 11/154,988.

(Continued)

*Primary Examiner* — Kristin Bianchi
(74) *Attorney, Agent, or Firm* — Stephen E. Reiter; Foley & Lardner LLP

(57) ABSTRACT

Compounds active on protein kinases are described, as well as methods of using such compounds to treat diseases and conditions associated with aberrant activity of protein kinases.

11 Claims, No Drawings

U.S. PATENT DOCUMENTS

| | | |
|---|---|---|
| 6,243,980 B1 | 6/2001 | Bronstein et al. |
| 6,258,606 B1 | 7/2001 | Kovacs |
| 6,261,776 B1 | 7/2001 | Pirrung et al. |
| 6,277,489 B1 | 8/2001 | Abbott et al. |
| 6,277,628 B1 | 8/2001 | Johann et al. |
| 6,288,234 B1 | 9/2001 | Griffin |
| 6,294,330 B1 | 9/2001 | Michnick et al. |
| 6,310,074 B1 | 10/2001 | Depreux et al. |
| 6,350,786 B1 | 2/2002 | Albano et al. |
| 6,545,014 B2 | 4/2003 | Verner |
| 6,858,860 B2 | 2/2005 | Hosono et al. |
| 7,259,165 B2 | 8/2007 | Bernotas et al. |
| 7,361,763 B2 | 4/2008 | Arnold et al. |
| 7,361,764 B2 | 4/2008 | Arnold et al. |
| 7,452,993 B2 | 11/2008 | Arnold et al. |
| 7,498,342 B2 | 3/2009 | Ibrahim et al. |
| 7,504,509 B2 | 3/2009 | Ibrahim et al. |
| 7,582,637 B2 | 9/2009 | Arnold et al. |
| 7,601,839 B2 | 10/2009 | Arnold et al. |
| 7,626,021 B2 | 12/2009 | Arnold et al. |
| 7,645,769 B2 * | 1/2010 | Khan et al. ............ 514/300 |
| 7,846,941 B2 | 12/2010 | Zhang et al. |
| 7,863,288 B2 | 1/2011 | Ibrahim et al. |
| 7,863,289 B2 | 1/2011 | Spevak et al. |
| 2001/0008765 A1 | 7/2001 | Shinoki et al. |
| 2001/0012537 A1 | 8/2001 | Anderson et al. |
| 2001/0014448 A1 | 8/2001 | Chappa et al. |
| 2001/0014449 A1 | 8/2001 | Nerenberg et al. |
| 2001/0016322 A1 | 8/2001 | Caren et al. |
| 2001/0018642 A1 | 8/2001 | Balaban et al. |
| 2001/0019827 A1 | 9/2001 | Dawson et al. |
| 2003/0003004 A1 | 1/2003 | Stones et al. |
| 2004/0002534 A1 | 1/2004 | Lipson et al. |
| 2004/0022534 A1 | 2/2004 | Amano et al. |
| 2004/0077595 A1 | 4/2004 | Cheng et al. |
| 2004/0142864 A1 | 7/2004 | Bremer et al. |
| 2004/0167030 A1 | 8/2004 | Bernotas et al. |
| 2005/0085463 A1 | 4/2005 | Weiner et al. |
| 2005/0154014 A1 | 7/2005 | Bloxham et al. |
| 2005/0164300 A1 | 7/2005 | Artis et al. |
| 2005/0170431 A1 | 8/2005 | Ibrahim et al. |
| 2005/0256151 A1 | 11/2005 | Salom et al. |
| 2006/0035898 A1 | 2/2006 | Arnold et al. |
| 2006/0058339 A1 | 3/2006 | Ibrahim et al. |
| 2006/0058340 A1 | 3/2006 | Ibrahim et al. |
| 2007/0032519 A1 | 2/2007 | Zhang et al. |
| 2007/0049615 A1 | 3/2007 | Ibrahim et al. |
| 2007/0287711 A1 | 12/2007 | Arnold et al. |
| 2008/0167338 A1 | 7/2008 | Spevak et al. |
| 2008/0188514 A1 | 8/2008 | Wu et al. |
| 2009/0005356 A1 | 1/2009 | Blaney et al. |
| 2009/0076046 A1 | 3/2009 | Zhang et al. |
| 2009/0143352 A1 | 6/2009 | Arnold et al. |
| 2009/0306056 A1 | 12/2009 | Arnold et al. |

FOREIGN PATENT DOCUMENTS

| | | |
|---|---|---|
| DE | 24 13 258 A1 | 10/1975 |
| EP | 0 154 734 | 8/1990 |
| EP | 0 465 970 | 1/1992 |
| EP | 1057826 | 12/2000 |
| EP | 0 870 768 | 5/2002 |
| EP | 1749829 | 2/2007 |
| FR | 2264804 A1 | 10/1975 |
| GB | 2 292 143 | 2/1996 |
| GB | 2 292 145 | 2/1996 |
| GB | 2 298 198 | 8/1996 |
| GB | 2 299 581 | 10/1996 |
| JP | 06-135946 | 5/1994 |
| JP | 10-130269 | 5/1998 |
| JP | 2001-278886 | 10/2001 |
| JP | 15-073357 | 3/2003 |
| WO | WO-93/13099 | 7/1993 |
| WO | WO-94/14808 | 7/1994 |
| WO | WO-94/20459 | 9/1994 |
| WO | WO-95/04742 | 2/1995 |
| WO | WO-95/07910 | 3/1995 |
| WO | WO-95/28387 | 10/1995 |
| WO | WO-96/00226 | 1/1996 |
| WO | WO-96/11929 | 2/1996 |
| WO | WO-96/05200 | 4/1996 |
| WO | WO-96/17958 | 6/1996 |
| WO | WO-96/18738 | 6/1996 |
| WO | WO-96/38131 | 12/1996 |
| WO | WO-97/46313 | 12/1997 |
| WO | WO-97/46558 | 12/1997 |
| WO | WO-97/49703 | 12/1997 |
| WO | WO-98/06433 | 2/1998 |
| WO | WO-98/22457 | 5/1998 |
| WO | WO-98/47899 | 10/1998 |
| WO | WO-99/00386 | 1/1999 |
| WO | WO-99/09217 | 2/1999 |
| WO | WO-99/51231 | 10/1999 |
| WO | WO-99/51232 | 10/1999 |
| WO | WO-99/51233 | 10/1999 |
| WO | WO-99/51234 | 10/1999 |
| WO | WO-99/51595 | 10/1999 |
| WO | WO-99/51596 | 10/1999 |
| WO | WO-99/51773 | 10/1999 |
| WO | WO-00/09162 | 2/2000 |
| WO | WO-00/12074 | 3/2000 |
| WO | WO-00/12514 | 3/2000 |
| WO | WO-00/29411 | 5/2000 |
| WO | WO-00/53582 | 9/2000 |
| WO | WO-00/55153 | 9/2000 |
| WO | WO-00/64898 | 11/2000 |
| WO | WO-00/71537 | 11/2000 |
| WO | WO-00/75139 | 12/2000 |
| WO | WO-01/09121 | 2/2001 |
| WO | WO-01/24236 | 4/2001 |
| WO | WO-01/29036 | 4/2001 |
| WO | WO-01/46196 | 6/2001 |
| WO | WO-01/60822 | 8/2001 |
| WO | WO-01/62255 | 8/2001 |
| WO | WO-01/74786 | 11/2001 |
| WO | WO-01/98299 | 12/2001 |
| WO | WO-02/00657 | 1/2002 |
| WO | WO-02/18346 | 3/2002 |
| WO | WO-02/083175 | 10/2002 |
| WO | WO-02/085896 | 10/2002 |
| WO | WO-02/102783 | 12/2002 |
| WO | WO-03/000258 | 1/2003 |
| WO | WO-03/003004 A2 | 1/2003 |
| WO | WO-03/006459 | 1/2003 |
| WO | WO-03/008422 | 1/2003 |
| WO | WO-03/011868 | 2/2003 |
| WO | WO-03/020698 | 3/2003 |
| WO | WO-03/028724 | 4/2003 |
| WO | WO-03/037862 | 5/2003 |
| WO | WO-03/051838 | 6/2003 |
| WO | WO 03/064413 | 8/2003 |
| WO | WO-03/068221 | 8/2003 |
| WO | WO-03/082289 | 10/2003 |
| WO | WO-03/082868 | 10/2003 |
| WO | WO-03/082869 | 10/2003 |
| WO | WO-03/087087 | 10/2003 |
| WO | WO-03/101990 | 12/2003 |
| WO | WO-2004/009600 | 1/2004 |
| WO | WO 2004/009601 | 1/2004 |
| WO | WO-2004/016609 | 2/2004 |
| WO | WO-2004/016610 | 2/2004 |
| WO | WO 2004/024895 | 3/2004 |
| WO | WO-2004/054581 | 7/2004 |
| WO | WO-2004/065393 | 8/2004 |
| WO | WO-2004/065394 | 8/2004 |
| WO | WO-2004/069138 | 8/2004 |
| WO | WO-2004/074286 | 9/2004 |
| WO | WO-2004/078756 | 9/2004 |
| WO | WO 2004/078923 | 9/2004 |
| WO | WO-2004/101565 | 11/2004 |
| WO | WO-2005/028475 | 3/2005 |
| WO | WO 2005/028624 | 3/2005 |
| WO | WO 2005/044181 | 5/2005 |
| WO | WO-2005/058891 | 6/2005 |
| WO | WO 2005/062795 | 7/2005 |
| WO | WO-2005/063746 | 7/2005 |
| WO | WO-2005/063747 | 7/2005 |

| | | |
|---|---|---|
| WO | WO-2005/066347 | 7/2005 |
| WO | WO-2005/082367 | 9/2005 |
| WO | WO-2005/085244 | 9/2005 |
| WO | WO 2005/095400 | 10/2005 |
| WO | WO 2005/103050 | 11/2005 |
| WO | WO-2005/115363 | 12/2005 |
| WO | WO-2006/004984 | 1/2006 |
| WO | WO-2006/009755 | 1/2006 |
| WO | WO-2006/009797 | 1/2006 |
| WO | WO-2006/015123 | 2/2006 |
| WO | WO-2006/015124 | 2/2006 |
| WO | WO-2006/114180 | 11/2006 |
| WO | WO-2006/127587 | 11/2006 |
| WO | WO 2007/002325 | 1/2007 |
| WO | WO 2007/002433 | 1/2007 |
| WO | WO 2007/013896 | 2/2007 |
| WO | WO-2007/106236 | 9/2007 |

OTHER PUBLICATIONS

Price et al., Summary report on the ISOBM TD-4 Workshop: analysis of 56 monoclonal antibodies against the MUC1 mucin, (1998) Tumour Biology 19 Suppl 1:1-20.
Sambrook, et al., Introduction of Recombinant Vectors into Mammalian Cells 1D Molecular Cloning: A Laboratory Manual 2:16.30-16.37 (1989).
Shan et al., Prodrug strategies based on intramolecular cyclization reactions. Journal of Pharmaceutical Sciences, 86:7, 765-767, 1997.
Steinman, L., Multiple Sclerosis: A Coordinated Immunological Attack Against Myelin in the Central Nervous System 1D Cell 85:299-302 (1996).
Vachon and Nairn, The influence of microencapsulation using Eudragit® RS100 on the hydrolysis kinetics of acetylsalicylic acid. J.Microencapsulation, 14:281-301, 1997.
Vandelli et al., Analysis of release data in the evaluation of the physical state of progesterone in matrix systems. J. Microencapsulation, 10:1, 55-65, 1993.
Balak, et. al., Novel D761Y and common secondary T790M mutations in epidermal growth factor receptor-mutant lung adenocarcinomas with acquired resistance to kinase inhibitors. Clin. Cancer Res. 12:6494-501 (2006).
Bouzakri, K. and Zierath, J.R., MAP4K4 Gene silencing in Human Skeletal Muscle Prevents Tumor Necrosis Factor-α-induced Insulin Resistance, J. Biol. Chem. 282:7783-7789 (2007).
Chou, T. and Talalay, P., Quantitative analysis of Dose-Effect Relationships: The Combined Effects of Multiple Drugs or Enzyme Inhibitors, Adv. Enzyme Regul. 22: 27-55 (1984).
Chou et al., Computerized Quantitation of Synergism and Antagonism of Taxol, Topotecan, and Cisplatin Against Human Teratocarcinoma Cell Growth: a Rational Approach to Clinical Protocol Design, J. Natl. Cancer Inst. 86:1517-24 (1994).
Collins et al., A small interfereing RNA screen for modulators of tumor cell motility identifies MAP4K4 as a prommigratory kinase, Proc. Natl. Acad. Sci. USA, 103: 3775-3780 (2006).
Coulie et al, Recombinant Human Neurotropic Factors Accelerate Colonic Transit and Relieve Constipation in Humans, Gastroenterology 119:41-50 (2000).
Crump, M., Inhibition of Raf Kinase in the Treatment of Acute Myeloid Leukemia, Curr. Pharm. Design 8(25):2243-8 (2002).
Douma, S. et al, Suppression of anoikis and induction of metastasis by the neurotropic receptor TrkB, Nature 430:1034-9 (2004).
Chou, T. et al., Chemotherapeutic Synergism, Potentiation and Antagonism, Encyclopedia of Human Biology, Academic Press, 2:371-9 (1991).
Halvorson, K.G. et al., A Blocking Antibody to Nerve Growth Factor Attenuates Skeletal Pain Induced by Prostate Tumor Cells Growing in Bone, Cancer Res. 65:9426-35 (2005).
Hood, J.D. et al., Tumor Regression by Targeted Gene Delivery to the Neovasculature, Science 296, 2404 (2002).
Kassel, O. et al., Local increase in the number of mast cells and expression of nerve growth factor in the bronchus of asthmatic patients after repeated inhalation of allergen at low-dose, Clin. Exp. Allergy 31:1432-40 (2001).

Kunnimalaiyaan, M. and Chen, H. et al., The Raf-1 pathway: a molecular target for treatment of select neuroendocrine tumors? Anticancer Drugs 17(2):139-42 (2006).
Machida, N. et al., Mitogen-activated Protein Kinase Kinase Kinase Kinase 4 as a Putative Effector of Rap2 to Activate the c-Jun N-terminal Kinase, J. Biol. Chem. 279: 15711-15714 (2004).
Mack, K.D. et al., Functional identification of kinases essential for T-cell activation through a genetic suppression screen, Immunol. Lett. 96, 129-145 (2005).
Matayoshi, S. et al, Actions of brain-derived neurotrophic factor on spinal nociceptive transmission during inflammation in the rat, J Physiol. 569:685-95 (2005).
Mazeas, et. al., Synthesis of new melatoninergic ligands including azaindole moiety. *Heterocycles*, 50:1065 (1999).
Nakagawara, A. et al., Expression and Function of *TRK-B* an *BDNF* in Human Neuroblastomas, Mol. Cell Biol. 14:759-767 (1994).
Nassentein, C. et al, The Neurotrophins Nerve Growth Factor, Brain-derived Neurotrophic Factor, Neurotrophin-3, and Neurotrophin-4 Are Survival and Activation Factors for Eosinophils in Patients with Allergic Bronchial Asthma, J. Exp. Med. 198:455-467 (2003).
Niihori, T. et al., Germline *KRAS* and *BRAF* mutations in cardio-facio-cutaneous syndrome, Nature Genet. 38(3):294-6 (2006).
Ochs, G. et al, A phase I/II trial of recombinant methionyl human brain derived neurotrophic factor administered by intrathecal infusion to patients with amyotrophic lateral sclerosis, Amyotroph Lateral Scler Other Motor Neuron Disord. 1:201-6 (2000).
Petty et al, The effect of systemically administered recombinant human nerve growth factor in healthy human subjects. Ann Neurol. 36:244-6 (1994).
Sclabas, G.M. et al, Overexpression of Tropomysin-Related Kinase B in Metastatic Human Pancreatic Cancer Cells, Clin. Cancer. Res. V11:440-449 (2005).
Chou, T.C. and Rideout, D.C., Synergism and Antagonism in Chemotherapy, Academic Press, 61-102 (1991).
Tang, X. et al., An RNA interference-based screen identifies MAP4K4/NIK as a negative regulator of PPARγ, adipogenesis, and insulin-responsive hexose transport, Proc. Natl. Acad. Sci. U. S. A. 103:2087-2092 (2006).
Wendt, et al, Identification of novel binding interactions in the development of potent, selective 2-naphthamidine inhibitors of urokinase, synthesis, structural analysis, and SAR of N-Phenyl amide 6-substitution. *J. Med. Chem.*, 47(2):303 (2004).
Wild, K.D. et al, Antibodies to Nerve Growth Factor Reverse Established Tactile Allodynia in Rodent Models of Neuropathic Pain without Tolerance, J. Pharmacol. Exp. Ther. 322:282-287 (2007).
Wright, J.H. et al., The STE20 Kinase KGK is Broadly Expressed in Human tumor Cells and Can Modulate Cellular Transformation, Invasion, and Adhesion, Mol. Cell. Biol. 23: 2068-2082 (2003).
Yang, Z.F. et al, Identification of Brain-Derived Neurotrophic Factor as a Novel Functional Protein in Hepatocellular Carcinoma, Cancer Res. 65:219-225 (2005).
Yang et. al., Synthesis of some 5-substituted indoles. Heterocycles, 34:1169 (1992).
Yao, Z. et al., A Novel Human STE20-related Protein Kinase, HGK, That Specifically Activates the c-Jun N-terminal Kinase Signaling Pathway, J. Biol. Chem. 274: 2118-2125 (1999)
International Search Report for PCT Patent Application No. PCT/US2007/088243, 2008.
Alfthan, K., Surface Plasmon Resonance Biosensors as a Tool in Antibody Engineering, Biosensors & Bioelectronics 13:653-663 (1998).
Allegretti, et al., Palladium-Catalysed Functionalisation at 4- and 6-Position of the 7-Azaindole System, Synlett 5:609-612 (2001).
Al-Obeidi, et al., Peptide and Peptidomimetic Libraries, Mol Biotechnol 9:205-223, 1998.
Alvarez, et al., Synthesis of 3-Aryl- and 3-Heteroaryl-7-Azaindoles, Synthesis 4:615-620 (1999).
Amersdorfer and Marks, Phage Libraries for Generation of Anti-Botulinum scFv Antibodies, Methods in Molecular Biology 145:219-240, 2000.
Anderson, et al., Cooperative Catalyst Effects in Palladium-Mediated Cyanation Reactions of Aryl Halides and Triflates, J. Org. Chem. 63:8224-8228 (1998).

Antonini, et al., Synthesis of 4-Amino-1-β-D-Ribofuranosyl-1H-pyrrolo[2,3-b]pyridine (1-Deazatubercidin) as a Potential Antitumor Agent, J. Med. Chem. 25:1258-1261 (1982).

Ashman et al., The biology of stem cell factor and its receptor C-kit, The International Journal of Biochemistry & Cell Biology, 31:1037-1051, 1999.

Baghestanian, et al., A Case of Malignant Mastocytosis with Circulating Mast Cell Precursors: Biologic and Phenotypic Characterization of the Malignant Clone, Leuk. 10:159-166 (1996).

Bagshaw et al, Measurement of Ligand Binding to Proteins Spectrophotometry and Spectrofluorimetry, 4:91-113, 1987.

Bagshawe, Antibody-Directed Enzyme Prodrug Therapy: A Review; 1995, Drug Dev. Res., 34:220-230.

Bancalari, et al., Blood Markers of Early and Late Airway Responses to Allergen in Asthmatic Subjects. Relationship with Functional Findings Allergy 52:32-40, 1997.

Bartlett, et al., CAVEAT: A Program to Facilitate the Structure-Derived Design of Biologically Active Molecules Royal Society of Chemistry 78:I80-I96, 1989.

Barton et al, The chemistry of pentavalent organobismuth reagents. Part X. Studies on the phenylation and oxidation of phenols, Tetrahedron, vol. 43, No. 2, 1987, pp. 323-332.

Basta et al, High-dose Intravenous Immunoglobulin Exerts its Beneficial Effect in Patients with Dermatomyositis by Blocking Endomysial Deposition of Activated Complement Fragments; J Clin Invest 1994, 94:1729-1735.

Bedi, et al., BCR-ABL-Mediated Inhibition of Apoptosis With Delay of G2/M Transition After DNA Damage: A Mechanism of Resistance to Multiple Anticancer Agents; Blood 1995, 86:1148-1158.

Bell, (1981) Spectroscopy in Biochemistry, vol. I, pp. 155-194, CRC Press.

Bellone, et al., Growth Stimulation of Colorectal Carcinoma Cells Via the c-Kit Receptor is Inhibited by TGF-β1, J. Cell Physiol. 172:1-11 (1997).

Berdel, et al., Recombinant Human Stem Cell Factor Stimulates Growth of a Human Glioblastoma Cell Line Expressing c-kit Protooncogene, Canc. Res. 52:3498-3502 (1992).

Bertolini et al., A new Rational Hypothesis for the Pharmacophore of the Active Metabolite of Leflunomide, a Potent Immunosuppressive Drug; 1997, J. Med. Chem., 40:2011-2016.

Bjorntorp, Neuroendocrine Pertuirbations as a Cause of Insulin Resistance; Diabetes Metab. Res. Rev., 1999, 15: 427-441.

Bloom, A. and Day. A.R., The Preparation of 2-Alkylaminobenzimidazoles, J. Org. Chem. 14, 17 (1939).

Blundell et al., Knowledge-Based Protein Modelling and Design Eur. J. Biochem. 172:513-520 1988.

Bode, et al, Modern Pathology, (2006), 19:541-547.

Böhm, H., On the Use of LUDI to Search the Fine Chemicals Directory for Ligands of Proteins of Known Three-Dimensional Structure, J. Comp. Aided Molec. Design 8:623-632, 1994.

Bokenmeyer, et al., Expression of Stem-Cell Factor and Its Receptor c-kit Protein in Normal Testicular Tissue and Malignant Germ-Cell Tumours, J. Cancer Res. Clin. Oncol. 122:301-306 (1996).

Bolger et al, Computer Modeling of Combining Site Structure of Anti-Hapten Monoclonal Antibodies, Methods Enz., 203:21-45, 1991.

Bongarzone, et al., High Frequency of Activation of Tyrosine Kinase Oncogenes in Human Papillary Thyroid Carcinoma, Oncogene 4(12):1457-1462 (1989).

Bothwell, M., Keeping Track of Neurotrophin Receptors Cell, 65:915-918, 1991.

Bowtell, D., Options Available From Start to Finish for Obtaining Expression Data by Microarray, Nature Genetics Supp. 21:25-32 (1999).

Brenner et al., Encoded Combinatorial Chemistry, Proc. Natl. Acad. Sci. USA 89:5381-5383, 1992.

Broudy, V., Stem Cell Factor and Hematopoiesis, Blood 90:1345-1364 (1997).

Brünger, A., Free R Value: a Novel Statistical Quantity for Assessing the Accuracy of Crystal Structures Nature 355:472-475 (1992).

Buchschacher, Human Immunodeficiency Virus Vectors for Inducible Expression of Foreign Genes; (1992) J. Virol. 66:2731-2739.

Capon, et al., Designing CD4 Immunoadhesins for AIDS Therapy, Nature 337:525-531 (1989).

Carell et al., New Promise in Combinatorial Chemistry: Synthesis, Characterization, and Screening of Small-Molecule Libraries in Solution, Chem. Biol. 2:171-183 (1995).

Carpino, et al., p62dok: A Constitutively Tyrosine-Phosphorylated, GAP-Associated Protein in Chronic Myelogenous Leukemia Progenitor Cells; Cell 1997, 88:197-204.

Castells, et al., The Presence of Membrane-Bound Stem Cell Factor on Highly Immature Nonmetachromatic Mast Cells in the Peripheral Blood of a Patient with Aggressive Systemic Mastocytosis, J. Aller. Clin. Immunol. 98:831-840 (1996).

Chabala, J., Solid-Phase Combinatorial Chemistry and Novel Tagging Methods for Identifying Leads, Curr Opin Biotechnol 6:632-639 (1995).

Chayer, et al., Synthesis of Carboranylpyrroles, Tetrahedron Lett. 42(44):7759-7761 (2001).

Checovich, et al., Fluorescence Polarization—A New Tool for Cell and Molecular Biology, Nature 375:254-256 (1995).

Clark, et al., PRO_LIGAND: An Approach to De Novo Molecular Design. 1. Application to the Design of Organic Molecules, J. Comp. Aided Molec. Design 9:13-32 (1995).

Clohisy et al, Review of Cellular Mechanisms of Tumor Osteolysis; Clin. Orthop. 2000, 373: 104-14.

Coe, et al., Solution-Phase Combinatorial Chemistry, Mol Divers. 4:31-38 (1999).

Cohen, et al., Expression of Stem Cell Factor and C-Kit in Human Neuroblastoma; 1994, Blood 84:3465-3472.

Collioud et al., Oriented and Covalent Immobilization of Target Molecules to Solid Supports: Synthesis and Application of a Light-Activatable and Thiol-Reactive Cross-Linking Reagent; (1993) Bioconjugate Chem. 4:528-536.

Colman, P.M., Structure-Based Drug Design, Current Opinion in Struc. Biol. 4: 868-874 (1994).

Columbo, et al., The Human Recombinant c-kit Receptor Ligand, rhSCF, Induces Mediator Release From Human Cutaneous Mast Cells and Enhances IgE-Dependent Mediator Release From Both Skin Mast Cells and Peripheral Blood Basophils, J. Immunol 149:599-608 (1992).

Costa, et al., The Cells of the Allergic Response, JAMA 278:1815-1822 (1997).

Coste, et al., Coupling N-Methylated Amino Acids Using PyBroP1 and PyCloP Halogenophosphonium Salts: Mechanism and Fields of Application, Journal of Organic Chemistry 59:2437-2446 (1994).

Creighton, T., An Empirical Approach to Protein Conformation Stability and Flexibility, Biopolymers 22(1):49-58 (1983).

Crouch et al., The use of ATP bioluminescence as a measure of cell proliferation and cytotoxicity. Journal of Immunological Methods, 160:81-8 (1993).

Curtin et al., Discovery and Evaluation of a Series of 3-Acylindole Imidazopyridine Platelet-Activating Factor Antagonists, J. Med. Chem., vol. 41, 1998, pp. 74-95.

Cwirla et al., Peptides on Phage: A Vast Library of Peptides for Identifying Ligands, Biochemistry 87:6378-6382 (1990).

Dai et al., Targeted disruption of the mouse colony-stimulating factor 1 receptor gene results in osteopetrosis, mononuclear phagocyte deficiency, increased primitive progenitor cell frequencies, and reproductive defects; Blood, 2002, 99: 111-120.

Dandliker, et al., Equilibrium and Kinetic Inhibition Assays Based Upon Fluorescence Polarization, Methods in Enzymology 74:3-28 (1981).

Dastych, et al., Stem Cell Factor Induces Mast Cell Adhesion to Fibronectin; 1994, J. Immunol. 152:213-219.

Demetri, Targeting c-kit mutations in solid tumors: Scientific rationale and novel therapeutic options, Seminars in Oncology, 28(5), Supp. 17, 19-26, 2001.

Dewar et al., Inhibition of c-fms by Imatinib Expanding the Spectrum of Treatment; Cell Cycle 2005, 4(7):851-3.

Dobeli, H., et al., Recombinant Fusion Proteins for the Industrial Production of Disulfide Bridge containing Peptides: Purification, Oxidation without Cancatamer Formation, and Selective Cleavage; (1998) Protein Expr. Purif. 12:404-414.

Dolle et al., Comprehensive Survey of Combinatorial Library Synthesis: 1998, J Comb Chem 1:235-282 (1999).
Donis-Keller, et al., Mutations in the RET Proto-Oncogene are Associated with MEN 2A and FMTC, Hum Mol Genet. 2(7):851-856 (1993).
Doyle and Bryker, Alkyl Nitrite-metal halide Deamination Reactions. 6. Direct Synthesis of Arenediazonium Tetrafluoroborate Salts from Aromatic Amines, tert-Butyl Nitrite, and Boron Trifluoride Etherate in Anhydrous Media; J. Org. Chem. 1979, 44:1572.
Dube aand Scholte, Reductive N-Alkylation of Amides, Carbamates and Ureas, Tetrahedron Lett. 40:2295-2298 (1999).
Durbec, et al., GDNF Signalling Through the Ret Receptor Tyrosine Kinase, Nature 381:789-793 (1996).
Dyson, et al., The Human Papilloma Virus 13 16 E7 Oncoprotein is Able to Bind to the Retinoblastoma Gene Product, Science 243:934-937 (1989).
Eklund and Joensuu, Treatment of rheumatoid arthritis and imatinib mesylate: clinical improvements in three refractory cases, Annals of Medicine, 35:362-367, 2003.
Eliseev et al, Dynamic Combinatorial Chemistry: Evolutionary Formation and Screening of Molecular Libraries, Current Topics in Microbiology & Immunology 243:159-172 (1999).
Enjalbal, et al., Mass Spectrometry in Combinatorial Chemistry, Mass Spectrometry Reviews. 19:139-161 (2000).
Escribano, et al., Expression of the c-kit (CD117) Molecule in Normal and Malignant Hematopoiesis, Leuk. Lymph. 30:459-466 (1998).
Felder, E.R., The Challenge of Preparing and Testing Combinatorial Compound Libraries in the Fast Lane, at the Front End of Drug Development, Chimia 48:531-541 (1994).
Feng et al, Tyrosines 559 and 807 in the Cytoplasmic Tail of the Macrophage colony-Stimulating Factor Receptor Play Distinct Roles in Osteoclast Differentiation and Function; Endocrinology 2002, 143: 4868-74.
Feng, et al., Stable in Vivo Gene Transduction Via a Novel Adenoviral/Retroviral Chimeric Vector, Nature Biotechnology 15:866-870 (1997).
Finotto, et al., Glucocorticoids Disease Tissue Mast Cell Number by Reducing the Production of the c-kit Ligand, Stem Cell Factor, by Resident Cells, J. Clin. Invest. 99:1721-1728 (1997).
Flanagan & Lader, Macrophages and the various isoforms of macrophage colony-stimulating factor; Curr Opin Hematol. 1998, 5:181-5.
Franz and Martin, Sulfuranes. X. A Reagent for the Facile Cleavage of Secondary Amides, JACS, 95(6):2017-2019 (1973).
Furitsu, et al., Identification of Mutations in the Coding Sequence of the Proto-oncogene c-kit in a Human Mast Cell Leukemia Cell Line Causing Ligand-independent Activation of the c-kit Product; 1993, J. Clin. Invest. 92:1736-1744.
Furuta, et al., Stem Cell Factor Influences Mast Cell Mediator Release in Response to Eosinophil-Derived Granule Major Basic Protein, Blood 92:1055-1061 (1998).
Gallop et al., Applications of Combinatorial Technologies to Drug Discovery. 1. Background and Peptide Combinatorial Libraries, J. Med. Chem. 37:1233-1251 (1994).
Gassman et al., Specific Ortho Substitution of Aromatic Heterocyclic Amines, J American Chemical Society, (1973), 95(13), pp. 4453-4455.
Girgis, N. et.al., The Synthesis of 5-Azaindoles by Substitution-Rearrangement of 7-Azaindoles upon Treatment with Certain Primary Amines; J. Heterocyclic. Chem. 1989, 26:317-325.
Golkar, et al., Mastocytosis, Lancet 349:1379-1385 (1997).
Goodford, P.J., A Computational Procedure for Determining Energetically Favorable Binding Sites on Biologically Important Macromolecules, J. Med. Chem. 28:849-857 (1985).
Goodsell et al, Automated Docking of Substrates to Proteins by Simulated Annealing, Proteins: Structure, Function, and Genetics 8:195-202 (1990).
Gordon et al., Applications of Combinatorial Technologies to Drug Discovery. 2. Combinatorial Organic Synthesis, Library Screening Strategies, and Future Directions, J. Med. Chem. 37:1384-1401 (1994).
Gordon, and Ford, Detection of Peroxides and Their Removal, The Chemist's Companion: A Handbook of Practical Data, Techniques, and References p. 437 (1972).
Gram H., Phage Display in Proteolysis and Signal Transduction, Combinatorial Chemistry & High Throughput Screening 2:19-28 (1999).
Gravert et al, Synthesis on Soluble Polymers: New Reactions and the Construction of Small Molecules, Curr Opin Chem Biol 1:107-113 (1997).
Greer, J., Model Structure for the Inflammatory Protein C5a, Science 228:1055-1060 (1985).
Grieco, et al., PTC is a Novel Rearranged Form of the ret Proto-Oncogene and is Frequently Detected in Vivo in Human Thyroid Papillary Carcinomas, Cell 60(4):557-563 (1990).
Guida, W., Software for Structure-Based Drug Design, Current Opinion in Struc. Biol. 4:777-781 (1994).
Hafner, et al., Isothermal Amplification and Multimerization of DNA by Bst DNA Polymerase, Biotechniques Apr. 2001;30(4):852-867.
Hallek, et al., Interaction of the Receptor Tyrosine Kinase p145c-kit with the p210bcr/abl Kinase in Myeloid Cells, Brit. J Haem. 94:5-16 (1996).
Hamel, et al., The Road Less Traveled: c-kit and Stem Cell Factor, J. Neuro-Onc. 35:327-333 (1997).
Hands et. al., A convenient Method for the Preparation of 5-, 6- and 7-Azaindoles and Their Derivatives; Synthesis 1996, 877-882.
Hanselman, et al., A cDNA-Dependent Scintillation Proximity Assay for Quantifying Apolipoprotein A-1, J. Lipid Res. 38:2365-2373 (1997).
Hassan and Zander, Stem Cell Factor as a Survival and Growth Factor in Human Normal and Malignant Hematopoiesis, Acta. Hem. 95:257-262 (1996).
Hassan, et al., Expression of Protooncogene c-kit and Its Ligand Stem Cell Factor (SCF) in Gastric Carcinoma Cell Lines; 1998, Digest. Dis. Science 43:8-14.
Hayashi, et al., Dichloro[1,1 19-bis(diphenylophosphino)ferrocene]palladium-(II), An Effective Catalyst for Cross-Coupling of Secondary and Primary Alkyl Grignard and Alkylzinc Reagents with Organic Halides, J. Am. Chem. Soc. 106:158-163 (1984).
Heacock et al., Orientation and Relative Reaction rate Factors in aromatic Substitution by the Benzensulfonimido Radical, J. Am. Chem. Soc., vol. 82, 1960, pp. 3460-3463.
Heim, et al., Engineering Green Fluorescent Protein for Improved Brightness, Longer Wavelengths and Fluorescence Resonance Energy Transfer, Curr. Biol. 6:178-182 (1996).
Heinrich et al., PDGFRA Activating Mutations in Gastrointestinal Stromal Tumors; (Science 2003, 299:708-10).
Heinrich, M. C. et al., "Inhibition of KIT Tyrosine Kinase Activity: A Novel Molecular Approach to the Treatment of KIT-Positive Malignancies," J. Clin. Oncol., vol. 20, No. 6, pp. 1692-1703, Mar. 15, 2002.
Herbst, et al., Differential Effects of W Mutations on p145c-kit Tyrosine Kinase Activity and Substrate Interaction, J. Biol. Chem. 267:13210-13216 (1992).
Hibi, et al., Coexpression of the stem cell factor and the c-kit genes in small-cell lung cancer; 1991, Oncogene 6:2291-2296.
Hirota, et al., Gain-of-function Mutations of c-kit in Human Gastrointestinal Stromal Tumors; 1998, Science 279:577-580.
Hoffmann, m-Trifluoromethylbenzenesulfonyl Chloride, Organic Syntheses , Coll. vol. 60, p. 121-126, 1981.
Hogaboam, et al., Novel Role of Transmembrane SCF for Mast Cell Activation and Eotaxin Production in Mast Cell-Fibroblast Interactions, J. Immunol. 160:6166-6171 (1998).
Houghten, et al., Generation and Use of Synthetic Peptide Combinatorial Libraries for Basic Research and Drug Discovery, Nature 354:84-86 (1991).
Houghten, R., Parallel Array and Mixture-Based Synthetic Combinatorial Chemistry: Tools for the Next Millennium, Annu Rev Pharmacol Toxicol 40:273-282 (2000).
Houghten, R., Peptide Libraries: Criteria and Trends, Trends Genet. 9:235-239 (1993).
Hudson, P. B. et al., A Simple Method for the Determination of Serum Acid Phosphatase, Journal of Urology 58:89-92 (1947).

Hughes-Jones, et al., Synthesis of Rh Fv Phage-Antibodies Using VH and VL Germline Genes, British Journal of Haematology 105:811-816 (1999).

Iemura, et al., The c-kit Ligand, Stem Cell Factor, Promotes Mast Cell Survival by Suppressing Apoptosis, Amer. J. Pathol 144:321-328 (1994).

Inoue, et al., Coexpression of the c-kit Receptor and the Stem Cell Factor in Gynecological Tumors, Cancer Res. 54:3049-3053 (1994).

International Search Report and Written Opinion of the ISA dated Oct. 24, 2006 for PCT Application No. PCT/U52006/024524.

International Search Report and Written Opinion of the ISA dated Apr. 4, 2007 for PCT Application No. PCT/U52006/018726.

International Search Report and Written Opinion of the ISA dated Apr. 20, 2006 for PCT Application No. PCT/US2005/021231.

International Search Report and Written Opinion of the ISA dated Jun. 4, 2008 for PCT Application No. PCT/US2007/088231.

International Search Report and Written Opinion of the ISA dated Jun. 4, 2008 for PCT Application No. PCT/US2007/088237.

International Search Report and Written Opinion of the ISA dated Jun. 5, 2008 for PCT Application No. PCT/US2007/083910.

International Search Report and Written Opinion of the ISA dated Jun. 5, 2008 for PCT Application No. PCT/US2007/085289.

International Search Report and Written Opinion of the ISA dated Jul. 25, 2008 for PCT Application No. PCT/US2007/088443.

International Search Report and Written Opinion of the ISA dated Jul. 28, 2008 for PCT Application No. PCT/US2007/085299.

International Search Report and Written Opinion of the ISA dated Oct. 24, 2006 for PCT Application No. PCT/US2006/024361.

International Search Report and Written Opinion of the ISA dated Nov. 17, 2008 for PCT Application No. PCT/US07/088412.

International Search Report and Written Opinion of the ISA dated Nov. 25, 2005 for PCT Application No. PCT/U504/42470.

Isbel et al., Local macrophage proliferation correlates with increased renal M-CSF expression in human glomerulonephritis; Nephrol Dial Transplant 2001, 16: 1638-1647.

Ishizaka, et al., Human ret Proto-Oncogene Mapped to Chromsome 10q11.2, Oncogene 4(12):1519-1521 (1989).

Isozaki, et al., Deficiency of c-kit cells in patients with a myopathic form of chronic idiopathic intestinal pseudo-obstruction; 1997, Amer. J. of Gast. 9 332-334.

Iwane, et al., Myosin Subfragment-1 is Fully Equipped with Factors Essential for Motor Function, Biochem. and Biophys. Res. Comm. 230:76-80 (1997).

Izouierdo, et al., Differential Expression of the c-kit Proto-Oncogene in Germ Cel Tumours, J. Pathol 177:253-258 (1995).

Jarugula et al., Nonlinear pharmacokinetics of 5-fluorouracil in rats. 1997, J Pharm Sci 86(7):756-757.

Jensen et al, Brit J Pharmacology, (2008), 154:1572-1582.

Jing, et al., GDNF-Induced Activation of the Ret Protein Tyrosine Kinase is Mediated by GDNFR-a, a Novel Receptor for GDNF, Cell 85:1113-1124 (1996).

Johann, S., et al., GLVR1, a Receptor for gibbon Ape Leukemia Virus, Is Homologous to a Phosphate Permease of *Neurospora crassa* and is Expressed at High Levels in the Brain and Thymus; (1992) J. Virol. 66:1635-1640.

Johnston, M., Gene Chips: Array of hope for understanding gene regulation; (1998) Curr. Biol. 8:R171-R174.

Jones, R., Biology and Treatment of Chronic Myeloid Leukemia, Curr. Opin. Onc. 9:3-7 (1997).

Jones, T., Interactive Computer Graphics: FRODO, Methods in Enzymology 115:157-171 (1985).

Jose et al., Blockade or Macrophage colony-Stimulating Factor Reduces Macrophage Proliferation and Accumulation in Renal Allograft Rejection; Am J Transplant 2003, 3(3):294-300.

Joseph-McCarthy, D., Computational Approaches to Structure-Based Ligand Design, Pharmacology & Therapeutics 84:179-191 (1999).

Kahl, et al., A Multiple-Approach Scintillation Proximity Assay to Measure the Association Between Ras and Raf, Anal. Biochem. 243:282-283 (1996).

Katritzky, et al., Regiospecific C-Acylation of Pyrroles and Indoles Using N-Acylbenzotriazoles, J. Org. Chem. 68:5720-5723 (2003).

Kay, et al., Eosinophils and Eosinophil-Associated Cytokines in Allergic Inflammation, Int. Arch. Aller. Immunol. 113:196-199 (1997).

Kern and Hampton, Direct Hybridization of Large-Insert Genomic Clones on High-Density Gridded cDNA Filter Arrays, Biotechniques 23:120-124 (1997).

Kim et al, A Merger of Rational Drug Design and Combinatorial Chemistry: Development and Application of Peptide Secondary Structure Mimetics, Combinatorial Chemistry & High Throughput Screening 3:167-183 (2000).

Kim et al, Database CAS on STN (Columbus, OH, USA) No. 138:55974, Preparation of 2-anilino-4-indolylpyrimidines as tyrosine kinase inhibitors, abstract, 2002) see whole article.

Kinashi and Springer, Steel Factor and c-kit Cell-Matrix Adhesion; Blood 83:1033-1038 (1994).

Kirkpatrick, et al., Structure-Based Drug Design: Combinatorial Chemistry and Molecular Modeling, Combinatorial Chemistry & High Throughput Screening 2:211-221 (1999).

Kitamura, et al., Synthesis of Quinolines and 2H-Dihydropyrroles by Nucleophilic Substitution at the Nitrogen Atom of Oxime Derivatives, Synthesis 15:2415-2426 (2003).

Kline et al., Studies by 1H Nuclear Magnetic Resonance and Distance Geometry of the Solution Conformation of the x-Amylase Inhibitor Tendamistat, J. Mol. Biol. 189:377-382 (1986).

Knighton, et al., Structural Basis of the Intrasteric Regulation of Myosin Light Chain Kinases, Science 258:130-135 (1992).

Kodama et al, Congenital Osteoclast Deficiency in Osteopetrotic (op/op) Mice is Cured by Injections of Macrophage colony-stimulating Factor; J. Exp,. Med. 1991, 173: 269-72.

Kolaskar et al, A Semi-Empirical Method for Prediction of Antigenic Determinants on Protein Antigens, FEBS Lett. 276:172-174 (1990).

Komoyira, S. et. al., Design, synthesis and biological activity of amidinobicyclic compounds (derivatives of DX-9065a) as a factor Xa inhibitors: SAR study of S1 and aryl binding sites, Bioorg. Med. Chem. 12, 2099 (2004).

Kondoh, et al., An in vivo model for receptor tyrosine kinase autocrine/paracrine activation: auto-stimulated Kit receptor acts as a tumor promoting factor in papillomavirus-induced tumorigenesis; 1995, Oncogene 10:341-347.

Kondoh, et al., Establishment and Further Characterization of a Line of Transgenic Mice Showing Testicular Tumorigenesis at 100% Incidence, J. Urol. 152:2151-2154 (1994).

Kondoh, et al., Very High Incidence of Germ Cell tumorigenesis (Seminomagenesis) in Human Papillomavirus Type 16 Transgenic Mice; 1991, J. Virol. 65:3335-3339.

Konishi, et al, Brit J Cancer, (2003), 88:1223-1228.

Kroll, David J., et al., A Malfunctional Prokaryotic Protein Expression System: Overproduction, Affinity Purification, and Selective Detection; (1993) DNA Cell. Biol. 12:441-53.

Kundu, et al., Combinatorial Chemistry: Polymer Supported Synthesis of Peptide and Non-Peptide Libraries, Progress in Drug Research 53:89-156 (1999).

Kunisada, et al., Murine Cutaneous Mastocytosis and Epidermal Melanocytosis Induced by Keratinocyte Expression of Transgenic Stem Cell Factor; 1998, J. Exp. Med. 187:1565-1573.

Kunkel, T., Rapid and Efficient Site-Specific Mutagenesis Without Phenotypic Selection, Proc. Natl. Acad. Sci. USA 82:488-492 (1985).

Kuntz, et al., A Geometric Approach to Macromolecule-Ligand Interactions, J. Mol. Biol. 161:269-288 (1982).

Kuntz, et al., Structure-Based Molecular Design, Acc. Chem. Res. 27:117-123 (1994).

Lahm, et al., Interleukin 4 Down-Regulates Expression of c-kit and Autocrine Stem Cell Factor in Human Colorectal Carcinoma Cells, Cell Growth & Differ 6:1111-1118 (1995).

Lam et al., A new type of synthetic peptide library for identifying ligand-binding activity, Nature, 354: 82-84, 1991.

Langham et al., Metalation of Halogen-Metal Interconversion Reactions of Some Halogenated Phenyl Ethers, J. Am. Chem. Soc., vol. 63, 1941, pp. 545-549.

Lawicki et al., The pretreatment plasma level and disgnostic utility of M-CSF in benign breast tumor and breast cancer patients, Clinica Chimica Acta, 371: 112-116, 2006.

Le Meur et.al., Macrophage accumulation at a site of renal inflammation is dependent on the M-CSF/c-fms pathway; J Leukocyte Biology, 2002, 72: 530-537.
Lebl, et al., One-Bead-One-Structure Combinatorial Libraries, Biopolymers 37:177-198 (1995).
Lee, et al., HLA-DR-Triggered Inhibition of Hemopoiesis Involves Fas/Fas Ligand Interactions and is Prevented by c-kit Ligand, J. Immunol. 159:3211-3219 (1997).
Lee, et al., Mast Cells: A Cellular Link Between Autoantibodies and Inflammatory Arthritis, Science 297:1689-1692 (2002).
Levin, et al., Neoplasms of the Central Nervous System, Cancer Principles & Practice of Oncology 2:2022-2082 (1997).
Li, et al., Abrogation of c-kit/Steel Factor-Dependent Tumorigenesis by Kinase Defective Mutants of the c-kit Receptor: c-kit Kinase Defective Mutants as Candidate Tools for Cancer Gene Therapy, Canc. Res. 56:4343-4346 (1996).
Libby, Inflammation in atherosclerosis, Nature, 2002;420:868-874.
Liparoto, et al., Biosensor Analysis of the Interleukin-2 Receptor Complex, Journal of Molecular Recognition 12:316-321 (1999).
Lipinski, et al., Experimental and Computational Approaches to Estimate Solubility and Permeability in Drug Discovery and Development Settings, Advanced Drug Delivery Reviews 23:3-25 (1997).
Lipschultz et al., Experimental design for analysis of complex kinetics using surface plasmon resonance, Methods; (2000) 20(3):310-318.
London, et al., Expression of Stem Cell Factor Receptor (c-kit) by the Malignant Mast Cells from Spontaneous Canine Mast Cell Tumors, 1996, J. Compar. Pathol. 115:399-414.
Longley, et al., Altered Metabolism of Mast-cell Growth Factor (c-kit Ligand) in Cutaneous Mastocytosis, 1993, New Engl. J. Med. 328:1302-1307.
Longley, et al., Chymase Cleavage of Stem Cell Factor Yields a Bioactive Soluble Product, Proc. Natl. Acad. Sci. 94:9017-9021 (1997).
Longley, et al., Somatic c-KIT Activating Mutation in Urticaria Pigmentosa and Aggressive Mastocytosis: Establishment of Clonality in a Human Mast Cell Neoplasm, Nat. Gen. 12:312-314 (1996).
Loveland, et al., Stem Cell Factor and c-kit in the Mammalian Testis: Lessons Originating from Mother Nature 19s Gene Knockouts, J. Endocrinol 153:337-344 (1997).
Lu, et al., Oriented Immobilization of Fab 19 Fragments on Silica Surfaces, Anal. Chem. 67:83-87 (1995).
Lukacs, et al., Stem Cell Factor (c-kit Ligand) Influences Eosinophil Recruitment and Histamine Levels in Allergic Airway Inflammation, J. Immunol. 156:3945-3951 (1996).
Luo, et al., Close Linkage with the RET Proto-Oncogene and Boundaries of Deletion Mutations in Autosomal Dominant Hirschsprung Disease, Hum Mol Genet. 2(11):1803-1808 (1993).
Lyman, et al., c-kit Ligand and Flt3 Ligand: Stem/Progenitor Cell Factors With Overlapping Yet Distinct Activities, Blood 91:1101-1134 (1998).
Ma et al., Indolinone Derivatives Inhibit Constitutively Activated KIT Mutants and Kill Neoplastic Mast Cells, 2000, J Invest Dermatol. 114:392-394.
Ma, et al., The c-KIT Mutation Causing Human Mastocytosis is Resistant to ST1571 and Other KIT Kinase Inhibitors; Kinases with Enzymatic Site Mutations Show Different Inhibitor Sensitivity Profiles Than Wild-Type Kinases and Those With Regulatory-Type Mutations, Blood 99:1741-1744 (2002).
Madden, et al., Synthetic Combinatorial Libraries: Views on Techniques and Their Application Perspectives in Drug Discovery and Design 2:269-285 (1994).
Malmborg, et al., BIAcore as a Tool in Antibody Engineering, Journal of Immunological Methods 183:7-13 (1995).
Malmqvist, et al., Biomolecular Interaction Analysis: Affinity Biosensor Technologies for Functional Analysis of Proteins, Current Opinion in Chemical Biology 1:378-383 (1997).
Malmqvist., BIACORE: an affinity biosensor system for characterization of biomolecular interactions, (1999) Biochemical Society Transactions 27:335-40.
Markiewicz, et al., Synthetic Oligonucleotide Combinatorial Libraries and Their Applications, II Farmaco 55:174-177 (2000).

Martin, Y., Computer-Assisted Rational Drug Design, Methods Enz. 203:587-613 (1991).
McCall, et al., Characterization of Anti-Mouse FcyRII Single-Chain Fv Fragments Derived from Human Phage Display Libraries, Immunotechnology 4:71-87 (1998).
McPherson, A., Current Approaches to Macromolecule Crystallization, Eur. J. Biochem. 189:1-23 (1990).
Mekori, et al., Transforming Growth Factor-β Prevents Stem Cell Factor-Mediated Rescue of Mast Cells from Apoptosis After IL-3 Deprivation, 1994, J. Immunol 153:2194-2203.
Mekori, et al., The Role of c-Kit and Its Ligand, Stem Cell Factor, in Mast Cell Apoptosis, 1995, Int. Arch. Allergy Immunol. 107:136-138.
Meltzer, The pharmacological basis for the treatment of perennial allergic rhinitis and non-allergic rhinitis with topical corticosteroids, 1997, Aller. 52:33-40.
Meng, et al., Automated Docking with Grid-Based Energy Evaluation, J. Compt. Chem. 13:505-524 (1992).
Merour and Joseph, Synthesis and Reactivity of 7-Azaidoles (1H-Pyrrolo[2,3-b]pyridine), Curr. Org. Chem. 2001, 5:471-506.
Merritt, A., Solution Phase Combinatorial Chemistry, Comb Chem High Throughput Screen 1:57-72 (1998).
Metcalf, D., Lineage Commitment in the Progeny of Murine Hematopoietic Preprogenitor Cells: Influence of Thrombopoietin and Interleukin 5, Proc. Natl. Acad. Sci. USA 95:6408-6412 (1998).
Metcalfe, Classification and Diagnosis of Mastocytosis: Current Status, 1991, J. Invest. Derm 93:2S-4S.
Metcalfe, et al., Mast Cells, Physiol. Rev. 77:1033-1079 (1997).
Miller, et al., FLOG: A System to Select Quasi-Flexible Ligands Complementary to a Receptor of Known Three-Dimensional Structure, J. Comp. Aided Molec. Design 8:153-174 (1994).
Minakata et al., Functionalization of 1H-Pyrrolo[2,3-b]pyridine, Bulletin of the Chemical Society of Japan (1992), 65(11): 2992-2997.
Minakata, et al., Regioselective Funtionalization of 1H-Pyrrolo[2,3-b]pyridine Via its N-Oxide, Synthesis pp. 661-663 (1992).
Miranker et al, Functionality Maps of Binding Sites: A Multiple Copy Simultaneous Search Method, Proteins: Structure, Function, and Genetics 11:29-34 (1991).
Mitra, et al., Fluorescence Resonance Energy Transfer Between Blue-Emitting and Red-Shifted Excitation Derivatives of the Green Fluorescent Protein, Gene 173:13-17 (1996).
Miyaura and Suzuki, Palladium-Catalyzed Cross-Coupling Reactions of Organoboron Compounds, Chem. Rev. 1995, 95:2457.
Mokhtari, et al, Clinical Science, (2010), 118(4):241-247.
Mol, et al. Structural Basis for the Autoinhibition and STI-571 Inhibition of c-Kit Tyrosine Kinase, J. Biol. Chem. 279:31655-31663 (2004).
Mol, et al., Structure of a c-Kit Product Complex Reveals the Basis for Kinase Transactivation, J. Biol. Chem. 278:31461-31464 (2003).
Morgan, C., Pollard, J.W., and Stanley, E.R., Isolation and Characterization of a Cloned Growth Factor Dependent Macrophage Cell Line, BAC1.2F5, Journal of Cellular Physiology, 130:420-427 (1987).
Motoyoshi, Biological activities and clinical application of M-CSF, Int J Hematol. 1998, 67:109-22.
Murty, et al., A Genetic Perspective of Male Germ Cell tumors, 1998, Sem. Oncol. 25:133-144.
Naclerio, et al., Rhinitis and Inhalant Allergens, JAMA 278:1842-1848 (1997).
Nagafuji and Cushman, A General Synthesis of Pyrroles and Fused Pyrrole Systems from Ketones and Amino Acids, J. Org. Chem. 61:4999-5003 (1996).
Nagata, et al., Elevated Expression of the Proto-Oncogene c-kit in Patients with Mastocytosis, Leukemia 12:175-181 (1998).
Nahm and Weinreb, N-Methoxy-N-Methylamides as Effective Acylating Agents, Tetrahedron Lett. 22(39):3815-3818 (1981).
Navaza, J., AMoRe: an Automated Package for Molecular Replacement, Acta Cryst. A50:157-163 (1994).
Neidle, et al., Molecular Modeling to Study DNA Intercalation by Anti-Tumor Drugs, Methods Enz. 203:433-458 (1991).

Ng, et al., Engineering Protein-Lipid Interactions: Targeting of Histidine-Tagged Proteins to Metal-Chelating Lipid Monolayers, Langmuir 11:4048-4055 (1995).

Nicholls, et al., Protein Folding and Association: Insights From the Interfacial and Thermodynamic Properties of Hydrocarbons, Proteins 11:281-296 (1991).

Nichols, et al., Development of a Scintillation Proximity Assay for Peroxisome Proliferator-Activated Receptor γ Ligand Binding Domain, Anal. Biochem. 257:112-119 (1998).

Notice of Allowance dated Dec. 26, 2007 for U.S. Appl. No. 11/016,350.

Notice of Allowance dated Jun. 18, 2010 in U.S. Appl. No. 11/473,347.

Okada, et al., Gene Therapy Against an Experimental Glioma Using Adeno-Associated Virus Vectors, Gene Ther. 3:957-964 (1996).

Okayama, et al., Human Lung Mast Cells are Enriched in the Capacity to Produce Granulocyte-Macrophage Colony-Stimulating Factor in Response to IgE-Dependent Stimulation, Eur. J. Immunol. 28:708-715 (1998).

Okayama, et al., Activation of Eosinophils with Cytokines Produced by Lung Mast Cells, Int. Arch. Aller. Immunol. 114(suppl. 1):75-77 (1997).

Olah, et al., Synthetic Methods and Reactions: Part 209. Improved Preparation of Aldehydes and Ketones from N,N-Dimethylamides and Grignard Reagents, Synthesis pp. 228-230 (1984).

O'Shannessy and Winzor, Interpretation of Deviations from Pseudo-First-Order Kinetic Behavior in the Characterization of Ligand Binding by Biosensor Technology, Analytical Biochemistry 236:275-283 (1996).

O'Shannessy, Determination of kinetic rate and equilibrium binding constants for macromolecular interactions: a critique of the surface plasmon resonance literature, (1994) Current Opinions in Biotechnology, 5:65-71.

Ottoni, et al., Efficient and Simple Methods for the Introduction of the Sulfonyl, Acyl and Alkyl Protecting Groups of the Nitrogen of Indole and its Derivatives, Tetrahedron 54:13915-13928 (1998).

Otwinowski, Z., Maximum Likelihood Refinement of Heavy Atom Parameters, Dept. of Molecular Biophysics and Biochemistry pp. 80-86 (1991).

Owicki et al., Application of Fluorescence Polarization Assays in High-Throughput Screening, (1997), Genetic Engineering News, 17:27.

Parker, et al., Development of High Throughput Screening Assays Using Fluorescence Polarization: Nuclear Receptor-Ligand-Binding and Kinase/Phosphatase Assays, J Biomol Screen 5:77-88 (2000).

Perrin, D., Nucleic Acids for Recognition and Catalysis: Landmarks, Limitations, and Looking to the Future, Combinatorial Chemistry & High Throughput Screening 3:243-269 (2000).

Pflugrath, et al., Crystal Structure Determination, Refinement and the Molecular Model of the α-Amylase Inhibitor Hoe-467A, J. Mol. Biol. 189:383-386 (1986).

Pierce et al., Local anaesthetics. I. beta-Monoaklylaminoethyl Esters of Alkoxybenzoic Acids, J. Am. Chem. Soc., vol. 64, 1942, pp. 1691-1694.

Pignon, J.M., C-kit mutations and mast cell disorders A model of activating mutations of growth factor receptors, Hermatol Cell Ther 39:114-116 (1997).

Plunkett et al, A Silicon-Based Linker for Traceless Solid-Phase Synthesis, J. Org. Chem. 60:6006-6007 (1995).

Poul, et al., Selection of Tumor-Specific Internalizing Human Antibodies from Phage Libraries, J. Mol. Biol. 301:1149-1161 (2000).

Price et al.; Summary report on the ISOBM TD-4 Workshop: analysis of 56 monoclonal antibodies against the MUC1 mucin, (1998) Tumour Biology 19 Suppl 1:1-20.

Qiao, et. al., Role of Macrophage Colony-Stimulating Factor in Atherosclerosis, Am. J. Path. 1997;150:1687-1699.

Rajavashisth, et. al., Heterozygous Osteopetrotic (op) Mutation Reduces Atherosclerosis in LDL Receptor-deficient Mice, J. Clin. Invest. 1998;101:2702-2710.

Rajpert-de Meyts, et al., Expression of the c-kit Protein Product in Carcinoma-in-situ and Invasive Testicular Germ Cell Tumours, Int. J. Androl. 17:85-92 (1994).

Ricotti, et al., c-kit is Expressed in Soft Tissue Sarcoma of Neuroectodermic Origin and its Ligand Prevents Apoptosis of Neoplastic Cells, Blood 91:2397-2405 (1998).

Ridge et al, FMS mutations in myelodysplastic, leukemic, and normal subjects, Proc. Nat. Acad. Sci., 1990, 87:1377-1380.

Roberts, S., et al., Generation of an antibody with enhanced affinity and specificity for its antigen by protein engineering, (1987) Nature 328:731-734.

Robinson et al., Stimulation of Bone Marrow Colony Growth in Vitro by Human Urine; Blood, 1969, 33:396-9.

Robison et al, 7-Azaindole. I. Synthesis and Conversion to 7-Azatryptophan and Other Derivatives, J. Am. Chem. Soc. 77:457-460 (1955).

Rodan, G., et al., Therapeutic Approaches to Bone Diseases, Science. 2000;289:1508.

Rosenfeld, Human artificial chromosomes get real, (1997) Nat. Genet. 15:333-335.

Ryan, et al., Role for the Stem Cell Factor/KIT Complex in Schwann Cell Neoplasia and Mast Cell Proliferation Associated with Neurofibromatosis, 1994, J. Neuro. Res. 37:415-432.

Saify et al, Database CAS on STN (Columbus, OH, USA) No. 124:170379, Synthesis of some 2-azaindole derivatives: their cyctotoxicity and antibacterial activity, abstract, (1996), See RN 271-63-6.

Saify et al., Synthesis of some 7-azaindole derivatives: Their cytotoxicity and antibacterial activity, Pakistan Journal of Scientific and Industrial Research, 37(10): 439-441, 1994.

Saiki, Amplification of Genomic DNA, in PCR Protocols, Innis et al., Eds., Academic Press, San Diego, CA 1990, pp. 13-20.

Sambrook et al, Molecular Cloning: A Laboratory Manual, 1989, Cold Spring Harbor Laboratory Press, Cold Spring Harbor N.Y, pp. 16.30-16.37.

Sambrook, et al., 1CIntroduction of Recombinant Vectors into Mammalian Cells 1D Molecular Cloning: A Laboratory Manual 2:16.30-16.37 (1989).

Sandlow, et al., Expression of c-KIT and its Ligand, Stem Cell Factor, in Normal and Subfertile Human Testicular Tissue, 1996, J. Androl. 17:403-408.

Santoro, et al., The ret Proto-Oncogene is Consistently Expressed in Human Pheochromocytomas and Thyroid Medullary Carcinomas, Oncogene, 5(10):1595-1598 (1990).

Sawada et al., 4-(Benzoylindolizinyl)butyric acids; Novel nonsteroidal inhibitors of steroid 5;1-reductase. III, Chemical and Pharmaceutical Bulletin (2001), 49(7): 799-813.

Sawada, et al., Role of Cytokines in Leukemic type Growth of Myelodysplastic CD34+ Cells, 1996, Blood 88:319-327.

Sawai, et al., Aberrant growth of granulocyte-macrophage progenitors in juvenile chronic myelogenous leukemia in serum-free culture, 1996, Exp. Hem. 2:116-122.

Scheffner, et al., The E6 Oncoprotein Encoded by Human Papillomavirus Types 16 and 18 Promotes the Degredation of p53, Cell 63:1129-1136 (1990).

Schiemann and Winkelmüller, p-Fluorobenzoic Acid, Org. Syn. Coll. vol. 2:299, 1943.

Schneider, et al., Functional Purification of a Bacterial ATP-Binding Cassette Transporter Protein (MaIK) from the Cytoplasmic Fraction of an Overproducing Strain, (1995) Protein Expr. Purif. 6435:10.

Schneller, et al., Synthesis of 4-Amino-1 H-pyrrolo[2,3-b]pyridine {1,7-Dideazaadenine) and 1H-Pyrrolo[2,3-b]pyridine-4-ol (1,7-Dideazahypoxanthine), J. Org. Chem. 1980, 45:4045.

Schuhmann, et al., Immobilization of Enzymes on Langmuir-Blodgett Films via a Membrane-Bound Receptor. Possible Applications for Amperometric Biosensors, Adv. Mater. 3:388-391 (1991).

Schummer, et al., Inexpensive Handheld Device for the Construction of High-Density Nucleic Acid Arrays, Biotechniques 23:1087-1092 (1997).

Schweizer, et al., Combinatorial Synthesis of Carbohydrates, Curr Opin. Chem. Biol., 3:291-298 (1999).

Secor, et al., Mast cells are essential for early onset and severe disease in a murine model of multiple sclerosis. J. Exp. Med. 5:813-821 (2000).

Selvin, P., Fluorescence Resonance Energy Transfer, Meth. Enzymol. 246:300-345 (1995).

Sheets, et al., Efficient Construction of a Large Nonimmune Phage Antibody Library: The Production of High-Affinity Human Single-Chain Antibodies to Protein Antigens, Proc Natl Acad Sci USA 95:6157-6162 (1998).

Shibata et al, Alveolar macrophage deficiency in osteopetrotic mice deficient in macrophage colony-stimulating factor is spontaneously corrected with age and associated with matrix metalloproteinase expression and emphysema, Blood 2001, 98: pp. 2845-2852.

Siegel, et al., Mass Spectral Analysis of a Protein Complex Using Single-Chain Antibodies Selected on a Peptide Target: Applications to Functional Genomics, Journal of Molecular Biology 302:285-293 (2000).

Sigal, et al., A Self-Assembled Monolayer for the Binding and Study of histidine-Tagged Proteins by Surface Plasmon Resonance, (1996) Anal. Chem. 68:490-497.

Smalley et al., c-KIT signaling as the driving oncogenic event in sub-groups of melanomas. Histol Histopathol, 24:643-650, 2009.

Solinas-Toldo, et al., Matrix-Based Comparative Genomic Hybridization Biochips to Screen for Genomic Imbalances, Genes, Chromosomes & Cancer 20:399-407 (1997).

Song et al., Isomerism of Bis(7-azaindolyl)methane, Organic Letters (2002), 4:23, 4049-4052, Table of content p. 1-16 and Supporting information p. 1-15.

Sperling, et al., Expression of the Stem Cell Factor Receptor C-Kit (CD117) in Acute Leukemias, Haemat 82:617-621 (1997).

Stanulla, et al., Coexpression of Stem Cell Factor and its Receptor c-Kit in Human Malignant Glioma Cell Lines, Act Neuropath 89:158-165 (1995).

Steinman, Multiple sclerosis: A coordinated immunological attack against myelin in the central nervous system. Cell 85:299-302 (1996).

Strohmeyer, et al., Expression of the C-kit Proto-Oncogene and its Ligand Stem Cell Factor (SCF) in Normal and Malignant Human Testicular Tissue, 1995, J. Urol. 153:511-515.

Strohmeyer, et al., Expression of the hst-1 and c-kit Protooncogenes in Human Testicular Germ Cell Tumors, Canc. Res. 51:1811-1816 (1991).

Su & Tsou, Synthesis of bromo-substituted Idoxyl Esters for Cytochemical Demonstration of Enzyme Activity, J. Am. Chem. Soc.,82, 1960, 1187.

Sun, C., Recent Advances in Liquid-Phase Combinatorial Chemistry, Comb. Chem. & High Throughput Screening 2:299-318 (1999).

Sun, et al., Design, Synthesis, and Evaluations of Substituted 3-[(3- or 4-Carboxyethylpyrrol-2-yl) Methylidenyl]indolin-2-Ones as Inhibitors of VEGF, PGF, and PDGF Receptor Tyrosine Kinases, J. Med. Chem. 42:5120-5130 (1999).

Supplemental Notice of Allowance dated Jul. 23, 2008 for U.S. Appl. No. 11/154,988.

Supplemental Notice of Allowance dated Sep. 8, 2008 for U.S. Appl. No. 11/154,988.

Supplementary Search Report dated Aug. 4, 2009 for European Application No. 04814626.0.

Tada, et al., Analysis of Cytokine Receptor Messenger RNA Expression in Human Glioblastoma Cells and Normal Astrocytes by Reverse-Transcription Polymerase Chain Reaction, J. Neuro 80:1063-1073 (1994).

Takahashi et al, ret Transforming Gene Encodes a Fusion Protein Homologous to Tyrosine Kinases, Mol Cell Biol. 7:1378-1385 (1987).

Takahashi, et al., Activation of a Novel Human Transforming Gene, ret, by DNA Rearrangement, Cell 42(2):581-588 (1985).

Takahashi, et al., Cloning and Expression of the ret Proto-Oncogene Encoding a Tyrosine Kinase with Two Potential Transmembrane Domains, Oncogene 3(5):571-578 (1988).

Taylor et al. The Rapid Generation of Oligonucleotide-directed Mutations at High Frequency Using Phosphorothloate-Modified DNA; (1985) Nucl. Acids Res. 13:8764-8785.

Teitelbaum, Bone Resorption by Osteoclasts, Science. 2000;289:1504.

Thibault et. al., Concise and Efficient Synthesis of 4-fluoro-1H-pyrrolo[2,3-b] pyridine, Org. Lett. 2003, 5:5023-5025.

Thomas et al, The Eosinophil and its Role in Asthma, Gen. Pharmac 27:593-597 (1996).

Thomas, et. al., Light-Emitting Carbazole Derivatives: Potential Electroluminescent Materials, J. Am. Chem. Soc. 123:9404-9411 (2001).

Toste, et al., A Versatile Procedure for the Preparation of Aryl Thiocyanates Using N-Thiocyanatosuccinimide (NTS), Synth. Comm. 25(8):1277-1286 (1995).

Toyota, et al., Expression of c-kit and kit Ligand in Human Colon Carcinoma Cells, 1993, Turn Biol 14:295-302.

Trupp, et al., Functional Receptor for GDNF Encoded by the c-ret Proto-Oncogene, Nature 381:785-789 (1996).

Tsujimura, et al., Substitution of an Aspartic Acid Results in Constitutive Activation of c-kit Receptor Tyrosine Kinase in a Rat Tumor Mast Cell Line RBL-2H3, 1995, Int. Arch. Aller. Immunol 106:377-385.

Tsujimura, et al.,Ligand-Independent Activation of c-kit Receptor Tyrosine Kinase in a Murine Mastocytoma Cell Line P-815 Generated by a Point Mutation, Blood 9:2619-2626 (1994).

Tsujimura, T., Role of c-kit Receptor Tyrosine Kinase in the Development, Survival and Neoplastic Transformation of Mast Cells, Pathol Int 46:933-938 (1996).

Turner, et al., Nonhematopoeietic Tumor Cell Lines Express Stem Cell Factor and Display c-kit Receptors, 1992, Blood 80:374-381.

Undenfriend, et al., Scintillation Proximity Assay: A Sensitive and Continuous Isotopic Method for Monitoring Ligand/Receptor and Antigen/Antibody Interactions, Anal. Biochem., 161:494-500 (1987).

Uritskaya et al., STN Accession No. 1974-27133; Document No. 08:27133; Abstract of Khimiya Geterotsiklicheskikh Soedinenii (1973, (10), 1370-3).

US Notice of Allowance dated Jul. 27, 2010 in related U.S. Appl. No. 11/435,381.

US Notice of Allowance dated Aug. 11, 2010 in U.S. Appl. No. 11/960,590.

US Notice of Allowance dated Aug. 13, 2010 in related U.S. Appl. No. 11/962,044.

US Notice of Allowance dated Aug. 6, 2010 in U.S. Appl. No. 11/986,667.

US Notice of Allowance dated May 27, 2010 in related U.S. Appl. No. 11/435,381.

US Office Action dated Jan. 4, 2008 for U.S. Appl. No. 11/154,988.
US Office Action dated Jun. 6, 2007 for U.S. Appl. No. 11/016,350.
US Office Action dated Aug. 22, 2007 for U.S. Appl. No. 11/487,134.
US Office Action dated Sep. 22, 2009 for U.S. Appl. No. 11/986,667.
US Office Action dated Sep. 23, 2009 for U.S. Appl. No. 11/962,044.
US Office Action dated Oct. 19, 2007 for U.S. Appl. No. 11/154,988.
US Office Action dated Oct. 26, 2007 for U.S. Appl. No. 11/016,350.
US Office Action dated Feb. 17, 2010 for U.S. Appl. No. 11/962,044.
US Office Action dated Jul. 22, 2010 in related U.S. Appl. No. 12/244,730.
US Office Action dated Aug. 2, 2007 in related U.S. Appl. No. 11/016,350.
US Office Action dated Feb. 19, 2010 for U.S. Appl. No. 11/435,381.
US Office Action dated Feb. 26, 2010 for U.S. Appl. No. 11/986,667.
US Office Action dated Jun. 1, 2009 for U.S. Appl. No. 11/435,381.
US Office Action dated Mar. 4, 2009 for U.S. Appl. No. 11/435,381.
US Office Action dated May 15, 2008 in related U.S. Appl. No. 11/487,134.
US Office Action Dec. 18, 2009 for U.S. Appl. No. 11/473,347.

Valent, P., Biology, Classification and Treatment of Human Mastocytosis, Wein/Klin Wochenschr 108:385-397 (1996).

Van Heyningen,V., One Gene—Four Syndromes, Nature 367:319-320 (1994).

Van Regenmortel, Use of biosensors to characterize recombinant proteins. (1994), Developments in Biological Standardization, 83:143-51.

Vely F. et al., BIAcore® analysis to test phosphopeptide-SH2 domain interactions, (2000), Methods in Molecular Biology, 121:313-21.

Verfaillie, Chronic myelogenous leukemia: too much or too little growth, or both?; Leukemia, 1998, 12:136-138.

Viskochil, D., It Takes Two to Tango: Mast Cell and Schwann Cell Interactions in Neurofibromas, J Clin Invest., 112:1791-1793 (2003).

Vliagoftis, et al., The protooncogene c-kit and c-kit ligand in human disease, Journ. Clin. Immunol, 100:435-440 (1997).

Weber, P., Physical Principles of Protein Crystallization, Adv. Protein Chem., 41:1-36 (1991).
Werness, et al., Association of Human Papillomavirus Types 16 and 18 E6 Proteins with p53, Science 248:76-79 (1990).
Wessjohann, L., Synthesis of Natural-Product-Based Compound Libraries, Curr Opin Chem Biol., 4:303-309 (2000).
Wharam, et al., Specific Detection of DNA and RNA Targets Using a Novel Isothermal Nucleic Acid Amplification Assay Based on the Formation of a Three-Way Junction Structure, Nucleic Acids Res., 29:1-8 (2001).
Williams et al., Dissection of the Extracellular Human Interferon γ Receptor a-Chain into two Immunoglobulin-like domains. Production in an *Escherichia coli* Thioredoxin Gene Fusion Expression system and Recognition by Neutralizing Antibodies, (1995) Biochemistry 34:1787-1797.
Woon, et al., Construction and Characterization of a 10-Fold Genome Equivalent Rat P1-Derived Artificial Chromosome Library, Genomics, 50:306-316 (1998).
Wuthrich, K., Chapter 10: Three-Dimensional Protein Structures by NMR, NMR of Proteins and Nucleic Acids, 10:176-199 (1986).
Wyckoff et al., Direct visualization of macrophage-assisted tumor cell intravasation in mammary tumors. Cancer Research, 67(6): 2649-2656, 2007.
Xu et al, Modulation of Endothelial Cell function by Normal Polyspecific Human Intraveneous immunoglobulins, Am. J. Path. 1998;153:1257-1266.
Yakhontov et al., Derivatives of 7-azaindole. XV. Electrophilic substitution of 4-methyl-7-azaindole and its derivatives, Zhurnal Obshchei Khimii (1965), 1(11): 2032-2040. (English abstract only)
Yang et al., Nf1-Dependent tumors require a microenvironment containing Nf1+/_-and c-kit-Dependent bone marrow, Cell, 135:437-448, 2008.
Yang, et al., Neurofibromin-Deficient Schwann Cells Secrete a Potent Migratory Stimulus for NF1+/– Mast Cells, J Clin Invest., 112:1851-1861 (2003).
Yee, et al., Role of kit-Ligand in Proliferation and Suppression of Apoptosis in Mast Cells: Basis for Radiosensitivity of White Spotting and Steel Mutant Mice, J. Exp. Med., 179:1777-1787 (1994).
Yeung et al., Friedel-Crafts acylation of indoles in acidic imidazolium chloroaluminate ionic liquid at room temperature, Tetrahedron Letters, (2002), 43(33), 5793-5795.
Yuan, et al., Human Peripheral Blood Eosinophils Express a Functional c-kit Receptor for Stem Cell Factor that Stimulates Very Late Antigen 4 (VLA-4)-Mediated Cell Adhesion to Fibronectin and Vascular Cell Adhesion Molecule 1 (VCAM-1), J. Exp. Med. 186:313-323 (1997).
Zanon, et. al., Copper-Catalyzed Domino Halide Exchange-Cyanation of Aryl Bromides, J. Am. Chem. Soc. 125:2890-2891 (2003).
Zhang et al., An effective procedure for the acylation of azaindoles at C-3, Journal of Organic Chemistry (2002), 67(17): 6226-6227 and p. S1-S30.
US Notice of Allowance dated Jan. 6, 2011 in U.S. Appl. No. 12/244,730.
Amiel, et al., Hirschsprung disease, associated syndromes and genetics: a review, J Med Genet, (2008), 45:1-14.
Castellone, et al., A novel de novo germ-line V292M mutation in the extracellular region of RET in a patient with phaeochromocytoma and medullary thyroid carcinoma: functional characterization, Clinical Endocrinology, (2010), 73:529-534.
Coelho, et al., Studies of RET gene expression and acetylcholinesterase activity in a series of sporadic Hirschsprung's disease, Pediatr Surg Int, (2008), 24:1017-21.
Communication pursuant to Article 94(3) EPC dated Jun. 6, 2011 in EP application 04814626.
Galofre, et al., Evaluation and Treatment of Thyroid Nodules: A Clinical Guide, (2008), Mt Sinai J Med, 75:299-311.
International Search Report dated Oct. 5, 2010 for PCT Application No. PCT/US2010/029489.
Leuner, et al., Improving drug solubility for oral delivery using solid dispersions. European Journal of Pharma. and Biopharma., 50:47-60, 2000.
Machens, et al., Modification of multiple endocrine neoplasia 2A phenotype by cell membrane proximity of RET mutations in exon 10, Endocrine-Related Cancer, (2009), 16:171-177.
Matsumoto and Zografi, Physical properties of solid molecular dispersions of indomethacine with poly(vinylpyrrolindone) and poly(vinylpyrrolidone-co-vinyl-acetate) in relation to indomethacin crystallization. Pharmaceutical Research, 16:11, 1722-1728, 1999.
Notice of Allowance for U.S. Appl. No. 12/082,665 dated Jul. 26, 2011.
Shan, et al., Prodrug strategies based on intramolecular cyclization reactions. Journal of Pharmaceutical Sciences, 86:7, 765-767, 1997.
Supplemental Notice of Allowance dated Sep. 8, 2010 in U.S. Appl. No. 11/473,347.
US Office Action dated Nov. 8, 2010 in U.S. Appl. No. 12/082,665.
Vachon and Naim, The influence of microencapsulation using Eudragit RS100 on the hydrolysis kinetics of acetylsalicylic acid. J.Microencapsulation, 14:281-301 (1997).
Vandelli, et al., Analysis of release data in the evaluation of the physical state of progesterone in matrix systems. J. Microencapsulation, 10:1, 55-65, 1993.
Wells, et al, Targeting the RET Pathway in Thyroid Cancer, Clin Cancer Res, (2009), 15(23):7119-7123.
U.S. Appl. No. 60/692,960, filed Jun. 22, 2005, Ibrahim et al.
U.S. Appl. No. 60/731,528, filed Oct. 28, 2005, Ibrahim et al.
Das-Gupta et al., "Acridine Derivatives, Part VI," J. Indian Chem. Society, (1941), 18:25-28.
Dutcher et al., "Studies of the C11H8N2OS Degradation Product of Gliotoxin," J. Am. Chem. Soc., (1951), 73:4139-4141.
Extended European Search Report dated Mar. 6, 2012 in related EP Application No. 1117370.1.
Haydock et al., "Analogues of clofibrate and clobuzarit containing fluorine in the side chains," Eur. J. Med. Chem., (1984), 19(3):205-214.
Haydock, et al., Analogues of clofibrate and clobuzarit containing fluorine in the side chains, European Journal of Medicinal Chemistry, 19:205-214 (1984).
Jones et al., "Antiestrogens. 2. Structure-Activity Studies in a Series of 3-Aroyl-2-arylbenzo[b]thiophene Derivatives Leading to [6-Hydroxy-2-(4-hydroxyphenyl)benzo[b]thien-3-yl][4-[2-(1-piperidinyl)ethoxy]-phenyl]methanone Hydrochloride (LY156758), a Remarkably Effective Estrogen Antagonist with Only Minimal Intrinsic Estrogenicity," J. Med. Chem., (1984), 27(8):1057-1066.
Nakai et al., "New Potent Antagonists of Leukotrienes C4 and D4. 01. Synthesis and Structure-Activity Relationships," J. Med. Chem., (1988), 31:(1):84-91.
Non Final Office Action dated Apr. 18, 2012 in related U.S. Appl. No. 12/958,376.
US Notice of Allowance dated Dec. 8, 2011 in related U.S. Appl. No. 13/216,200.
US Office Action dated Feb. 9, 2012 in U.S. Appl. No. 12/616,079.

* cited by examiner

COMPOUNDS AND METHODS FOR KINASE MODULATION, AND INDICATIONS THEREFOR

RELATED PATENT APPLICATIONS

This application claims priority to U.S. Provisional App. No. 60/876,744, entitled "Compounds and Methods for Kinase Modulation, and Indications Therefor", filed Dec. 21, 2006, and is related to U.S. patent application Ser. No. 11/473,347, entitled "Compounds and Methods for Kinase Modulation, and Indications Therefor", filed Jun. 21, 2006, which claims the benefit of U.S. Provisional App. No. 60/731,528, entitled "Compounds and Methods for Kinase Modulation, and Indications Therefor", filed Oct. 28, 2005, and U.S. Provisional App. No. 60/692,960, entitled "Compounds and Methods for Kinase Modulation, and Indications Therefor", filed Jun. 22, 2005, all of which are incorporated herein by reference in their entireties and for all purposes.

FIELD OF THE INVENTION

The present invention relates to kinases and compounds which modulate kinases, and uses therefor. Particular embodiments contemplate disease indications which are amenable to treatment by modulation of kinase activity by the compounds of the present invention.

BACKGROUND OF THE INVENTION

The information provided herein is intended solely to assist the understanding of the reader. None of the information provided nor references cited is admitted to be prior art to the present invention. Each of the references cited herein is incorporated in its entirety.

Receptor protein kinases regulate key signal transduction cascades that control or are involved in the control of a plethora of physiological functions including cellular growth and proliferation, cell differentiation, cellular development, cell division, cell adhesion, stress response, short-range contact-mediated axonal guidance, transcription regulation, aberrant mitogenesis, angiogenesis, abnormal endothelial cell-cell or cell-matrix interactions during vascular development, inflammation, lymphohematopoietic stem cell activity, protective immunity against specific bacteria, allergic asthma, aberrant tissue-specific responses to the activation of the JNK signal transduction pathway, cell transformation, memory, apoptosis, competitive activity-dependent synapse modification at the neuromuscular synapse, immunological mediation of disease, and calcium regulation.

Specific disease states associated with aberrant regulation of protein kinases include, for example without limitation, acrocephalo-syndactyly type I, acute myeloid leukemia, AIDS-induced non-Hodgkin's lymphoma, Alzheimer's disease, amyotrophic lateral sclerosis, arthritis, asthma, atherosclerosis, atopic dermatitis, autoimmune diseases, bacterial infection, bladder cancer, cancer of the breast, cancer of the central nervous system, cancer of the colon, cancer of the endometrium, cancer of the fallopian tube, cancer of the gastrointestinal tract, cancer of the ovary, heart failure, chronic myeloid leukemia, colon carcinoma, colorectal cancer, chronic obstructive pulmonary disease (COPD), Crouzon Syndrome, diabetes, diabetic nephropathy, emphysema, endometriosis, epidermoid cancer, fibrotic disorders, gastrointestinal stromal tumor (GIST), glomerulonephritis, Graves' disease, head injury, hepatocellular carcinoma, Hirschsprung's disease, human gliomas, immunodeficiency diseases, inflammatory disorders, ischemic stroke, Jackson-Weiss syndrome, leiomyosarcoma, leukemias, lupus nephritis, malignant melanoma, malignant nephrosclerosis, mastocytosis, mast cell tumors, melanoma of the colon, MEN2 syndromes, metabolic disorders, migraine, multiple sclerosis, myeloproliferative disorders, nephritis, neurodegenerative diseases, neurotraumatic diseases, non small cell lung cancer, organ transplant rejection, osteoporosis, pain, Parkinson's disease, Pfeiffer Syndrome, polycystic kidney disease, primary lymphoedema, prostate cancer, psoriasis, vascular restenosis, rheumatoid arthritis, dermal and tissue scarring, selective T-cell defect (STD), severe combined immunodeficiency (SCID), small cell lung cancer, spinal cord injury, squamous cell carcinoma, systemic lupus erythematosis, testicular cancer, thrombotic microangiopathy syndromes, Wegener's granulomatosis, X-linked agammaglobulinemia, viral infection, diabetic retinopathy, alopecia, erectile dysfunction, macular degeneration, chronic lymphocytic leukemia (CLL), myelodysplastic syndrome (MDS), neurofibromatosis, and tuberous sclerosis.

This application is related to the following published patent applications: WO 2004024895, US 20040142864, WO 2004078923, US 20050170431, WO 2005028624, US 20050164300, and WO 2005062795, each of which are hereby incorporated by reference herein in their entireties including all specifications, figures, and tables, and for all purposes.

SUMMARY OF THE INVENTION

Compounds are contemplated that are active on protein kinases in general, including, but not limited to, Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, Ephf2, EphB4, Erk2, Fak, FGFR1, FGF 2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, LCK, MAP2K1, MAP2K2, MAP4K4, MAPKAPK2, Met, Mnk1, MLK1, p38, PDGFRRA, PDGFRB, PDPK1, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and/or Zap70, including any mutations of these kinases. In some aspects, compounds are of Formula I (including Formulae Ia-It, and all sub-embodiments thereof) as described below.

Also contemplated in accordance with the present invention are methods for the use of the above-described compounds in treating diseases and conditions associated with regulation of the activity of the above-described kinases. Thus, the use of compounds for therapeutic methods involving modulation of protein kinases are provided, as well as compounds that can be used for therapeutic methods involving modulation of protein kinases.

In some embodiments, compounds have the structure according to the following Formula I:

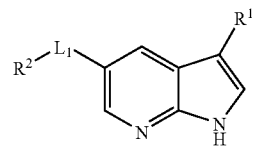

Formula I all salts, prodrugs, tautomers and isomers thereof, wherein:

$L_1$ is —O—, —S—, —S(O)—, or —S(O)$_2$—;

$R^1$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, and -L-$R^3$.

$R^3$ is selected from the group consisting of hydrogen, provided, however, that hydrogen is not bound to any of S(O), S(O)$_2$, C(O) or C(S) of L, optionally substituted lower alkyl, optionally substituted lower alkenyl, provided, however, that when $R^3$ is optionally substituted lower alkenyl, no alkene carbon thereof is bound to N, S, O, S(O), S(O)$_2$, C(O) or C(S) of L, optionally substituted lower alkynyl, provided, however, that when $R^3$ is optionally substituted lower alkynyl, no alkyne carbon thereof is bound to N, S, O, S(O), S(O)$_2$, C(O) or C(S) of L, optionally substituted cycloalkyl, optionally substituted heterocycloalkyl, optionally substituted aryl, and optionally substituted heteroaryl, $R^2$ is selected from the group consisting of -Cy, -alk-Cy, -alk-X-(alk)$_b$-Cy, -alk-NR$^4$-(alk)$_b$-Cy, -alk-C(X)-(alk)$_b$-Cy, -alk-S(O)-(alk)$_b$-Cy, -alk-S(O)$_2$-(alk)$_b$-Cy, -alk-OC(X)-(alk)$_b$-Cy, -alk-C(X) O-(alk)$_b$-Cy, -alk-C(X) NR$^4$-(alk)$_b$-Cy, -alk-S(O)$_2$N 4-(alk)$_b$-Cy, -alk-NR$^4$C(X)-(alk)$_b$-Cy, -alk-NR$^4$S(O)$_2$-(alk)$_b$-Cy, -alk-NR$^4$C(X)O-(alk)$_b$-Cy, -alk-OC(X) NR$^4$-(alk)$_b$-Cy, -alk-NR$^4$C(X) NR$^4$-(alk)$_b$-Cy, -alk-NR$^4$S(O)$_2$NR$^4$-(alk)$_b$-Cy, and $C_{2-4}$ alkyl, wherein $C_{2-4}$ alkyl is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, and di-alkylamino, L at each occurrence is independently selected from the group consisting of -(alk), —X-(alk)$_b$-, -(alk)$_a$-NR$^4$-(alk)$_b$-, -(alk)$_a$-C(X)-(alk)$_b$-, -(alk)$_a$-S(O)-(alk)$_b$-, -(alk)$_a$-S(O)$_2$-(alk)$_b$-, -(alk)$_a$-OC(X)-(alk)$_b$-, -(alk)$_a$-C(X)O-(alk)$_b$-, -(alk)$_a$-C(X)NR$^4$-(alk)$_b$-, -(alk)$_a$-S(O)$_2$NR$^4$-(alk)$_b$-, -(alk)$_a$-NR$^4$C(X)-(alk)$_b$-, -(alk)$_a$-NR$^4$S(O)$_2$-(alk)$_b$-, -(alk)$_a$-NR$^4$C(X)O-(alk)$_b$-, -(alk)$_a$-OC(X)NR$^4$-(alk)$_b$-, -(alk)$_a$-NR$^4$C(X) NR$^4$-(alk)$_b$-, and -(alk)$_a$-NR$^4$S(O)$_2$NR$^4$-(alk)$_b$-;

a and b are independently 0 or 1;

alk is $C_{1-3}$ alkylene or $C_{1-3}$ alkylene substituted with one or more substituents selected from the group consisting of fluoro, —OH, —NH$_2$, lower alkyl, lower alkoxy, lower alkylthio, mono-alkylamino, di-alkylamino, and —NR$^5$R$^6$, wherein lower alkyl or the alkyl chain(s) of lower alkoxy, lower alkylthio, mono-alkylamino or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution of the alkyl chain carbon bound to O of alkoxy, S of thioalkyl or N of mono- or di-alkylamino is fluoro;

X is O or S;

Cy is optionally substituted cycloalkyl, optionally substituted heterocycloalkyl, optionally substituted aryl, or optionally substituted heteroaryl;

$R^4$ at each occurrence is independently selected from the group consisting of hydrogen, optionally substituted lower alkyl, optionally substituted cycloalkyl, optionally substituted heterocycloalkyl, optionally substituted aryl, and optionally substituted heteroaryl; and $R^5$ and $R^6$ combine with the nitrogen to which they are attached to form a 5-7 membered heterocycloalkyl optionally substituted with one or more substituents selected from the group consisting of fluoro, —OH, —N$_2$, lower alkyl, fluoro substituted lower alkyl, lower alkoxy, fluoro substituted lower alkoxy, lower alkylthio, and fluoro substituted lower alkylthio, provided, however, that the compound is not

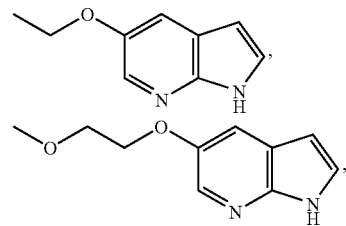

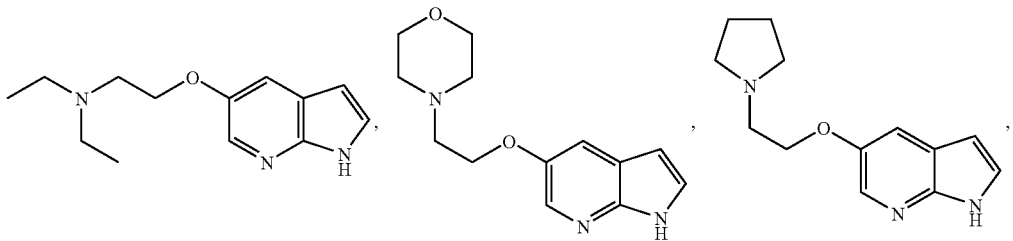

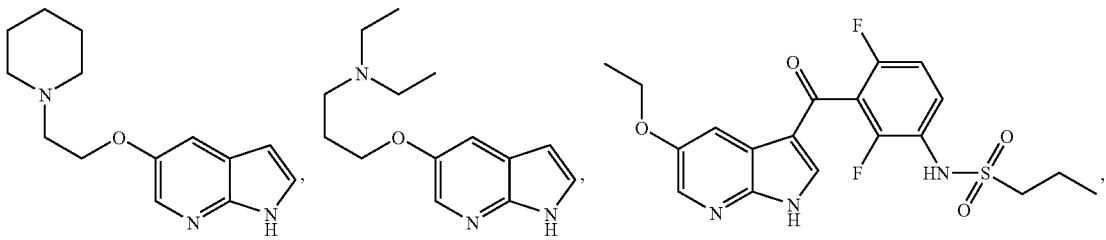

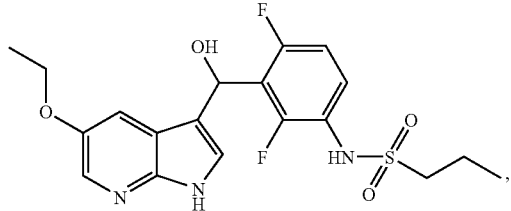
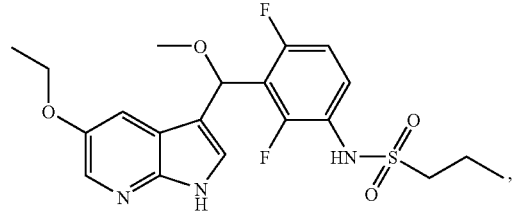
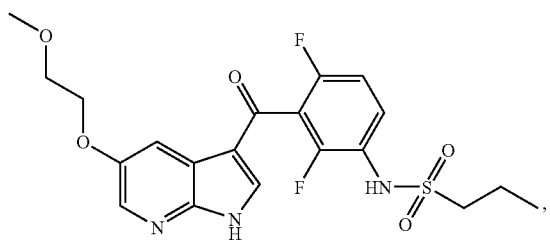
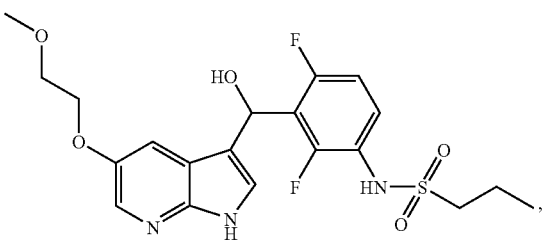
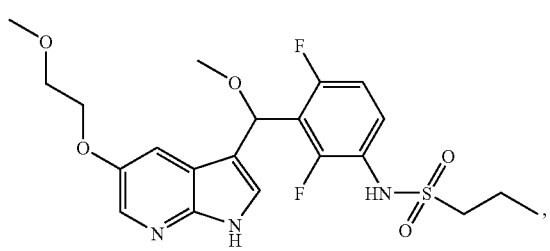
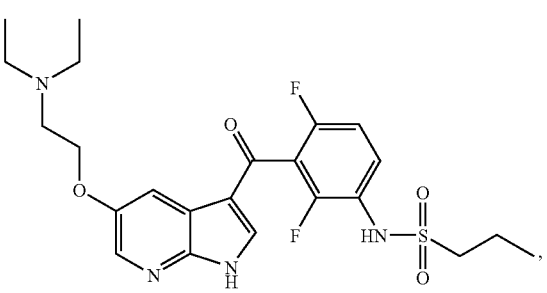
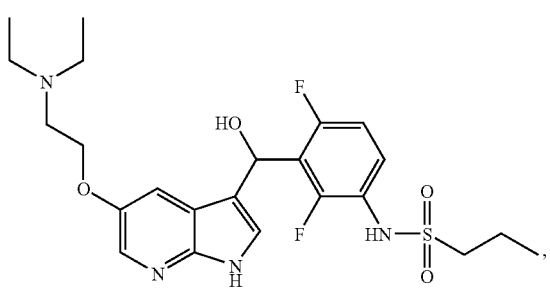
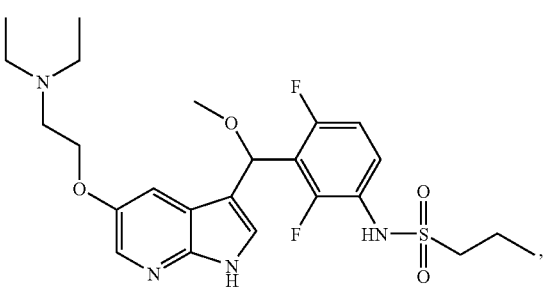
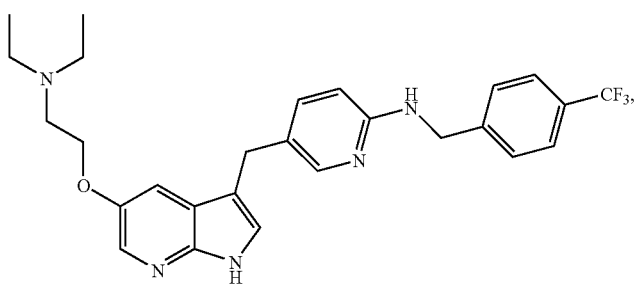
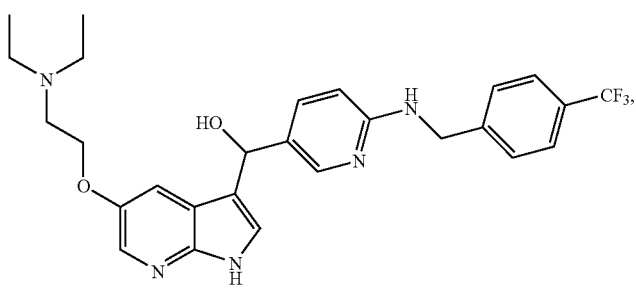

-continued
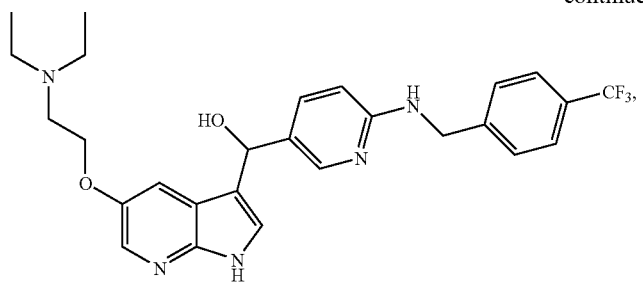
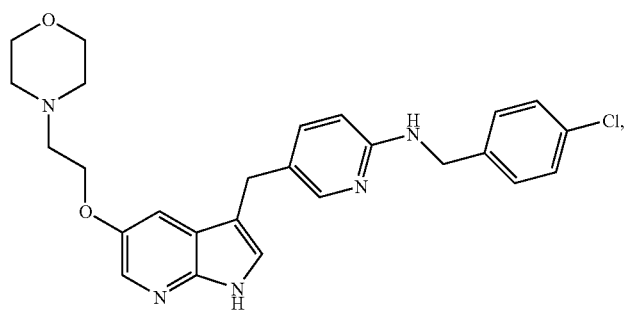
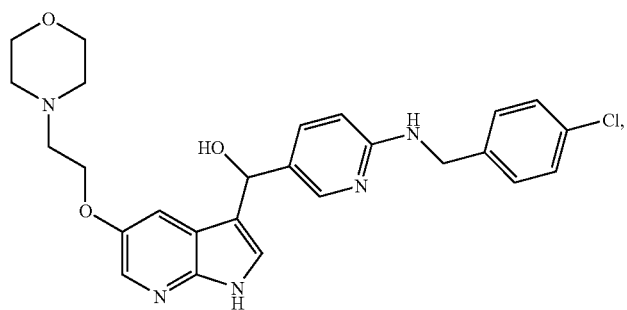
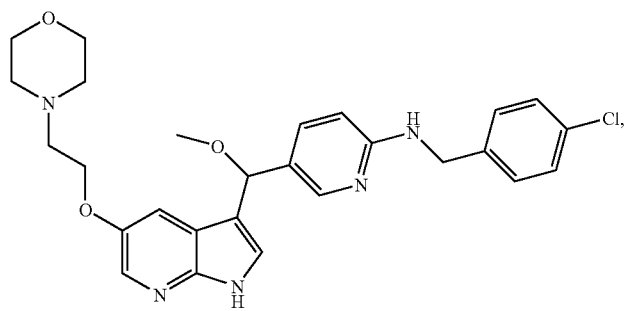
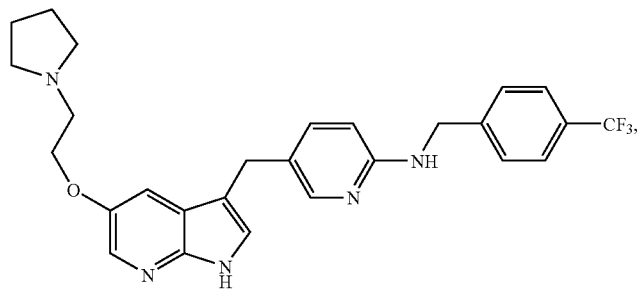

-continued
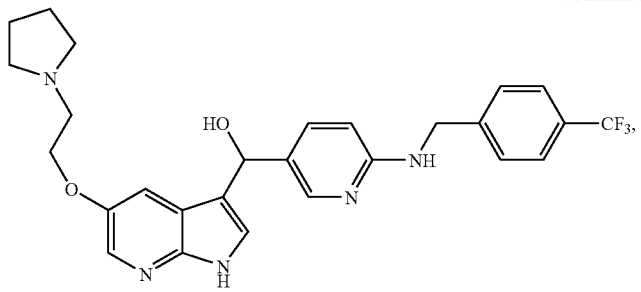
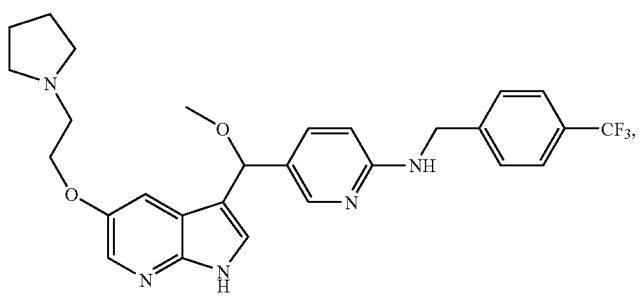
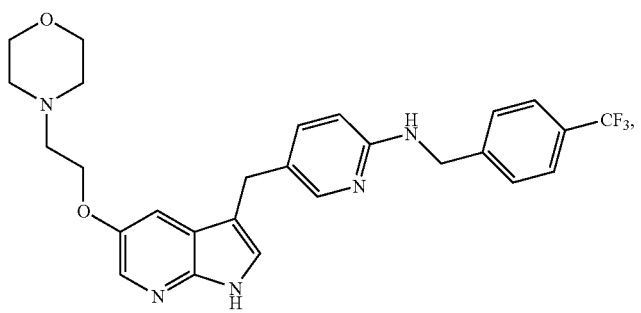
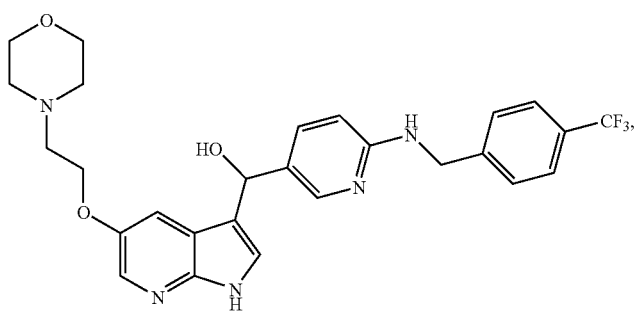
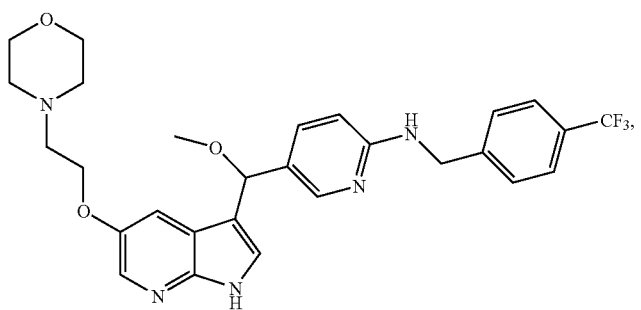

-continued
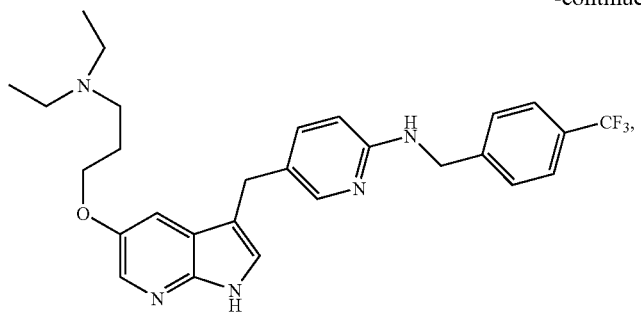
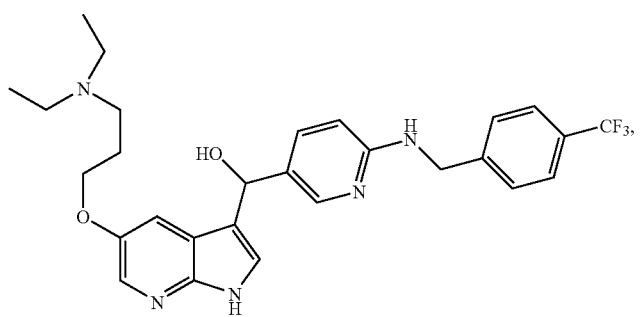
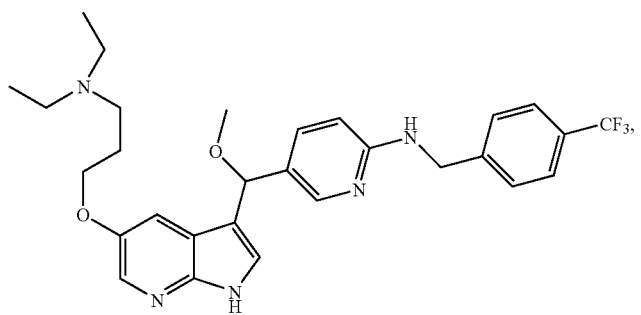
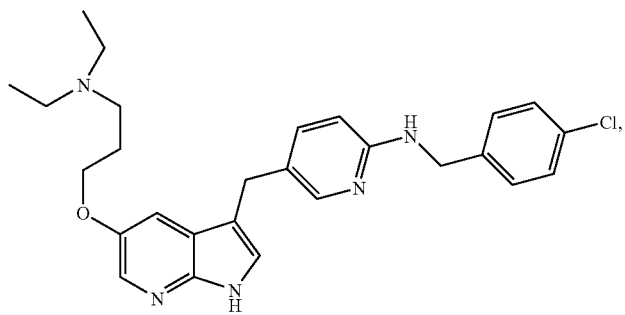
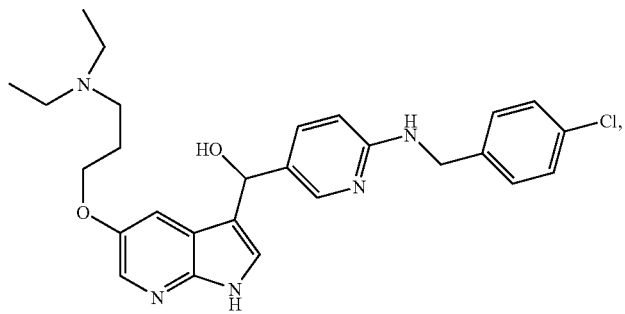

-continued
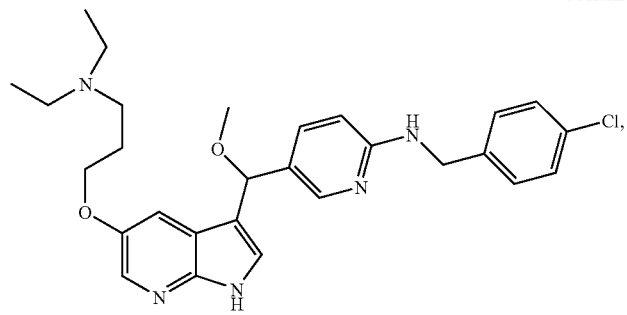
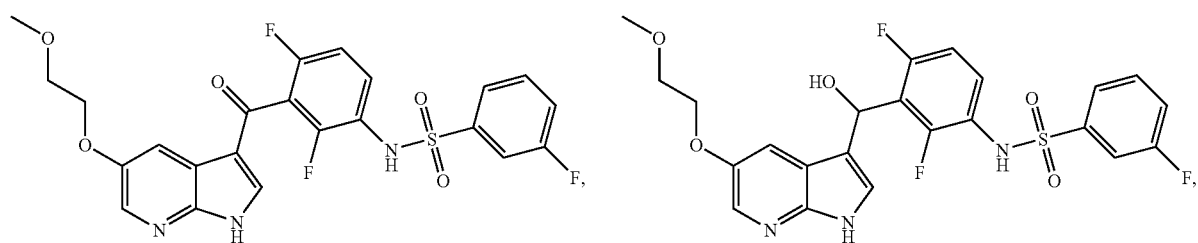
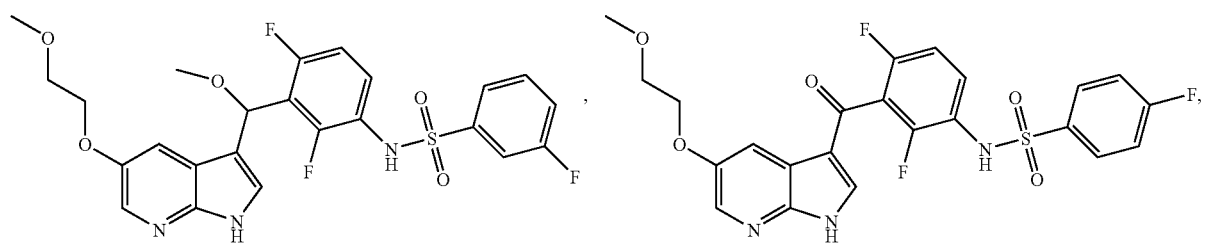
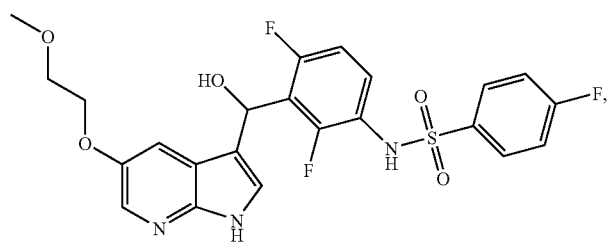
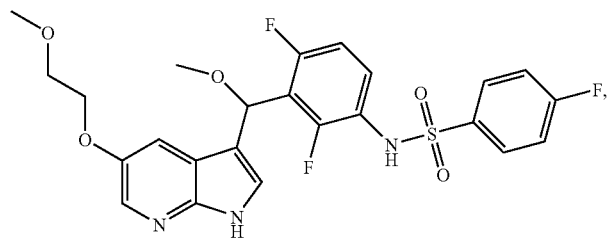
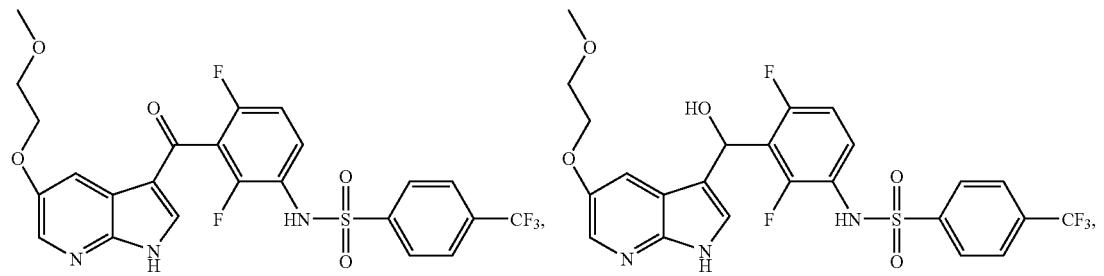

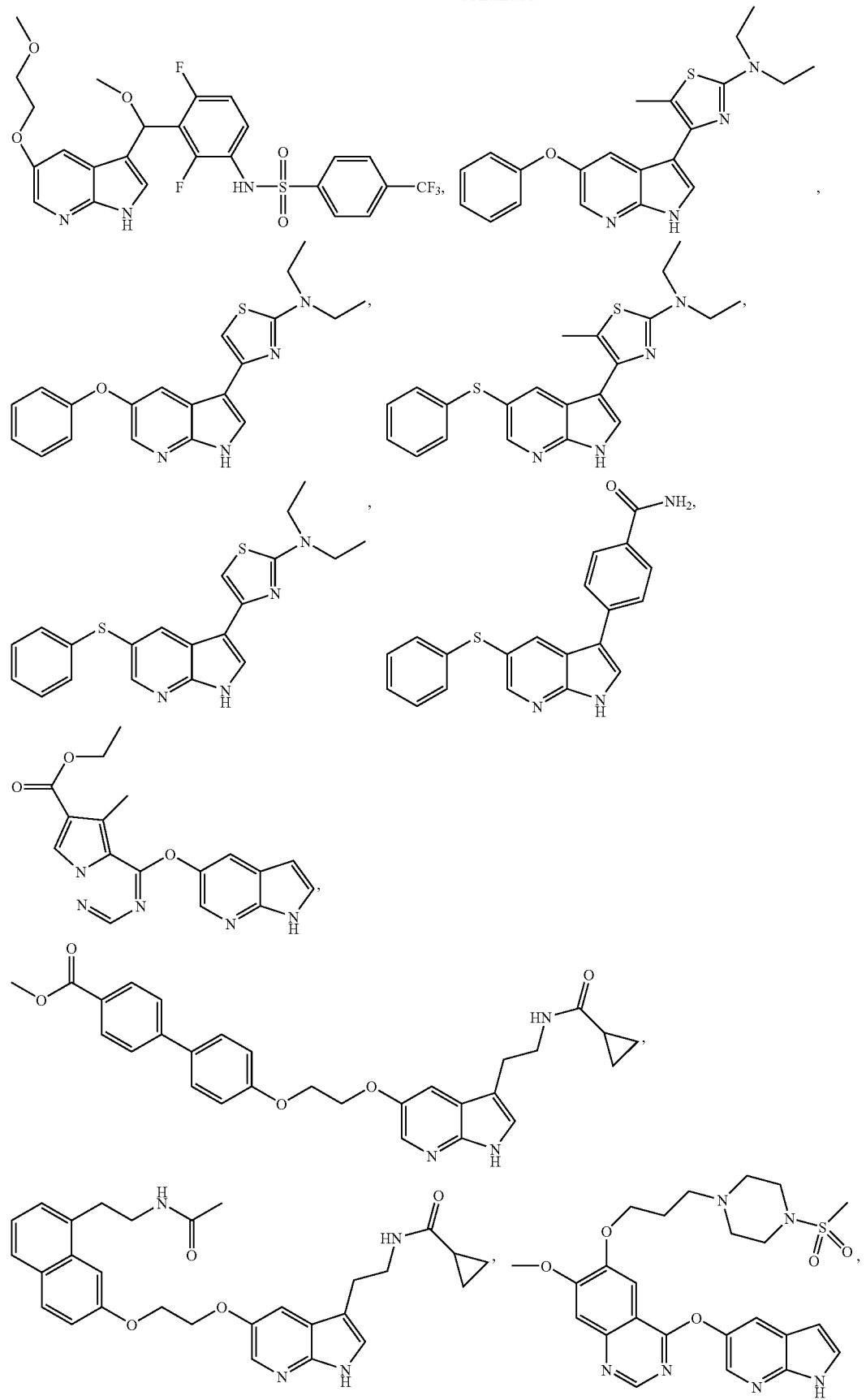

-continued
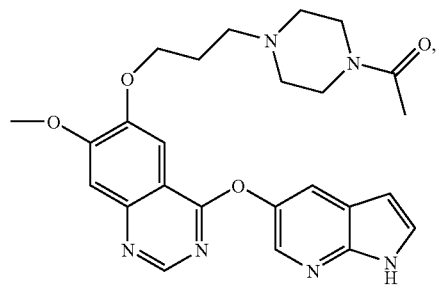
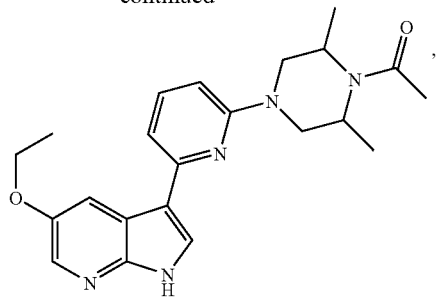
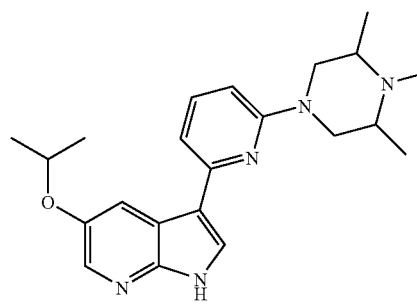
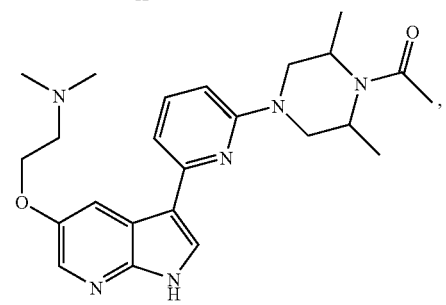
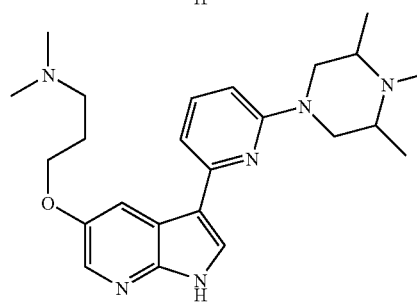
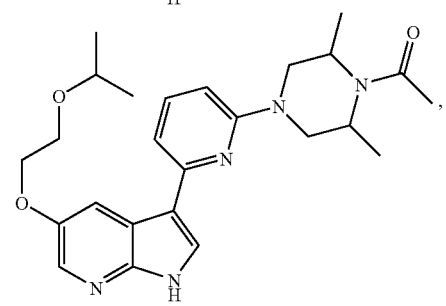
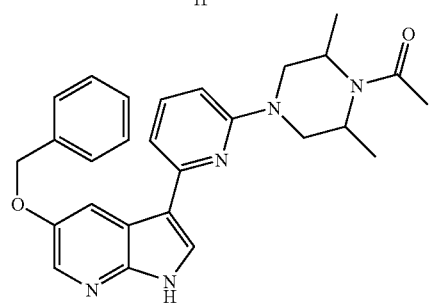
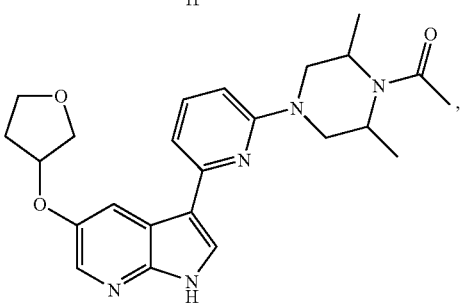
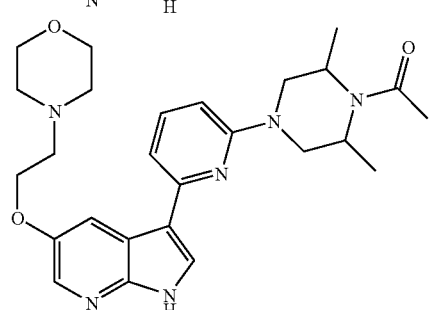
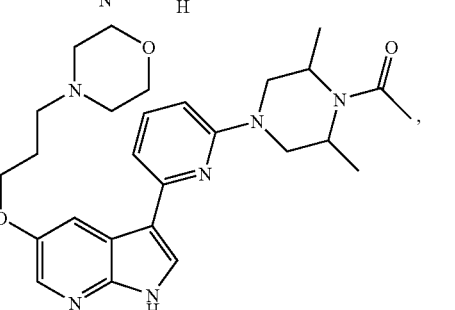
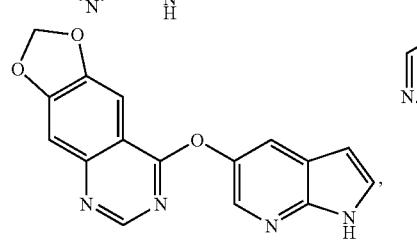
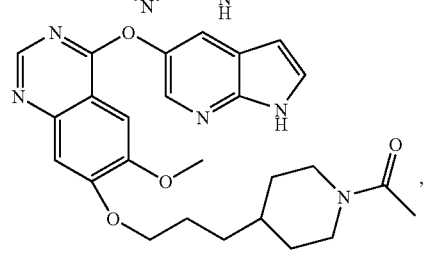

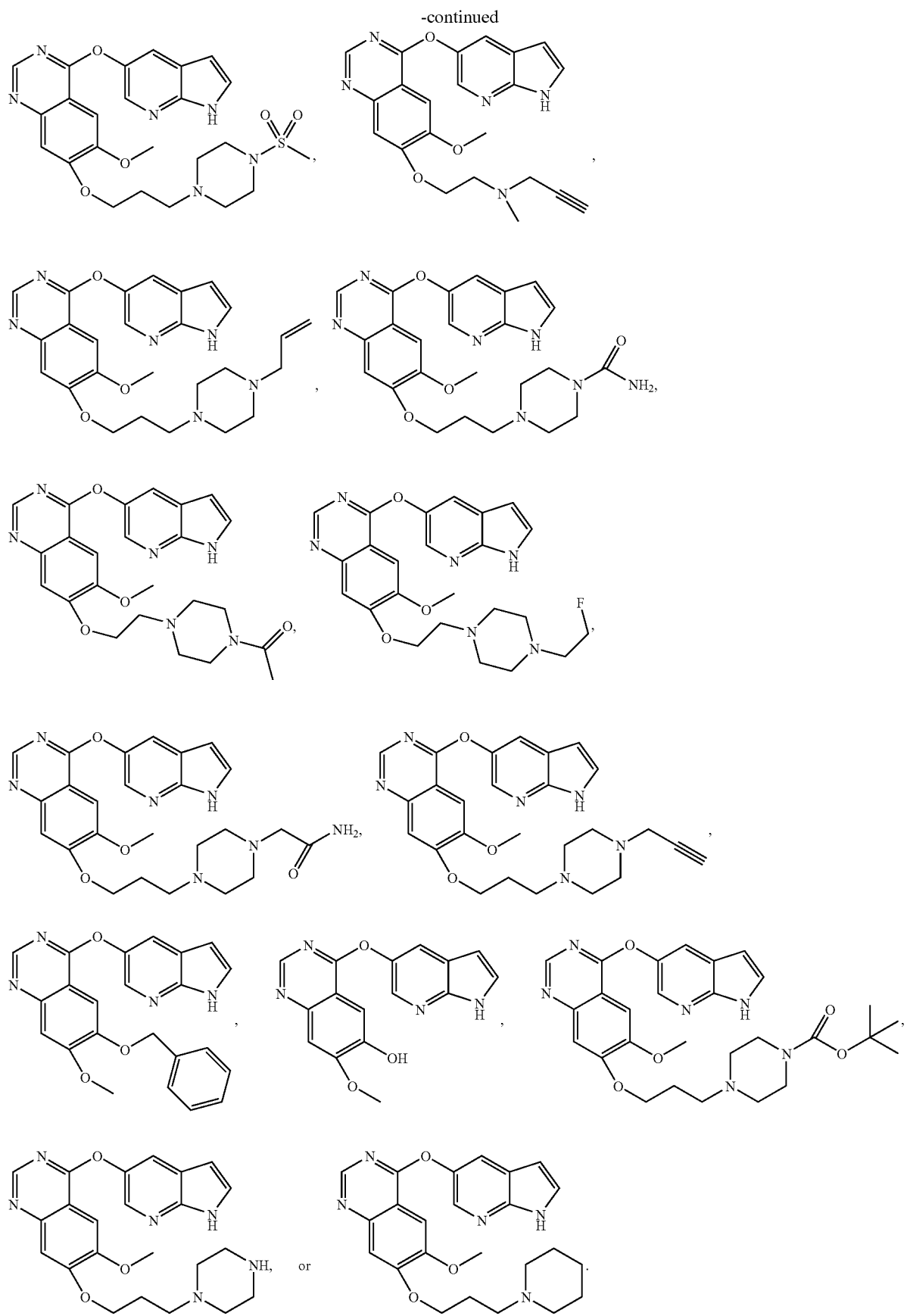

In some embodiments, compounds of Formula I have the sub-generic structure according to owing Formula Ia:

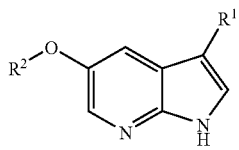

Formula Ia all salts, prodrugs, tautomers and isomers thereof, wherein $R^1$ and $R^2$ are as defined for Formula I.

In some embodiments, compounds of Formula I have the sub-generic structure according to the following Formula Ib:

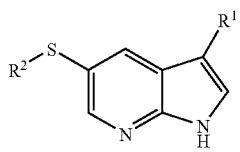

Formula Ib all salts, prodrugs, tautomers and isomers thereof, wherein $R^1$ and $R^2$ are as defined for Formula I.

In some embodiments, compounds of Formula I have the sub-generic structure according to wing Formula Ic:

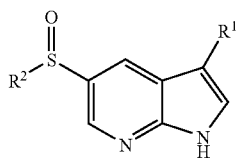

Formula Ic all salts, prodrugs, tautomers and isomers thereof, wherein $R^1$ and $R^2$ are as defined for Formula I.

In some embodiments, compounds of Formula I have the sub-generic structure according to the following Formula Id:

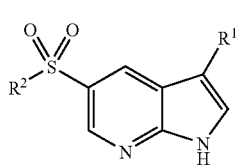

Formula Id all salts, prodrugs, tautomers and isomers thereof, wherein $R^1$ and $R^2$ are as defined for Formula I.

In some embodiments, compounds of Formula I have the sub-generic structure according to the following Formula Ie:

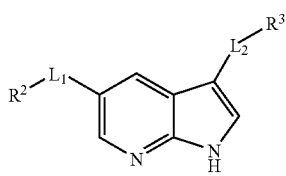

Formula Ie all salts, prodrugs, tautomers and isomers thereof,
wherein
 $L_2$ is L or optionally substituted methylene; and
 L, $L_1$, $R^2$ and $R^3$ are as defined for Formula I.

In some embodiments, compounds of Formula I have the sub-generic structure according to the following Formula If:

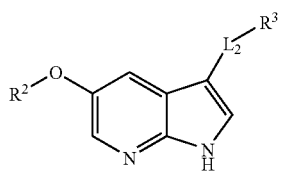

Formula If all salts, prodrugs, tautomers and isomers thereof,
wherein
 $L_2$ is as defined for Formula Ie; and
 $R^2$ and $R^3$ are as defined for Formula I.

In some embodiments, compounds of Formula I have the sub-generic structure according to the following Formula Ig:

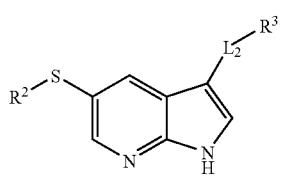

Formula Ig all salts, prod rugs, tautomers and isomers thereof,
wherein
 $L_2$ is as defined for Formula Ie; and
 $R^2$ and $R^3$ are as defined for Formula I.

In some embodiments, compounds of Formula I have the sub-generic structure according to the following Formula Ih:

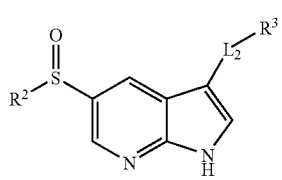

Formula Ih all salts, prodrugs, tautomers and isomers thereof,
wherein
 $L_2$ is as defined for Formula Ie; and
 $R^2$ and $R^3$ are as defined for Formula I.

In some embodiments, compounds of Formula I have the sub-generic structure according to the following Formula Ii:

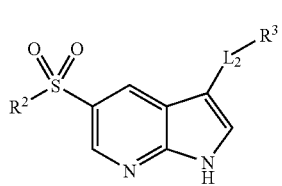

Formula Ii all salts, prodrugs, tautomers and isomers thereof,
wherein
 $L_2$ is as defined for Formula Ie; and
 $R^2$ and $R^3$ are as defined for Formula I.

In some embodiments, compounds of Formula I have the sub-generic structure according to the following Formula Ij:

Formula Ij all salts, prodrugs, tautomers and isomers thereof, wherein

- $L_3$ is selected from the group consisting of —O—, —S—, —$CR^aR^b$—, —$NR^4$—, —C(O)—, —C(S)—, —S(O)—, and —$S(O)_2$—;
- $R^a$ and $R^b$ at each occurrence are independently selected from the group consisting of hydrogen, fluoro, —OH, —$NH_2$, lower alkyl, lower alkoxy, lower alkylthio, mono-alkylamino, di-alkylamino, and —$NR^5R^6$, wherein the alkyl chain(s) of lower alkyl, lower alkoxy, lower alkylthio, mono-alkylamino, or di-alkylamino are optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro; or
- $R^a$ and $R^b$ combine to form a 3-7 membered monocyclic cycloalkyl or 5-7 membered monocyclic heterocycloalkyl, wherein the monocyclic cycloalkyl or monocyclic heterocycloalkyl are optionally substituted with one or more substituents selected from the group consisting of halogen, —OH, —$NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; and
- $L_1$, $R^2$, $R^3$, $R^4$, $R^5$ and $R^6$ are as defined for Formula I.

In some embodiments, compounds of Formula I have the sub-generic structure according to the following Formula Ik:

Formula Ik all salts, prodrugs, tautomers and isomers thereof, wherein

- $L_3$ is as defined for Formula Ij; and
- $R^2$ and $R^3$ are as defined for Formula I.

In some embodiments, compounds of Formula I have the sub-generic structure according to the following Formula Im:

Formula Im all salts, prodrugs, tautomers and isomers thereof, wherein

- $L_3$ is as defined for Formula Ij; and
- $R^2$ and $R^3$ are as defined for Formula I.

In some embodiments, compounds of Formula I have the sub-generic structure according to the following Formula In:

Formula In all salts, prodrugs, tautomers and isomers thereof, wherein

- $L_3$ is as defined for Formula Ij; and
- $R^2$ and $R^3$ are as defined for Formula I.

In some embodiments, compounds of Formula I have the sub-generic structure according to the following Formula Io:

Formula Io all salts, prodrugs, tautomers and isomers thereof, wherein

- $L_3$ is as defined for Formula Ij; and
- $R^2$ and $R^3$ are as defined for Formula I.

In some embodiments of compounds of Formula I, Formula Ia, Formula Ib, Formula Ic, Formula Id, Formula Ie, Formula If, Formula Ig, Formula Ih, Formula Ii, Formula Ij, Formula Ik, Formula Im, Formula In or Formula Io. $R^2$ is selected from the group consisting of -Cy, -alk-Cy, -alk-X-$(alk)_b$-Cy, -alk-$NR^4$-$(alk)_b$-Cy, -alk-C(X)-$(alk)_b$-Cy, -alk-S(O)-$(alk)_b$-Cy, -alk-$S(O)_2$-$(alk)_b$-Cy, -alk-OC(X)-$(alk)_b$-Cy, -alk-C(X) O-$(alk)_b$-Cy, -alk-C(X)$NR^4$-$(alk)_b$-Cy, -alk-$S(O)_2$ $NR^4$-$(alk)_b$-Cy, -alk-$NR^4$C(X)-$(alk)_b$-Cy, -alk-$NR^4$$S(O)_2$-$(alk)_b$-Cy, -alk-$NR^4$C(X) O-$(alk)_b$-Cy, -alk-OC(X)$NR^4$-$(alk)_b$-Cy, -alk-$NR^4$C(X)$NR^4$-$(alk)_b$-Cy, and -alk-$NR^4$$S(O)_2$ $NR^4$-$(alk)_b$-Cy. In one embodiment, $R^2$ is selected from the group consisting of -Cy, -alk-Cy, -alk-X-$(alk)_b$-Cy, -alk-$NR^4$-$(alk)_b$-Cy, -alk-C(X)-$(alk)$b-Cy, -alk-S(O)-$(alk)_b$-Cy, -alk-S$(O)_2$-$(alk)_b$-Cy, -alk-OC(X)-$(alk)_b$-Cy, -alk-C(X) O-$(alk)_b$-Cy, -alk-C(X)$NR^4$-$(alk)_b$-Cy, -alk-$S(O)_2$$NR^4$-$(alk)_b$-Cy, -alk-$NR^4$C(X)-$(alk)_b$-Cy, -alk-$NR^4$$S(O)_2$-$(alk)_b$-Cy, -alk-$NR^4$C(X)O-$(alk)_b$-Cy, -alk-OC(X)$NR^4$-$(alk)_b$-Cy, -alk-$NR^4$C(X) $NR^4$-$(alk)_b$-Cy, and -alk-$NR^4$$S(O)_2$$NR^4$-$(alk)_b$-Cy, and Cy is optionally substituted cycloalkyl, optionally substituted aryl or optionally substituted heteroaryl. In one embodiment, $R^2$ is selected from the group consisting of -Cy, -alk-Cy, -alk-X-$(alk)_b$-Cy, -alk-$NR^4$-$(alk)_b$-Cy, -alk-C(X)-$(alk)_b$-Cy, -alk-S(O)-$(alk)_b$-Cy, -alk-$S(O)_2$-$(alk)_b$-Cy, -alk-OC(X)-$(alk)_b$-Cy, -alk-C(X)O-$(alk)_b$-Cy, -alk-C(X)$NR^4$-$(alk)_b$-Cy, -alk-$S(O)_2$ $NR^4$-$(alk)_b$-Cy, -alk-$NR^4$C(X)-$(alk)_b$-Cy, -alk-$NR^4$$S(O)_2$-$(alk)_b$-Cy, -alk-$NR^4$C(X)O-$(alk)_b$-Cy, -alk-OC(X)$NR^4$-$(alk)_b$ -Cy, -alk-$NR^4$C(X) $NR^4$-$(alk)_b$-Cy, and -alk-$NR^4$$S(O)_2$ $NR^4$-$(alk)_b$-Cy, and Cy is optionally substituted aryl or optionally substituted heteroaryl.

In some embodiments, compounds of Formula I have the sub-generic structure according to the following Formula Ip:

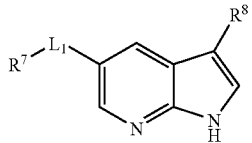

Formula Ip all salts, prodrugs, tautomers and isomers thereof;
wherein $R^7$ is selected from the group consisting of -$Cy_1$, -alk-$Cy_1$, -alk-X-(alk)$_b$-$Cy_1$, -alk-$NR^{12}$-(alk)$_b$-$Cy_1$, -alk-C(X)-(alk)$_b$-$Cy_1$, -alk-S(O)-(alk)$_b$-$Cy_1$, -alk-$S(O)_2$-(alk)$_b$-$Cy_1$, -alk-OC(X)-(alk)$_b$-$Cy_1$, -alk-C(X) O-(alk)$_b$-$Cy_1$, -alk-C(X)$NR^{12}$-(alk)$_b$-$Cy_1$, -alk-$S(O)_2NR^{12}$-(alk)$_b$-$Cy_1$, -alk-$NR^{12}$C(X)-(alk)$_b$-$Cy_1$, -alk-$NR^{12}S(O)_2$-(alk)$_b$-$Cy_1$, -alk-$NR^{12}$C(X)O-(alk)$_b$-$Cy_1$-alk-OC(X)$NR^{12}$-(alk)$_b$-$Cy_1$, -alk-$NR^{12}$C(X)$NR^{12}$—(alk)$_b$-$Cy_1$, -alk-$NR^{12}S(O)_2NR^{12}$-(alk)$_b$-$Cy_1$, and $C_{2-4}$ alkyl, wherein $C_{2-4}$ alkyl is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, and di-alkylamino;

$R^8$ is selected from the group consisting of hydrogen, halogen, lower alkyl, lower alkenyl, lower alkynyl, cycloalkyl, heterocycloalkyl, aryl, heteroaryl, —$OR^9$, —$SR^9$, —$CR^{10}R^{11}R^9$, —$NR^{12}R^9$, —$C(O)R^9$, —$C(S)R^9$, —$S(O)R^9$, and —$S(O)_2R^9$, wherein lower alkyl, lower alkenyl, or lower alkynyl are optionally substituted with one or more substituents selected from the group consisting of fluoro, —OH, —$NH_2$, —C(O)OH, —$C(O)NH_2$, —$OR^{13}$, —$SR^{13}$, —$NR^{12}R^{13}$, —C(O) $OR^{13}$, —$C(O)NR^{12}R^{13}$, cycloalkyl, heterocycloalkyl, aryl, and heteroaryl, and wherein cycloalkyl, heterocycloalkyl, aryl, or heteroaryl as $R^8$, or a substituent of lower alkyl, lower alkenyl, or lower alkynyl are optionally substituted with one or more substituents selected from the group consisting of —OH, —$NH_2$, —CN, —$NO_2$, —C(O)OH, —$S(O)_2NH_2$, —$C(O)NH_2$, —$C(S)NH_2$, —$NHC(O)NH_2$, —$NHC(S)NH_2$, —$NHS(O)_2NH_2$, —$OR^{13}$, —$SR^{13}$, —$NR^{12}R^{13}$, —$C(O)R^{13}$, —$C(S)R^{13}$, —$C(O)OR^{13}$, —$C(O)NR^{12}R^{13}$, —$C(S)NR^{12}R^{13}$, —$S(O)_2NR^{12}R^{13}$, —$NR^{12}C(O)R^{13}$, —$NR^{12}C(S)R^{13}$, —$NR^{12}S(O)_2R^{13}$, —$NR^{12}C(O)NR^{12}R^{13}$, —$NR^{12}C(S)NR^{12}R^{13}$, —$NR^{12}S(O)_2NR^{12}R^{13}$, —$S(O)R^{13}$, —$S(O)_2R^{13}$, halogen, lower alkyl, fluoro substituted lower alkyl, and cycloalkylamino.

$R^9$ is selected from the group consisting of lower alkyl, lower alkenyl, lower alkynyl, cycloalkyl, heterocycloalkyl, aryl, and heteroaryl, wherein lower alkyl, lower alkenyl, and lower alkynyl are optionally substituted with one or more substituents selected from the group consisting of fluoro, —OH, —$NH_2$, —C(O)OH, —$C(O)NH_2$, —$OR^{13}$, —$SR^{13}$, —$NR^{12}R^{13}$, —C(O) $OR^{13}$—$C(O)NR^{12}R^{13}$ cycloalkyl, heterocycloalkyl, aryl, and heteroaryl, and wherein cycloalkyl, heterocycloalkyl, aryl, and heteroaryl as $R^9$, or a substituent of lower alkyl, lower alkenyl, or lower alkynyl are optionally substituted with one or more substituents selected from the group consisting of —OH, —$NH_2$, —CN, —$NO_2$,—C(O)OH, —$S(O)_2NH_2$,—$C(O)NH_2$,—C(S) $NH_2$, —$NHC(O)NH_2$, —$NHC(S)NH_2$, —$NHS(O)_2$ $NH_2$,—$OR^{13}$,—$SR^{13}$,—$NR^{12}R^{13}$,—$C(O)R^{13}$,—C(S) $R^{13}$, —$C(O)OR^{13}$, —$C(O)NR^{12}R^{13}$, —C(S) $NR^{12}R^{13}$, —$S(O)_2NR^{12}R^{13}$, —$NR^{12}C(O)R^{13}$, —$NR^{12}C(S)R^{13}$—$NR^{12}S(O)_2R^{13}$, —$NR^{12}C(O)$ $NR^{12}R^{13}$, —$NR^{12}C(S)NR^{12}R^{13}$, —$NR^{12}S(O)_2$ $NR^{12}R^{13}$, —$S(O)R^{13}$, —$S(O)_2R^{13}$, halogen, lower alkyl, fluoro substituted lower alkyl, and cycloalkylamino;

$Cy_1$ is cycloalkyl, heterocycloalkyl, aryl or heteroaryl, wherein cycloalkyl, heterocycloalkyl, aryl, and heteroaryl are optionally substituted with one or more substituents selected from the group consisting of —OH, —$NH_2$, —CN, —$NO_2$, —C(O)OH, —$S(O)_2NH_2$, —$C(O)NH_2$, —$C(S)NH_2$, —$NHC(O)NH_2$, —$NHC(S)$ $NH_2$, —$NHS(O)_2NH_2$, —$OR^{13}$, —$SR^{13}$,—$NR^{12}R^{13}$, —$C(O)R^{13}$, —$C(S)R^{13}$, —$C(O)OR^{13}$, —C(O) $NR^{12}R^{13}$, —$C(S)NR^{12}R^{13}$, —$S(O)_2NR^{12}R^{13}$, —$NR^{12}C(O)R^{13}$, —$NR^{12}C(S)R^{13}$, —$NR^{12}S(O)_2R^{13}$, —$NR^{12}C(O)NR^{12}R^{13}$, —$NR^{12}C(S)NR^{12}R^{13}$, —$NR^{12}S(O)_2NR^{12}R^{13}$, —$S(O)R^{13}$, —$S(O)_2R^{13}$, halogen, lower alkyl, fluoro substituted lower alkyl, and cycloalkylamino;

$R^{10}$ and $R^{11}$ are independently selected from the group consisting of hydrogen, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; or $R^{10}$ and $R^{11}$ combine to form a 3-7 membered monocyclic cycloalkyl or 5-7 membered monocyclic heterocycloalkyl, wherein the monocyclic cycloalkyl or monocyclic heterocycloalkyl is optionally substituted with one or more substituents selected from the group consisting of halogen, —OH, —$NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^{12}$ at each occurrence is independently hydrogen, lower alkyl or fluoro substituted lower alkyl;

$R^{13}$ at each occurrence is independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, provided, however, that any substitution of the alkyl carbon bound to O, S, or N of —$OR^{13}$, —$SR^{13}$, —$NR^{12}R^{13}$, —$C(O)OR^{13}$, —$C(O)NR^{12}R^{13}$, or —$S(O)_2$ $NR^{12}R^{13}$ is fluoro, cycloalkyl, heterocycloalkyl, aryl or heteroaryl, and wherein cycloalkyl, heterocycloalkyl, aryl, and heteroaryl as $R^{13}$ or as substituents of lower alkyl are optionally substituted with one or more substituents selected from the group consisting of —OH, —$NH_2$, —CN, —$NO_2$, —C(O)OH, —$S(O)_2$ $NH_2$,—$C(O)NH_2$, $OR^{14}$, $SR^{14}$,—$NR^{12}R^{14}$,—$NR^{12}C$ $(O)R^{14}$, —$NR^{12}S(O)_2R^{14}$, —$S(O)_2R^{14}$, —$C(O)R^{14}$, —$C(O)OR^{14}$, —$C(O)NR^{12}R^{14}$, —$S(O)_2NR^{12}R^{14}$, halogen, lower alkyl, fluoro substituted lower alkyl, and cycloalkylamino;

$R^{14}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl carbon bound to O, S, or N of —$OR^{14}$, —$SR^{14}$,—$NR^{12}R^{14}$,—$C(O)OR^{14}$,—$C(O)NR^{12}R^{14}$, or —S(O)$_2$NR$^{12}$R$^{14}$ is fluoro, and wherein heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy; and L$_1$, alk, X, and b are as defined for Formula I.

In some embodiments, compounds of Formula I have the sub-generic structure according to the following Formula Iq:

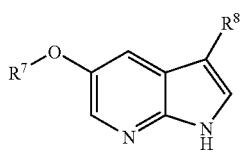

Formula Iq all salts, prodrugs, tautomers and isomers thereof, wherein

R$^7$ and R$^8$ are as defined for Formula Ip.

In some embodiments, compounds of Formula I have the sub-generic structure according to the following Formula Ir:

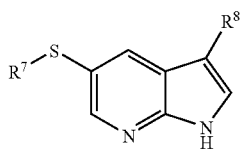

Formula Ir all salts, prodrugs, tautomers and isomers thereof, wherein

R$^7$ and R$^8$ are as defined for Formula Ip.

In some embodiments, compounds of Formula I have the sub-generic structure according to the following Formula Is:

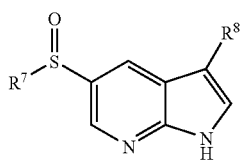

Formula Is all salts, prodrugs, tautomers and isomers thereof, wherein

R$^7$ and R$^8$ are as defined for Formula Ip.

In some embodiments, compounds of Formula I have the sub-generic structure according to the following Formula It:

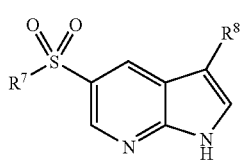

Formula It all salts, prodrugs, tautomers and isomers thereof, wherein

R$^7$ and R$^8$ are as defined for Formula Ip.

In some embodiments of compounds of Formula Ip, Formula Iq, Formula Ir, Formula Is, or Formula It, R$^7$ is selected from the group consisting of -Cy$_1$, -alk-Cy$_1$, -alk-X-(alk)$_b$-Cy$_1$, -alk-NR$^{12}$-(alk)$_b$-Cy$_1$, -alk-C(X)-(alk)$_b$-Cy$_1$, -alk-S(O)-(alk)$_b$-Cy , -alk-S(O)$_2$-(alk)$_b$-Cy$_1$, -alk-OC(X)-(alk)$_b$-Cy$_1$, -alk-C(X)O-(alk)$_b$-Cy$_1$, -alk-C(X)NR$^{12}$-(alk)$_b$-Cy$_1$, -alk-S(O)$_2$NR$^{12}$-(alk)$_b$-Cy$_1$, -alk-NR$^{12}$C(X)-(alk)$_b$-Cy$_1$, -alk-NR$^{12}$S(O)$_2$-(alk)$_b$-Cy$_1$, -alk-NR$^{12}$C(X)O-(alk)$_b$-Cy$_1$, -alk-OC(X)NR$^{12}$-(alk)$_b$-Cy$_1$, -alk-NR$^{12}$C(X)NR$^{12}$-(alk)$_b$-Cy$_1$, and -alk-NR$^{12}$S(O)$_2$NR$^{12}$-(alk)$_b$-Cy$_1$; R$^8$ is selected from the group consisting of hydrogen, —OR$^9$, —SR$^9$, —CR$^{10}$R$^{11}$R$^9$, —NR$^2$R$^9$, —C(O)R$^9$, —C(S)R$^9$, —S(O)R$^9$, and —S(O)$_2$R$^9$; and R$^9$ is aryl or heteroaryl, wherein aryl or heteroaryl are optionally substituted with one or more substituents selected from the group consisting of —OH, —NH$_2$, —CN, —NO$_2$, —C(O)OH, —S(O)$_2$NH$_2$, —C(O)NH$_2$, —C(S)NH$_2$, —NHC(O)NH$_2$, —NHC(S)NH$_2$, —NHS(O)$_2$NH$_2$, —OR$^{13}$, —SR$^{13}$, —NR$^{12}$R$^{13}$, —C(O)R$^{13}$, —C(S)R$^{13}$, —C(O)OR$^{13}$, —C(O)NR$^{12}$R$^{13}$, —C(S)NR$^{12}$R$^{13}$, —S(O)$_2$NR$^{12}$R$^{13}$, —NR$^{12}$C(O)R$^{13}$, —NR$^{12}$C(S)R$^{13}$, —NR$^{12}$S(O)$_2$R$^{13}$, —NR$^{12}$C(O)NR$^{12}$R$^{13}$. —NR$^{12}$C(S)NR$^{12}$R$^{13}$, —NR$^{12}$S(O)$_2$NR$^{12}$R$^{13}$, —S(O)R$^{13}$, —S(O)$_2$R$^{13}$, halogen, lower alkyl, fluoro substituted lower alkyl, and cycloalkylamino.

In some embodiments of compounds of Formula Ip, Formula Iq, Formula Ir, Formula Is, or Formula It, R$^7$ is -Cy$_1$ or -alk-Cy$_1$, Cy, is cycloalkyl, heterocycloalkyl, aryl or heteroaryl, wherein cycloalkyl, heterocycloalkyl, aryl or heteroaryl are optionally substituted with one or more substituents selected from the group consisting of —OH, —NH$_2$, —CN, —NO$_2$, —C(O)OH, —S(O)$_2$NH$_2$, —C(O)NH$_2$, —C(S)NH$_2$, —NHC(O)NH$_2$, —NHC(S)NH$_2$, NHS(O)$_2$NH$_2$, —OR$^{13}$, —SR$^{13}$, —NR$^{12}$R$^{13}$, —C(O)R$^{13}$, —C(S)R$^{13}$, —C(O)OR$^{13}$, —C(O)NR$^{12}$R$^{13}$, —C(S)NR$^{12}$R$^{13}$, —S(O)$_2$NR$^{12}$R$^{13}$, —NR$^{12}$C(O)R$^{13}$, —NR$^{12}$C(S)R$^{13}$, —NR$^{12}$S(O)$_2$R$^{13}$, —NR$^{12}$C(O)NR$^{12}$R$^{13}$, —NR$^{12}$C(S)NR$^{12}$R$^{13}$, —NR$^{12}$S(O)$_2$NR$^{12}$R$^{13}$, —S(O)R$^{13}$, —S(O)$_2$R$^{13}$, halogen, lower alkyl, fluoro substituted lower alkyl, and cycloalkylamino; R$^8$ is selected from the group consisting of hydrogen, —OR$^9$, —SR$^9$, —CR$^{10}$R$^{11}$R$^9$, —NR$^{12}$R$^9$, —C(O)R$^9$, —C(S)R$^9$, —S(O)R$^9$, and —S(O)$_2$R$^9$; and R$^9$ is aryl or heteroaryl, wherein aryl and heteroaryl are optionally substituted with one or more substituents selected from the group consisting of —OH, —NH$_2$, —CN, —NO$_2$, —C(O)OH, —S(O)$_2$NH$_2$, —C(O)NH$_2$, —C(S)NH$_2$, —NHC(O)NH$_2$, —NHC(S)NH$_2$, —NHS(O)$_2$NH$_2$, —OR$^{13}$, —SR$^{13}$, —NR$^{12}$R$^{13}$, —C(O)R$^{13}$, —C(S)R$^{13}$, —C(O)OR$^{13}$, —C(O)NR$^{12}$R$^{13}$, —C(S) NR$^{12}$R$^{13}$, —S(O)$_2$NR$^{12}$R$^{13}$, —NR$^{12}$C(O)R$^{13}$—NR$^{12}$C(S) R$^{13}$, —NR$^{12}$S(O)$_2$R$^{13}$, —NR$^{12}$C(O)NR$^{12}$R$^{13}$, —NR$^{12}$C(S) NR$^{12}$R$^{13}$, —NR$^{13}$S(O)$_2$NR$^{12}$R$^{13}$, —S(O)R$^{13}$, —S(O)$_2$R$^{13}$, halogen, lower alkyl fluoro substituted lower alkyl, and cycloalkylamino.

In some embodiments of compounds of Formula Ip, Formula Iq, Formula Ir, Formula Is, or Formula It, R$^7$ is -Cy$_1$ or -alk-Cy$_1$, Cy, is cycloalkyl, heterocycloalkyl, aryl or heteroaryl, wherein cycloalkyl, heterocycloalkyl, aryl or heteroaryl are optionally substituted with one or more substituents selected from the group consisting of —OH, —NH$_2$, —CN, —NO$_2$, —S(O)$_2$NH$_2$, —C(O)NH$_2$, —OR$^{13}$, —NR$^{12}$R$^{13}$, —C(O)R$^{13}$, —C(O)NR$^{12}$R$^{13}$, —S(O)$_2$NR$^{12}$R$^{13}$, —NR$^{12}$C(O)R$^{13}$, —NR$^{12}$S(O)$_2$R$^{13}$, —S(O)$_2$R$^{13}$, halogen, lower alkyl, fluoro substituted lower alkyl, and cycloalkylamino; R$^8$ is selected from the group consisting of hydrogen, —OR$^9$, —SR$^9$, —CR$^{10}$R$^{11}$, R$^9$, —NR$^{12}$R$^9$, —C(O)R$^9$, —C(S)R$^9$, —S(O)R$^9$, and —S(O)$_2$R$^9$; and R$^9$ is aryl or heteroaryl, wherein aryl and heteroaryl are optionally substituted with one or more substituents selected from the group consisting of —OH, —NH$_2$, —CN, —NO$_2$, —S(O)$_2$NH$_2$, —C(O)NH$_2$, —NHC(O)NH$_2$, —NHS(O)$_2$NH$_2$, —OR$^{13}$, —SR$^{13}$, —NR$^{12}$R$^{13}$, —C(O)R$^{13}$, —C(O)NR$^{12}$R$^{13}$, —S(O)$_2$NR$^{12}$R$^{13}$, —NR$^{12}$C(O)R$^{13}$, —NR$^{12}$S(O)$_2$R$^{13}$, —NR$^{12}$C(O)NR$^{12}$R$^{13}$, —NR$^{12}$S(O)$_2$NR$^{12}$R$^{13}$, —S(O)$_2$R$^{13}$, halogen, lower alkyl, fluoro substituted lower alkyl, and cycloalkylamino.

In some embodiments of the above compounds, compounds are excluded where N (except where N is a heteroaryl ring atom), O, or S is bound to a carbon that is also bound to N (except where N is a heteroaryl ring atom), O, or S, except where the carbon forms a double bond with one of the heteroatoms, such as in an amide, carboxylic acid, and the like; or where N (except where N is a heteroaryl ring atom), O, C(S), C(O), or S(O)$_n$ (n is 0-2) is bound to an alkene carbon of an alkenyl group or bound to an alkyne carbon of an alkynyl group; accordingly, in some embodiments compounds which include linkages such as the following are excluded from the compounds provided: —NR—CH$_2$—NR—, —O—CH$_2$—NR—, —S—CH$_2$—NR—, —NR—CH$_2$—O—, —O—C$_2$—O—, —S—CH$_2$—O—, —NR—CH$_2$—S—, —O—CH$_2$—S—, —S—CH$_2$—S—, —NR—CH=CH—, —CH=CH—NR—, —NR—C≡C—, —C≡C—NR—, —O—CH=CH—, —CH=CH—O—, —O—C≡C—, —C≡C—O—, —S(O)$_{0-2}$—CH=CH—, —CH=CH—S(O)$_{0-2}$—, —S(O)$_{0-2}$—C≡C—, —C≡C—S(O)$_{0-2}$—, —C(O)—CH=CH—, —CH=CH—C(O)—, —C≡C—C(O)—, or —C(O)—C≡C—, —C(S)—CH=CH—, —CH=CH—C(S)—, —C≡C—C(S)—, or —C(S)—C≡C—.

In reference to compounds herein, unless clearly indicated to the contrary, specification of a compound or group of compounds includes pharmaceutically acceptable salts of such compound(s), prodrug(s), and all stereoisomers thereof. In reference to compositions, kits, methods of use, etc. of compounds of Formula I described herein, it is understood that a compound of Formula I includes all sub-embodiments thereof, including compounds of Formula Ia-It, unless indicated otherwise.

In one aspect, methods are provided for treating a protein kinase mediated disease or condition in an animal subject, wherein the method involves administering to the subject an effective amount of one or more compounds of Formula I. The terms "treat," "therapy," and like terms refer to the administration of material, e.g., one or more compounds of Formula I, in an amount effective to prevent, alleviate, or ameliorate one or more symptoms of a disease or condition, i.e., indication, and/or to prolong the survival of the subject being treated. The term "protein kinase mediated disease or condition" refers to a disease or condition in which the biological function of a protein kinase affects the development, course and/or symptoms of the disease or condition, and/or in which modulation of the protein kinase alters the development, course, and/or symptoms of the disease or condition. A protein kinase mediated disease or condition includes a disease or condition for which modulation provides a therapeutic benefit, e.g. wherein treatment with protein kinase inhibitors, including compounds described herein, provides a therapeutic benefit to the subject suffering from or at risk of the disease or condition. In one aspect, the method involves administering to the subject an effective amount of one or more compounds of Formula I in combination with one or more other therapies for the disease or condition.

In one aspect, methods are provided for treating a protein kinase mediated disease or condition in an animal subject, wherein the method involves administering to the subject an effective amount of one or more compounds of Formula I.

In one aspect, methods are provided for treating a protein kinase mediated disease or condition in an animal subject, wherein the method involves administering to the subject an effective amount of one or more compounds of Formula I. The terms "protein kinase mediated disease or condition," and the like refer to a disease or condition in which the biological function of a protein kinase, or any mutation thereof, affects the development, course, and/or symptoms of the disease or condition, and/or in which modulation of the protein kinase alters the development, course, and/or symptoms of the disease or condition. A protein kinase mediated disease or condition includes a disease or condition for which the protein kinase inhibition provides a therapeutic benefit, e.g. wherein treatment with protein kinase inhibitors, including compounds described herein, provides a therapeutic benefit to the subject suffering from or at risk of the disease or condition. In one aspect, the method involves administering to the subject an effective amount of one or more compounds of Formula I in combination with one or more other therapies for the disease or condition.

In some embodiments, a compound of Formula I will have an $IC_{50}$ of less than 500 nm, less than 100 nM, less than 50 nM, less than 20 nM, less than 10 nM, less than 5 nM, or less than 1 nM as determined in a generally accepted kinase activity assay. In some embodiments, a compound of any of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, LCK, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70, including any mutations thereof.

In some embodiments, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Ab1, Akt1, Akt2, Akt3, ALK, Alk5, A-Raf, B-Raf, Btk, Cdk2, CDK4, CDK5, CDK6, CHK1, c-Raf-1, Csk, EGFR, EphA1, EphA2, EphB2, EphB4, Erk2, Fak, Fms, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk13, Kit, LCK, MAP2K1, MAP2K2, MAP4K4, MAPKAPK2, Met, Mnk1, MLK1, p38, PDPK1, Pim1, Pim2, Pim3, PKC alpha, PKC beta, PKC theta, Plk1, Pyk2, Ron, Src, Stk6, Syk, TEC, Tie2, TrkA, TrkB, Yes, and Zap70, including any mutations thereof.

In some embodiments, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Ab1, A-Raf, B-Raf, Btk, c-Raf-1, EGFR, EphB2, Erk2, Fak, FGFR1, Flt1, Flt3, Flt4, Fms, Irak4, Jnk1, Jnk2, Jnk3, Kdr, Kit, MAP2K1, MAPKAP kinase 2, Met, p38, PDGFRB, Pim1, PKC theta, Pyk2, Ret, Src, Stk6, Yes, and Zap70, including any mutations thereof.

In some embodiments, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Ab1, A-Raf; B-Raf, Btk, c-Raf-1, EGFR, EphB2, Erk2, Fak, Fms, Irak4, Jnk1, Jnk2, Jnk3, Kit, MAP2K1, MAPKAP kinase 2, Met, p38, Pim1, PKC theta, Pyk2, Src, Stk6, Yes, and Zap70, including any mutations thereof.

Further to any of the above mentioned embodiments, a compound will also inhibit the effects of a mutation of the kinase, including, but not limited to, a mutation that is related to a disease state, such as a cancer.

Further to any of the above embodiments, a compound may selectively inhibit one kinase relative to one or more other kinases, where preferably inhibition is selective with respect to any of the other kinases, whether a kinase discussed herein, or other kinases. Selective inhibition of one kinase relative to another is such that the $IC_{50}$ for the one kinase may be at least about 2-fold, also 5-fold, also 10-fold, also 20-fold, also 50-fold, or at least about 100-fold less than the $IC_{50}$ for any of the other kinases as determined in a generally accepted kinase activity assay.

In another aspect, compositions are provided that include a therapeutically effective amount of one or more compounds of Formula I and at least one pharmaceutically acceptable carrier, excipient, and or diluent. The composition can include a plurality of different pharmacologically active compounds, which can include a plurality of compounds of Formula I, In another aspect, the composition can include one or more compounds of Formula I along with one or more compounds that are therapeutically effective for the same disease indication. In one aspect, the composition includes one or more compounds of Formula I along with one or more compounds that are therapeutically effective for the same disease indication, wherein the compounds have a synergistic effect on the disease indication.

In another aspect, compositions are provided that include a therapeutically effective amount of at least one compound of Formula I and at least one pharmaceutically acceptable carrier, excipient, and/or diluent including combinations of any two or more compounds of Formula I. The composition can further include a plurality of different pharmacologically active compounds, which can include one or more compounds of Formula I. In another aspect, the composition can include one or more compounds of Formula I along with one or more compounds that are therapeutically effective for the same disease indication. In one aspect, the composition includes one or more compounds of Formula I along with one or more compounds that are therapeutically effective for the same disease indication, wherein the compounds have a synergistic effect on the disease indication.

In another aspect, methods are provided for modulating the activity of a protein kinase selected from the group consisting of Ab1, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, LCK, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, or Zap70 by contacting the protein kinase with an effective amount of one or more compounds of Formula I.

In another aspect, methods are provided for treating a protein kinase mediated disease or condition in an animal subject, wherein the method involves administering to the subject an effective amount of a composition including one or more compounds of Formula I.

In one aspect, methods are provided for treating a disease or condition mediated by a protein kinase selected from the group consisting of Ab1, Akt1, Akt2, Akt3, ALK, Alk5, A-Raf, B-Raf, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, LCK, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, ROCK1, ROCK2, Ron, Src, Stk6, Syk, TEC, Tie2, TrkA, TrkB, Yes, and Zap70 by administering to the subject an effective amount of a composition including one or more compounds of Formula I.

In one aspect, the invention provides methods for treating a disease or condition mediated by a protein kinase selected from the group consisting of Ab1, Akt1, Akt2, Akt3, ALK, Alk5, A-Raf, B-Raf, Btk, Cdk2, CDK4, CDK5, CDK6, CHK1, c-Raf-1, Csk, EGFR, EphA1, EphA2, EphB2, EphB4, Erk, Fak, Fms, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kit, LCK, MAP2K1, MAP2K2, MAP4K4, MAPKAPK2, Met, Mnk1, MLK1, p38, PDPK1, Pim1, Pim2, Pim3, PKC alpha, PKC beta, PKC theta, Plk1, Pyk2, Ron, Src, Stk6, Syk, TEC, Tie2, TrkA, TrkB, Yes, and Zap70 by administering to the subject an effective amount of a composition including one or more compounds of Formula I.

In one aspect, the invention provides methods for treating a disease or condition mediated by a protein kinase selected from the group consisting of Ab1, A-Raf, B-Raf, Btk, c-Raf-1, EGFR, EphB2, Erk2, Fak, FGFR1, Flt1, Flt3, Flt4, Fms, Irak4, Jnk1, Jnk2, Jnk3, Kdr, Kit, MAP2K1, MAPKAPK2, Met, p38, PDGFRB, Pim1, PKC theta, Pyk2, Ret, Src, Stk6, Yes, and Zap70 by administering to the subject an effective amount of a composition including one or more compounds of Formula I.

In one aspect, the invention provides methods for treating a disease or condition mediated by a protein kinase selected from the group consisting of Ab1, A-Raf, B-Raf, Btk, c-Raf-1, EGFR, EphB2, Erk2, Fak, Fms, Jak4, Jnk1, Jnk2, Jnk3, Kit, MAP2K1, MAPKAPK2, Met, p38, Pim1, PKC theta, Pyk2, Src, Stk6, Yes, and Zap70 by administering to the subject an effective amount of a composition including one or more compounds of Formula I.

In one aspect, the invention provides methods for treating a disease or condition mediated by a protein kinase selected from the group consisting of A-Raf, B-Raf, B-Raf V600E mutant, c-Raf-1, FGFR1, FGFR2, FGFR3, FGFR4, Jnk1, Jnk2, Jnk3, Met, Pim1, Pim2, Pim3, Pyk2, Kdr and Ret by administering to the subject an effective amount of a composition including one or more compounds of Formula I.

In one aspect, the invention provides a method of treating a cancer by administering to the subject an effective amount of a composition including one or more compounds of Formula I, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one aspect, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or a particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, and bone marrow and stem cell transplantation.

In a preferred embodiment, the invention provides a method of treating a cancer by administering to the subject an effective amount of a composition including one or more compounds of Formula I, in combination with one or more suitable chemotherapeutic agents. In one aspect, the one or more suitable chemotherapeutic agents is selected from an alkylating agent, including, but not limited to, adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; an antibiotic, including, but not limited to, bleomycin, dactinomycin, daunorubicin, doxorubicin, epirubicin, idarubicin, menogaril, mitomycin, mitoxantrone, neocarzinostatin, pentostatin, and plicamycin; an antimetabolite, including, but not limited to, azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; an immunotherapy, including, but not limited to, alemtuzumab, bevacizumab, cetuximab, galiximab, gemtuzumab, panitumumab, pertuzumab, rituximab, tositumomab, trastuzumab, and 90 Y ibritumomab tiuxetan; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-92', docetaxel, TPI 287, paclitaxel and DHA-paclitaxel; a retinoid, including, but not limited to, alitretinoin, bexarotene, fenretinide, isotretinoin, and tretinoin; an alkaloid, including, but not limited to, etoposide, homoharringtonine, teniposide, vinblastine, vincristine, vindesine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, edotecarin, exatecan, irinotecan (also active metabolite SN-38 (7-ethyl-10-hydroxycamptothecin)), rubitecan, topotecan, and 9-aminocamptothecin; a kinase inhibitor, including, but not limited to, erlotinib, gefitinib, flavopiridol, imatinib mesylate, lapatinib, sorafenib, sunitinib malatc, AEE-788, AG-013736, AMG 706, AMN107, BMS-354825, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), aminoglutethimide, asparaginase, bryostatin-1, cilengitide, E7389, ixabepilone, procarbazine, sulindac, temsirolimus, tipifarnib. Preferably, the method of treating a cancer involves administering to the subject an effective amount of a composition of Formula I in combination with a chemotherapeutic agent selected from 5-fluorouracil, carboplatin, dacarbazine, gefitinib, oxaliplatin, paclitaxel, SN-38, temozolomide, vinblastine, bevacizumab, cetuximab, or erlotinib.

In another aspect, the invention provides a method of treating or prophylaxis of a disease or condition in a mammal, by administering to the mammal a therapeutically effective amount of one or more compounds of Formula I, a prodrug of such compound, or a pharmaceutically acceptable salt of such compound or prodrug. The compound can be alone or can be part of a composition. In another aspect, the invention provides a method of treating or prophylaxis of a disease or condition in a mammal, by administering to the mammal a therapeutically effective amount of one or more compounds of Formula I, a prodrug of such compound, or a pharmaceutically acceptable salt of such compound or prodrug in combination with one or more other suitable therapies for the disease or condition.

In a related aspect, the invention provides kits that include a composition as described herein. In some embodiments, the composition is packaged, e.g., in a vial, bottle, flask, which may be further packaged, e.g., within a box, envelope, or bag; the composition is approved by the U.S. Food and Drug Administration or similar regulatory agency for administration to a mammal, e.g., a human; the composition is approved for administration to a mammal, e.g., a human , for a protein kinase mediated disease or condition; the invention kit includes written instructions for use and/or other indication that the composition is suitable or approved for administration to a mammal, e.g., a human, for a protein kinase-mediated disease or condition; and the composition is packaged in unit dose or single dose form, e.g., single dose pills, capsules, or the like.

In aspects involving treatment or prophylaxis of a disease or condition with the compounds of Formula I, the disease or condition is, for example without limitation, neurologic diseases, including, but not limited to, cerebrovascular ischemia, multi-infarct dementia, head injury, spinal cord injury Alzheimer's disease (AD), Parkinson's disease, amyotrophic lateral sclerosis, dementia, senile chorea, and Huntington's disease; neoplastic diseases and associated complications, including, but not limited to, chemotherapy-induced hypoxia, gastrointestinal stromal tumors (GISTs), prostate tumors, mast cell tumors (including canine mast cell tumors), acute myeloid leukemia, acute lymphocytic leukemia, chronic myeloid leukemia, chronic lymphocytic leukemia, multiple myeloma, melanoma, mastocytosis, gliomas, glioblastoma, astrocytoma, neuroblastoma, sarcomas (e.g. sarcomas of neuroectodermal origin, leiomyosarcoma), carcinomas (e.g. lung, breast, pancreatic, colon, hepatocellular, renal, female genital tract, squamous cell, carcinoma in situ), lymphoma (e.g. histiocytic lymphoma, non-Hodgkin's lymphoma), MEN2 syndromes, neurofibromatosis (including Schwann cell neoplasia), myelodysplastic syndrome, myelofibrosis, leukemia, tumor angiogenesis, cancers of the thyroid, liver, bone, skin, brain, central nervous system, pancreas, lung (e.g. small cell lung cancer, non small cell lung cancer), breast, colon, bladder, prostate, gastrointestinal tract, endometrium, fallopian tube, testes and ovary, and metastasis of tumors to other tissues; pain of neuropathic or inflammatory origin, including, but not limited to, acute pain, chronic pain, bone pain, cancer-related pain and migraine; cardiovascular diseases, including, but not limited to, heart failure, ischemic stroke, cardiac hypertrophy, thrombosis (e.g. thrombotic microangiopathy syndromes), atherosclerosis, reperfusion injury and ischemia (e.g. cerebrovascular ischemia, liver ischemia); inflammation including, but not limited to, age-related macular degeneration, rheumatoid arthritis, allergic rhinitis, inflammatory bowel disease (IBD), ulcerative colitis, Crohn's disease, systemic lupus erythematosis, Sjogren's Syndrome, Wegener's granulomatosis, Kawasaki's Disease, hemophagocytic syndrome (macrophage activation syndrome), multicentric reticulohistiocytosis, psoriasis, scleroderma, chronic thyroiditis, Grave's disease, myasthenia gravis, multiple sclerosis, osteoarthritis, endometriosis, scarring (e.g. dermal, tissue), vascular restenosis, fibrotic disorders, hypereosinophilia, CNS inflammation, pancreatitis, nephritis, atopic dermatitis, and hepatitis; immunodeficiency diseases including, but not limited to, severe combined immunodeficiency (SCID), organ transplant rejection, and graft versus host disease; renal or prostatic diseases, including, but not limited to, diabetic nephropathy, polycystic kidney disease, nephrosclerosis, glomerulonephritis, interstitial nephritis, Lupus nephritis, prostate hyperplasia, chronic renal failure, tubular necrosis, diabetes-associated renal complications, and renal hypertrophy; metabolic diseases, including, but not limited to, type 1 diabetes, type 2 diabetes, metabolic syndrome, obesity, hepatic steatosis, insulin resistance, hyperglycemia, lipolysis and obesity; infection, including, but not limited to, *Helicobacter pylori, Hepatitis* and *Influenza* viruses, fever, and sepsis; pulmonary diseases, including, but not limited to, chronic obstructive pulmonary disease (COPD), acute respiratory distress syndrome (ARDS), asthma, allergy, bronchitis, emphysema, and pulmonary fibrosis; genetic developmental diseases, including, but not limited to, Noonan's syndrome, Crouzon syndrome, acrocephalo-syndactyly type I, Pfeiffer's syndrome, Jackson-Weiss syndrome. Costello syndrome, (faciocutaneoskeletal syndrome), LEOPARD syndrome, cardio-faciocutaneous syndrome (CFC) and neural crest syndrome abnormalities causing cardiovascular, skeletal, intestinal, skin, hair and endocrine diseases; disorders of bone structure, mineralization and bone reformation and resorption, including, but not limited to, osteoporosis, increased risk of fracture, Paget's disease, hypercalcemia, infection-mediated osteolysis (e.g. osteomyelitis), peri-prosthetic or wear-debris-mediated osteolysis, and metastatis of cancer to bone; Grave's disease; Hirschsprung's disease; lymphoedema; selective T-cell defect (STD); X-linked agammaglobulinemia; diabetic retinopathy; alopecia; erectile dysfunction; tuberous sclerosis, and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

The compounds of Formula I with kinase activity $IC_{50}$ less than 10 µM as determined in a standard assay described herein can be used to treat protein kinase mediated diseases and conditions related to the following protein kinases, for example without limitation:

Ab1, related to chronic myeloid leukemia (CML), acute lymphoblastic leukemia (ALL) and acute myelogenous leukemia (AML);

Akt1, related to gastric, prostate, colorectal, ovarian, pancreatic and breast cancer, glioblastoma and leukemia, as well as schizophrenia and bipolar disorders, and also use in combination with other chemotherapeutic drugs;

Akt2, related to hyperglycemia due to peripheral insulin resistance and nonsuppressible hepatic glucose production accompanied by inadequate compensatory hyperinsulinemia, also related to pancreatic, ovarian and breast cancer;

Akt3, related to melanoma, prostate and breast cancer;

ALK, related to non-Hodgkin lymphomas such as diffuse large B-cell lymphoma and anaplastic large cell lymphoma;

Alk5, related to pancreatic and biliary cancers, and cutaneous T-cell lymphoma;

A-Raf, related to neurologic diseases including, but not limited to, multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myelodysplastic syndrome, leukemia, tumor angiogenesis; pain of neuropathic or inflammatory origin, including, but not limited to, acute pain, chronic pain, cancer-related pain and migraine; and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharynlgeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenital paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

B-Raf or c-Raf-1, related to neurologic diseases, including, but not limited to, multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma) neurofibromatosis, acute myeloid leukemia, myelodysplastic syndrome, leukemia, tumor angiogenesis, neuroendocrine tumors such as medullary thyroid cancer, carcinoid, small cell lung cancer and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, reperfusion injury; inflammation including, but not limited to, psoriasis, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease; renal or prostatic diseases, including, but not limited to, diabetic nephropathy, polycystic kidney disease, nephrosclerosis, glomerulonephritis, prostate hyperplasia; metabolic disorders, including, but not limited to, obesity; infection, including, but not limited to, *Helicobacter pylori*, *Hepatitis* and *Influenza* viruses, fever, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases.

Brk, related to breast and colon cancer, and head and neck squamous cell carcinoma;

Btk, related to X-linked agammaglobulinemia, acute lymphocytic leukemia, autoimmune diseases such as multiple sclerosis, systemic lupus erythematosis, rheumatoid arthritis, and Graves' disease, immune suppression in organ transplant, and drug sensitivity of B-lineage cells;

Cdk2, related to prostate, breast, colorectal and ovarian cancer;

Cdk4, related to glioblastoma (e.g. glioblastoma multiforme), anaplastic astrocytoma, and breast cancer;

Cdk5, related to Alzheimer's disease, amyotrophic lateral sclerosis and Lewy body disease;

Cdk6, related to glioblastoma multiforme, non-Hodgkin's lymphoma, splenic marginal zone lymphoma, T-cell lymphoblastic lymphoma (T-LBL) and T-cell acute lymphoblastic leukemia (T-ALL);

CHK1, related to DNA damage repair, sensitizes cells to chemotherapeutic agents;

Csk, related to colon and pancreatic carcinomas and autoimmune pathology such as type I diabetes, rheumatoid arthritis and systemic lupus erythematosus;

EGFR, related to breast, colorectal, bladder, prostate and non small cell lung cancer, squamous cell carcinomas of the head and neck cancer, oral cavity, and esophagus, and glioblastoma multiforme;

EphA1, related to head and neck squamous cell carcinoma, hepatoma and lung cancer;

EphA2, related to aberrant short-range contact-mediated axonal guidance, bladder, breast, prostate, colon, skin, cervical, ovarian, pancreatic and lung cancers, and metastatic melanoma;

EphB2, related to angiogenesis disorder (e.g. ocular angiogenesis disease such as retinopathy), and cancer (e.g. glioblastoma, breast and liver cancer);

EphB4, related to colorectal cancer (CRC), head and neck squamous cell carcinoma, and tumours of the prostate, breast, endometrium, and bladder;

Erk2, related to aberrant proliferation, differentiation, transcription regulation and development, and may be useful in treating inflammation, for example inflammation associated with Lyme neuroborreliosis, and in treating cancers, such as gastric cancer;

Fak, related to colon and breast tumors, and is also related to esophageal squamous cell carcinoma, melanoma, anaplastic astrocytoma, glioblastoma, ductal carcinoma in situ, prostate and hepatocellular carcinoma, and tumor metastases, and may also provide synergistic effects when used with other chemotherapeutic drugs;

FGFR1, related to 8p11 myeloproliferative syndrome;

FGFR2, related to Crouzon Syndrome, Jackson-Weiss Syndrome, Apert Syndrome, craniosynostosis, Pfeiffer Syndrome, acrocephalo syndactyly type V, and Beare-Stevenson Cutis Gyrata Syndrome;

FGFR3, related to angiogenesis, wound healing, achondroplasia, Muenke craniosynostosis, Crouzon syndrome, acanthosis nigricans, thanatophoric dysplasia, bladder carcinomas, and multiple myeloma;

FGFR4, related to cancer of the breast, lung, colon, medullary thyroid, pancreas, ovary, prostate, endometrium, and fallopian tube, head and neck squamous cell carcinomas and leiomyosarcoma;

Flt1, related to non-small cell lung carcinoma, prostate carcinoma, and colorectal cancer;

Flt3, related to acute myeloid leukemia, myelodysplastic syndrome, acute lymphoblastic leukemia;

Flt4, related to primary lymphoedema;

Fms, related to immune disorders, including, but not limited to, rheumatoid arthritis, systemic lupus erythematosis (SLE), and transplant rejection; inflammatory diseases including, but not limited to, osteoarthritis, inflammatory bowel syndrome, ulcerative colitis, Crohn's disease, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, increased risk of fracture, Paget's disease, hypercalcemia, infection-mediated osteolysis (e.g. osteomyelitis), peri-prosthetic or wear-debris-mediated osteolysis, and metastasis of cancer to bone; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, stroke, Alzheimer's disease and Parkinson's disease; inflammatory and chronic pain, including, but not limited to, bone pain; and cancers, including, but not limited to, multiple myeloma, acute myeloid leukemia (AML), chronic myeloid leukemia (CML), prostate cancer, breast cancer, ovarian cancer, melanoma, glioblastoma multiforme, metastasis of tumors to other tissues, and other chronic myeloproliferative diseases such as myelofibrosis;

Frk, related to acute myeloid leukemia and type 1 diabetes;

Fyn, related to Alzheimer's disease, schizophrenia and prevention of metastases, e.g. in melanoma and squamous cell carcinoma;

GSK3 (Gsk3α and/or Gsk3β), related to CNS disorders such as Alzheimer's disease, Parkinson's disease, amyotrophic lateral sclerosis, diabetes type II, bipolar disorders, stroke, cancer, chronic inflammatory disease, leucopenia, schizophrenia, chronic pain, neuropathic pain, and traumatic head injury;

HCK, related to chronic myelogenous leukemia and acute lymphocytic leukemia;

Her2/Erbb2, related to prostate and breast cancer;

Her4/Erbb4, related to childhood medulloblastoma;

IGF1R, related to prostate cancer, hepatocellular carcinoma;

IKK beta, related to leukemia of T-cells, necrosis, insulin resistance, and malignant neoplasms;

Irak4, related to bacterial infections, immunodeficiency syndrome, Crohn's disease, ulcerative colitis, asthma, chronic bronchitis, cardio hypertrophy, and kidney hypertension;

Itk, related to allergic asthma;

Jak1, related to Hepatitis C virus infection;

Jak2, related to myeloproliferative disorders such as polycythaemia vera, myelofibrosis, essential thrombocythemia, myeloid metaplasia and leukemias, including, but not limited to, acute lymphoblastic leukemia, chronic neutrophilic leukemia, juvenile myelomonocytic leukemia, CMML, Philadelphia chromosome-negative CML, megakaryocytic leukemia, and acute erythroid leukemia;

Jak3, related to X-linked severe combined immunodeficiency, myeloproliferative disorders, transplant rejection and autoimmune diseases such as rheumatoid arthritis, inflammatory bowel syndrome, Crohn's disease, systemic lupus erythematosus, ulcerative colitis, psoriasis and multiple sclerosis;

Jnk (Jnk1, Jnk2, Jnk3), related to metabolic diseases including, but not limited to, type 1 diabetes, type 2 diabetes, metabolic syndrome, obesity, and hepatic steatosis; cardiovascular diseases such as atherosclerosis, ischemia (e.g. cerebrovascular ischemia, liver ischemia), reperfusion injury, cardiac hypertrophy; renal diseases such as chronic renal failure; neoplastic diseases and associated complications, including, but not limited to chemotherapy-induced hypoxia, prostate tumors, myeloid leukemia and cancers of the liver, bone, skin, brain, pancreas, lung breast, colon, prostate and ovary; transplant rejection; pain of neuropathic or inflammatory origin including, but not limited to, acute and chronic pain; inflammatory and autoimmune diseases including, but not limited to, age-related macular degeneration, rheumatoid arthritis, inflammatory bowel disease, ulcerative colitis, Crohn's disease, systemic lupus erythematosus, Sjogren's Syndrome, psoriasis, sclerodenna, chronic thyroiditis, Grave's disease, myasthenia gravis, and multiple sclerosis, and inflammation in other organs including, but not limited to, CNS inflammation, pancreatitis, nephritis, atopic dermatitis, and hepatitis; airway inflammatory diseases such as asthma, allergy, bronchitis, pulmonary fibrosis, chronic obstructive pulmonary disease; neurologic diseases such as stroke, cerebrovascular ischemia, neurodegenerative diseases such as Parkinson's disease, Alzheimer's disease, amyotrophic lateral sclerosis, dementia, senile chorea, head and spinal cord trauma, and Huntington's disease. More particularly, Jnk1 is related to type 1 diabetes, type 2 diabetes, metabolic syndrome, obesity and hepatic steatosis, Jnk2 is related to atherosclerosis, and Jnk3 is related to inflammatory diseases including, but not limited to, autoimmune diseases such as rheumatoid arthritis, inflammatory bowel syndrome, Crohn's disease, systemic lupus erythematosis, Sjogren's Syndrome, psoriasis and multiple sclerosis, airway inflammatory diseases such as asthma, allergy, pulmonary fibrosis, and chronic obstructive pulmonary disease, and inflammation in other organs, such as CNS inflammation, pancreatitis, nephritis, and hepatitis; neurologic diseases such as stroke, cerebrovascular ischemia, and neurodegenerative diseases such as Parkinson's disease, Alzheimer's disease, and Huntington's disease; and neoplastic diseases such as prostate tumors and myeloid leukemia;

Kdr, related to anti-angiogenesis for treating solid tumor growth (e.g. ovarian, lung, breast, pancreatic, prostate, colon, gastrointestinal stromal tumor, non small cell lung cancer, and epidermoid cancer), metastasis, psoriasis, rheumatoid arthritis, diabetic retinopathy and age related macular degeneration;

Kit, related to malignancies, including, but not limited to, mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, melanoma, and canine mast cell tumors, and inflammatory diseases, including, but not limited to, asthma, rheumatoid arthritis, allergic rhinitis, multiple sclerosis, inflammatory bowel syndrome, transplant rejection, and hypereosinophilia;

LCK, related to acute lymphoblastic leukemia, T-cell lymphoma, lymphopenia, renal carcinoma, colon carcinoma, severe combined immunodeficiency, multiple sclerosis, inflammatory bowel and type I diabetes;

MAP2K1, related to acute myeloid leukemia, breast, ovarian and liver cancer;

MAP2K2, related to cancer and inflammation;

MAP4K4, related to metabolic indications, including, but not limited to, re-sensitizing fat and muscle cells to insulin, ameliorating the pathology in adipocytes, ameliorating the pathology in muscle cells, metabolic syndrome, and type II diabetes; a broad range of oncology indications, including, but not limited to, blocking the migration, invasion and metastasis in many different tumor types; and T-cell mediated autoimmune diseases;

MAPKAPK2, cancer (e.g. prostate, breast), stroke, menengitis, and inflammatory disorders;

Met, related to kidney, breast, bladder, non-small-cell lung, colorectal, and bladder cancers, and hepatocellular carcinoma;

Mnk1, related to conditions associated with heat shock, nutrient deprivation, oxidative or osmotic stress, and infection of mammalian cells (e.g. with viruses such as adenovirus (Ad) or influenza virus), and autoimmune diseases;

MLK1, related to neurodegenerative diseases such as Alzheimer's disease and Parkinson's disease, and inflammatory disorders;

p38, related to acute coronary syndrome, stroke, atherosclerosis, and inflammatory autoimmune diseases such as rheumatoid arthritis, inflammatory bowel disease, and Crohn's disease;

PDGFR (PDGFRA, PDGFRB), related to idiopathic hypereosinophilic syndrome, chronic eosinophilic leukemia, glioma, gastrointestinal stromal tumors (GISTs), juvenile myelomonocytic leukemia, metastatic medulloblastoma, atherogenesis, and restenosis. More particularly, PDGFRA related to idiopathic hypereosinophilic syndrome, chronic eosinophilic leukemia, glioma, gastrointestinal stromal tumors (GISTs), juvenile myelomonocytic leukemia, metastatic medulloblastoma, atherogenesis, and restenosis, and PDGFRB related to idiopathic hypereosinophilic syndrome, chronic eosinophilic leukemia, juvenile myelomonocytic leukemia, and metastatic medulloblastoma;

PDPK1, related to cancer and diabetes;

Pim1, related to cancers such as hematopoietic (e.g. acute myeloid and acute lymphoid leukemias) and prostate cancers, and non-Hodgkin's lymphomas;

Pim2, related to lymphomas;

Pim3, related to hepatocellular carcinoma;

PKC alpha, related to pituitary tumors and prefrontal cortical dysfunction such as distractibility, impaired judgment, impulsivity, and thought disorder, also may be used to sensitize chemotherapy in breast, colon, and non small cell lung cancers;

PKC beta, related to diabetic retinopathy,

PKC-theta, related to insulin resistance, T-cell lymphoma;

Plk1, related to cancers (e.g. lymphoma of the thyroid, non-Hodgkin's lymphomas, colorectal cancers, leukemias and melanoma), also useful as sensitizer in chemotherapy;

Pyk2, related to inflammation (e.g. osteoporosis, polycystic kidney disease, rheumatoid arthritis and inflammatory bowel disease), CNS disease (e.g. Parkinson's disease and Alzheimer's disease), stroke and cancers (e.g. gliomas, breast cancer, and pancreatic cancer);

Ret, related to cancer of the thyroid, neuroblastoma, familial medullary thyroid carcinoma (FMTC), multiple endocrine neoplasia type IIA and IIB (MEN2A, MEN2B), and neurodegenerative disorders (e.g. Hirschsprung's disease, Parkinson's disease, Alzheimer's disease, and amyotrophic lateral sclerosis);

ROCK (ROCK-1, ROCK-2), related to cancers (e.g. ovarian cancer, hepatocellular carcinoma, pancreatic cancer), ocular disease (e.g. glaucoma), cardiac hypertrophy, improved renal perfusion, transplant rejection, and acute respiratory distress syndrome;

Ron, related to cancer and inflammation;

Src, related to cancer and osteoporosis;

Stk6, related to gastric, bladder, breast, lung, CNS, ovarian, kidney, colon, prostate, pancreas, and cervical cancers, melanoma, leukemia, and neuroblastoma;

Syk, related to lymphomas (e.g. mantle cell lymphoma);

TEC, related to sepsis, septic shock, inflammation, rheumatoid arthritis, Crohn's disease, irritable bowel disease (IBD), and ulcerative colitis;

Tie2 (TEK), related to cancer, arthritis (e.g. rheumatoid arthritis), and atherosclerosis;

TrkA, related to pain (e.g. chronic pain, neuropathic pain), cancer (e.g. prostate cancer, lung cancer, pancreatic cancer), allergic disorders (e.g. asthma), arthritis, diabetic retinopathy, macular degeneration and psoriasis;

TrkB, related to obesity, hyperphagia, developmental delays, cancer (e.g. prostate cancer, lung cancer, Wilms tumors, neuroblastoma, pancreatic cancer), various neuropathies (e.g. stroke, multiple sclerosis, transverse myelitis, and encephalitis), and diabetes.

Yes, related to various cancers including, but not limited to, esophageal squamous cell carcinoma; and Zap70, related to AIDS, systemic lupus erythematosus, myasthenia gravis, atherosclerosis, rejection of transplanted organs or tissues, allograft rejection including, but not limited to, acute and chronic allograft rejection, graft versus host disease, rheumatoid arthritis, psoriasis, systemic sclerosis, atopic dermatitis, eczematous dermatitis, alopecia, and inflammation of the nasal mucus membrane, including all forms of rhinitis.

Additional aspects and embodiments will be apparent from the following Detailed Description and from the claims.

DETAILED DESCRIPTION OF THE PREFERRED EMBODIMENTS

As used herein the following definitions apply unless clearly indicated otherwise:

"Halogen" refer to all halogens, that is, chloro (Cl), fluoro (F), Bromo (Br), or iodo (I).

"Hydroxyl" or "hydroxy" refer to the group —OH,

"Thiol" refers to the group —SH.

"Lower alkyl" alone or in combination means an alkane-derived radical containing from 1 to 6 carbon atoms (unless specifically defined) that includes a straight chain alkyl or branched alkyl, The straight chain or branched alkyl group is attached at any available point to produce a stable compound. In many embodiments, a lower alkyl is a straight or branched alkyl group containing from 1-6, 1-4, or 1-2, carbon atoms, such as methyl, ethyl, propyl, isopropyl, butyl, t-butyl, and the like. A "substituted lower alkyl" denotes lower alkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR°, —SR°, —OC(O)R°, —OC(S)R°, —C(O)R°, —C(S)R°, —C(O)OR°, —C(S)OR°, —S(O)R°, —S(O)$_2$R°, —C(O)NHR°, —C(S)NHR°, —C(O)NR°R°, —C(S)NR°R°, —S(O)$_2$NHR°, —S(O)$_2$NR°R°, —C(NH)NHR°, —C(NH)NR$^p$R°, —NHC(O)R°, —NHC(S)R°, —NR°C(O)R°, —NR°C(S)R°, —NHS(O)$_2$R°, —NR°S(O)$_2$R°, —NHC(O)NHR°, —NHC(S)NHR°, —NR°C(O)NH$_2$, —NR°C(S)NH$_2$, —NR°C(O)NHR°, —NR°C(S)NHR°, —NHC(O)R°R°, —NHC(S)NR°R°, —NR°C(O)NR°R°, —NR°C(S)NR°R°, —NHS(O)$_2$NHR°, NR°S(O)$_2$NH$_2$, —NR°S(O)$_2$NHR°, —NHS(O)$_2$NR°R°, —NR°S(O)$_2$NR°R°, —NHR°, —NR°R°, —R$^e$, —R$^f$, and —R$^g$. Furthermore, possible substitutions include subsets of these substitutions, such as are indicated herein, for example, in the description of compounds of Formula I attached at any available atom to produce a stable compound. For example "fluoro substituted lower alkyl" denotes a lower alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. While it is understood that substitutions are attached at any available atom to produce a stable compound, when optionally substituted alkyl is an R group of a moiety such as OR (e.g. alkoxy), —SR (e.g. thioalkyl), —NHR (e.g. alkylamino), —C(O)NHR, and the like, substitution of the alkyl R group is such that substitution of the alkyl carbon bound to any O, S, or N of the moiety (except where N is a heteroaryl ring atom) excludes substituents that would result in any O, S, or N of the substituent (except where N is a heteroaryl ring atom) being bound to the alkyl carbon bound to any O, S, or N of the moiety. "$C_{2-6}$ alkyl" denotes lower alkyl containing 2-6 carbon atoms. A "substituted $C_{2-6}$alkyl" denotes optionally substituted lower alkyl containing 2-6 carbon atoms, A "substituted methyl" denotes methyl that is independently substituted, unless indicated otherwise, with 1, 2, or 3 substituents, wherein the substituents are selected as per optionally substituted lower alkyl.

"$C_{1-3}$ alkylene" refers to a divalent alkane-derived radical containing 1-3 carbon atoms, straight chain or branched, from which two hydrogen atoms are taken from the same carbon atom or from different carbon atoms. $C_{1-3}$ alkylene includes methylene —CH$_2$—, ethylene —CH$_2$CH$_2$—, propylene —CH$_2$CH$_2$CH$_2$—, and isopropylene —CH(CH$_3$)CH$_2$— or —CH$_2$CH(CH$_3$)—. $C_{1-3}$alkylene substituted with one or more substituents indicates $C_{1-3}$ alkylene that is independently substituted, with one or more, preferably 1, 2, 3, 4 or 5, also 1, 2, or 3 substituents as indicated, attached at any available atom to produce a stable compound.

"Lower alkenyl" alone or in combination means a straight or branched hydrocarbon containing 2-6 carbon atoms (unless specifically defined) and at least one, preferably 1-3, more preferably 1-2, most preferably one, carbon to carbon double bond. Carbon to carbon double bonds may be either contained within a straight chain or branched portion. Examples of lower alkenyl groups include ethenyl, propenyl, isopropenyl, butenyl, and the like. A "substituted lower alkenyl" denotes lower alkenyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)$_2$, —NHC(S)NH$_2$, —NHS(O)$_2$, —C(NH)NH$_2$, —OR°, —SR°, —OC(O)R°, —OC(S)R°, —C(O)R°, —C(S)R°, —C(O)OR°, —C(S)OR°, —S(O)R°, —S(O)$_2$R°, —C(O)NHR°, —C(S)NHR°, —C(O)NR°R°, —C(S)NR°R°, —S(O)$_2$NHR°, —S(O)$_2$NR°R°, —C(NH)NR°, —C(NH)NR°R°, —NHC(O)R°, —NHC(S)R°, —NR°C(O)R°, —NR°C(S)R°, —NHS(O)$_2$R°, —NR°S(O)$_2$R°, —NHC(O)NHR°, —NHC(S)NHR°, —NR°C(O)NH$_2$, —NR°C(S)NH$_2$, —NR°C(O)NHR°, —NR°C(S)NHR°, —NHC(O)NR°R°, —NHC(S)NR°R°, —NR°C(O)NR°R°, —NR°C(S)NR°R°, —NHS(O)$_2$(O)NHR°, —NR°S(O)$_2$NH$_2$, —NR°S(O)$_2$NHR°, —NHS(O)$_2$NR°R°, —NR°S(O)$_2$NR°R°, —NHR°, —NR°R°, —R$^d$—R$^f$, and —R$^g$. Further, possible substitutions include subsets of these substitutions, such as are indicated herein, for example, in the description of compounds of Formula I, attached at any available atom to produce a stable compound. For example "fluoro substituted lower alkenyl" denotes a lower alkenyl group substituted with one or more fluoro atoms, where preferably the lower alkenyl is substituted with 1, 2, 3, 4 or 5 fluoro atoms, also 1, 2, or 3 fluoro atoms. While it is understood that substitutions are attached at any available atom to produce a stable compound, substitution of alkenyl groups are such that —F, —C(O)—, —C(S)—, —C(NH)—, —S(O)—, —S(O)$_2$—, —O—, —S—, or N (except where N is a heteroaryl ring atom), are not bound to an alkene carbon thereof: Further, where alkenyl is a substituent of another moiety or an R group of a moiety such as —OR, —NHR, —C(O)R, and the like, substitution of the moiety is such that any —C(O)—, —C(S)—, —S(O)—, —S(O)$_2$—, —O—, —S—, or N thereof (except where N is a heteroaryl ring atom) are not bound to an alkene carbon of the alkenyl substituent or R group. Further, where alkenyl is a substituent of another moiety or an R group of a moiety such as —OR, —NHR, —C(O)NHR, and the like, substitution of the alkenyl R group is such that substitution of the alkenyl carbon bound to any O, S, or N of the moiety (except where N is a heteroaryl ring atom) excludes substituents that would result in any O, S, or N of the substituent (except where N is a heteroaryl ring atom) being bound to the alkenyl carbon bound to any O, S, or N of the moiety. An "alkenyl carbon" refers to any carbon within an alkenyl group, whether saturated or part of the carbon to carbon double bond. An "alkene carbon" refers to a carbon within an alkenyl group that is part of a carbon to carbon double bond.

"Lower alkynyl" alone or in combination means a straight or branched hydrocarbon containing 2-6 carbon atoms (unless specifically defined) containing at least one, preferably one, carbon to carbon triple bond. Examples of alkynyl groups include ethynyl, propynyl, butynyl, and the like. A "substituted lower alkynyl" denotes lower alkynyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR°, —SR°, —OC(O)R°, —OC(S)R°, —C(O)R°, —C(S)R°, —C(O)OR°, —C(S)OR°, —S(O)R°, —S(O)$_2$R°, —C(O)NHR°, —C(S)NHR°, —C(O)NR°R°, —C(S)NR°R°, —S(O)$_2$NHR°, —S(O)$_2$NR°R°, —C(NH)NHR°, —C(NH)NR$^p$R$^c$, —NHC(O)R°, —NHC(S)R°, —NR°C(O)R°, —NR°C(S)R°, —NHS(O)$_2$R°, —NR°S(O)$_2$R°, —NHC(O)NHR°, —NH(S)NHR°, —NR°C(O)NH$_2$, —NR°C(S)NH$_2$, —NR°C(O)NHR°, —NR°C(S)NHR°, —NHC(O)NR°R°, —NHC(S)NR°R°, —NR°C(O)NR°R°, —NR°C(S)NR°R°, —NHS(O)$_2$NHR°, —NR°S(O)$_2$NH$_2$, —NR°S(O)$_2$NHR°, —NHS(O)$_2$NR°R°, —NR°S(O)$_2$NR°R°, —NHR°, —NR°R°, R$^d$, —R$^e$, and —R$^g$. Further, possible substitutions include subsets of these substitutions, such as are indicated herein, for example, in the description of compounds of Formula I, attached at any available atom to produce a stable compound. For example "fluoro substituted lower alkynyl" denotes a lower alkynyl group substituted with one or more fluoro atoms, where preferably the lower alkynyl is substituted with 1, 2, 3, 4 or 5 fluoro atoms, also 1, 2, or 3 fluoro atoms. While it is understood that substitutions are attached at any available atom to produce a stable compound, substitution of alkynyl groups are such that —F, —C(O)—, —C(S)—, —C(NH)—, —S(O)—, —S(O)$_2$—, —O—, —S—, or N (except where N is a heteroaryl ring atom) are not bound to an alkyne carbon thereof. Further, where alkynyl is a substituent of another moiety or an R group of a moiety such as —OR, —NHR, —C(O)R, and the like, substitution of the moiety is such that any —C(O)—, —C(S)—, —S(O)—, —S(O)$_2$—, —O—, —S—, or N thereof (except where N is a heteroaryl ring atom) are not bound to an alkyne carbon of the alkynyl substituent or R group. Further, where alkynyl is a substituent of another moiety or an R group of a moiety such as —OR, —NHR, —C(O)NHR, and the like, substitution of the alkynyl R group is such that substitution of the alkynyl carbon bound to any O, S, or N of the moiety (except where N is a heteroaryl ring atom) excludes substituents that would result in any O, S, or N of the substituent (except where N is a heteroaryl ring atom) being bound to the alkynyl carbon bound to any O, S, or N of the moiety. An "alkynyl carbon" refers to any carbon within an alkynyl group, whether saturated or part of the carbon to carbon triple bond. An "alkyne carbon" refers to a carbon within an alkynyl group that is part of a carbon to carbon triple bond.

"Cycloalkyl" refers to saturated or unsaturated, non-aromatic monocyclic, bicyclic or tricyclic carbon ring systems of 3-10, also 3-8, more preferably 3-6, ring members per ring, such as cyclopropyl, cyclopentyl, cyclohexyl, adamantyl, and the like. A "substituted cycloalkyl" is a cycloalkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^o$, —SR$^o$, —OC(O)R$^o$, —OC(S)R$^o$, —C(O)R$^o$, —C(S)R$^o$, —C(O)OR$^o$, —C(S)OR$^o$, —S(O)R$^o$, —S(O)$_2$R$^o$, —C(O)NHR$^o$, —C(S)NHR$^o$, —C(O)NR$^o$R$^o$, —C(S)NR$^o$R$^o$, —S(O)$_2$NHR$^o$, —S(O)$_2$NR$^o$R$^o$, —C(NH)NHR$^o$, —C(NH)NR$^p$R$^c$, —NHC(O)R$^o$, —NHC(S)R$^o$, —NR$^o$C(O)R$^o$, —NR$^o$C(S)R$^o$, —NHS(O)$_2$R$^o$, —NR$^o$S(O)$_2$R$^o$, —NHC(O)NHR$^o$, —NHC(S)NHR$^o$, —NR$^o$C(O)NH$_2$, —NR$^o$C(S)NH$_2$, —NR$^o$C(O)NHR$^o$, —NR$^o$C(S)NHR$^o$, —NHC(O)NR$^o$R$^o$, —NHC(S)NR$^o$R$^o$, —NR$^o$C(O)NR$^o$R$^o$, —NR$^o$C(S)NR$^o$R$^o$, —NHS(O)$_2$NHR$^o$, —NR$^o$S(O)$_2$NH$_2$, —NR$^o$S(O)$_2$NHR$^o$, —NHS(O)$_2$NR$^o$R$^o$, —NR$^o$S(O)$_2$NR$^o$R$^o$, —NHR$^o$, —NR$^o$R$^o$, —R$^d$, —R$^e$, —R$^f$, and —R$^g$.

"Heterocycloalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which a ring carbon may be oxo substituted, i.e. the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, pyrrolidonyl, piperazinyl, dihydrobenzofuryl, and dihydroindolyl. A "substituted heterocycloalkyl" is a heterocycloalkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^o$, —SR$^o$, —OC(O)R$^o$, —OC(S)R$^o$, —C(O)R$^o$, —C(S)R$^o$, —C(O)OR$^o$, —C(S)OR$^o$, —S(O)R$^o$, —S(O)$_2$R$^o$, —C(O)NHR$^o$, —C(S)NHR$^o$, —C(O)NR$^o$R$^o$, —C(S)NR$^o$R$^o$, —S(O)$_2$NHR$^o$, —S(O)NR$^o$R$^o$, —C(NH)NHR$^o$, —C(NH)NR$^p$R$^c$, —NHC(O)R$^o$, —NHC(S)R$^o$, —NR$^o$C(O)R$^o$, —NR$^o$C(S)R$^o$, —NHS(O)$_2$R$^o$, —NR$^o$S(O)$_2$R$^o$, —NHC(O)NHR$^o$, —NHC(S)NHR$^o$, —NR$^o$C(O)NH$_2$, —NR$^o$C(S)NH$_2$, —NR$^o$C(O)NHR$^o$, —NR$^o$C(S)NHR$^o$, —NHC(O)NR$^o$R$^o$, —NHC(S)NR$^o$R$^o$, —NR$^o$C(O)NR$^o$R$^o$, —NR$^o$C(S)NR$^o$R$^o$, —NHS(O)$_2$NHR$^o$, —NR$^o$S(O)$_2$NH$_2$, —NR$^o$S(O)$_2$NHR$^o$, —NHS(O)$_2$NR$^o$R$^o$, —NR$^o$S(O)$_2$NR$^o$R$^o$, —NHR$^o$, —NR$^o$R$^o$, R$^d$, —R$^e$, —R$^f$, and —R$^g$.

"Aryl" alone or in combination refers to a monocyclic or bicyclic ring system containing aromatic hydrocarbons such as phenyl or naphthyl, which may be optionally fused with a cycloalkyl of preferably 5-7, more preferably 5-6, ring members. "Arylene" is a divalent aryl. A "substituted aryl" is an aryl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NT-T$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^o$, —SR$^o$, —OC(O)R$^o$, —OC(S)R$^o$, —C(O)R$^o$, —C(S)R$^o$, —C(O)OR$^o$, —C(S)OR$^o$, —S(O)R$^o$, —S(O)$_2$R$^o$, —C(O)NHR$^o$, —C(S)NHR$^o$, —C(O)NR$^o$R$^o$, —C(S)NR$^o$R$^o$, —S(O)$_2$NHR$^o$, —S(O)$_2$NR$^o$R$^o$, —C(NH)NHR$^o$, —C(NH)NR$^p$R$^c$, —NHC(O)R$^o$, —NHC(S)R$^o$, —NR$^o$C(O)R$^o$, —NR$^o$C(S)R$^o$, —NHS(O)$_2$R$^o$, —NR$^o$S(O)$_2$R$^o$, —NHC(O)NHR$^o$, —NHC(S)NHR$^o$, —NR$^o$C(O)NH$_2$, —NR$^o$C(S)NH$_2$, —NR$^o$C(O)NHR$^o$, —NR$^o$C(S)NHR$^o$, —NHC(O)NR$^o$R$^o$, —NHC(S)NR$^o$R$^o$, —NR$^o$C(O)NR$^o$R$^o$, —NR$^o$C(S)NR$^o$R$^o$, —NHS(O)$_2$NHR$^o$, —NR$^o$S(O)$_2$NH$_2$, —NR$^o$S(O)$_2$NHR$^o$, —NHS(O)$_2$NR$^o$R$^o$, —NR$^o$S(O)$_2$NR$^o$R$^o$, —NHR$^o$, —NR$^o$R$^o$, —R$^d$, —R$^e$, —R$^f$, and —R$^g$. A "substituted arylene" is a divalent substituted aryl.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. "Nitrogen containing heteroaryl" refers to heteroaryl wherein any heteroatoms are N. "Heteroarylene" is a divalent heteroaryl. A "substituted heteroaryl" is a heteroaryl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^o$, —SR$^o$, —OC(O)R$^o$, —OC(S)R$^o$, —C(O)R$^o$, —C(S)R$^o$, —C(O)OR$^o$, —C(S)OR$^o$, —S(O)R$^o$, —S(O)$_2$R$^o$, —C(O)NHR$^o$, —C(S)NHR$^o$, —C(O)NR$^o$R$^o$, —C(S)NR$^o$R$^o$, —S(O)$_2$NHR$^o$, —S(O)$_2$NR$^o$R$^o$, —C(NH)NHR$^o$, —C(NH)NR$^p$R$^c$, —NHC(O)R$^o$, —NHC(S)R$^o$, —NR$^o$C(O)R$^o$, —NR$^o$C(S)R$^o$, —NHS(O)$_2$R$^o$, —NR$^o$S(O)$_2$R$^o$, —NHC(O)NHR$^o$, —NHC(S)NHR$^o$, —NR$^o$C(O)NH$_2$, —NR$^o$C(S)NH$_2$, —NR$^o$C(O)NHR$^o$, —NR$^o$C(S)NHR$^o$, —NHC(O)NR$^o$R$^o$, —NHC(S)NR$^o$R$^o$, —NR$^o$C(O)NR$^o$R$^o$, —NR$^o$C(S)NR$^o$R$^o$, —NHS(O)$_2$NHR$^o$, —NR$^o$S(O)$_2$NH$_2$, —NR$^o$S(O)$_2$NHR$^o$, —NHS(O)$_2$NR$^o$R$^o$, —NR$^o$S(O)$_2$NR$^o$R$^o$, —NHR$^o$, —NHR$^o$R$^o$, —R$^d$, —R$^e$, —R$^f$, and —R$^g$. "Substituted heteroarylene" is a divalent substituted heteroaryl.

The variables $R^o$, $R^p$, $R^c$, $R^d$, $R^e$, $R^f$ and $R^g$ as used in the description of optional substituents for alkyl, alkenyl, alkynyl, cycloalkyl, heterocycloalkyl, aryl and heteroaryl are defined as follows:

each $R^o$, $R^p$, and $R^c$ are independently selected from the group consisting of $R^d$, $R^e$, $R^f$, and $R^g$, or $R^p$ and $R^c$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, —OR$^u$, —SR$^u$, —NR$^u$, —NR$^u$R$^u$, —R$^x$, and —R$^y$;

each $R^d$ is independently lower alkyl, wherein lower alkyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —O(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —O(O)NR$^k$R$^k$, C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^i$, and —R$^j$;

each $R^e$ is independently lower alkenyl, wherein lower alkenyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, NHC(O)R$^k$, NHC(S)R$^k$, NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)NH$_2$, NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^h$, and —R$^j$;

each $R^f$ is independently lower alkynyl, wherein lower alkynyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NM)NR$^k$R$^k$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^h$, and —R$^j$;

each $R^g$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$k, —C(NH)NHR$^k$, —C(NH)NR$^m$R$^n$, —NHC(O)R$^k$, —NHC(S)R$^k$, —NR$^k$C(O)R$^k$, NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NHS(O)$_2$NR$^k$R$^k$, —NHR$^k$, —NR$^k$R$^k$, —R$^h$, —R$^i$, and —R$^j$;

wherein $R^k$, $R^m$, and $R^n$ at each occurrence are independently selected from the group consisting of $R^h$, $R^i$, and $R^j$, or $R^m$ and $R^n$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more preferably 1, 2, 3, 4 or 5, also 1, 2, or 3 substituents selected from the group consisting of halogen, —NO$_2$, —CN, —OH, —NH$_2$, OR$^u$, —SR$^u$, —NHR$^u$, —NR$^u$R$^u$, —R$^x$, and —R$^y$;

wherein each $R^h$ is independently lower alkyl optionally substituted with one or more, preferably 1, 2, 3, 4 or 5, also 1, 2, or 3 substituents selected from the group consisting of fluoro, —OH, —NH$_2$, —NO$_2$—CN, —C(O)OH, —C(S)OH, —C(O)NH$_2$, —C(S)NH$_2$, —S(O)$_2$NH$_2$, —NHC(O)NH$_2$, —NC(S)NH$_2$, —NHS(O)$_2$NH$_2$, —C(NH)NH$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR'R$^r$, —C(S)NR'R$^r$, —S(O)$_2$NHR$^r$, —S(O)$_2$NR'R$^r$, —C(NH)NHR$^r$, —C(NH)NR$^s$R$^t$, —NHC(O)R$^r$, —NHC(S)R$^r$, —NR'C(O)R$^r$, —NR'C(S)R$^r$, —NHS(O)$_2$R$^r$, —NR'S(O)$_2$R$^r$, —NHC(O)NHR$^r$, —NHC(S)NHR$^r$, —NR'C(O)NH$_2$, —NR'C(S)NH$_2$, —NR'C(O)NHR$^r$, —NR'C(S)NHR$^r$, —NHC(O)NR'R$^r$, —NHC(S)NR'R$^r$, —NR'C(O)NR'R$^r$, —NR'C(S)NR$^r$, —NHS(O)$_2$NHR$^r$, —NR'S(O)$_2$NH$_2$, —NR'S(O)$_2$NHR$^r$, —NHS(O)$_2$NR'R$^r$, —NR'S(O)$_2$NR'R$^r$, —NHR$^r$, —NR'R$^r$, —R$^i$, and —R$^j$;

wherein each $R^i$ is independently selected from the group consisting of lower alkenyl and lower alkynyl, wherein lower alkenyl or lower alkynyl are optionally substituted with one or more, preferably 1, 2, 3, 4 or 5, also , 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR'R$^r$, —C(S)NR'R$^r$, —S(O)$_2$NHR$^r$, —S(O)$_2$NR'R$^r$, —C(NH)NHR$^r$, —C(NH)NR'R$^r$, —NHC(O)R$^r$, —NHC(S)R$^r$, —NR'C(O)R$^r$, —NR'C(S)R$^r$, —NHS(O)$_2$R$^r$, —NR'S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NR$^r$C(S)NHR$^r$, —NHC(O)NR$^r$R$^r$, —NHC(S)NR$^r$R$^r$, —NR$^r$C(O)NR$^r$R$^r$, —NR$^r$C(S) NR$^r$R$^r$, —NHS(O)$_2$NHR$^r$, —NR$^r$S(O)$_2$NH$_2$, —NR$^r$S (O)$_2$NHR$^r$, —NHS(O)$_2$NR$^r$R$^r$, —NR$^r$S(O)$_2$NR$^r$R$^r$, —NHR$^r$, —NR$^r$R$^r$, and —R$^j$;

wherein each R$^j$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR$^r$R$^r$, —C(S)NR$^r$R$^r$, —S(O)$_2$NHR$^r$, —S(O)$_2$NR$^r$R$^r$, —C(NH)NHR$^r$, —C(NH)NR$^s$R$^t$, —NHC(O)R$^r$, —NHC(S)R$^r$, —NR$^r$C(O)R$^r$, —NR$^r$C(S)R$^r$, —NHS(O)$_2$R$^r$, —NR$^r$S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NR$^r$C(S)NHR$^r$, —NHC(O)NR$^r$R$^r$, —NHC(S)NR$^r$R$^r$, —NR$^r$C(O)NR$^r$R$^r$, —NR$^r$C(S)NR$^r$R$^r$, —NHS(O)$_2$NHR$^r$, —NR$^r$S(O)$_2$NH$_2$, —NR$^r$S(O)$_2$HR$^r$, —NHS(O)$_2$NR$^r$R$^r$, —NR$^r$S(O)$_2$NR$^r$R$^r$, —NHR$^r$, —NR$^r$R$^r$, cycloalkylamino, and —R$^x$;

wherein each R$^r$, R$^s$, and R$^t$ at each occurrence are independently selected from the group consisting of lower alkyl, C$_{3-6}$ alkenyl, C$_{3-6}$ alkynyl, cycloalkyl, heterocycloalkyl, aryl and heteroaryl, wherein lower alkyl is optionally substituted with one or more, preferably 1, 2, 3, 4 or 5, also 1, 2, or 3 substituents selected from the group consisting of —R$^y$, fluoro, —OH, —N$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the lower alkyl carbon bound to any O, S, or N, of —OR$^r$, —SR$^r$, —C(O)OR$^r$, —C(S)OR$^r$, —C(O)NHR$^r$, —C(S)NHR$^r$, —C(O)—NR$^r$R$^r$, —C(S)NR$^r$R$^r$, —S(O)$_2$NHR$^r$, —S(O)$_2$NR$^r$R$^r$, —C(NH)NHR$^r$, —NR$^r$C(O)R$^r$, —NR$^r$C(S)R$^r$, —NR$^r$S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NR$^r$C(S)NHR$^r$, —NC(O)NR$^r$R$^r$, —NHC(S)NR$^r$R$^r$, —NR$^r$C(O)NR$^r$R$^r$, —NR$^r$C(S)NR$^r$R$^r$, —NHS(O)$_2$NHR$^r$, —NR$^r$S(O)$_2$NH$_2$, —NR$^r$S(O)$_2$NHR$^r$, —NHS(O)$_2$NR$^r$R$^r$, —NR$^r$S(O)$_2$NR$^r$R$^r$, —NHR$^r$, or —NR$^r$R$^r$ is selected from the group consisting of fluoro and —R$^y$, and wherein C$_{3-6}$ alkenyl or C$_{3-6}$ alkynyl are optionally substituted with one or more, preferably 1, 2, 3, 4 or 5, also 1, 2, or 3 substituents selected from the group consisting of —R$^y$, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, provided, however, that any substitution of the C$_{3-6}$ alkenyl or C$_{3-6}$ alkynyl carbon bound to any O, S, or N, of —OR$^r$, —SR$^r$, —C(O)OR$^r$, —C(S)OR$^r$, —C(O)NHR$^r$, —C(S)NHR$^r$, —C(O)NR$^r$R$^r$, —C(S)NR$^r$R$^r$, —S(O)$_2$NHR$^r$, —S(O)$_2$NR$^r$R$^r$, —C(NH)NHR$^r$, —NR$^r$C(O)R$^r$, —NR$^r$C(S)R$^r$, —NR$^r$S(O)$_2$R$^r$, —NHC(O)NHR$^r$, —NHC(S)NHR$^r$, —NR$^r$C(O)NH$_2$, —NR$^r$C(S)NH$_2$, —NR$^r$C(O)NHR$^r$, —NR$^r$C(S)NHR$^r$, —NHC(O) NR$^r$R$^r$, —NHC(S)NR$^r$R$^r$, —NR$^r$C(O)NR$^r$R$^r$, —NR$^r$C(S)NR$^r$R$^r$, —NHS(O)$_2$NHR$^r$, —NR$^r$S(O)$_2$NH$_2$, —NR$^r$S(O)$_2$NHR$^r$, —NHS(O)$_2$NR$^r$R$^r$, —NR$^r$S(O)$_2$NR$^r$R$^r$, —NHR$^r$, or —NR$^r$R$^r$ is selected from the group consisting of fluoro, lower alkyl, fluoro substituted lower alkyl, and —R$^y$, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, or R$^s$ and R$^t$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, OR$^u$, —SR$^u$, —NHR$^u$, —NR$^u$R$^u$, —R$^x$, and —R$^y$;

wherein each R$^u$ is independently selected from the group consisting of lower alkyl, C$_{3-6}$ alkenyl, C$_3$—alkynyl, cycloalkyl, heterocycloalkyl, aryl, and heteroaryl, wherein lower alkyl is optionally substituted with one or more, preferably 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided, however, that any substitution of the lower alkyl carbon bound to the O of —OR$^u$, S of —SR$^u$, or N of —NHR$^u$ is fluoro or —R$^y$, and wherein C$_{3-6}$ alkenyl or C$_{3-6}$ alkynyl are optionally substituted with one or more, preferably 1, 2, 3, 4 or 5, also 1, 2, or 3 substituents selected from the group consisting of —R$^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, provided, however that any substitution of the C$_{3-6}$ alkenyl or C$_{3-6}$ alkynyl carbon bound to the O of —OR$^u$, S of —SR$^u$, or N of —NHR$^u$ is fluoro, lower alkyl, fluoro substituted lower alkyl, or —R$^y$, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each R$^x$ is selected from the group consisting of lower alkyl, lower alkenyl and lower alkynyl, wherein lower alkyl is optionally substituted with one or more, preferably 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein lower alkenyl or lower alkynyl are optionally substituted with one or more, preferably 1, 2, 3, 4 or 5, also 1, 2, or 3 substituents selected from the group consisting of —R$^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each R$^y$ is selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted C$_{2-6}$ alkyl, optionally substituted lower alkenyl, or optionally substituted lower alkynyl are optionally substituted with one or more, also 1, 2 or 3 groups or substituents selected from the group consisting of fluoro, —NO$_2$, —CN, —OR$^{1a}$, —SR$^{1a}$, —NR$^{1a}$R$^{1a}$, —OC(O)R$^{1a}$, —OC(S)R$^{1a}$, —C(O)R$^{1a}$, —C(S)R$^{1a}$, —C(O)OR$^{1a}$, —C(S)OR$^{1a}$, —C(O)NR$^{1a}$R$^{1a}$, —C(S)NR$^{1a}$R$^{1a}$, —S(O)$_2$NR$^{1a}$R$^{1a}$, —C(O)NR$^{1a}$R$^{1a}$, —NR$^{1a}$C(O)R$^{1a}$, —NR$^{1a}$C(S)R$^{1a}$, —NR$^{1a}$S(O)$_2$R$^{1a}$, —NR$^{1a}$C(O)NR$^{1a}$NR$^{1a}$, —NR$^{1a}$C(S)NR$^{1a}$R$^{1a}$, —NR$^{1a}$S(O)$_2$NR$^{1a}$R$^{1a}$, —S(O)R$^{1a}$, —S(O)$_2$R$^{1a}$, cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —NO$_2$, —CN, —OR$^{1a}$, —SR$^{1a}$, —NR$^{1a}$R$^{1a}$, —OC(O)R$^{1a}$, —OC(S)R$^{1a}$, C(O)R$^{1a}$, —C(S)R$^{1a}$, —C(O)OR$^{1a}$, —C(S)OR$^{1a}$, —C(O)NR$^{1a}$R$^{1a}$, —C(S)NR$^{1a}$R$^{1a}$, —S(O)$_2$NR$^{1a}$R$^{1a}$, —C(NH)NR$^{1a}$R$^{1a}$, NR$^{1a}$C(O)R$^{1a}$, —NR$^{1a}$C(S)R$^{1a}$, —NR$^{1a}$S(O)$_2$R$^{1a}$, —NR$^{1a}$C(O)NR$^{1a}$R$^{1a}$, —NR$^{1a}$C(S)NR$^{1a}$R$^{1a}$, —NR$^{1a}$S(O)$_2$NR$^{1a}$R$^{1a}$, —S(O)R$^{1a}$, —S(O)$_2$R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, and all occurrences of optionally substituted cycloalkyl, optionally substituted heterocycloalkyl, optionally substituted 5-7 membered heterocycloalkyl, optionally substituted aryl, optionally substituted arylene, optionally substituted heteroaryl, optionally substituted heteroarylene, or optionally substituted 5 or 7 membered nitrogen containing heteroaryl are optionally substituted with one or more, also 1, 2, or 3 substituents selected from the group consisting of halogen, —NO$_2$, —CN, —OR$^{1a}$, —SR$^{1a}$, —NR$^{1a}$R$^{1a}$, —OC(O)R$^{1a}$, —OC(S)R$^{1a}$, —C(O)R$^{1a}$, —C(S)R$^{1a}$, —C(O)OR$^{1a}$, —C(S)OR$^{1a}$, —C(O)NR$^{1a}$R$^{1a}$, —C(S)NR$^{1a}$R$^{1a}$, —S(O)$_2$NR$^{1a}$R$^{1a}$, —C(NH)NR$^{1a}$R$^{1a}$, —NR$^{1a}$C(O)R$^{1a}$, —NR$^{1a}$C(S)R$^{1a}$, —NR$^{1a}$S(O)$_2$R$^{1a}$, —NR$^{1a}$C(O)NR$^{1a}$R$^{1a}$, —NR$^{1a}$C(S)NR$^{1a}$R$^{1a}$, —NR$^{1a}$S(O)$_2$NR$^{1a}$R$^{1a}$, —S(O)R$^{1a}$, —S(O)$_2$R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, wherein R$^{1a}$ is selected from the group consisting of hydrogen, provided, however, that hydrogen is not bound to any of C(S), C(O), S(O), or S(O)$_2$ of —OC(O)R$^{1a}$, —OC(S)R$^{1a}$, —C(O)R$^{1a}$, —C(S)R$^{1a}$, —NR$^{1a}$C(O)R$^{1a}$, —NR$^{1a}$C(S)R$^{1a}$, —NR$^{1a}$S(O)$_2$R$^{1a}$, —S(O)R$^{1a}$, or —S(O)$_2$R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, provided, however, that any substitution of the alkyl carbon bound to O, S, or N of —OR$^{1a}$, —SR$^{1a}$, —NR$^{1a}$R$^{1a}$, —C(O)OR$^{1a}$, —C(S)OR$^{1a}$, —C(O)NR$^{1a}$R$^{1a}$, —C(S)NR$^{1a}$R$^{1a}$, —S(O)$_2$NR$^{1a}$R$^{1a}$, —C(NH)NR$^{1a}$, —NR$^{1a}$C(O)R$^{1a}$, —NR$^{1a}$C(S)R$^{1a}$, —NR$^{1a}$S(O)$_2$R$^{1a}$, —NR$^{1a}$C(O)NR$^{1a}$R$^{1a}$, —NR$^{1a}$C(S)NR$^{1a}$R$^{1a}$, or —NR$^{1a}$S(O)$_2$NR$^{1a}$R$^{1a}$, is fluoro or —R$^{1b}$, and wherein —R$^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —NH$_2$, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted C$_{2-6}$, alkyl, optionally substituted lower alkenyl, or optionally substituted lower alkynyl are optionally substituted with one or more, also 1, 2 or 3 groups or substituents selected from the group consisting of fluoro, —CN, —OR$^{1a}$, —SR$^{1a}$, —NR$^{1a}$R$^{1a}$, —C(O)R$^{1a}$, —C(S)R$^{1a}$, —C(O)OR$^{1a}$, —C(O)NR$^{1a}$R$^{1a}$, —C(S)NR$^{1a}$R$^{1a}$, —S(O)$_2$NR$^{1a}$R$^{1a}$, —NR$^{1a}$C(O)R$^{1a}$, —NR$^{1a}$C(S)R$^{1a}$, —NR$^{1a}$S(O)$_2$R$^{1a}$, —S(O)R$^{1a}$, —S(O)$_2$R$^{1a}$, cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OR$^{1a}$, —SR$^{1a}$, —NR$^{1a}$R$^{1a}$, —C(O)R$^{1a}$, —C(S)R$^{1a}$, —C(O)OR$^{1a}$, —C(O)NR$^{1a}$R$^{1a}$, —C(S)NR$^{1a}$R$^{1a}$, —S(O)$_2$NR$^{1a}$R$^{1a}$, —NR$^{1a}$C(O)R$^{1a}$, —NR$^{1a}$C(S)R$^{1a}$, —NR$^{1a}$S(O)$_2$R$^{1a}$, —S(O)R$^{1a}$, —S(O)$_2$R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, and all occurrences of optionally substituted cycloalkyl, optionally substituted heterocycloalkyl, optionally substituted 5-7 membered heterocycloalkyl, optionally substituted aryl, optionally substituted arylene, optionally substituted heteroaryl, optionally substituted heteroarylene, or optionally substituted 5 or 7 membered nitrogen containing heteroaryl are optionally substituted with one or more, also 1, 2, or 3 substituents selected from the group consisting of halogen, —CN, —OR$^{1a}$, —SR$^{1a}$, —NR$^{1a}$R$^{1a}$, —C(O)R$^{1a}$, —C(S)R$^{1a}$, —C(O)OR$^{1a}$, —C(O)NR$^{1a}$R$^{1a}$, —C(S)NR$^{1a}$R$^{1a}$, —S(O)$_2$NR$^{1a}$R$^{1a}$, —NR$^{1a}$C(O)R$^{1a}$, —NR$^{1a}$C(S)R$^{1a}$, —NR$^{1a}$S(O)$_2$R$^{1a}$, —S(O)R$^{1a}$, —S(O)$_2$R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, wherein R$^{1a}$ is selected from the group consisting of hydrogen, provided, however, that hydrogen is not bound to any of C(S), C(O), S(O), or S(O)$_2$ of —C(O)R$^{1a}$, —C(S)R$^{1a}$, —NR$^{1a}$C(O)R$^{1a}$, —NR$^{1a}$C(S)R$^{1a}$, —NR$^a$S(O)$_2$R$^{1a}$, —S(O)R$^{1a}$, or —S(O)$_2$R$^{1a}$, —R$^{1b}$, and lower alkyl optionally substituted with one or more, also 1, 2 or 3 groups or substituents selected from the group consisting of fluoro, —OH, —N$_2$, lower alkoxy, fluoro substituted lower alkoxy, lower alkylthio, fluoro substituted lower alkylthio, mono-alkylamino, di-alkylamino, and —$R^{1b}$, provided, however, that any substitution of the alkyl carbon bound to O, S, or N of —$OR^{1a}$, —$SR^{1a}$, —$NR^{1a}R^{1a}$, —$C(O)OR^{1a}$, —$C(O)NR^{1a}$, —$C(S)NR^{1a}R^{1a}$, —$S(O)_2NR^{1a}$, —$NR^{1a}C(O)R^{1a}$, —$NR^{1a}C(S)R^{1a}$, or —$NR^{1a}S(O)_2R^{1a}$, is fluoro or —$R^{1b}$, and wherein —$R^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —$NH_2$, lower alkoxy, fluoro substituted lower alkoxy, lower alkylthio, fluoro substituted lower alkylthio, mono-alkylamino, di-alkylamino, and cycloalkylamino.

"Lower alkoxy" denotes the group —$OR^z$, where $R^z$ is lower alkyl. "Substituted lower alkoxy" denotes lower alkoxy in which $R^z$ is lower alkyl substituted with one or more substituents as indicated herein, for example, in the description of compounds of Formula I, including descriptions of substituted cycloalkyl, cycloheteroalkyl, aryl and heteroaryl, attached at any available atom to produce a stable compound. Preferably, substitution of lower alkoxy is with 1, 2, 3, 4, or 5 substituents, also 1, 2, or 3 substituents. For example "fluoro substituted lower alkoxy" denotes lower alkoxy in which the lower alkyl is substituted with one or more fluoro atoms, where preferably the lower alkoxy is substituted with 1, 2, 3, 4 or 5 fluoro atoms, also 1, 2, or 3 fluoro atoms. While it is understood that substitutions on alkoxy are attached at any available atom to produce a stable compound, substitution of alkoxy is such that O, S, or N (except where N is a heteroaryl ring atom), are not bound to the alkyl carbon bound to the alkoxy O. Further, where alkoxy is described as a substituent of another moiety, the alkoxy oxygen is not bound to a carbon atom that is bound to an O, S, or N of the other moiety (except where N is a heteroaryl ring atom), or to an alkene or alkyne carbon of the other moiety.

"Lower alkylthio" denotes the group —$SR^{aa}$, where $R^{aa}$ is lower alkyl, "Substituted lower alkylthio" denotes lower alkylthio in which $R^{aa}$ is lower alkyl substituted with one or more substituents as indicated herein, for example, in the description of compounds of Formula I, including descriptions of substituted cycloalkyl, cycloheteroalkyl, aryl and heteroaryl, attached at any available atom to produce a stable compound. Preferably, substitution of lower alkylthio is with 1, 2, 3, 4, or 5 substituents, also 1, 2, or 3 substituents. For example "fluoro substituted lower alkylthio" denotes lower alkylthio in which the lower alkyl is substituted with one or more fluoro atoms, where preferably the lower alkylthio is substituted with 1, 2, 3, 4 or 5 fluoro atoms, also 1, 2, or 3 fluoro atoms. While it is understood that substitutions on alkylthio are attached at any available atom to produce a stable compound, substitution of alkylthio is such that O, S, or N (except where N is a heteroaryl ring atom), are not bound to the alkyl carbon bound to the alkylthio S. Further, where alkylthio is described as a substituent of another moiety, the alkylthio sulfur is not bound to a carbon atom that is bound to an O, S, or N of the other moiety (except where N is a heteroaryl ring atom), or to an alkene or alkyne carbon of the other moiety.

"Amino" or "amine" denotes the group —$NH_2$. "Mono-alkylamino" denotes the group —$NHR^{bb}$ where $R^{bb}$ is lower alkyl. "Di-alkylamino" denotes the group —$NR^{bb}R^{cc}$, where $R^{bb}$ and $R^{cc}$ are independently lower alkyl. "Cycloalkylamino" denotes the group —$NR^{dd}R^{ee}$, where $R^{dd}$ and $R^{ee}$ combine with the nitrogen to form a 5-7 membered heterocycloalkyl, where the heterocycloalkyl may contain an additional heteroatom within the ring, such as O, N, or S, and may also be further substituted with lower alkyl. Examples of 5-7 membered heterocycloalkyl include, but are not limited to, piperidine, piperazine, 4-methylpiperazine, morpholine, and thiomorpholine. While it is understood that when mono-alkylamino, di-alkylamino, or cycloalkylamino are substituents on other moieties that are attached at any available atom to produce a stable compound, the nitrogen of mono-alkylamino, di-alkylamino, or cycloalkylamino as substituents is not bound to a carbon atom that is bound to an O, S, or N of the other moiety.

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

As used herein, the terms "ligand" and "modulator" are used equivalently to refer to a compound that changes (i.e., increases or decreases) the activity of a target biomolecule, e.g., an enzyme such as a kinase. Generally a ligand or modulator will be a small molecule, where "small molecule refers to a compound with a molecular weight of 1500 daltons or less, or preferably 1000 daltons or less, 800 daltons or less, or 600 daltons or less. Thus, an "improved ligand" is one that possesses better pharmacological and/or pharmacokinetic properties than a reference compound, where "better" can be defined by one skilled in the relevant art for a particular biological system or therapeutic use.

In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10,000-fold greater affinity.

As used herein in connection with compounds of the invention, the term "synthesizing" and like terms means chemical synthesis from one or more precursor materials.

By "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

As used herein in connection with amino acid or nucleic acid sequence, the term "isolate" indicates that the sequence is separated from at least a portion of the amino acid and/or nucleic acid sequences with which it would normally be associated.

In connection with amino acid or nucleic sequences, the term "purified" indicates that the subject molecule constitutes a significantly greater proportion of the biomolecules in a composition than the proportion observed in a prior composition, e.g., in a cell culture. The greater proportion can be 2-fold, 5-fold, 10-fold, or more than 10-fold, with respect to the proportion found in the prior composition.

The present invention concerns compounds of Formula I and all sub-generic formulae that are modulators of protein kinases, for example without limitation, the compounds are modulators of at least one of the kinases selected from the group consisting of Ab1, Akt1, Akt2, Akt3, ALK, Alk5, A-Raf, B-Raf. Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, LCK, MAP2K1, MAP2K2, MAP4K4, MAPKAPK2, Met, Mnk1, MLK1, p38, PDGFRA, PDGFRB, PDPK1, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and Zap70, and the use of such compounds in the treatment of diseases or conditions.

II. Kinase Targets and Indications of the Invention

Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Description of specific target protein kinases contemplated by the present invention may be found, for example, in U.S. patent application Ser. No. 11/473,347 (PCT publication WO2007002433), the disclosure of which is hereby incorporated by reference in its entirety, in addition to the following:

Exemplary Diseases Associated with Raf Kinases

A-Raf: Target kinase A-Raf (i.e., v-raf murine sarcoma 3611 viral oncogene homolog 1) is a 67.6 kDa serine/threonine kinase encoded by chromosome Xp11.4-p11.2 (symbol: ARAF). The mature protein comprises RED (i.e., Ras binding domain) and phorbol-ester/DAG-type zinc finger domain and is involved in the transduction of mitogenic signals from the cell membrane to the nucleus. A-Raf inhibitors may be useful in treating neurologic diseases including, but not limited to, multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myelodysplastic syndrome, leukemia, tumor angiogenesis; pain of neuropathic or inflammatory origin, including, but not limited to, acute pain, chronic pain, cancer-related pain and migraine; and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenital central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

B-Raf: Target kinase B-Raf (i.e., v-raf murine sarcoma viral oncogene homolog B1) is a 84.4 kDa serine/threonine kinase encoded by chromosome 7q34 (symbol: BRAF). The mature protein comprises RBD (i.e., Ras binding domain), C1 (i.e., protein kinase C conserved region 1) and STK (i.e., serine/threonine kinase) domains.

Target kinase B-Raf is involved in the transduction of mitogenic signals from the cell membrane to the nucleus and may play a role in the postsynaptic responses of hippocampal neurons. As such, genes of the RAF family encode kinases that are regulated by Ras and mediate cellular responses to growth signals. Indeed, B-Raf kinase is a key component of the RAS>Raf>MEK>ERK/MAP kinase signaling pathway, which plays a fundamental role in the regulation of cell growth, division and proliferation, and, when constitutively activated, causes tumorigenesis. Among several isoforms of Raf kinase, the B-type, or B-Raf, is the strongest activator of the downstream MAP kinase signaling.

The BRAF gene is frequently mutated in a variety of human tumors, especially in malignant melanoma and colon carcinoma. The most common reported mutation was a missense thymine (T) to adenine (A) transversion at nucleotide 1796 (T1796A; amino acid change in the B-Raf protein is Val<600> to Glu<600>) observed in 80% of malignant melanoma tumors. Functional analysis reveals that this transversion is the only detected mutation that causes constitutive activation of B-Raf kinase activity, independent of RAS activation, by converting B-Raf into a dominant transforming protein. Based on precedents, human tumors develop resistance to kinase inhibitors by mutating a specific amino acid in the catalytic domain as the "gatekeeper". (Balak, et. al., Clin Cancer Res. 2006, 12:6494-501). Mutation of Thr-529 in BRAF to Ile is thus anticipated as a mechanism of resistance to BRAY inhibitors, and this can be envisioned as a transition in codon 529 from ACC to ATC.

Niihori et al., report that in 43 individuals with cardio-facio-cutaneous (CFC) syndrome, they identified two heterozygous KRAS mutations in three individuals and eight BRAF mutations in 16 individuals, suggesting that dysregulation of the RAS-RAY-ERK pathway is a common molecular basis for the three related disorders (Niihori et al., Nat. Genet. 2006, 38(3):294-6).

c-Raf-1: Target kinase c-Raf-1 (i.e., v-raf murine sarcoma viral oncogene homolog 1) is a 73.0 kDa STK encoded by chromosome 3p25 (symbol: RAF1). c-Raf-1 can be targeted to the mitochondria by BCL2 (i.e., oncogene B-cell leukemia 2) which is a regulator of apoptotic cell death. Active c-Raf-1 improves BCL2-mediated resistance to apoptosis, and c-Raf-1 phosphorylates BAD (i.e., BCL2-binding protein), c-Raf-1 is implicated in carcinomas, including, but not limited to, colorectal, ovarian, lung and renal cell carcinoma. C-Raf-1 is also implicated as an important mediator of tumor angiogenesis (flood, J. D. et al., 2002. Science 296, 2404). C-Raf-1 inhibitors may also be useful for the treatment of acute myeloid leukemia and myelodysplastic syndromes (Crump, Curr Pharm Des 2002, 8(25):2243-8). Raf-1 activators may be useful as treatment for neuroendocrine tumors, such as medullary thyroid cancer, carcinoid, small cell lung cancer and pheochromocytoma (Kunnimalaiyaan et al., Anticancer Drugs 2006, 17(2):139-42).

B-Raf and/or C-Raf inhibitors may be useful in treating A-Raf-mediated, B-Raf-mediated or c-Raf-1-mediated disease or condition selected from the group consisting of neurologic diseases, including, but not limited to, multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma) neurofibromatosis, acute myeloid leukemia, myelodysplastic syndrome, leukemia, tumor angiogenesis, neuroendocrine tumors such as medullary thyroid cancer, carcinoid, small cell lung cancer and pheochromocytoma; pain of neuropathic or inflammatory origin, including, but not limited to, acute pain, chronic pain, cancer-related pain, and migraine; cardiovascular diseases, including, but not limited to, hear failure, ischemic stroke, cardiac hypertrophy, thrombosis (e.g. thrombotic microangiopathy syndromes), atherosclerosis, and reperfusion injury; inflammation including, but not limited to, psoriasis, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease; renal or prostatic diseases, including, but not limited to, diabetic nephropathy, polycystic kidney disease, nephrosclerosis, glomerulonephritis, prostate hyperplasia; metabolic disorders, including, but not limited to, obesity; infection, including, but not limited to, *Helicobacter pylori*, *Hepatitis* and *Influenza* viruses, fever, and sepsis; pulmonary diseases, including, but not limited to, chronic obstructive pulmonary disease (COPD) and acute respiratory distress syndrome (ARDS); genetic developmental diseases, including, but not limited to, Noonan's syndrome, Costello syndrome, (facio-cutaneoskeletal syndrome), LEOPARD syndrome, cardio-faciocutaneous syndrome (CFC) and neural crest syndrome abnormalities causing cardiovascular, skeletal, intestinal, skin, hair and endocrine diseases.

Exemplary Diseases Associated with c-Kit.

The compounds described herein are useful for treating disorders related to c-kit e.g. diseases related to unregulated kinase signal transduction, including cell proliferative disorders, fibrotic disorders and metabolic disorders, among others. As described in more detail below and in Lipson et al., U.S. 20040002534 (U.S. application Ser. No. 10/600,868, filed Jun. 23, 2003) which is incorporated herein by reference in its entirety, cell proliferative disorders which can be treated by the present invention include cancers, and mast cell proliferative disorders.

The presence of c-kit has also been associated with a number of different types of cancers. In addition, the association between abnormalities in c-kit and disease are not restricted to cancer. As such, c-kit has been associated with malignancies, including, but not limited to, mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, melanoma, and canine mast cell tumors, and inflammatory diseases, including, but not limited to, asthma, rheumatoid arthritis, allergic rhinitis, multiple sclerosis, inflammatory bowel syndrome, transplant rejection, and hypereosinophilia.

Exemplary Diseases Associated with c-fms

The presence of c-fms has been associated with a number of different types of diseases. As such, c-fms has been associated with immune disorders, including rheumatoid arthritis, systemic lupus erythematosis (SLE), and transplant rejection; inflammatory diseases including, but not limited to, osteoarthritis, inflammatory bowel syndrome, ulcerative colitis, Crohn's disease, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, increased risk of fracture, Paget's disease, hypercalcemia, infection-mediated osteolysis (e.g. osteomyelitis), peri-prosthetic or wear-debris-mediated osteolysis, and metastasis of cancer to bone; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, stroke, Alzheimer's disease and Parkinson's disease; inflammatory and chronic pain, including, but not limited to, bone pain; and cancers, including, but not limited to, multiple myeloma, acute myeloid leukemia (AML), chronic myeloid leukemia (CML), prostate cancer, breast cancer, ovarian cancer, melanoma, glioblastoma multiforme, metastasis of tumors to other tissues, and other chronic myeloproliferative diseases such as myelofibrosis.

Exemplary Diseases Associated with TrkA and TrkB

TrkA: Target kinase TrkA (i.e., neurotrophic tyrosine kinase, receptor, type 1) is a 140 kDa tyrosine kinase encoded by chromosome 1q21-q22 (symbol: NTRK1). TrkA inhibitors may be useful in treating pain (e.g. chronic pain, neuropathic pain), cancer (e.g. prostate cancer, lung cancer, myeloid leukemia, pancreatic cancer), allergic disorders (e.g. asthma), arthritis, diabetic retinopathy, macular degeneration and psoriasis.

TrkA is a plasma member receptor composed of an extracellular domain (responsible for high affinity binding to nerve growth factor, NGF), a transmembrane segment and an intracellular protein tyrosine kinase domain (responsible to transmit the NGF signal to initiate and coordinate neuronal responses). NGF binding induces TrkA clustering on the membrane and activates the kinase. The kinase initiates a cascade of protein phosphorylation events through multiple pathways including SHC/Ras/MAPK, PI3K and PLCg1. A TrkA kinase inhibitor would not prevent NGF/TrkA binding, but could prevent down-stream signal transduction.

Nerve Growth Factor (NGF) is produced by a number of tissues and inflammatory cells during tissue injury and host immune response. It initiates and maintains hypersensitivity to incoming stimulus (hyperalgesia) and the perception of non-noxious stimuli (allodynia). Through its high-affinity receptor TrkA, NGF increases the excitation state of sensory neurons leading to the central nervous system (peripheral sensitization), and increases transmitter release from the dorsal spinal cord (central sensitization). In clinical trials, a single NGF subcutaneous injection generated local hyperalgesia persisting up to 7 weeks. At doses above 0.1 microgram/kg, NGF caused muscle pain that varied from mild to moderate, primarily in the bulbar and truncal musculature. Intravenous NGF produced earlier and more pronounced systemic effects (Petty et al, 1994, Ann Neurol. 36: 244-6). Conversely, TrkA kinase inhibitors could be used to treat diseases of enhanced states of nociception.

In Complete Freund's Adjuvant (CFA)-induced hind-paw inflammation, spinal nerve ligation and streptozoticin-induced neuropathic pain models, a single intraperitoneal injection of anti-NGF reversed established tactile allodynia from day 3 to day 7 following treatment. In the mouse CCI model, anti-NGF reversed tactile allodynia when administered 2 weeks after surgery. Repeated administration of this antibody to CCI mice for 3 weeks produced a sustained reversal of tactile allodynia (Wild et al, 2007, J. Pharmacol. Exp. Ther. 322:282-287).

Prostate tumors that have metastasized to bone frequently induce bone pain which can be difficult to fully control as it seems to be driven simultaneously by inflammatory, neuropathic, and tumorigenic mechanisms. Anti-NGF produced a significant reduction in both early and late stage bone cancer pain-related behaviors. This therapy did not influence tumor-induced bone remodeling, osteoblast proliferation, osteoclastogenesis, tumor growth, or markers of sensory or sympathetic innervation in the skin or bone. All nerve fibers that innervate the bone express TrkA and p75, and these are the receptors through which NGF sensitizes and/or activates nociceptors (Halvorson et al, 2005, Cancer Res. 65:9426-35).

In patients with mild asthma due to exposure to cat allergen, NGF expression was strongly induced in epithelial cells, fibroblasts, blood vessels, and a few infiltrating cells. TrkA mRNA and protein levels in bronchial biopsies were increased significantly after allergen exposure in infiltrating mast cells before the onset of symptoms (Kassel et al, 2001, Clin Exp Allergy 31:1432-40).

The late phase reaction in asthma following allergen provocation is dominated by an influx of activated eosinophils into the bronchial lumen, which correlates with the release of eosinophilic products into the airways to increase disease severity. The viability and activation of eosinophils from patients with mild asthma were significantly enhanced after NGF stimulation. Addition of neutralizing anti-NGF antibodies ex vivo abrogated the effects (Nassentein et al, 2003, J Exp Med 198:455-467). TrkA kinase inhibitors could decrease this paracrine loop between the respiratory tract and infiltrating mast cells as well as endobronchial eosinophils, and thus be useful for the treatment of asthma and other allergic disorders.

TrkB: Target kinase TrkB (i.e., neurotrophic tyrosine kinase, receptor, type 2) is a 145 kDa tyrosine kinase encoded by chromosome 9q22.1 (symbol: NTRK2). TrkB inhibitors may be useful in treating various cancers and their metastases (e.g. prostate cancer, lung cancer, Wilms tumors, neuroblastoma, and pancreatic cancer), and various neuropathies (e.g. stroke, multiple sclerosis, transverse myelitis, and encephalitis).

In clinical trials with recombinant BDNF, paresthesia was developed at the site of subcutaneous injection (Coulie et al, 2000, Gastroenterology 119:41-50). Intrathecal infusion of BDNF in humans also induced paresthesia and warmth as side effects (Ochs et al, 2000, Amyotroph Lateral Scler Other Motor Neuron Disord. 1:201-6). Chronic paresthesia is often a symptom of an underlying neurological disease or traumatic nerve damage. Paresthesia can be caused by disorders affecting the central nervous system, such as stroke and transient ischemic attacks (mini-strokes), multiple sclerosis, transverse myelitis, and encephalitis. Since BDNF binds to TrkB specifically with high affinity these neuropath effects are mediated through TrkB signaling. Thus Trkb kinase inhibitors could be used to treat certain patients with neuropathy.

BDNF is known to act at the synapses between primary sensory and spinal dorsal horn neurons to affect pain transmission during inflammation. The primary afferent is the only source of BDNF in the spinal cord, and it is up-regulated in the dorsal root ganglion (DRG) by peripheral NGF a few days after inflammation, and is transported and released into the superficial dorsal horn in an activity-dependent manner. TrkB expression in the dorsal horn also increases for a few days after inflammation. These findings suggest that BDNF may act during the restricted period in the early phase of inflammation. Through TrkB, BDNF activates two distinct channels: (1) transient receptor potential canonicals (TRPC3), which produces a slow response by opening of a non-selective cation channel; and (2) Na+ channel, which mediates a rapid depolarization in the hippocampus. These channels have been strongly associated with inflammatory pain. Anti-BDNF significantly increased the withdrawal threshold in CFA-treated rats, a model of inflammatory pain. Since the swelling at the site of CFA injection was not affected by antiserum, the residual component might be due to peripheral sensitization (Matayoshi et al, 2005, J. Physiol. 569:685-95).

In patients with neuroblastomas, co-expression of TrkB and BDNF, co-expression of TrkB with N-Myc amplification, and expression of truncated TrkB are found to be associated with poorer clinical outcome (Nakagawara et al, 1994, Mol Cell Biol. 14:759-767). Co-expression of TrkB with its ligand BDNF could generate a positive feedback loop through autocrine and paracrine loops. Also TrkB truncations found in these tumors generate activated forms of the intracellular protein tyrosine kinase. The constitutively active TrkB signals through multiple pathways to promote cancer initiation, progression and metastasis. These truncated TrkB kinases were also found in hepatocellular carcinoma (Yang et al, 2005, Cancer. Res 65:219-225). Thus TrkB inhibitors could be used to treat a sub-population of cancer patients with an activated TrkB pathway.

In patients with pancreatic cancer, TrkB expression is correlated with perineural invasion, positive retroperitoneal margin, and shorter latency to development of liver metastasis (Sclabas et al, 2005, Clin. Cancer. Res V11:440-449). Mechanistically, TrkB activates the PI3K pathway to suppress anoikis (apoptosis resulting from loss of cell-matrix interactions) which is one of the physiological barriers to metastasis. TrkB kinase inhibition could break down resistance to anoikis of metastasizing tumors (Douma et al, 2004, Nature 430: 1034-9). Therefore, TrkB inhibitors could have utility in a broad range of tumor types.

Exemplary Diseases Associated with MAPK4K

MAP4K4: Target kinase MAP4K4 (i.e., Mitogen-activated protein kinase kinase 4, aka Hematopoietic progenitor kinase/Germinal center kinase-like Kinase) is a 130 kDa serine/threonine kinase encoded by chromosome 2q11.2-q12 (symbol: MAP4K4) and is also known as HGK. It is a member of the human STE20/mitogen-activated protein kinase kinase kinase kinase (MAP4K) family of serine/threonine kinases and is the human ortholog of mouse NIK (Nck-interacting kinase). The N-terminus of the mature HGK protein has a catalytic kinase domain that shares 47% and 48% amino acid sequence identity to the catalytic domain of Hematopoietic progenitor kinase 1 (HPK1) and Germinal center kinase (GCK), respectively. Yao et al. (J. Biol. Chem. 274: 2118-2125, 1999) identified 2 HGK isoforms, one of which has no proline-rich domains, and another, longer variant that contains such domains and appears to be expressed in brain only. Northern blot analysis revealed expression of 3 HGK transcripts of approximately 4.6, 6.5, and 8.5 kb in hear, brain, skeletal muscle, pancreas, placenta, liver, lung, and kidney. By Western blot analysis with a polyclonal antibody, Yao et al. (J. Biol. Chem. 274: 2118-2125, 1999) found that the 130-4) protein is expressed in multiple cell lines.

Expression of HGK in transfected cell lines resulted in strong JNK activation and, in turn, c-jun transcriptional activity (Yao et al. J. Biol. Chem. 274: 2118-2125, 1999). 1GK-induced JNK activation was inhibited by dominant-negative MAP2K4, MAP2K7, and TAK1 mutants. TNF-alpha also stimulated 1GK kinase activity. HGK was identified as a putative effect of Rap2 to activate AK (Machida et al. J. Biol. Chem. 279: 15711-15714, 2004). This link establishes HGK as a potential target for a range of metabolic indications, since the AK pathway clearly antagonizes insulin signaling. An HGK inhibitor could re-sensitize fat and muscle cells to insulin.

HGK is found to be broadly expressed in human tumor cells and can modulate cellular transformation, invasion, and adhesion (Wright et al. Mol. Cell. Biol. 23: 2068-2082, 2003). Wright et al showed HGK to be highly expressed in most tumor cell lines relative to normal tissue. An active role for this kinase in transformation was suggested by an inhibition of H-Ras(V12)-induced focus formation by expression of inactive, dominant-negative mutants of HGK in both fibroblast and epithelial cell lines. Expression of an inactive mutant of HGK also inhibited the anchorage-independent growth of cells yet had no effect on proliferation in monolayer culture. Expression of HGK mutants modulated integrin receptor expression and had a striking effect on hepatocyte growth factor-stimulated epithelial cell invasion. Together, these results suggest an important role for HGK in cell transformation and invasiveness. More recently, a small interfering RNA screen for modulators of tumor cell motility identifies MAP4K4 as a promigratory kinase (Collins et al. Proc. Natl. Acad. Sci. USA, 103: 3775-3780, 2006). Collins et al. showed that the knockdown of the HGK transcript inhibited the migration of multiple carcinoma cell lines, indicating a broad role in cell motility, and potently suppressed the invasion of SKOV-3 cells in vitro. The effect of HGK on cellular migration was found to be mediated through JK kinase, independent of AP1 activation and downstream transcription. Accordingly, small molecule inhibition of c-Jun N-terminal kinase suppressed SKOV-3 cell migration, underscoring the potential therapeutic utility of mitogen-activated protein kinase pathway inhibition in cancer progression (Collins et al. Proc. Natl. Acad. Sci, USA, 103: 3775-3780, 2006). These studies strongly support HGK as a target in a broad range of oncology indications. In particular, an HGK inhibitor could have utility in blocking the migration, invasion and metastasis in many different tumor types.

Activation of T-cells by antigens initiates a complex series of signal-transduction events that are critical for immune responses. Mack et al. (Immunol. Lett. 96, 129-145, 2005) developed a genetic screen to survey the functional roles of kinases in antigen mediated T-cell activation and identified 19 protein kinases that were previously implicated in T-cell signaling processes and 12 kinases that were not previously linked to T-cell activation, including HGK. siRNA studies showed a role for HGK in antigen mediated T-cell responses in Jurkat and primary T-cells. In addition, by analyzing multiple promoter elements using reporter assays, Mack et al. have shown that MAP4K4 is implicated in the activation of the TN -alpha promoter. Therefore, inhibition of HGK could have broad therapeutic utility for T-cell-mediated autoimmune diseases.

Insulin-regulated glucose transporter GLUT4 is a key modulator of whole body glucose homeostasis, and its selective loss in adipose tissue or skeletal muscle causes insulin resistance and diabetes. Using an RNA interference-based screen, Tang et al. (Proc Natl Acad Sci USA. 103:2087-2092, 2006) found 4 negative regulators of insulin-responsive glucose transport in mouse adipocytes: Pctk1, Pftk1, Ikbka (CHUK), and HGK. HGK suppressed expression of adipogenic transcription factors, C/EBPA, C/EBPB, and PPARZG, and it suppressed surface expression of GLUT4 (SLC2A4), resulting in attenuated membrane hexose transport activity. RNA interference-mediated depletion of HGK early in differentiation enhanced adipogenesis and triglyceride deposition; in fully differentiated adipocytes, loss of HGK upregulated GLUT4 expression. Conversely, conditions that inhibited adipogenesis, such as TNF-alpha treatment or PPARG depletion, markedly upregulated HGK. Tang et al. (Proc Natl Acad Sci USA. 103:2087-2092, 2006) concluded that MAP4K4-dependent signaling inhibited PPARG-responsive gene expression, adipogenesis, and insulin-stimulated glucose transport. Furthermore, TNF-alpha signaling to down-regulate GLUT4 is impaired in the absence of HGK, indicating that HGK expression is required for optimal TNF-alpha action. This study further supports HGK as a target in metabolic disease, and suggests a role for HGK inhibition in ameliorating the pathology in adipocytes.

In a separate study (Bouzakri and Zierath J. Biol. Chem. 282:7783-7789, 2007), using small interfering RNA (siRNA) to suppress the expression of HGK protein 85% in primary human skeletal muscle cells, TNF-alpha-induced insulin resistance on glucose uptake was completely prevented. HCK silencing inhibited TNF-alpha-induced negative signaling inputs by preventing excessive JNK and ERK-1/2 phosphorylation, as well as IRS-1 serine phosphorylation. These results highlight the HGK/JNK/ERK/IRS module in the negative regulation of insulin signaling to glucose transport in response to TNF-alpha. Depletion of HGK also prevented TNF-alpha-induced insulin resistance on AKT and the AKT substrate 160 (AS160), providing evidence that appropriate insulin signaling inputs for glucose metabolism were rescued. The authors suggested that strategies to inhibit HGK may be efficacious in the prevention of TNT-alpha-induced inhibitory signals that cause skeletal muscle insulin resistance on glucose metabolism in humans. Moreover, in myotubes from insulin-resistant type II diabetic patients, siRNA against HGK restored insulin action on glucose uptake to levels observed in healthy subjects. This study further supports HGK as a target in metabolic diseases such as type II diabetes, and suggests a role for HGK inhibition in ameliorating the pathology in muscle cells.

HGK inhibitors may be useful in treating metabolic indications, including re-sensitizing fat and muscle cells to insulin, ameliorating the pathology in adipocytes, ameliorating the pathology in muscle cells, metabolic syndrome and type IT diabetes; a broad range of oncology indications, including blocking the migration, invasion and metastasis in many different tumor types; and T-cell mediated autoimmune diseases.

Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases describe assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

Organic Synthetic Techniques

A wide array of organic synthetic techniques exist in the art to facilitate constructing potential modulators. Many of these organic synthetic methods are described in detail in standard reference sources utilized by those skilled in the art. One example of such a reference is March, 1994, *Advanced Organic Chemistry; Reactions, Mechanisms and Structure*, New York, McGraw Hill. Thus, the techniques useful to synthesize a potential modulator of kinase function are readily available to those skilled in the art of organic chemical synthesis.

Regarding the synthetic examples described herein, solvents include polar and non-polar solvents known to those of skill in the art, including polar aprotic and polar protic solvents. Polar solvents include, without limitation, protic solvents such as methanol, ethanol, isopropyl alcohol, t-butanol, n-butanol, acetic acid, formic acid or water, or aprotic solvents such as tetrahydrofuran (THF), acetonitrile, dioxane, methylene chloride, dimethylsulfoxide (DMSO), acetone, N,N-dimethylformamide (DMF), N,N-dimethylacetamide (DMA), ethyl acetate, 1,2-dimethoxyethane, 1,2-dichloroethane, chloroform, 1,2-dichloroethane, or pyridine. Polar solvents include a mixture of water with any of the above, or a mixture of any two or more of the above. Apolar solvents include, without limitation, toluene, benzene, chlorobenzene, xylenes and hexanes.

Regarding the synthetic examples described herein, reducing agent includes, without limitation, a reducing agent such as catalytic reducing agents using hydrogen and transition metal catalysts such as palladium, platinum, rhodium, etc. (e.g. Pt/acetic acid/$H_2$); a mixture of trifluoroacetic acid and triethylsilane, borane tetrahydrofuran complex, diborane, borane dimethylsulfide complex, and a combination of sodium borohydride and boron trifluoride; metals such as reduced iron, zinc powder, magnesium etc.; metal hydrogen complex compounds such as alkali metal borohydrides (for example, potassium borohydride, sodium borohydride, lithium borohydride, zinc borohydride, sodium triacetoxyborohydride, etc.), aluminum lithium hydride, etc.; metal hydrides such as sodium hydride, etc.; organic tin compounds (triphenyltin hydride, etc.); and metal salts such as nickel compounds, zinc compounds, tin compounds (for example tin(II) chloride), and samarium iodide/pivalic acid/hexamethylphosphoric triamide.

Regarding the synthetic examples described herein, oxidizing agent includes, without limitation, an oxidizing agent such as Dess-Martin reagent, TEMPO (2,2,6,6-tetramethylpiperidine-N-oxide), DDQ (2,3-Dichloro-5,6-dicyano-1,4-benzoquinone), PDC (pyridinium dichromate), PCC (pyridinium chlorochromate), Pyridine.SO3, Chromium trioxide, p-nitroperbenzoic acid, magnesium monoperoxyphthalate, sodium periodate, potassium periodate, hydrogen peroxide, urea peroxide, alkali metal bromates, cumene hydroperoxide, tert-butyl peroxide, peracids such as performic acid, peracetic acid, pertrifluoroacetic acid, perbenzoic acid, m-chloroperbenzoic acid, o-carboxyperbenzoic acid and the like; sodium metaperiodate, bichromic acid; bichromates such as sodium bichromate, potassium bichromate; permanganic acid; permanganates such as potassium permanganate, sodium permanganate; and lead salts such as lead tetraacetate.

Regarding the synthetic examples described herein, a nitrogen protecting group is a chemical group covalently bound to a nitrogen atom of a compound that is used to protect the nitrogen from reaction during a synthetic step. The nitrogen protecting group may be added to a compound and removed in a subsequent step by methods known to those of skill in the art. Nitrogen protecting groups include, without limitation, carbamates, amides, N-sulfonyl derivatives, groups of formula —C(O)OR, wherein R is, for example, methyl, ethyl, t-butyl, benzyl, phenylethyl, $CH_2=CHCH_2—$, and the like, groups of the formula —C(O)R', wherein R' is, for example, methyl, phenyl, trifluoromethyl, and the like, groups of the formula —$SO_2$R", wherein R" is, for example, tolyl, phenyl, trifluoromethyl, 2,2,5,7,8-pentamethylchroman-6-yl, 2,3,6-trimethyl-4-methoxyphenyl, and the like, and silanyl containing groups, such as 2-trimethylsilylethoxymethyl, t-butyldimethylsilyl, triisopropylsilyl, and the like. Other suitable nitrogen protecting groups may be found in texts such as T. W. Greene & P. G. M. Wuts, *Protective Groups in Organic Synthesis*, John Wiley & Sons, 1991.

Alternative Compound Forms or Derivatives

Compounds contemplated herein are described with reference to both generic formulae and specific compounds. In addition, invention compounds may exist in a number of different forms or derivatives, all within the scope of the present invention. Alternative forms or derivatives, such as (a) Isomers, Prodrugs, and Active Metabolites (b) Tautomers, Stereoisomers, Regioisomers, and Solvated Forms (c) Prodrugs and Metabolites (d) Pharmaceutically acceptable salts and (e) Polymorphic forms, are described, for example, in U.S. patent application Ser. No. 11/473,347 (see also, PCT publication WO2007002433), the disclosure of which is hereby incorporated by reference in its entirety.

Administration

The methods and compounds will typically be used in therapy for human subjects. However, they may also be used to treat similar or identical indications in other animal subjects. In this context, the terms "subject," "animal subject," and the like refer to human and non-human vertebrates, e.g. mammals, such as non-human primates, sports and commercial animals, e.g., equines, bovines, porcines, ovines, rodents, and pets, e.g., canines and felines. A description of possible methods and routes of administration may be found, for example, in U.S. patent application Ser. No. 11/473,347 (see also, PCT publication WO2007002433), the disclosure of which is hereby incorporated by reference in its entirety.

EXAMPLES

Examples related to the present invention are described below. In most cases, alternative techniques can be used. The examples are intended to be illustrative and are not limiting or restrictive to the scope of the invention. In some examples, the mass spectrometry result indicated for a compound may have more than one value due to the isotope distribution of an atom in the molecule, such as a compound having a bromo or chloro substituent.

Unless specifically indicated otherwise, the Formula enumeration and R group enumeration used in the following examples is not related to such enumeration in other sections of this application. The reagents and solvents used in these examples can be readily substituted with appropriate alternatives as are known in the art and isolation of products is readily achieved by methods known in the art, including, but not limited to, extraction, crystallization, and chromatographic methods. In addition to the following Examples, exemplary methods which may be employed for synthesis of compounds of the present invention may be found in U.S. patent application Ser. No. 11/473,347 (see also, PCT publication WO2007002433), the disclosure of which is hereby incorporated by reference. The 1H-pyrrolo[2,3-b]pyridine core of compounds described in the examples may also be referred to as 7-azaindole in the examples.

Example 1

Synthesis of Compounds of Formula X

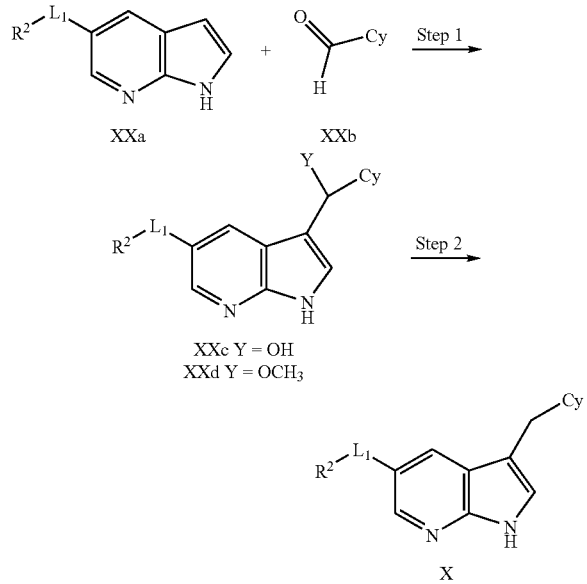

Step 1—Preparation of Compounds of Formula XXc and XXd

To a compound of Formula XXa ($L_1$ and $R^2$ is as defined in paragraph [0008]) and a compound of Formula XXb (Cy is optionally substituted cycloalkyl, optionally substituted heterocycloalkyl, optionally substituted aryl or optionally substituted heteroaryl) is added an appropriate solvent (e.g. methanol) followed by an appropriate base (e.g. potassium hydroxide, sodium methoxide). The reaction is typically allowed to stir at room temperature overnight. Isolation by conventional means (e.g. extraction, washing and filtering) affords a mixture of compounds of Formula XXc and XXd, which may be separated by silica gel chromatography if desired.

Step 2—Preparation of Compounds of Formula X

To a compound of Formula XXc or XXd in an appropriate solvent (e.g. acetonitrile) is added a reducing agent (e.g. trifluoroacetic acid and triethylsilane). Typically, the reaction is allowed to stir at room temperature overnight. Isolation by conventional means (e.g. extraction and silica gel column chromatography) affords compounds of Formula X.

Example 2

Synthesis of Compounds of Formula XI

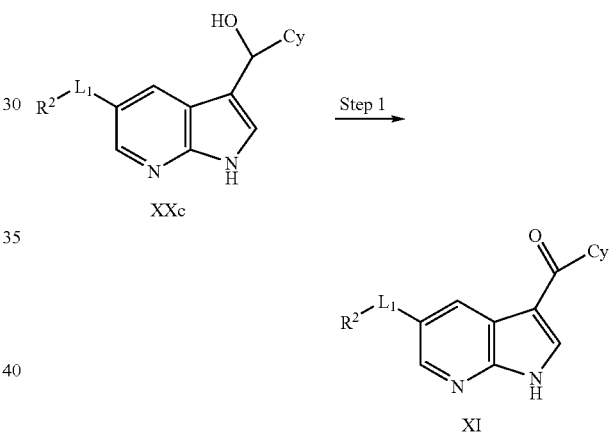

Step 1—Preparation of Compounds of Formula XI

To a compound of Formula XXc (See Example 1) in an appropriate solvent (e.g. tetrahydrofuran) is added an oxidizing agent (e.g. Dess-Martin periodane, TEMPO, DDQ). Typically, the reaction is allowed to stir at room temperature for 20 minutes. Isolation by conventional means (e.g. extraction and silica gel column chromatography) affords compounds of Formula XI.

Example 3

Synthesis of Compounds of Formula XI

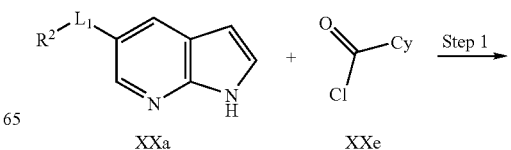

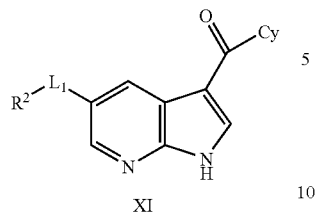

XI

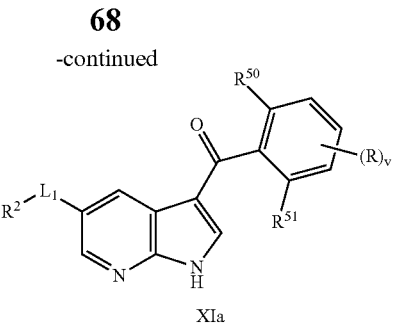

XIa

Step-1—Synthesis of Compound of Formula XI

Compound of Formula XI is synthesized by reacting a compound of Formula XXa with a compound of Formula XXe (Cy is as defined in Example 1, e.g. benzoyl chloride) in the presence of a Lewis acid (e.g. aluminum trichloride) in an inert solvent (e.g. dichloromethane) under an inert atmosphere (e.g. argon) at room temperature or with heating up to reflux for 1-18 hours. The desired compound XI is isolated by extraction and silica gel column chromatography.

Example 4

Synthesis of Compounds of Formula XIa

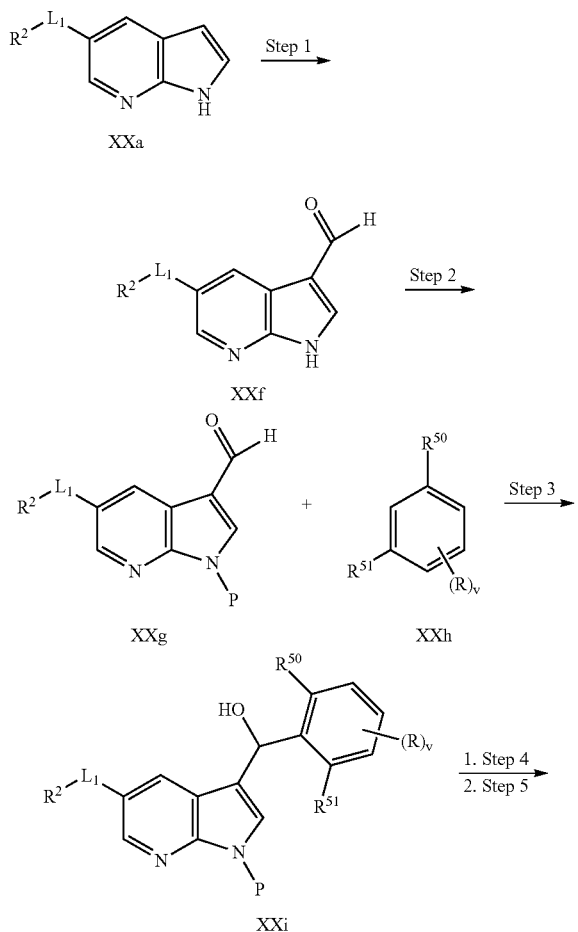

Step-1—Synthesis of Compound XXf

Compound of Formula XXf can be synthesized by reacting a compound of Formula XXa with hexamethyltetramine and acetic acid in water with heating to reflux for two hours. After cooling, the desired compound precipitates and may be collected by filtration.

Step-2—Synthesis of Compound of Formula XXg

Compound of Formula XXg, where P is a nitrogen protecting group, is synthesized by reacting a compound XXf with an appropriate reagent to introduce a protecting group (e.g. triisopropylsilylchloride) and a base (e.g. sodium hydride) in a solvent (e.g. tetrahydrofuran) typically at room temperature for 8-12 hours. The desired compound is isolated by conventional means (e.g. extraction).

Step-3—Synthesis of Compound of Formula XXi

Compound of Formula XXi is synthesized by reacting a compound of Formula XXg in a solvent (e.g. tetrahydrofuran) with an organolithium reagent (e.g. phenyl lithium) in a solvent (e.g. tetrahydrofuran) under an inert atmosphere, cooled to −78° C. An appropriate organolithium reagent can also be prepared by reacting compounds of Formula XXh, where $R^{50}$ and $R^{51}$ are independently fluoro or chloro, R and v are consistent with optional substituent of an aryl group as defined in paragraph [0061], with an organolithium reagent (e.g. butyllithium) in a solvent (e.g. tetrahydrofuran) under an inert atmosphere, cooled to −78° C. The reaction is typically allowed to warm to room temperature and stirred for 30 minutes. The desired compound is isolated by conventional means (e.g. extraction).

Step-4—Synthesis of an Intermediate of Compound of Formula XIa

An intermediate of compound of Formula XIa is synthesized by reacting a compound of Formula XXi with an appropriate reagent to remove the protecting group, P, (e.g. tetra-n-butyl ammonium fluoride) in an appropriate solvent (e.g. tetrahydrofuran). The desired compound is isolated by standard procedures (e.g. extraction).

Step-5—Synthesis of Compound of Formula XIa

Compound of Formula XIa is synthesized by reacting the intermediate from Step 4 with an oxidizing agent (e.g. Dess-Martin periodane, TEMPO) in an aprotic solvent (e.g. tetrahydrofuran) typically at room temperature for 20 minutes.

The desired compound is isolated by conventional means (e.g. extraction and silica gel chromatography).

Example 5

Synthesis of Compound of Formula XXj, where $R^{50}$ and $R^{51}$ are Independently Fluoro or Chloro

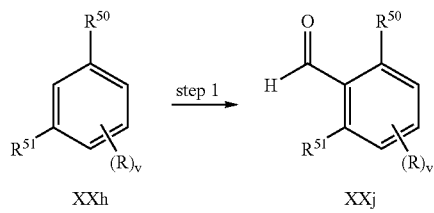

XXh  →  XXj

Step 1—Synthesis of Compound of Formula XXj

Compound of Formula XXj may be synthesized by reacting a compound of Formula XXh with an organolithium reagent (e.g. n-butyllithium, lithium diisopropylamine) in an inert solvent (e.g. tetrahydrofuran), followed by the addition of a formylating reagent (e.g. dimethyl formamide). The reaction is allowed to proceed, typically at −78° C., for 1-2 hours and the desired compound is isolated by standard procedures (e.g. extraction, silica gel chromatography).

Example 6

Synthesis of Compounds of Formula XXm

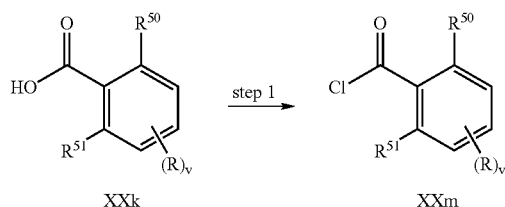

XXk  →  XXm

Step 1—Synthesis of Compound of Formula XXm

Compound of Formula XXm may be synthesized by reacting a compound of Formula XXk, where $R^{50}$ and $R^{51}$ are independently fluoro or chloro, R and v are consistent with optional substituent of an aryl group as defined in paragraph [0061], with thionyl chloride. The reaction is allowed to proceed, typically under reflux, for 3 hours and the desired compound is isolated by standard procedures (e.g. evaporation).

Example 7

Synthesis of Compounds of Formula XXa where $L_1$ is O

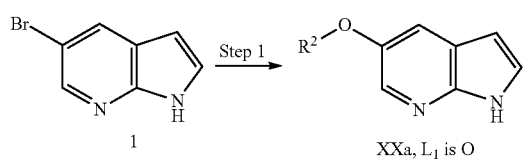

1  →  XXa, $L_1$ is O

Step-1—Synthesis of Compound of Formula XXa

A compound of Formula XXa (where $L_1$ is O), is synthesized by reacting compound 1 with a reagent of formula $R^2OH$ (e.g. phenol) in the presence of base (e.g. sodium methoxide) and copper (I) bromide in a solvent (e.g. N,N-dimethylformamide) typically with heating to reflux for 2-8 hours as described by Mazeas, et. al. in *Heterocycles*, 1999, 50:1065. The desired intermediate is purified by conventional means (e.g. silica gel column chromatography).

Example 8

Synthesis of Compounds of Formula XXa where $L_1$ is O

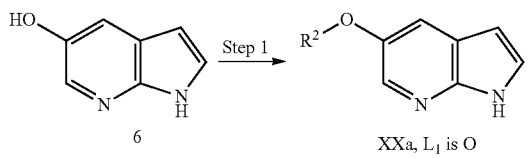

6  →  XXa, $L_1$ is O

Step-1—Synthesis of Compound of Formula XXa

A compound of Formula XXa (where $L_1$ is O), is synthesized by reacting compound 6 with a reagent of formula $R^2OH$ in the presence of an azodicarboxylate such as diethyl azodicarboxylate and a phosphine such as triphenylphosphine in a suitable solvent in a manner similar to the procedure described by Wendt, et al, *J. Med. Chem.*, 2004, 47(2), 303.

Example 9

Synthesis of Compounds of Formula XXa where $L_1$ is S

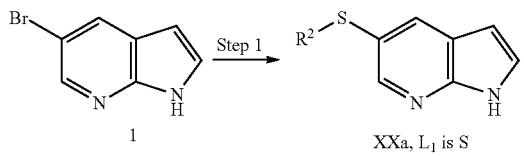

1  →  XXa, $L_1$ is S

Compound of Formula XXa (where $L_1$ is O), can be prepared by reacting compound 1 with a strong base (e.g. potassium hydride or t-butyl lithium) and dialkyldisulfides (e.g. dimethyldisulfane) or thiophenols (e.g. 4-methoxythiophenol) in a polar aprotic solvent (e.g. N,N-dimethylformamide) in an inert atmosphere following the procedure described by Yang et. al., Heterocycles, 1992, 34, 1169, by substituting 5-bromo-7-azaindole for 5-bromo-indole.

Example 10

Synthesis of Compounds of Formula XXa where $L_1$ is S(O) or S(O)$_2$

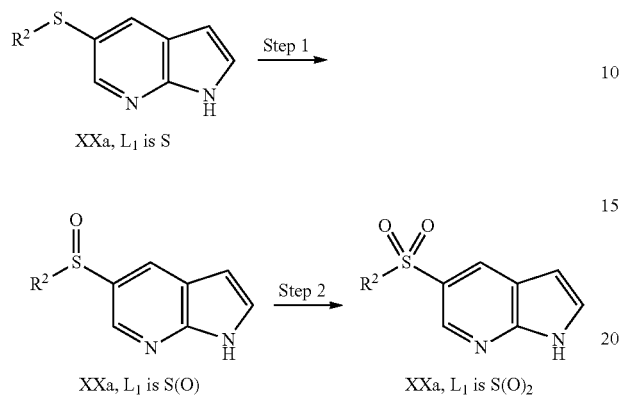

Compounds of Formula XXa (where $L_1$ is S(O) or S(O)$_2$), can be prepared by reacting compound of Formula XXa (where $L_1$ is S), with 1 or 2 equivalents of oxidizing agent (e.g. Oxone), respectively, in a polar solvent (e.g. dimethyl formamide), using standard procedures.

Example 11

Synthesis of 5-Methoxy-1H-pyrrolo[2,3-b]pyridine 2 and related compounds

5-Methoxy-1H-pyrrolo[2,3-b]pyridine 2 was synthesized in one step from 5-bromo-1H-pyrrolo[2,3-b]pyridine 1 as described in Scheme 1.

Scheme 1

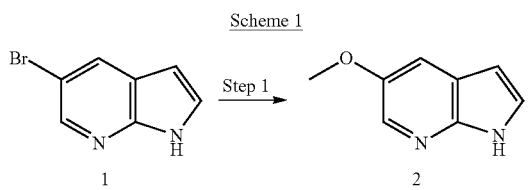

Step 1—Preparation of 5-Methoxy-1H-pyrrolo[2,3-b]pyridine (2)

To 5-bromo-7-azaindole (1, 500.0 mg, 2.53 mmol) in N,N-dimethylformamide (8 mL) were added copper(I) iodide (966 mg, 5.08 mmol) and sodium methoxide in methanol (3 M, 5 mL). The reaction was stirred overnight at 120° C. under an atmosphere of Argon. The reaction was poured into water, and extracted with ethyl acetate. The organic layer was dried over anhydrous sodium sulfate, filtered. The filtrate was concentrated and purified with silica gel column chromatograph eluting with 20% ethyl acetate in hexane to give white solid (2, 140 mg, 28%). MS (FSI) [M+H$^+$]$^+$=149.1. In an alternative method, 2.3 g (11.7 mmol) 5-bromo-7-azaindole (1, 2.3 g, 11.7 mmol) was dissolved in 75 mL N,N-dimethylformamide and 50 mL methanol (50 mL), adding sodium methoxide (32 g, 0.6 mol) and copper-(I) bromide (3.2 g, 22.4 mmol) at room temperature. The reaction was stirred for three hours at 100° C. under an atmosphere of argon. The mixture was diluted with ethyl acetate and poured into a solution of ammonium chloride:ammonium hydroxide (4:1). The organic layer was extracted with ammonium chloride:ammonium hydroxide (4:1), washed with brine, dried over anhydrous sodium sulfate, filtered and concentrated. The desired compound was isolated by silica gel column chromatography eluting with 30% to 70% ethyl acetate in hexanes to give a yellow solid (2, 0.27 g, 15.6%). MS (ESI) [M+H$^+$]$^+$=149.2.

5-Ethoxy-1H-pyrrolo[2,3-b]pyridine 3

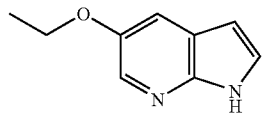

was prepared using the protocol of Scheme 1, substituting methanol with ethanol and sodium methoxide with sodium ethoxide.

5-(2-Methoxy-ethoxy)-1H-pyrrolo[2,3-b]pyridine 4

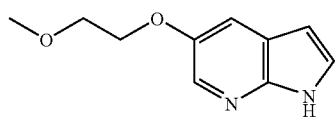

was prepared using the protocol of Scheme 1, substituting methanol with 2-methoxy-ethanol and sodium methoxide with sodium 2-methoxy-ethoxide (prepared from 2-methoxy-ethanol and sodium hydride). MS (ESI) [M+H$^+$]$^+$= 193.3.

Diethyl-[2-(1H-pyrrolo[2,3-h]pyridin-5-yloxy)-ethyl]-amine 5

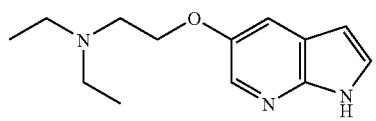

was prepared using the protocol of Scheme 1, substituting methanol with 2-diethylamino-ethanol and sodium methoxide with sodium 2-diethylamino-ethoxide (prepared from 2 2-diethylamino-ethanol and sodium hydride). MS (ESI) [M+H$^+$]$^+$=234.5.

Example 12

Synthesis of 5-cyclopentyloxy-1-pyrrolo[2,3-b]pyridine (P-0001)

5-cyclopentyloxy-1H-pyrrolo[2,3-b]pyridine P-0001 was synthesized in one step from 1H-Pyrrolo[2,3-b]pyridin-5-ol 6 and cyclopentanol 7 as shown in Scheme 2.

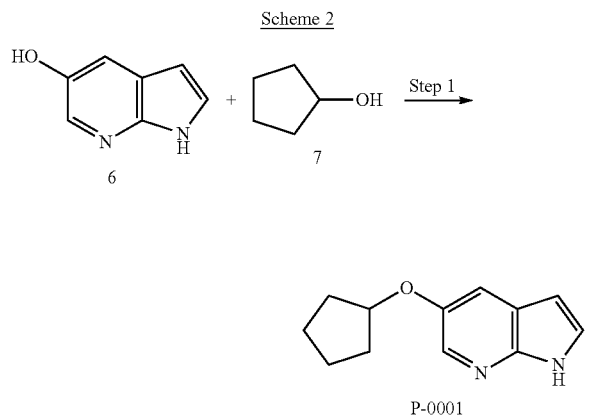

Scheme 2

Step 1—Preparation of 5-cyclopentyloxy-1H-pyrrolo[2,3-b]pyridine (P-0001)

1H-Pyrrolo[2,3-b]pyridin-5-ol (6, 0.250 g 1.86 mmol), triphenylphosphine (0.587 g, 2.24 mmol), and cyclopentanol (7, 0.203 mL, 2.24 mmol) were dissolved in tetrahydrofuran (5 mL, 0.06 mol). Diethyl azodicarboxylate (0.352 mL, 2.24 mol) was then added dropwise over 1 minute. The reaction became hot. The solution was allowed to stir at room temperature overnight. The reaction was poured into water with added 0.1 N HCl and extracted with ethyl acetate. The organic layer was washed with brine, dried over anhydrous magnesium sulfate and filtered. The filtrate was concentrated and purified by silica gel column chromatography eluting with a gradient of 0-80% ethyl acetate in hexanes to give crude compound that was purified by HPLC to give P-0001 (314 mg, 83% yield). MS (ESI) $[M+H^+]^+$=203.2.

Additional compounds were prepared following the protocol of Scheme 2, replacing cyclopentanol 7 with an appropriate alcohol. The following compounds were made following this procedure:

5-(benzyloxy)-1H-pyrrolo[2,3-b]pyridine (P-0002),
5-(3-methoxybenzyloxy)-1H-pyrrolo[2,3-b]pyridine (P-0003),
5-(cyclopropylmethoxy)-1H-pyrrolo[2,3-b]pyridine (P-0004),
5-((pyridin-3-yl)methoxy)-1H-pyrrolo[2,3-b]pyridine (P-0005),
5-(cyclopentylmethoxy)-1H-pyrrolo[2,3-b]pyridine (P-0006),
5-(4-fluorobenzyloxy)-1H-pyrrolo[2,3-b]pyridine (P-0007),
5-(2,4-dimethoxybenzyloxy)-1H-pyrrolo[2,3-b]pyridine (P-0008),
5-(2-methoxyethoxy)-1H-pyrrolo[2,3-b]pyridine (P-0009),
5-(4-methoxybenzyloxy)-1H-pyrrolo[2,3-h]pyridine (P-0010),
5-(4-butoxybenzyloxy)-1H-pyrrolo[2,3-b]pyridine (P-0011),
5-(4-chlorobenzyloxy)-1H-pyrrolo[2,3-b]pyridine (P-0012),
5-(2-(piperidin-1-yl)ethoxy)-1H-pyrrolo[2,3-b]pyridine (P-0013),
5-(4-(difluoromethoxy)benzyloxy)-1H-pyrrolo[2,3-b]pyridine (P-0014),
5-(4-morpholinobenzyloxy)-1H-pyrrolo[2,3-b]pyridine (P-0015),
5-(4-(4-methylpiperazin-1-yl)benzyloxy)-1H-pyrrolo[2,3-b]pyridine (P-0016),
5-((1-methyl-1H-imidazol-5-yl)methoxy)-1H-pyrrolo[2,3-b]pyridine (P-0017),
5-(cyclohexyloxy)-1H-pyrrolo[2,3-b]pyridine (P-0018),
5-((tetrahydro-2H-pyran-4-yl)methoxy)-1H-pyrrolo[2,3-b]pyridine (P-0019),
5-(tetrahydro-2H-pyran-4-yloxy)-1H-pyrrolo[2,3-b]pyridine (P-0020),
5-((1-methylpiperidin-4-yl)methoxy)-1H-pyrrolo[2,3-b]pyridine (P-0021),
5-((1-(2-methoxyethyl)-1H-imidazol-5-yl)methoxy)-1H-pyrrolo[2,3-b]pyridine (P-0022),
3-((1H-pyrrolo[2,3-b]pyridin-5-yloxy)methyl)-2-methylH-imidazo[1,2-a]pyridine (P-0023),
2-((1H-pyrrolo[2,3-b]pyridin-5-yloxy)methyl)H-imidazo[1,2-a]pyridine (P-0024),
2-(1H-pyrrolo[2,3-b]pyridin-5-yloxy)-N-(4-ethoxyphenyl) propanamide (P-0025),
5-((S)-1-benzylpyrrolidin-3-yloxy)-1H-pyrrolo[2,3-b]pyridine (P-0026),
5-((R)-tetrahydrofuran-3-yloxy)-1H-pyrrolo[2,3-b]pyridine (P-0027),
5-(2-(tetrahydro-2H-pyran-4-yl)ethoxy)-1H-pyrrolo[2,3-b]pyridine (P-0028),
5-(2-(4-methylpiperazin-1-yl)ethoxy)-1H-pyrrolo[2,3-b]pyridine (P-0029),
5-(4-(methylsulfonyl)benzyloxy)-1H-pyrrolo[2,3-b]pyridine (P-0030),
5-(2,5-dimethoxybenzyloxy)-1H-pyrrolo[2,3-b]pyridine (P-0031),
5-(2-(5-methoxy-1H-indol-3-yl)ethoxy)-1H-pyrrolo[2,3-b]pyridine (P-0032),
5-(Pyrrolidin-3-ylmethoxy)-1H-pyrrolo[2,3-b]pyridine (P-0042),
5-(3-Chloro-4-methoxy-benzyloxy)-1H-pyrrolo[2,3-b]pyridine (P-0043, and
5-(Imidazo[2,1-b]thiazol-6-ylmethoxy)-1H-pyrrolo[2,3-b]pyridine (P-0044).

The alcohol used in this procedure is indicated in column 2 of the following table, with the compound structure indicated in column 3. Column 1 provides the compound reference number and Column 4 the experimental mass spectrometry result.

| | Alcohol | Compound | MS(ESI) [M + H⁺]⁺ observed |
|---|---|---|---|
| P-0002 | benzyl alcohol | 5-(benzyloxy)-7-azaindole | |
| P-0003 | 3-methoxybenzyl alcohol | 5-(3-methoxybenzyloxy)-7-azaindole | 255.5 |
| P-0004 | cyclopropylmethanol | 5-(cyclopropylmethoxy)-7-azaindole | 189.0 |
| P-0005 | pyridin-3-ylmethanol | 5-(pyridin-3-ylmethoxy)-7-azaindole | 226.3 |
| P-0006 | cyclopentylmethanol | 5-(cyclopentylmethoxy)-7-azaindole | 217.5 |
| P-0007 | 4-fluorobenzyl alcohol | 5-(4-fluorobenzyloxy)-7-azaindole | 243.1 |
| P-0008 | 2,4-dimethoxybenzyl alcohol | 5-(2,4-dimethoxybenzyloxy)-7-azaindole | 285.1 |
| P-0009 | 2-methoxyethanol | 5-(2-methoxyethoxy)-7-azaindole | 193.0 |

-continued
| | Alcohol | Compound | MS(ESI) [M + H⁺]⁺ observed |
|---|---|---|---|
| P-0010 | 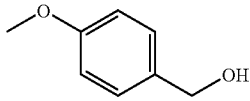 | 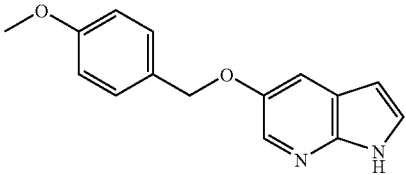 | 255.5 |
| P-0011 | 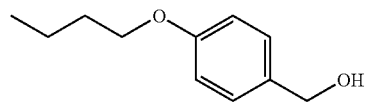 | 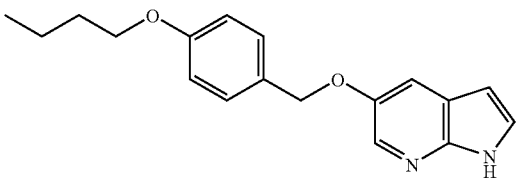 | 297.5 |
| P-0012 | 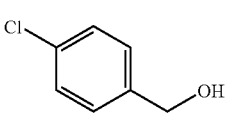 | 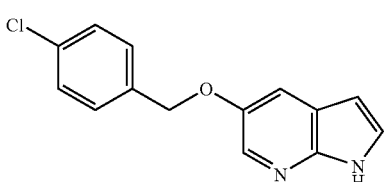 | 259.1 |
| P-0013 | 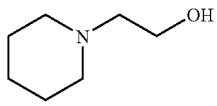 | 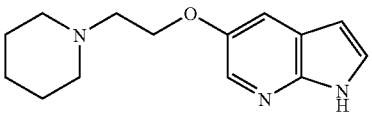 | 246.3 |
| P-0014 |  | 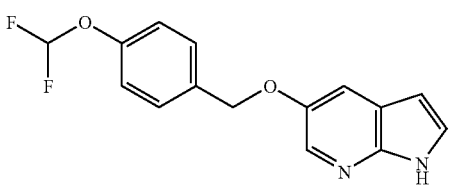 | 291.1 |
| P-0015 | 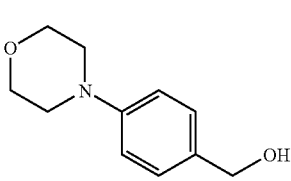 | 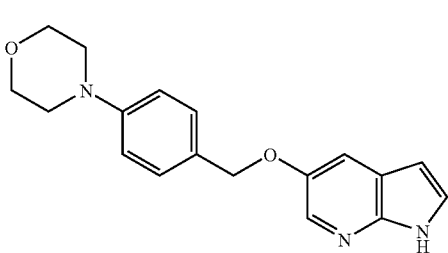 | 310.3 |
| P-0016 | 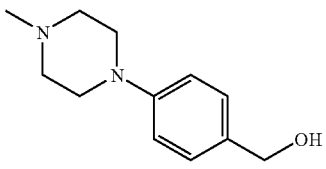 | 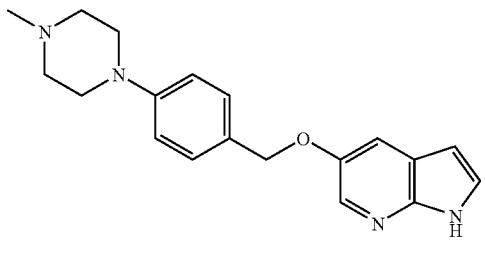 | 323.1 |
| P-0017 | 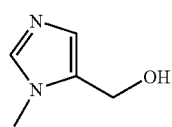 | 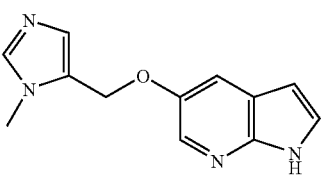 | 229.5 |

-continued

| | Alcohol | Compound | MS(ESI) [M + H⁺]⁺ observed |
|---|---|---|---|
| P-0018 | cyclohexanol | cyclohexyloxy-7-azaindole | 217.5 |
| P-0019 | (tetrahydropyran-4-yl)methanol | (tetrahydropyran-4-ylmethoxy)-7-azaindole | 233.1 |
| P-0020 | tetrahydropyran-4-ol | (tetrahydropyran-4-yloxy)-7-azaindole | 219.1 |
| P-0021 | (1-methylpiperidin-4-yl)methanol | (1-methylpiperidin-4-ylmethoxy)-7-azaindole | 246.3 |
| P-0022 | (1-(2-methoxyethyl)-1H-imidazol-5-yl)methanol | (1-(2-methoxyethyl)-1H-imidazol-5-ylmethoxy)-7-azaindole | 273.1 |
| P-0023 | (2-methylimidazo[1,2-a]pyridin-3-yl)methanol | (2-methylimidazo[1,2-a]pyridin-3-ylmethoxy)-7-azaindole | 279.1 |
| P-0024 | imidazo[1,2-a]pyridin-2-ylmethanol | (imidazo[1,2-a]pyridin-2-ylmethoxy)-7-azaindole | 265.1 |
| P-0025 | N-(4-ethoxyphenyl)-2-hydroxypropanamide | N-(4-ethoxyphenyl)-2-(7-azaindol-5-yloxy)propanamide | 326.3 |

-continued

| | Alcohol | Compound | MS(ESI) [M + H⁺]⁺ observed |
|---|---|---|---|
| P-0026 | | | 294.3 |
| P-0027 | | | 205.0 |
| P-0028 | | | 247.1 |
| P-0029 | | | 261.1 |
| P-0030 | | | 303.1 |
| P-0031 | | | 285.1 |
| P-0032 | | | 308.3 |
| P-0042 | | | 218.1 |

| | Alcohol | Compound | MS(ESI) [M + H⁺]⁺ observed |
|---|---|---|---|
| P-0043 | 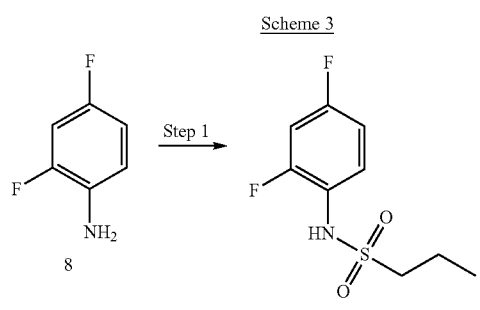 | | 289.5 |
| P-0044 | 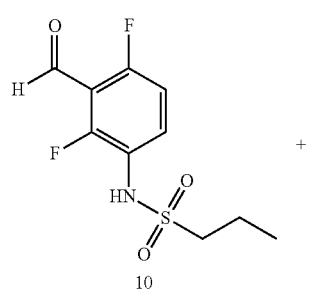 | | 271.6 |

Example 13

Preparation of propane-1-sulfonic acid [3-(5-cyclopentyloxy-1-pyrrolo[2,3-b]pyridine-3-carbonyl)-2,4-difluoro-phenyl]-amide P-0033

Propane-1-sulfonic acid [3-(5-cyclopentyloxy-1H-pyrrolo[2,3-h]pyridine-3-carbonyl)-2,4-difluoro-phenyl]-amide P-0033 was synthesized in four steps from 2,4-difluorophenylamine 8 as shown in Scheme 3.

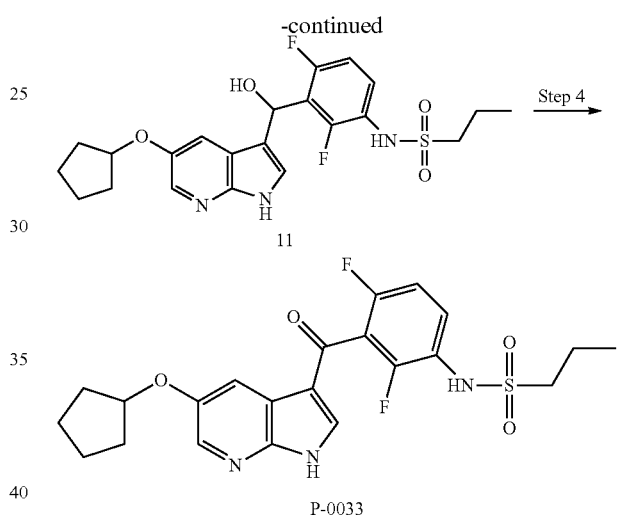

Step 1—Preparation of propane-1-sulfonic acid (2,4-difluoro-phenyl)-amide (9)

To 2,4-difluoro-phenylamine (8, 11.8 g, 91.4 mmol) in dichloromethane (110 mL) were added pyridine (8.13 mL, 100 mmol) and propane-1-sulfonyl chloride (11.3 mL. 100 mmol). The reaction was stirred overnight. The reaction was poured into water and extracted with ethyl acetate. The organic layer was washed with 1M HCl solution and brine, dried over anhydrous sodium sulfate and filtered. The filtrate was concentrated and purified by silica gel column chromatography eluting with 10% ethyl acetate in hexane to give a solid (9, 19.98 g, 93%). MS (ESI) [M−H⁺]⁻=234.1.

Step 2—Preparation of propane-1-sulfonic acid (2,4-difluoro-3-formyl-phenyl)-amide (10)

To diisopropyl amine (0.210 mL, 1.49 mmol) in tetrahydrofuran (3 mL) was added n-butyllithium (2.50 M in hexane, 0.600 mL, 1.49 mmol) at −78° C. under an atmosphere of nitrogen. After 30 minutes, propane-1-sulfonic acid (2,4-difluoro-phenyl)-amide (9, 113 mg, 0.480 mmol) in tetrahydrofuran (2 mL) was added at −78° C. under am atmosphere of nitrogen. After 1 hour, N,N-dimethylformamide (0.050 mL, 0.64 mmol) was added. The reaction was stirred for 1 hour, then allowed to come to room temperature for 15 minutes. The reaction was poured into water, acidified with 1M HCl (aq.) to pH=1, and extracted with ethyl acetate. The organic layer was washed with brine, dried over anhydrous sodium sulfate and filtrated. The filtrate was concentrated and purified by silica gel column chromatography eluting with 30% ethyl acetate in hexane to give a solid (10, 25 mg, 20%). MS (ESI) [M−H$^+$]$^−$=262.0.

Step 3—Preparation of propane-1-sulfonic acid {3-[(5-cyclopentyloxy-1H-pyrrolo[2,3-b]pyridin-3-yl)-hydroxy-methyl]-2,4-difluoro-phenyl}-amide (11)

To propane-1-sulfonic acid (2,4-difluoro-3-formyl-phenyl)-amide (10, 102 mg, 0.32 mmol) in methanol (1.5 mL) was added 5-cyclopentyloxy-1H-pyrrolo[2,3-b]pyridine (P-0001, 65 mg, 0.32 mmol, prepared as described in Example 12) and potassium hydroxide (54 mg, 0.96 mmol) under an atmosphere of nitrogen. The reaction was stirred at room temperature for 3 hours. The reaction was poured into water and extracted with ethyl acetate. The organic layer was washed with brine, dried over sodium sulfate and filtrated. The filtrate was concentrated and purified by silica gel column chromatography eluting with 50% ethyl acetate in hexane to give a solid (11, 102 mg, 68%). MS (ESI) [M+H$^+$]$^+$=466.2.

Step 4—Preparation of propane-1-sulfonic acid [3-(5-cyclopentyloxy-1H-pyrrolo[2,3-b]pyridine-3-carbonyl)-2,4-difluoro-phenyl]-amide (P-0033)

To propane-1-sulfonic acid {3-[(5-cyclopentyloxy-1H-pyrrolo[2,3-b]pyridin-3-yl)-hydroxy-methyl]-2,4-difluoro-phenyl}-amide (11, 95 mg, 0.20 mmol) in tetrahydrofuran (2 mL) was added Dess-Martin periodane (104 mg, 0.25 mmol). The reaction was stirred at room temperature for 30 minutes. The reaction was poured into sodium thiosulfate and potassium carbonate solution and extracted with ethyl acetate. The organic layer was washed with brine, dried over anhydrous sodium sulfate and filtrated. The filtrate was concentrated and purified by silica gel column chromatography eluting with 50% ethyl acetate in hexane to give the compound (P-0033, 48 mg, 51%). MS (ESI) [M+H$^+$]$^+$=464.2.

Additional compounds were prepared following the protocol of Scheme 3, optionally replacing propane-1-sulfonyl chloride with an appropriate acid chloride in Step 1 and/or 5-cyclopentyloxy-1H-pyrrolo[2,3-b]pyridine P-0001 with an appropriate azaindole in Step 3 (prepared as described in Example 11, 12, or 14). The following compounds were made following this procedure:

Propane-1-sulfonic acid [3-(5-ethoxy-1H-pyrrolo[2,3-b]pyridine-3-carbonyl)-2,4-difluoro-phenyl]-amide (13)

Propane-1-sulfonic acid {2,4-difluoro-3-[5-(2-methoxy-ethoxy)-1H-pyrrolo[2,3-b]pyridine-3-carbonyl]-phenyl}-amide (14), Propane-1-sulfonic acid {3-[5-(2-diethylamino-ethoxy)-1H-pyrrolo[2,3-b]pyridine-3-carbonyl]-2,4-difluoro-phenyl}-amide (15), N-{2,4-Difluoro-3-[5-(2-methoxy-ethoxy)-1H-pyrrolo[2,3-b]pyridine-3-carbonyl]-phenyl}-3-fluoro-benzenesulfonamide (16), N-{2,4-Difluoro-3-[5-(2-methoxy-ethoxy)-1H-pyrrolo[2,3-b]pyridine-3-carbonyl]-phenyl}-4-fluoro-benzenesulfonamide (17), and N-{2,4-Difluoro-3-[5-(2-methoxy-ethoxy)-1H-pyrrolo[2,3-b]pyridine-3-carbonyl]-phenyl}-4-trifluoromethyl-benzenesulfonamide (18) and Propane-1-sulfonic acid [3-(5-benzyloxy-1H-pyrrolo[2,3-b]pyridine-3-carbonyl)-2,4-difluoro-phenyl]-amide (P-0034), Propane-1-sulfonic acid {2,4-difluoro-3-[5-(2-morpholin-4-yl-ethoxy)-1H-pyrrolo[2,3-b]pyridine-3-carbonyl]-phenyl}-amide (P-0041), Propane-1-sulfonic acid {2,4-difluoro-3-[5-(tetrahydro-pyran-4-yloxy)-11H-pyrrolo[2,3-b]pyridine-3-carbonyl]-phenyl}-amide (P-0045), and Propane-1-sulfonic acid {2,4-difluoro-3-[5-(toluene-4-sulfonyl)-1H-pyrrolo[2,3-b]pyridine-3-carbonyl]-phenyl}-amide (P-0047).

The following table indicates the acid chloride (column 2) and the azaindole (column 3) used to afford the target compounds (column 4). Column provides the compound number and column 5 the observed mass. Compounds isolated after Step 3 of Scheme 17 are so noted in column 1.

| | Sulfonyl chloride | Azaindole | Compound | MS(ESI) [M + H$^+$]$^+$ observed |
|---|---|---|---|---|
| 13 | ⌒⌒SO$_2$Cl | 5-ethoxy-7-azaindole structure | product structure | 424.2 |
| 14 | ⌒⌒SO$_2$Cl | 5-(2-methoxyethoxy)-7-azaindole structure | product structure | 454.2 |

-continued

| | Sulfonyl chloride | Azaindole | Compound | MS(ESI) [M + H+]+ observed |
|---|---|---|---|---|
| 15 | | | | 495.3 |
| 16 | | | | 506.2 |
| 17 | | | | 506.2 |
| 18 | | | | 556.0 |
| P-0034 | | | | 486.1 |
| P-0041 | | | | 509.2 |

| Sulfonyl chloride | Azaindole | Compound | MS(ESI) [M + H⁺]⁺ observed |
|---|---|---|---|
| P-0045  |  |  | 480.1 |
| P-0047  |  |  | 533.9 |

Example 14

Synthesis of 5 oxy substituted 7-azaindoles 5-(2-Morpholin-4-yl-ethoxy)-1H-pyrrolo[2,3-b]pyridine 20 was synthesized in 1 Step from 5-bromo-azaindole 1 as shown in Scheme 4.

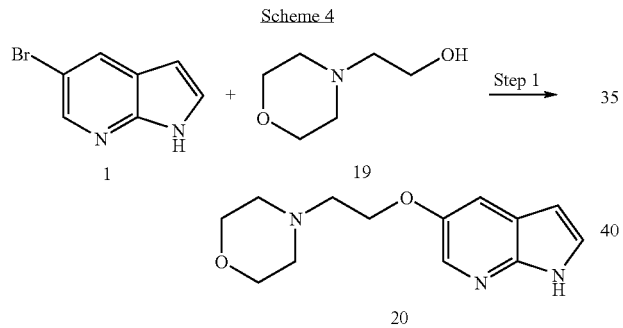

Step 1—5-(2-Morpholin-4-yl-ethoxy)-1H-pyrrolo[2, 3-b]pyridine (20)

To 2-morpholin-4-yl-ethanol (19, 30 mL, 0.2 mol) in N,N-dimethylformamide (30 mL), sodium hydride (7 g, 60% dispersion in mineral oil, 0.2 mol) was slowly added. After the solution turned clear, a solution of 5-bromo-7-azaindole (1, 1.0 g, 0.0051 mol) in N,N-dimethylformamide (5 mL) and copper(I) bromide (1.4 g, 0.0098 mol) were added. The reaction mixture was stirred at 120° C. under nitrogen for 2 hours. The reaction mixture was concentrated and the residue was dissolved in ethyl acetate and water. The organic layer was collected, washed with a solution of ammonium chloride and ammonium hydroxide (4:1), brine, and dried over magnesium sulfate. After removal of solvent, the residue was purified by silica gel column chromatography eluting with ethyl acetate in hexane to provide the compound as an off-white solid (20, 0.62 g, 50%). MS (ESI) [M+H⁺]⁺=248.25.

Additional 5-oxy-substituted 7-azaindoles were prepared following the protocol of Scheme 4, replacing 2-morpholin-4-yl-ethanol 19 with either 2-diethylamino-ethanol, 3-diethylamino-propan-1-ol, 2-piperidin-1-yl-ethanol, or 2-pyrolidin-1-yl-ethanol to provide diethyl-[2-(1H-pyrrolo[2,3-b]pyridin-5-yloxy)-ethyl]-amine, diethyl-[3-(1H-pyrrolo[2,3-b]pyridin-5-yloxy)-propyl]-amine, 5-(2-piperidin-1-yl-ethoxy)-1H-pyrrolo[2,3-b]pyridine, and 5-(2-pyrrolidin-1-yl-ethoxy)-1H-pyrrolo[2,3-b]pyridine, respectively.

Example 15

Synthesis of {5-[5-(2-Morpholin-4-yl-ethoxy)-1H-pyrrolo[2,3-b]pyridin-3-ylmethyl]-pyridin-2-yl}-(4-trifluoromethyl-benzyl)-amine 25

{5-[5-(2-Morpholin-4-yl-ethoxy)-1H-pyrrolo[2,3-b]pyridin-3-ylmethyl]-pyridin-2-yl}-(4-trifluoromethyl-benzyl)-amine 25 was synthesized in four Steps from (5-bromo-pyridin-2-yl)-(4-trifluoromethylbenzyl)-amine 21 as shown in Scheme 5.

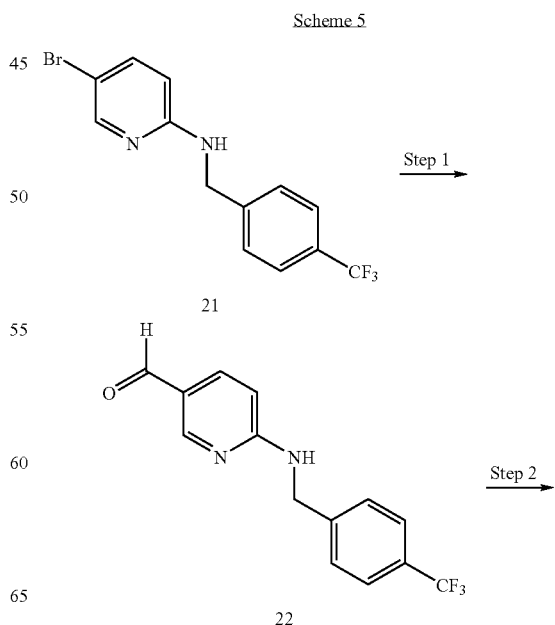

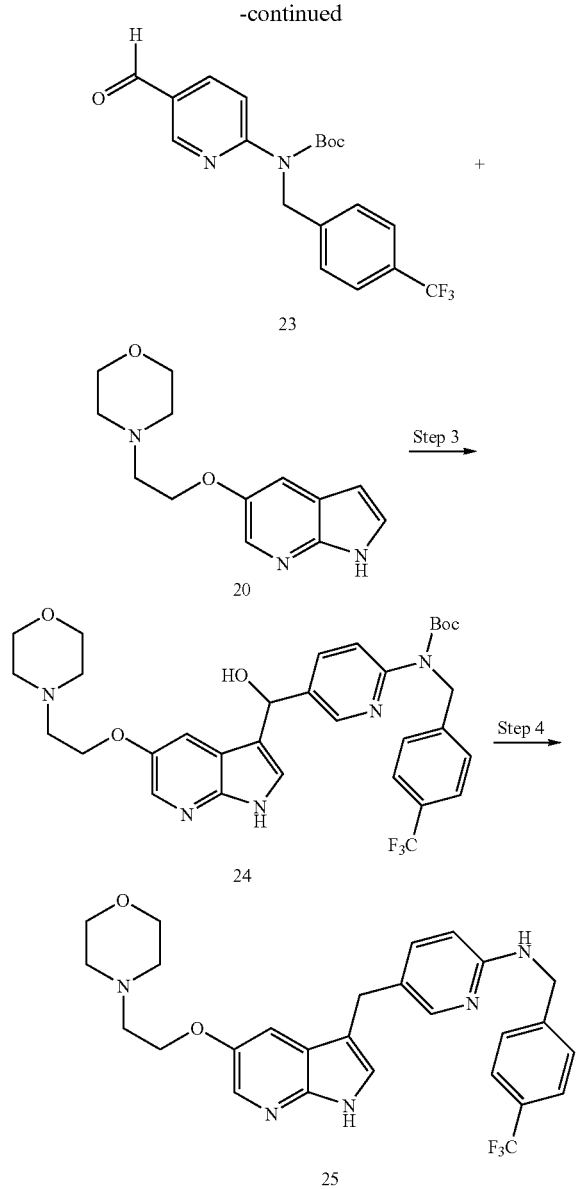

Step 1—Preparation of 6-(4-trifluoromethyl-benzylamino)-pyridine-3-carbaldehyde (22)

To a solution of (5-bromo-pyridin-2-yl)-(4-trifluoromethyl-benzyl)-amine (21, 3.55 g, 0.0107 mol) in tetrahydrofuran (150 mL), tert-butyllithium (13.2 mL, 1.70 M in pentane, 0.0224 mol) was added slowly under an atmosphere of nitrogen at −78° C. over 10 minutes. The reaction mixture was stirred at −78° C. for 90 minutes. N,N-Dimethylformamide (2.2 mL, 0.028 mol) was added slowly into the reaction mixture. The reaction mixture was stirred at −78° C. for 2 hours, then allowed to warm to room temperature. After stirring at room temperature for 2 hours, the reaction mixture was poured into ice water and extracted with ethyl acetate. The organic phase was washed with saturated sodium bicarbonate, brine, and dried over magnesium sulfate. After removal of solvent, the residue was purified by silica gel column chromatography eluting with ethyl acetate in hexane to provide the compound as a light yellow solid (22, 1.67 g, 56%).

Step 2—Preparation of (5-formyl-pyridin-2-yl)-(4-trifluoromethyl-benzyl)-carbamic acid tert-butyl ester (23)

To a solution of 6-(4-trifluoromethyl-benzylamino)-pyridine-3-carbaldehyde (22, 3.7 g, 0.013 mol) and di-tert-butyl-dicarbonate (3.4 g, 0.016 mol) in dichloromethane (100 mL) was added N,N-diisopropylethylamine (4.6 mL, 0.026 mol) and 4-diethylaminopyridine (0.2 g, 0.002 mol). The reaction mixture was stirred at room temperature overnight. The reaction mixture was concentrated and then dissolved in ethyl acetate. The solution was washed with hydrochloric acid (10%), saturated sodium bicarbonate, brine, and dried over magnesium sulfate. After removal of solvent, the residue was purified by silica gel column chromatography eluting with ethyl acetate in hexane to provide the compound as a white solid (23, 4.38 g, 87%).

Step 3—Preparation of (5-{Hydroxy-[5-(2-morpholin-4-yl-ethoxy)-1H-pyrrolo[2,3-b]pyridin-3-yl]-methyl}-pyridin-2-yl)-(4-trifluoromethyl-benzyl)-carbamic acid tert-butyl ester (24)

A mixture of (5-Formyl-pyridin-2-yl)-(4-trifluoromethyl-benzyl)-carbamic acid tert-butyl ester (23, 315 mg, 0.828 mmol), 5-(2-morpholin-4-yl-ethoxy)-1-pyrrolo[2,3-b]pyridine (20, 205 mg, 0.829 mmol, prepared as described in Example 14), and potassium hydroxide (70 mg, 1 mmol) in methanol (25 mL) was stirred at room temperature overnight. The reaction mixture was poured into ice water, extracted with ethyl acetate, washed with brine, and dried over sodium sulfate. After removal of solvent, the residue was purified by silica gel column chromatography eluting with methanol in dichloromethane to provide the compound as a yellow solid (24, 0.2 g, 40%). MS (ESI) [M+H$^+$]$^+$=628.42.

Step 4—Preparation of {5-[5-(2-Morpholin-4-yl-ethoxy)-1H-pyrrolo[2,3-b]pyridin-3-ylmethyl]-pyridin-2-yl}-(4-trifluoromethyl-benzyl)-amine (25)

A mixture of (5-{Hydroxy-[5-(2-morpholin-4-yl-ethoxy)-1H-pyrrolo[2,3-b]pyridin-3-yl]-methyl}-pyridin-2-yl)-(4-trifluoromethyl-benzyl)-carbamic acid tert-butyl ester (24, 0.2 g, 0.3 mmol), triethylsilane (4 mL, 0.02 mol), and trifluoroacetic acid (2 mL, 0.02 mol) in acetonitrile (30 mL) was refluxed for 2 hours. After removal of solvent, the residue was dissolved in ethyl acetate, washed with saturated sodium bicarbonate, brine, and dried over magnesium sulfate. After removal of solvent, the residue was purified by silica gel column chromatography eluting with methanol in dichloromethane to provide the compound as a light yellow solid (25, 17 mg, 10%). MS (ESI) [M+H$^+$]$^+$=512.42.

Additional compounds may be prepared using steps 3 and 4 of Scheme 5, using (5-formyl-pyridin-2-yl)-(4-trifluoromethyl-benzyl)-carbamic acid tert-butyl ester 23 or replacing it with (5-formyl-pyridin-2-yl)-(4-chloro-benzyl)-carbamic acid tert-butyl ester (58, prepared as described in Example 19) and replacing 5-(2-morpholin-4-yl-ethoxy)-1H-pyrrolo[2,3-b]pyridine 20 with an appropriate azaindole (see Examples 11 or 14). The following compounds were made following this procedure:

{5-[5-(2-Diethylamino-ethoxy)-1H-pyrrolo[2,3-b]pyridin-3-ylmethyl]-pyridin-2-yl}-(4-trifluoromethyl-benzyl)-amine (26), (4-Chloro-benzyl)-{5-[5-(2-morpholin-4-yl-ethoxy)-1H-pyrrolo[2,3-b]pyridin-3-ylmethyl]-pyridin-2-yl}-amine (27),
(5-[5-(2-Pyrrolidin-1-yl-ethoxy)-1H-pyrrolo[2,3-b]pyridin-3-ylmethyl]-pyridin-2-yl -(4-trifluoromethyl-benzyl)-amine (28),
{5-[5-(3-Diethylamino-propoxy)-1H-pyrrolo[2,3-h]pyridin-3-ylmethyl]-pyridin-2-yl}-(4-trifluoromethyl-benzyl)-amine (29), and (4-Chloro-benzyl)-{5-[5-(3-diethylamino-propoxy)-1H-pyrrolo[2,3-b]pyridin-3-ylmethyl]-pyridin-2-yl}-amine (30).

The aldehyde and azaindole used in step 4 of this procedure are indicated in columns 2 and 3 of the following table, respectively, with the compound structure indicated in column 4. Column 1 provides the compound reference number and Column 5 the experimental mass spectrometry result.

| | Aldehyde | Azaindole | Compound | MS(ESI) [M + H⁺]⁺ observed |
|---|---|---|---|---|
| 26 | 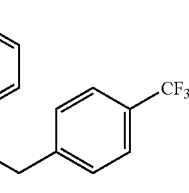 | 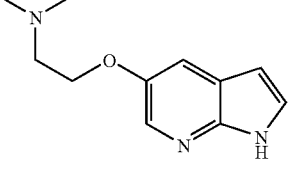 | 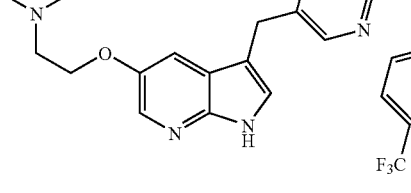 | 498.4 |
| 27 | 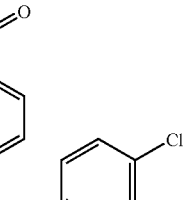 | 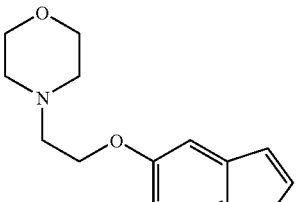 | 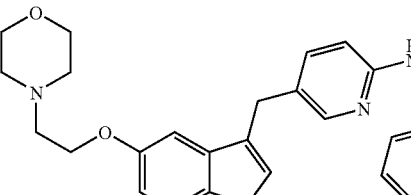 | 478.3 |
| 28 | 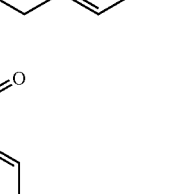 | 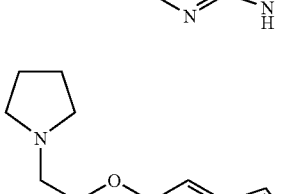 | 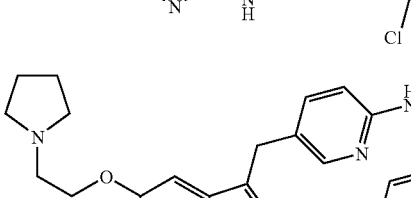 | 496.3 |
| 29 | 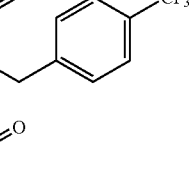 | 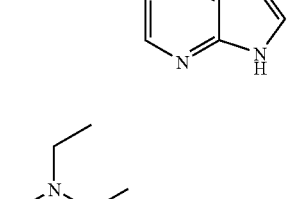 | 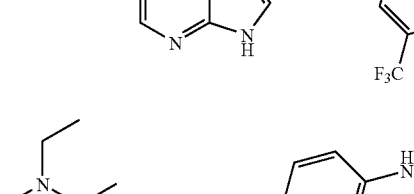 | 512.3 |
| 30 | 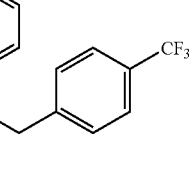 | 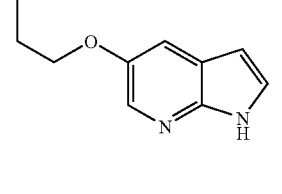 |  | 478.3 |

Example 16
Syntheses of (2,4-dichloro-phenyl)-(5-phenoxy-1H-pyrrolo[2,3-b]pyridin-3-yl)-methanone (P-0036) and 3-(2,4-dichloro-benzyl)-5-phenoxy-1H-pyrrolo[2,3-b]pyridine (P-0037)
Compounds P-0036 and P-0037 were synthesized in three steps from 1H-Pyrrolo[2,3-b]pyridin-5-ol 6 as shown in Scheme 6.
Scheme 6
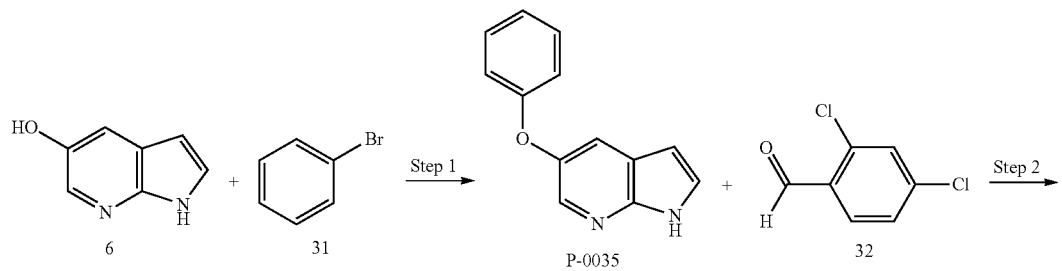
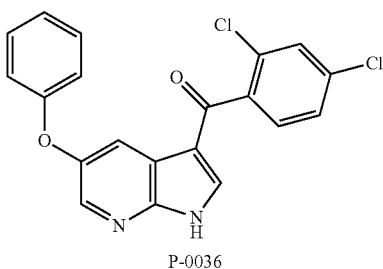
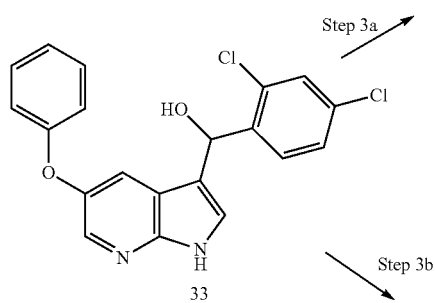
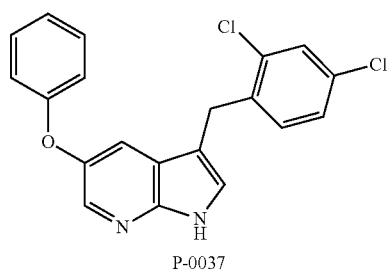

Step 1—Preparation of 5-phenoxy-1H-pyrrolo[2,3-b]pyridine (P-0035)

To 1H-Pyrrolo[2,3-b]pyridin-5-ol (6, 645 mg, 4.81 mol) and copper(I) oxide (860 mg, 6.0 mmol) in pyridine (10 mL), bromobenzene (31, 422 uL, 4.01 mmol) was added. The mixture was heated to 115° C. for 24 hours. The reaction mixture was treated with 1N HCl and extracted with ethyl acetate. The organic layer was washed with NH$_4$OH/NH$_4$Cl (1:4), saturated aqueous NH$_4$Cl twice, water, and brine, dried over anhydrous magnesium sulfate, filtrated and concentrated. The desired compound was isolated with silica gel column chromatography (50-70% ethyl acetate/hexane) to provide the compound (P-0035, 88 mg, 10%). MS (ESI) [M+H$^+$]$^+$=211.2.

Step 2—Preparation of (2,4-dichloro-phenyl)-(5-phenoxy-1H-pyrrolo[2,3-b]pyridin-3-yl)-methanol (33)

To [5-phenoxy-1H-pyrrolo[2,3-b]pyridine (P-0035, 80 mg, 0.38 mol) in methanol (2.0 mL), 2,4-dichloro-benzaldehyde (32, 133 mg, 0.76 mmol) and potassium hydroxide (74 mg, 1.3 mmol) were added. The reaction was stirred at room temperature for 2 hours. The reaction mixture resulted in a precipitate, which was collected with vacuum filtration to provide the compound (33, 104 mg, 71%). MS (ESI) [M+H$^+$]$^+$=385.1 and 387.1.

Step 3a—Preparation of (2,4-dichloro-phenyl)-(5-phenoxy-1H-pyrrolo[2,3-b]pyridin-3-yl)-methanone (P-0036)

To (2,4-dichloro-phenyl)-(5-phenoxy-1H-pyrrolo[2,3-b]pyridin-3-yl)-methanol (33, 48 mg, 0.12 mmol) in tetrahydrofuran (15 mL), Dess-Martin periodinane (58 mg, 0.137 mmol) was added. The reaction was stirred at room temperature for 40 minutes, then poured into water and extracted with ethyl acetate. The organic layer was washed with saturated sodium bicarbonate and brine, dried over anhydrous magnesium sulfate, filtrated and concentrated. The crude material was suspended in acetonitrile (1~2 mL). The precipitated material was collected with vacuum filtration to provide the compound (P-0036, 24 mg, 50%). MS (ESI) [M+H$^+$]$^+$=383.1 and 385.1.

Step 3b—Preparation of 3-(2,4-dichloro-benzyl)-5-phenoxy-1H-pyrrolo[2,3-b]pyridine (P-0037)

To (2,4-dichloro-phenyl)-(5-phenoxy-1H-pyrrolo[9,3-b]pyridin-3-yl)-methanol (33, 30 mg, 0.078 mmol) in acetonitrile (8 mL), triethylsilane (1 mL, 7 mmol) and trifluoroacetic acid (0.5 mL, 7 mmol) were added. The reaction solution was heated to reflux for 4 hours. Then, the reaction was poured into water and extracted with ethyl acetate. The organic layer was washed with saturated sodium bicarbonate, water, and brine, dried over anhydrous magnesium sulfate, filtrated and concentrated. The crude material was suspended in acetonitrile (1~2 mL). The precipitated material was collected with vacuum filtration to provide the compound (P-0037, 13 mg, 45%). MS (ESI) [M+H$^+$]$^+$=369.1 and 371.1.

(2-Chloro-4-fluoro-phenyl)-[5-(4-methanesulfonyl-phenoxy)-1H-pyrrolo[2,3-b]pyridin-3-yl]-methanone P-0038

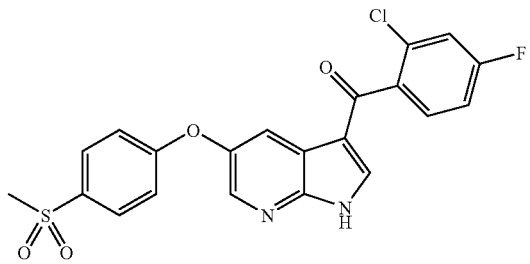

was prepared following the protocol of Scheme 7 using step 3a, replacing bromo-benzene 31 with 1-bromo-4-methanesulfonyl-benzene in Step 1 and 2,4-dichloro-benzaldehyde 32 with 2-chloro-4-fluoro-benzaldehyde in Step 2. MS (ESI) [M+H$^+$]$^+$=443.0 and 445.0.

{3-[3-(2-Chloro-4-fluoro-benzoyl)-1H-pyrrolo[2,3-b]pyridin-5-yloxy]-phenyl}-acetic acid P-0039

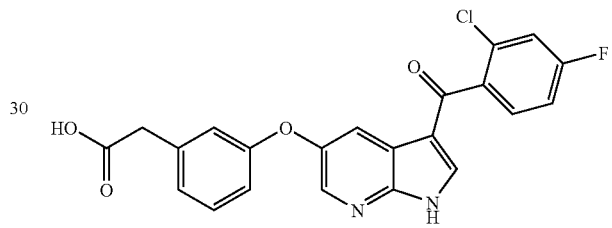

was prepared following the protocol of Scheme 7, using step 3a, replacing bromo-benzene 31 with (3-bromo-phenyl)-acetic acid in Step 1 and 2,4-dichloro-benzaldehyde 32 with 2-chloro-4-fluoro-benzaldehyde in Step 2. MS (ESI) [M+H$^+$]$^+$=425.1 and 427.1.

Example 17

Synthesis of aldehyde reagents for coupling to 5-oxy substituted 7-azaindoles Aldehyde compounds for coupling to the 3-position of a 5-oxy substituted 7-azaindole are shown in the following Schemes. 3-Methoxy-4-[4-(4-methyl-piperazin-1-ylmethyl)-benzyloxy]-benzaldehyde 37 was prepared in one Step as shown in Scheme 7.

Scheme 7

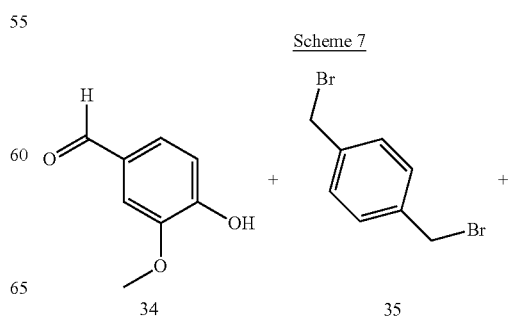

2,5-Difluoro-4-hydroxy-benzaldehyde 43 was synthesized in three steps from 2,5-difluorophenol 40 as shown in Scheme 9.

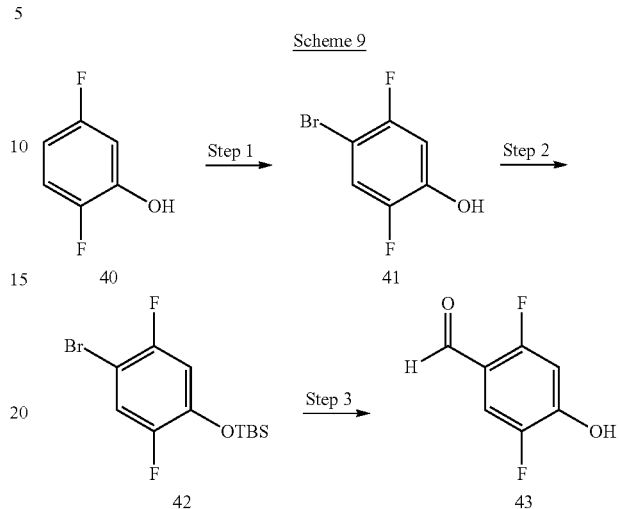

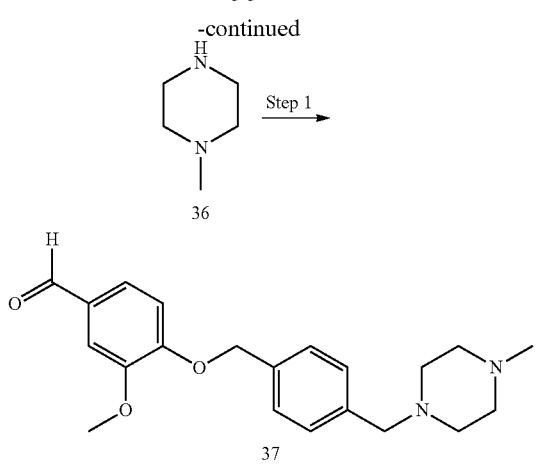

Step 1—Synthesis of 3-Methoxy-4-[4-(4-methyl-piperazin-1-ylmethyl)-benzyloxy]-benzaldehyde (37)

To 4-Hydroxy-3-methoxybenzaldehyde (34, 2.1 g, 0.014 mol) in N,N-dimethylformamide (40.0 mL) were added 1,4-bis(bromomethyl)-benzene (35, 4.00 g, 0.0152 mol) and potassium carbonate (5.0 g, 0.036 mol) under an atmosphere of nitrogen. After 12 hours 1-methyl-piperazine (36, 3.8 mL, 0.034 mol) was added to the reaction. After 2 hours, the reaction was poured into water and extracted with ethyl acetate. The organic layer was dried over anhydrous sodium sulfate and filtered. The filtrate was concentrated and purified by silica gel column chromatography eluting with 20% methanol in dichloromethane to give the compound (37, 1.2 g, 25.0%). MS (ESI) $[M+H^+]^+$=355.3.

2-Fluoro-4-hydroxy-5-methoxy-benzaldehyde 39 was synthesized in one step from 2-fluoro-4,5-dimethoxy-benzaldehyde 38 as shown in Scheme 8.

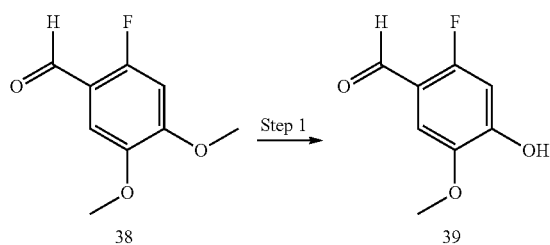

Step 1—Synthesis of 2-fluoro-4-hydroxy-5-methoxy-benzaldehyde (39)

To 2-fluoro-4,5-dimethoxy-benzaldehyde (38, 1.00 g, 5.43 mol) in dichloromethane (50.0 mL) was added aluminum trichloride (4.34 g, 32.6 mmol) under an atmosphere of nitrogen. The reaction was stirred at room temperature overnight. The reaction was poured into water and extracted with ethyl acetate. The organic layer was dried over anhydrous sodium sulfate and filtered. The filtrate was concentrated and washed with ethyl acetate and hexane to give a white solid (39, 0.70 g, 76.0%).

Step 1—Synthesis of 4-bromo-2,5-difluoro-phenol (41)

To 2,5-difluorophenol (40, 5.50 g, 0.0423 mol) in chloroform (110.0 mL), bromine (2.18 mL, 0.0423 mol) was added slowly. After 3 hours, the reaction was poured into a solution of sodium thiosulfate and extracted with ethyl acetate. The organic layer was dried over sodium sulfate, concentrated and purified with silica gel column chromatography eluting with 20% ethyl acetate in hexane to give a colorless oil (41, 6.20 g, 70.2%).

Step 2—(4-Bromo-2,5-difluoro-phenoxy)-tert-butyl-dimethyl-silane (42)

To 4-bromo-2,5-difluoro-phenol (41, 3.50 g, 0.0167 mol) in N,N-dimethylformamide (50.0 mL) were added tert-butyldimethylsilyl chloride (3.83 g, 0.0254 mol) and 1H-imidazole (6.00 g, 0.0529 mol). The reaction was stirred at room temperature overnight, then poured into water and extracted with ethyl acetate. The organic layer was dried over anhydrous sodium sulfate and filtered. The filtrate was concentrated and purified by silica gel column chromatography eluting with 20% ethyl acetate in hexane to give the compound (42, 3.0 g, 55.4%).

Step 3—2,5-Difluoro-4-hydroxy-benzaldehyde (43)

To (4-bromo-2,5-difluoro-phenoxy)-tert-butyl-dimethyl-silane (42, 3.00 g, 9.28 mmol) in tetrahydrofuran (37.5 mL), under an atmosphere of nitrogen at −78° C., n-butyllithium (3.90 mL, 2.50 M in hexane) was added slowly. After 30 minutes, N,N-dimethylformamide (0.825 mL, 0.0106 mol) was added to the reaction. One hour later, the reaction was allowed to come to room temperature. The reaction was poured into water and 1 NA HCl, then extracted with ethyl acetate. The organic layer was dried over anhydrous sodium sulfate and filtered. The filtrate was concentrated and purified by silica gel column chromatography eluting with 20% ethyl acetate in hexane to give the compound as an off-white solid (43, 0.86 g, 59.0%).

101

4-(4-Chloro-benzyloxy)-3-fluoro-benzaldehyde 46 was synthesized in one step from 3-fluoro-4-hydroxy-benzaldehyde 44 as shown in Scheme 10.

Scheme 10

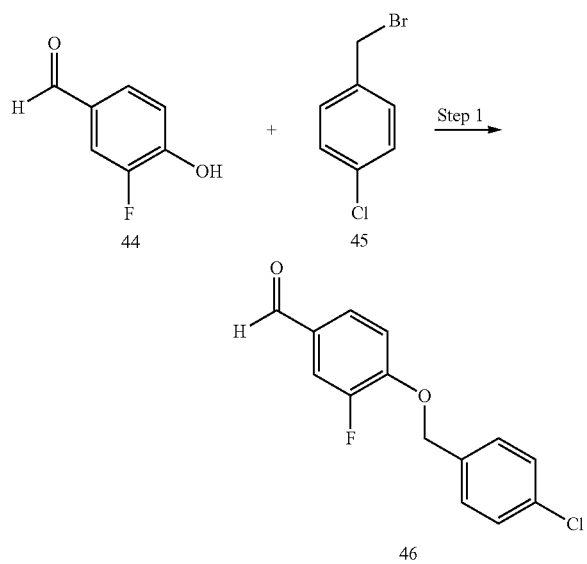

102

Step 1—Synthesis of 4-(4-chloro-benzyloxy)-3-fluoro-benzaldehyde (46)

To 3-fluoro-4-hydroxy-benzaldehyde (44, 0.800 g, 5.71 mmol) in N,N-dimethylformamide (50.0 mL) was added sodium hydride (260.0 mg, 60% in mineral oil, 6.50 mmol). After 15 minutes, 4-chlorobenzyl bromide (45, 1.29 g, 6.28 mmol) was added to the reaction mixture. The reaction was stirred at 80° C. for 5 hours. The reaction was poured into water and extracted with ethyl acetate. The organic layer was dried over anhydrous sodium sulfate and filtered. The filtrate was concentrated and purified by silica gel column chromatography eluting with 30% ethyl acetate in hexane to give the compound (46, 1.3 g, 86.0%).

Additional aldehydes were prepared using the protocol of Scheme 10, replacing either 4-chlorobenzyl bromide 45 with a suitable alkylating agent, and/or 3-fluoro-4-hydroxy-benzaldehyde 44 with a suitable aldehyde. The following table indicates the alkylating agent (column 1) and the starting aldehyde (column 2) used to afford the aldehyde (column 3) synthesized following this protocol.

| Alkylating agent | Aldehyde | Compound |
|---|---|---|

-continued

| Alkylating agent | Aldehyde | Compound |
|---|---|---|

Example 18

Synthesis of Aldehyde Reagents for Coupling to 5-oxy Substituted 7-azaindoles Propane-2-sulfonic acid (2,4-difluoro-3-formyl-phenyl)-amide 49 was synthesized in two steps from 2,4-difluorophenylamine 47 as shown in Scheme 11.

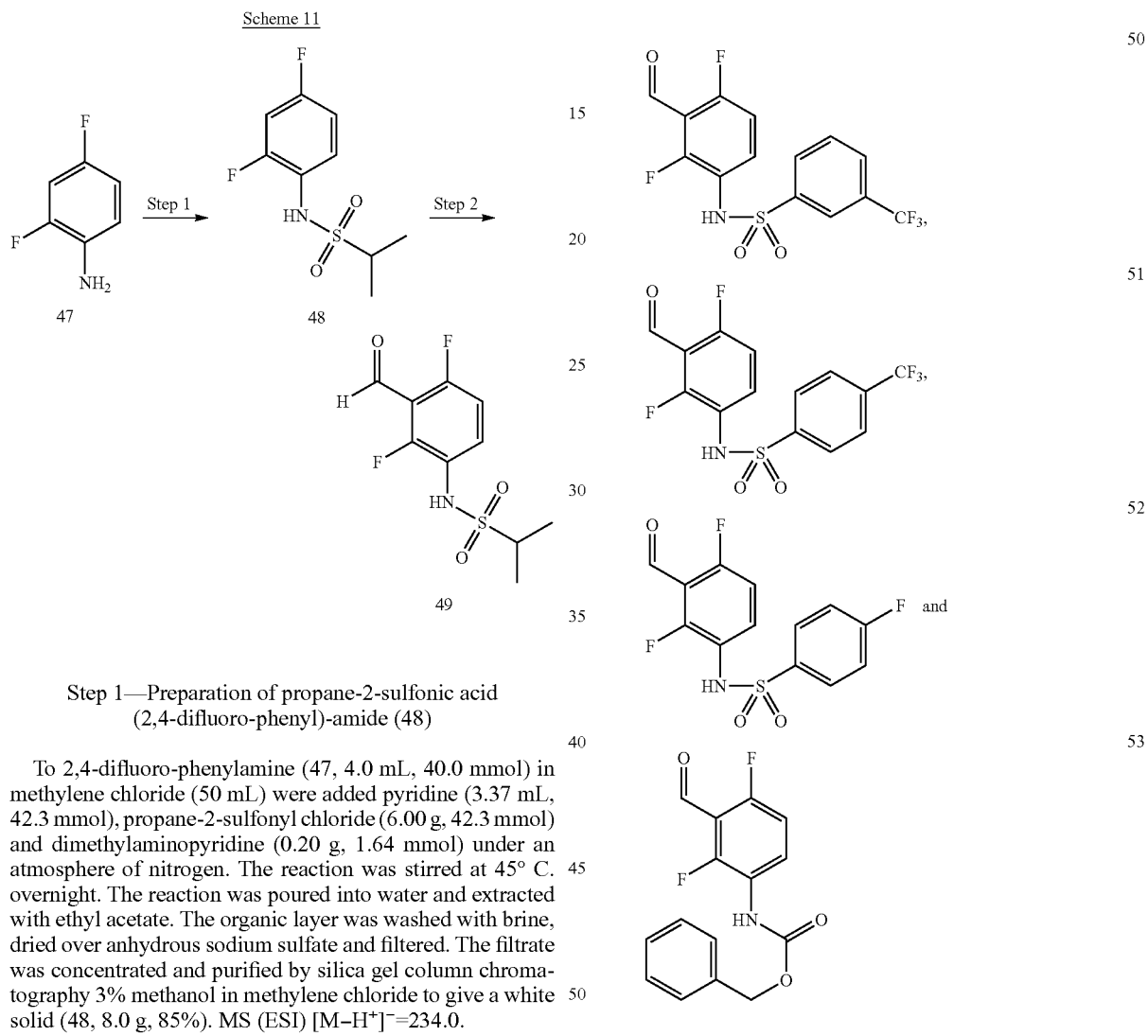

Step 1—Preparation of propane-2-sulfonic acid (2,4-difluoro-phenyl)-amide (48)

To 2,4-difluoro-phenylamine (47, 4.0 mL, 40.0 mmol) in methylene chloride (50 mL) were added pyridine (3.37 mL, 42.3 mmol), propane-2-sulfonyl chloride (6.00 g, 42.3 mmol) and dimethylaminopyridine (0.20 g, 1.64 mmol) under an atmosphere of nitrogen. The reaction was stirred at 45° C. overnight. The reaction was poured into water and extracted with ethyl acetate. The organic layer was washed with brine, dried over anhydrous sodium sulfate and filtered. The filtrate was concentrated and purified by silica gel column chromatography 3% methanol in methylene chloride to give a white solid (48, 8.0 g, 85%). MS (ESI) [M–H$^+$]$^-$=234.0.

Step 2—Preparation of propane-2-sulfonic acid (2,4-difluoro-3-formyl-phenyl)-amide (49)

To propane-2-sulfonic acid (2,4-difluoro-phenyl)-amide (48, 2.35 g, 9.95 mmol) in tetrahydrofuran (70 mL) under an atmosphere of nitrogen cooled with a dry ice/acetone bath was added 1.60 M of n-butyllithium (1.60 M in hexane, 6.53 mL, 10.45 mmol). The reaction was stirred for 40 minutes, and then another portion of n-butyllithium (1.60 M in hexane, 6.84 mL, 10.94 mmol). The reaction was stirred for 1 hour and N,N-dimethylformamide (0.92 mL, 11.9 mmol) was added. The reaction was allowed to warm to room temperature overnight. The reaction was poured into water extracted with ethyl acetate. The organic layer was washed with brine, dried over anhydrous sodium sulfate and filtrated. The filtrate was concentrated and purified by silica gel column chromatography (dichloromethane methanol 5%) to give the compound (49, 1.4 g, 53.4%). MS (ESI) [M–H$^+$]$^-$=263.4.

N-(2,4-Difluoro-3-formyl-phenyl)-3-trifluoromethyl-benzenesulfonamide 50, N-(2,4-difluoro-3-formyl-phenyl)-4-t fluoromethyl-benzenesulfonamide 51, and N-(2,4-difluoro-3-formyl-phenyl)-4-fluoro-benzenesulfonamide 52, and (2,4-difluoro-3-formyl-phenyl)-carbamic acid benzyl ester 53

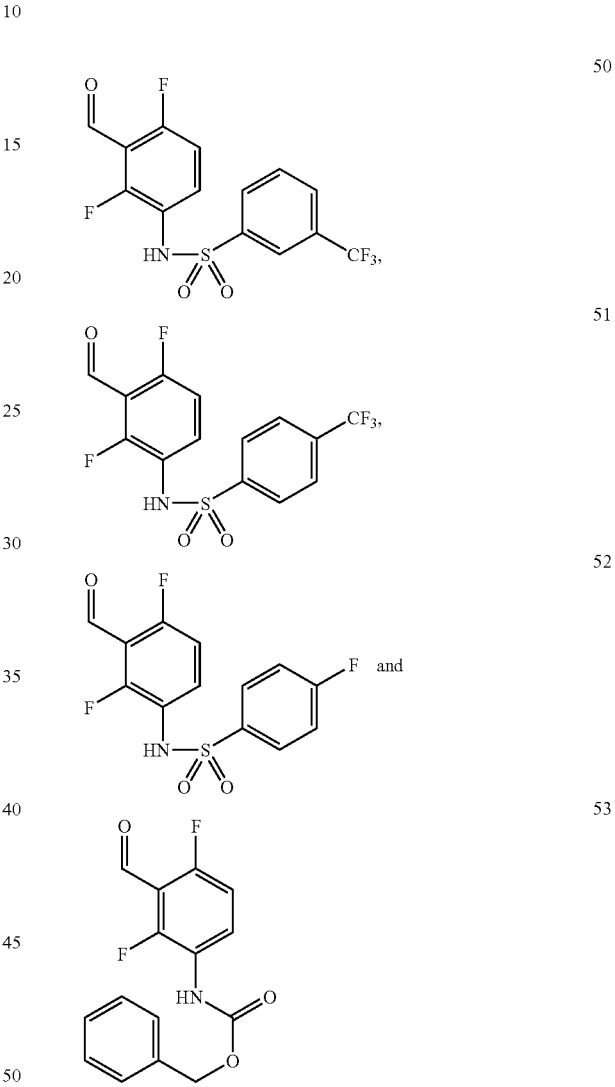

were prepared following the protocol of Scheme 11, substituting propane-2-sulfonyl chloride with 3-trifluoromethyl-benzenesulfonyl chloride, 4-trifluoromethyl-benzenesulfonyl chloride, 4-fluoro-benzenesulfonyl chloride, and benzyl chloroformate, respectively, in Step 1.

Example 19

Synthesis of (4-Chloro-benzyl)-(5-formyl-pyridin-2-yl)-carbamic acid tert-butyl ester 58

(4-Chloro-benzyl)-(5-formyl-pyridin-2-yl)-carbamic acid tert-butyl ester 58 was synthesized in three steps from 2-amino-5-bromopyridine 54 as shown in Scheme 12.

Scheme 12

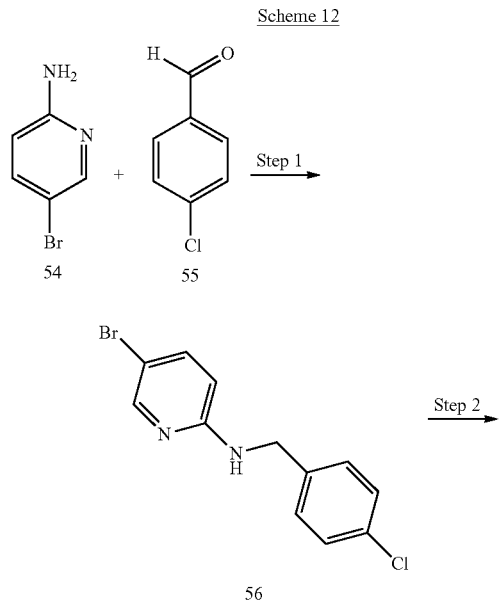

Step 1—Synthesis of (5-Bromo-pyridin-2-yl)-(4-chloro-benzyl)-amine (56)

To 2-amino-5-bromopyridine (54, 6.10 g, 0.0352 mol) in toluene (90.0 mL) were added 4-chlorobenzaldehyde (55, 5.00 g, 0.0356 mol), trifluoroacetic acid (8.0 mL, 0.10 mol) and triethylsilane (16.5 mL, 0.103 mol). The reaction was heated to reflux for 48 hours. The reaction was concentrated, poured into aqueous potassium carbonate and extracted with ethyl acetate. The organic layer was washed with brine, dried over sodium sulfate and concentrated. The crude residue was crystallized with ethyl acetate to give compound (56, 6.8 g, 65.4%).

Step 2—Synthesis of 6-(4-Chloro-benzylamino)-pyridine-3-carbaldehyde (57)

To (5-Bromo-pyridin-2-yl)-(4-chloro-benzyl)-amine (56, 10.00 g, 0.03360 mol) in tetrahydrofuran (400.0 mL) under an atmosphere of nitrogen at −78° C. was added n-butyllithium (17.5 mL, 2.00 M in cyclohexane). After 90 minutes, tert-butyllithium (42.00 mL, 1.70 M in hexane) was added to the reaction. After 80 minutes, N,N-dimethylformamide (6.9 mL, 0.089 mol) was added to the reaction. The reaction mixture was stirred at −78° C. for 2 hours, then allowed to warm to room temperature for 1 hour. The reaction mixture was poured into water and extracted with ethyl acetate. The organic layer was washed with brine, dried over sodium sulfate mid concentrated to give the crude compound, which was crystallized from tert-butoxyl methyl ether to provide compound (57, 7.66 g, 92.2%).

Step 3—Synthesis of (4-Chloro-benzyl)-(5-formyl-pyridin-2-yl)-carbamic acid tert-butyl ester (58)

To 6-(4-Chloro-benzylamino)-pyridine-3-carbaldehyde (57, 2.00 g, 8.11 mmol) in dichloromethane (20.0 mL) were added triethylamine (1.70 mL, 12.2 mmol), di-tert-butyldicarbonate (2.00 g, 9.16 mmol) and 4-dimethylaminopyridine (52.3 mg, 0.43 mmol). The reaction was stirred at room temperature for 48 hours. The reaction was concentrated and purified by silica gel column chromatography eluting with 20% ethyl acetate in hexane to give compound (58, 2.50 g, 89.3%).

Example 20

Synthesis of (5-cyclopentyloxy-1H-pyrrolo[2,3-b]pyridin-3-yl)-(1H-indol-6-yl)-methanone P-0040

(5-Cyclopentyloxy-1H-pyrrolo[2,3-b]pyridin-3-yl)-(1H-indol-6-yl)-methanone P-0040 was synthesized in three steps from 59 as shown in Scheme 13.

Scheme 13

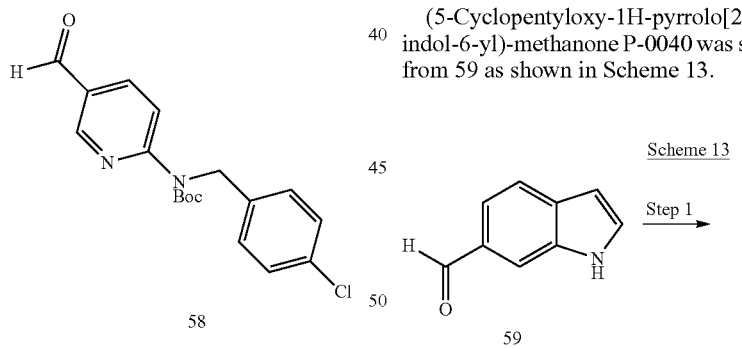

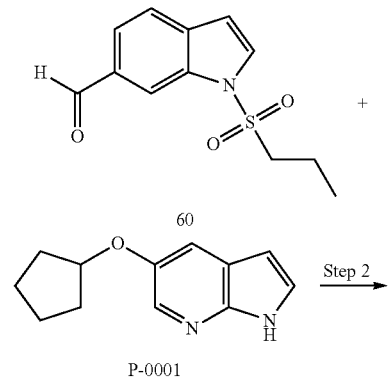

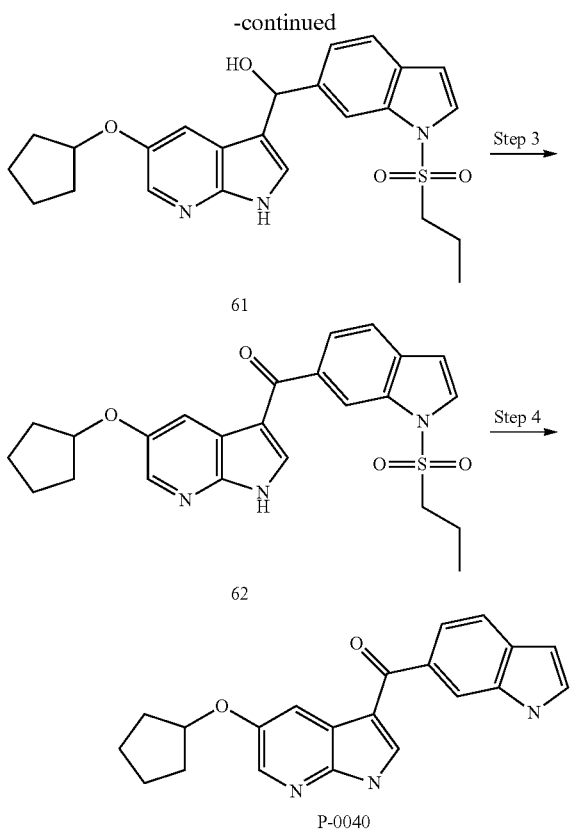

Step 1—Preparation of 1-(propane-1-sulfonyl)-1H-indole-6-carbaldehyde (60)

To sodium hydride (0.174 g, 4.35 mmol) in tetrahydrofuran (6.8 mL, 0.084 mol), 1H-Indole-6-carbaldehyde (59, 0.486 g, 3.35 mol) was added. After 30 minutes, propane-1-sulfonyl chloride (0.565 mL, 5.02 mol) was added. After two hours, it was quenched with 1M HCl (aqueous) and extracted twice with ethyl acetate. The combined organic layers were washed with brine, dried over anhydrous sodium sulfate and filtered. The filtrate was concentrated. The desired compound was purified by silica gel column chromatography eluting with a gradient of ethyl acetate in hexane to give 516 mg of desired compound. MS (ESI) $[M-H^+]^-=250.1$.

Step 2—Preparation of (5-Cyclopentyloxy-1H-pyrrolo[2,3-b]pyridin-3-yl)-[1-(propane-1-sulfonyl)-1H-indol-6-yl]-methanol (61)

Into a round bottom flask, was added 5-cyclopentyloxy-1H-pyrrolo[2,3-b]pyridine (P-0001, 0.110 g, 0.544 mol, prepared as describes in Example 12), 1-(propane-1-sulfonyl)-1H-indole-6-carbaldehyde (60, 0.169 g, 0.674 mol), potassium hydroxide (91.6 mg, 1.63 mmol) and methanol (2 mL, 0.05 mol). The reaction was allowed to stir at room temperature overnight. The reaction was poured into water and extracted with ethyl acetate. The organic layer was washed with brine, dried over anhydrous magnesium sulfate and filtered. The filtrate was concentrated and purified by silica gel column chromatography eluting with a gradient of ethyl acetate (with 4% acetic acid) in hexanes to provide 88 mg of the desired compound. MS (EST) $[M+H^+]^+=454.2$.

Step 3—Preparation of (5-Cyclopentyloxy-1H-pyrrolo[2,3-b]pyridin-3-yl)-[1-(propane-1-sulfonyl)-1H-indol-6-yl]-ethanone (62)

To (5-Cyclopentyloxy-1H-pyrrolo[2,3-b]pyridin-3-yl)-[1-(propane-1-sulfonyl)-1H-indol-6-yl]-methanol (61, 80.0 mg, 0.176 mmol) dissolved in tetrahydrofuran (20 mL, 0.2 mol), was added Dess-Martin periodinane (82 mg, 0.19 mmol). The resulting mixture was stirred at room temperature for 2 hours. The reaction mixture was extracted with ethyl acetate and water. The aqueous layer was extracted with ethyl acetate. The combined organic layers were washed with sodium bicarbonate followed by brine, dried with anhydrous magnesium sulfate and filtered. The volatiles were removed under vacuum. The filtrate was concentrated and purified by silica gel column chromatography eluting with 3% methanol in dichloromethane to give 65 mg of compound. MS (ESI) $[M+H^+]^+=452.2$.

Step 4—Preparation of (5-Cyclopentyloxy-1H-pyrrolo[2,3-b]pyridin-3-yl)-(1H-indol-6-yl)-methanone (P-0040)

To (5-Cyclopentyloxy-1H-pyrrolo[2,3-b]pyridin-3-yl)-[1-(propane-1-sulfonyl)-1H-indol-6-yl]-methanone (62, 0.065 g, 0.14 mmol) dissolved in tetrahydrofuran (5.10 mL, 0.0628 mol), 1.00 M tetra-n-butylammonium fluoride in tetrahydrofuran (0.475 mL) was added. The resulting solution was allowed to stir at 60° C. under an atmosphere of nitrogen. After 19 hours, the reaction was quenched with water, and the two layers were separated. The organic layer was extracted with 50% sat. NaHCO$_3$ (in water), followed by sat. bicarbonate, 1N HCl, and brine. The organic layer was dried with anhydrous magnesium sulfate and filtered. The filtrate was concentrated and purified by HPLC to give 1.7 mg of compound P-0040. MS (ESI) $[M+H^+]^+=346.2$.

Example 21

Synthesis of 5-(toluene 4-sulfonyl)-1H-pyrrolo[2,3-b]pyridine P-0046

5-(Toluene-4-sulfonyl)-1H-pyrrolo[2,3-b]pyridine P-0046 was synthesized in 1 step from 5-bromo-1H-pyrrolo[2,3-b]pyridine 1 as shown in Scheme 14.

Scheme 14

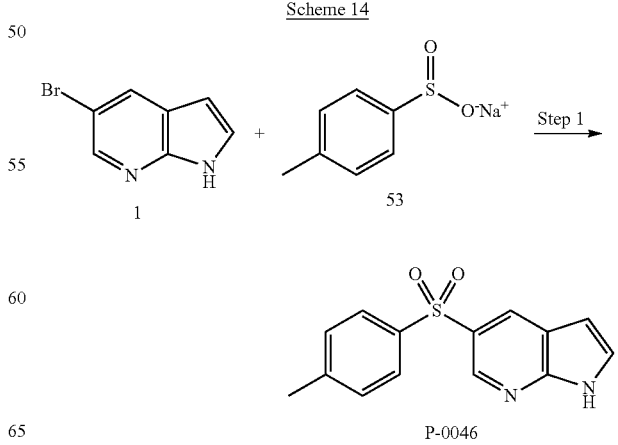

Step 1—Preparation of 5-(toluene-4-sulfonyl)-1H-pyrrolo[2,3-h]pyridine (P-0046)

5-Bromo-1H-pyrrolo[2,3-b]pyridine (1,480 mg, 2.44 mmol) and sodium p-toluene sulfinate (63, 521 mg, 2.92 mmol) were combined in a sealed tube, followed by adding copper (I) iodide (46 mg, 0.24 mmol), L-proline (56 mg, 0.49 mmol), sodium hydroxide (19.5 mg, 0.49 mmol) and dimethyl sulfoxide (7 mL, 0.1 mmol) under argon gas. The mixture was heated at 120° C. for 16 hours. Water was added and the reaction solution was extracted with ethyl acetate. The organic layer was washed with $NH_4OH/NH_4Cl$ (1:4), water, and brine, dried over anhydrous magnesium sulfate, filtrated and concentrated. The desired compound was isolated by silica gel column chromatography (ethyl acetate/hexane 100% and 20%) to give white crystal solid (P-0046, 181 mg, 27%). MS (ESI) $[M-H^+]^-=271.1$.

Example 22

Kinase Activity Assays

The effect of potential modulators of kinase activity of c-kit and other kinases can be measured in a variety of different assays known in the art, e.g., biochemical assays, cell-based assays, and in vivo testing (e.g. model system testing). Such in vitro and/or in vivo assays and tests can be used in the present invention. As an exemplary kinase assay, the kinase activity of c-kit or Fms is measured in AlphaScreening (Packard BioScience). Assays for the activity of various kinases are described, for example, in U.S. patent application Ser. No. 11/473,347 (see also, PCT publication WO2007002433), the disclosure of which is hereby incorporated by reference.

Representative compounds screened by at least one of the methods described in U.S. patent application Ser. No. 11/473,347 (PCT publication WO2007002433), or by similar methods, having $IC_{50}$ of less than 10 μM under the test conditions employed are shown in tables 1a (B-Raf), 1b (B-RafV600E), 1c (B-RafV600E/T529I), 1d (Btk), 1e (c-Raf-1), 1f (Flt1), 1g (Fms), 1h (Jnk1), 1i (Kdr), 1j (Kit), and 1k (Src).

TABLE 1a

Representative compounds with activity toward kinase B-Raf with $IC_{50} \leq 10$ μM under the test conditions employed.

| | |
|---|---|
| B-Raf | P-0009, P-0019, P-0026, P-0033, P-0034, P-0041, P-0045, P-0047 |

TABLE 1b

Representative compounds with activity toward kinase B-RafV600E with $IC_{50} \leq 10$ μM under the test conditions employed.

| | |
|---|---|
| B-RafV600E | P-0009, P-0019, P-0033, P-0034, P-0041, P-0045, P-0047 |

TABLE 1c

Representative compounds with activity toward kinase B-Raf V600E/T529I with $IC_{50} \leq 10$ μM under the test conditions employed.

| | |
|---|---|
| B-RafV600E T529I | P-0008, P-0033, P-0034, P-0039, P-0040, P-0045 |

TABLE 1d

Representative compounds with activity toward kinase Btk with $IC_{50} \leq 10$ μM under the test conditions employed.

| | |
|---|---|
| Btk: | P-0036, P-0039 |

TABLE 1e

Representative compounds with activity toward kinase c-Raf-1 with $IC_{50} \leq 10$ μM under the test conditions employed.

| | |
|---|---|
| c-Raf-1: | P-0033, P-0034 |

TABLE 1f

Representative compounds with activity toward kinase Flt1 with $IC_{50} \leq 10$ μM under the test conditions employed.

| | |
|---|---|
| Flt1: | P-0033, P-0034, P-0038, P-0040 |

TABLE 1g

Representative compounds with activity toward kinase Fms with $IC_{50} \leq 10$ μM under the test conditions employed.

| | |
|---|---|
| Fms: | P-0033, P-0035, P-0036, P-0037, P-0039, P-0040, P-0045 |

TABLE 1h

Representative compounds with activity toward kinase Jnk1 with $IC_{50} \leq 10$ μM under the test conditions employed.

| | |
|---|---|
| Jnk1: | P-0001, P-0002, P-0033, P-0040 |

TABLE 1i

Representative compounds with activity toward kinase Kdr with $IC_{50} \leq 10$ μM under the test conditions employed.

| | |
|---|---|
| Kdr: | P-0001, P-0002, P-0003, P-0014, P-0033, P-0034, P-0035, P-0036, P-0037, P-0038, P-0039, P-0040, P-0041, P-0045, P-0047 |

TABLE 1j

Representative compounds with activity toward kinase Kit with $IC_{50} \leq 10$ μM under the lest conditions employed.

| | |
|---|---|
| Kit: | P-0001, P-0002, P-0033, P-0035, P-0036, P-0037, P-0039, P-0040, P-0045 |

TABLE 1k

Representative compounds with activity toward kinase Src with $IC_{50} \leq 10$ μM under the test conditions employed.

| | |
|---|---|
| Src: | P-0033, P-0041, P-0045 |

Example 23

Efficacy of Compounds in Combination with Standard-of-Care Chemotherapeutic Agents in Four Human Cancer Cell Lines Compounds of the invention, such as compounds of Formula I, in combination with a standard chemotherapeutic agent, such as 5-fluorouracil, carboplatin, dacarbazine, gefitinib, oxaliplatin, paclitaxel, SN-38, temozolomide, or vinblastine, can be assessed for their effectiveness in killing human tumor cells. Human tumor cell lines, such as A-375 (malignant melanoma), SK-MEL-2 (malignant melanoma, skin metastasis), COLO 205 (colorectal adenocarcinoma, ascites metastasis) or SW-620 (colorectal adenocarcinoma, lymph node metastasis) can be treated with a compound of Formula I alone, or in combination with one of the above-mentioned chemotherapeutic agents.

Tumor cells are grown as a monolayer at 37° C. in a humidified atmosphere (5% $CO_2$, 95% air). Cells are grown in a suitable culture medium, e.g. RPMI 1640 (Ref BE12-702F, Cambrex, Verviers, Belgium) containing 2 mM L-glutamine and supplemented with 10% fetal bovine serum (Ref DE14-801E, Cambrex). For experimental use, the tumor cells are detached from the culture flask by a 5-minute treatment with trypsin-versene (Ref 02-007E, Cambrex), diluted in Hanks' medium without calcium or magnesium (Ref BE10-543F, Cambrex), Trypsin treatment is neutralized by culture medium addition. The cells are counted in a hemocytometer and their viability assessed by 0.25% trypan blue exclusion.

The cell lines are checked for mycoplasma contamination with the Mycotect assay kit (Ref 15672-017, Invitrogen, Cergy-Pontoise, France) in accordance with the manufacturer's instructions. The mycoplasma test is assayed from the culture supernatants of the cell lines and compared to negative and positive controls.

The tumor cells (10,000 per well) are plated in 96-well flat-bottom microtitration plates (Ref 055260, Nunc, Dutscher, Brumath, France) and incubated at 37° C. for 24 hours before treatment in 100 µl of drug-free culture medium supplemented with 10% FBS. In order to assess the $IC_{50}$ of each compound to be used for each cell line, the tumor cells are incubated in a 200 µl final volume of RPMI 1640 supplemented with 10% FBS and containing either a compound of Formula I or one of 5-fluorouracil, carboplatin, dacarbazine, gefitinib, oxaliplatin, paclitaxel, SN-38, temozolomide, or vinblastine. The compounds are tested in a suitable concentration range, such as $10^{-8}$ to $10^{-3}$ M for a compound of Formula I, 5-fluorouracil, dacarbazine or gefitinib, $10^{-9}$ to $10^{-4}$ M for carboplatin, oxaliplatin, or temozolomide, $10^{-11}$ to $10^{-6}$ M for paclitaxel or SN-38, and $10^{-11}$ to $10^{-10}$ M for vinblastine. Compounds of Formula I are dissolved in DMSO and diluted with culture medium to the desired concentrations. 5-fluorouracil (50 mg/ml, Dakota Pharm, LePlessis Robinson, France), carboplatin (10 mg/ml, Aguettant, Lyon, France), and paclitaxel (6 mg/ml, Bristol-Myers Squibb SpA, Rueil Malmaison, France), are diluted with culture medium to the desired concentrations. Dacarbazine (Sigma, Saint Quentin Fallavier, France) and vinblastine (Lilly France S. A., Saint Cloud, France) are dissolved in NaCl 0.9% and diluted with culture medium to the desired concentrations. Gefitinib is dissolved in a mixed solution of RPMI 1640 and DMSO and diluted with culture medium to the desired concentrations (maximum final DMSO of 0.1% v/v). SN-38 (LKT Laboratories, Inc., St. Paul, Minn.) is dissolved in DMSO and diluted with culture medium to the desired concentrations (maximum final DMSO of 0.1% v/v). Temozolomide (LKT Laboratories, Inc., St. Paul, Minn.) is dissolved in water for injection and diluted with culture medium to the desired concentrations. Cells are incubated for 96 hours in the presence of test substances at 37° C. under 5% $CO_2$. At the end of treatments, the cytotoxic activity is evaluated by an MTT assay.

For the MTT assay, at the end of the cells treatment, 20 µl of a 5 mg/ml solution 0.22 µm filtered tetrazolium reagent (MTT, Ref M2128, Sigma) in Phosphate Buffered Saline (PBS, Ref BE17-517Q, Cambrex), is added in each well. Culture plates are incubated for 2 h at 37° C. The resulting supernatant is removed and formazan crystals dissolved with 200 µl of DMSO per well. Absorbency (OD) is measured at 570 nm in each well using VICTOR³™ 1420 multilabeled counter (Wallac, PerkinElmer, Courtaboeuf, France).

The $IC_{50}$ for each compound on each cell line is determined from the OD measurements of each sample. The dose response inhibition of cell proliferation is expressed as:

$$IC = (OD \text{ of drug exposed cells}/OD \text{ of drug free wells}) \times 100.$$

The mean of multiple measurements for each concentration is plotted vs. the drug concentration. The dose-response curves are plotted using XLFit 3 (IDBS, United Kingdom). The $IC_{50}$ (drug concentration to obtain 50% inhibition of cell proliferation) determination values are calculated using the XLFit 3 from semi-log curves. The $IC_{51}$ value determined for each compound in each cell line is used to determine the concentration of a compound of Formula I and of the standard chemotherapeutic to be used in combination.

The cells are treated with a combination of five concentrations of a compound of Formula I and five concentrations of one of 5-fluorouracil, carboplatin, dacarbazine, gefitinib, oxaliplatin, paclitaxel, SN-38, temozolomide, or vinblastine, based on the $IC_{50}$ results. The compounds and cells are treated per the $IC_{50}$ determination described above and assayed by the MTT assay.

The results are assessed to determine whether the combination is synergistic or antagonistic. The compound interactions are calculated by multiple drug effect analysis and are performed by the median equation principle according to the methodology described by Chou and Talalay (Adv. Enzyme Regul. 1984, 22: 27-55).

The combination index (CI) will be calculated by the Chou et al. equation (Adv. Enzyme Regul. 1984, 22: 27-55, Encyclopaedia of human biology, Academic Press, 1991, 2: 371-9; Synergism and Antagonism in Chemotherapy, Academic Press, 1991, 61-102) which takes into account both the potency ($D_m$ or $IC_{50}$) and the shape of the dose-effect curve (the m value). The general equation for the CI of the two compounds is given by:

$$CI = \frac{(D)_1}{(D_x)_1} + \frac{(D)_2}{(D_x)_2} + \frac{(D)_1(D)_2}{(D_x)_1(D_x)_2}$$

where:
$(D_x)_1$ and $(D_x)_2$ in the denominators are the doses (or concentrations) for compound 1 and compound 2 alone which demonstrate x % of inhibition, whereas $(D)_1$ and $(D)_2$ in the numerators are doses of both compounds (1 and 2) in combination that also inhibit x % (iso-effective). CI<1, =1, and >1 indicate synergism, additive effect and antagonism, respectively.

The $(D_x)_1$ and $(D_x)_2$ can be calculated from the median-effect equation of Chou et al. (J. Natl. Cancer Inst. 1994, 86: 1517-24):

$$D_x = D_m \left( \frac{f_a}{(1-f_a)} \right)^{1/m}$$

where:
$D_m$ is the median-effect dose that is obtained from the anti-log of x-intercept of the median-effect plot, x=log(D) versus y=log $\{f_a/(1-f_a)\}$, or $D_m = 10^{-(y\text{-}intercept)/m}$; and m is the slope of the median-effect plot an $f_a$ is the fraction of cells affected by the treatment.
Each CI will be calculated with CalcuSyn software (Biosoft, UK) from the mean affected fraction at each drug ratio concentration.

Additional examples of certain methods contemplated by the present invention may be found in the following applications: U.S. Patent Publ. No. 2006/058339, application Ser. No. 11/154,287; U.S. Patent Publ. No. 2006/058340, application Ser. No. 11/154,988; U.S. Prov. App. No. 60/682,076, filed May 17, 2005; U.S. Prov. App. No. 60/682,058, filed May 17, 2005; U.S. Prov. App. No. 60/682,063, filed May 17, 2005; U.S. Prov. App. No. 60/682,051, filed May 17, 2005; U.S. Prov. App. No. 60/682,042, filed May 17, 2005; U.S. Prov. App. No. 60/692,750, filed Jun. 22, 2005; and U.S. Prov. App. No. 60/692,960, filed Jun. 22, 2005; U.S. Prov. App. No. 60/731,528, filed Oct. 28, 2005, U.S. patent application Ser. No. 11/435,381, filed May 16, 2006, and U.S. patent application Ser. No. 11/473,347, filed Jun. 21, 2006, each of which are hereby incorporated by reference herein in their entireties including all specifications, figures, and tables, and for all purposes.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to crystallization or co-crystallization conditions for Ret and Ret surrogate proteins and/or various kinase domain sequences can be used, Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:
1. A compound having the chemical structure of Formula I,

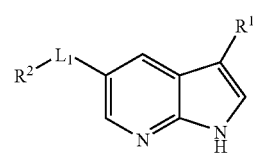

Formula I all salts, prodrugs, tautomers, stereoisomers or regioisomers thereof,
wherein:
$L_1$ is —O—, —S—, —S(O)—, or —S(O)$_2$—;
$R^1$ is -L-$R^3$;
$R^3$ is selected from the group consisting of hydrogen, provided, however, that hydrogen is not bound to any of S(O), S(O)$_2$, C(O) or C(S) of L, optionally substituted lower alkyl, optionally substituted lower alkenyl, provided, however, that when $R^3$ is optionally substituted lower alkenyl, no alkene carbon thereof is bound to N, S, O, S(O), S(O)$_2$, C(O) or C(S) of L, optionally substituted lower alkynyl, provided, however, that when $R^3$ is optionally substituted lower alkynyl, no alkyne carbon thereof is bound to N, S, O, S(O), S(O)$_2$, C(O) or C(S) of L, optionally substituted cycloalkyl, optionally substituted heterocycloalkyl, optionally substituted aryl, and optionally substituted heteroaryl;
$R^2$ is selected from the group consisting of -Cy, -alk-Cy, -alk-X-(alk)$_b$-Cy, -alk-NR$^4$-(alk)$_b$-Cy, -alk-C(X)-(alk)$_b$-Cy, -alk-S(O)-(alk)$_b$-Cy, -alk-S(O)$_2$-(alk)$_b$-Cy, -alk-OC(X)-(alk)$_b$-Cy, -alk-C(X)O-(alk)$_b$-Cy, -alk-C (X)NR⁴-(alk)_b-Cy, -alk-S(O)₂NR⁴-(alk)_b-Cy, -alk-NR⁴C(X)-(alk)_b-Cy, -alk-NR⁴S(O)₂-(alk)_b-Cy, -alk-NR⁴C(X)O-(alk)_b-Cy, -alk-OC(X)NR⁴-(alk)_b-Cy, -alk-NR⁴C(X)NR⁴-(alk)_b-Cy, -alk-NR⁴S(O)₂NR⁴-(alk)_b-Cy, and $C_{2-4}$ alkyl, wherein $C_{2-4}$ alkyl is optionally substituted with one or more substituents selected from the group consisting of fluoro, —OH, —NH₂, lower alkoxy, fluoro substituted lower alkoxy, lower alkylthio, fluoro substituted lower alkylthio, mono-alkylamino, and di-alkylamino;

L at each occurrence is independently selected from the group consisting of optionally substituted methylene, -(alk)_a-X-(alk)_b-, -(alk)_a-NR⁴-(alk)_b-, -(alk)_a-C(X)-(alk)_b-, -(alk)_a-S(O)-(alk)_b-, -(alk)_a-S(O)₂-(alk)_b-, -(alk)_a-OC(X)-(alk)_b-, -(alk)_a-C(X)O-(alk)_b-, -(alk)_a-C(X)NR⁴-(alk)_b-, -(alk)_a-S(O)₂NR⁴-(alk)_b-, -(alk)_a-NR⁴S(O)₂-(alk)_b-, -(alk)_a-NR⁴C(X)O-(alk)_b-, -(alk)_a-OC(X)NR⁴-(alk)_b-, -(alk)_a-NR⁴C(X)NR⁴-(alk)_b-, and -(alk)_a-NR⁴S(O)₂NR⁴-(alk)_b-;

a and b are independently 0 or 1;

alk is $C_{1-3}$ alkylene or $C_{1-3}$ alkylene substituted with one or more substituents selected from the group consisting of fluoro, —OH, —NH₂, lower alkyl, lower alkoxy, lower alkylthio, mono-alkylamino, di-alkylamino, and —NR⁵R⁶, wherein lower alkyl or the alkyl chain(s) of lower alkoxy, lower alkylthio, mono-alkylamino or di-alkylamino are optionally substituted with one or more substituents selected from the group consisting of fluoro, —OH, —NH₂, lower alkoxy, fluoro substituted lower alkoxy, lower alkylthio, fluoro substituted lower alkylthio, mono-alkylamino, di-alkylamino and cycloalkylamino, provided, however, that any substitution of the alkyl chain carbon bound to O of alkoxy, S of thioalkyl or N of mono- or di-alkylamino is fluoro;

X is O or S;

Cy is optionally substituted cycloalkyl, optionally substituted heterocycloalkyl, optionally substituted aryl, or optionally substituted heteroaryl;

R⁴ at each occurrence is independently selected from the group consisting of hydrogen, optionally substituted lower alkyl, optionally substituted cycloalkyl, optionally substituted heterocycloalkyl, optionally substituted aryl, and optionally substituted heteroaryl; and R⁵ and R⁶ combine with the nitrogen to which they are attached to form a 5-7 membered heterocycloalkyl optionally substituted with one or more substituents selected from the group consisting of fluoro, —OH, —NH₂, lower alkyl, fluoro substituted lower alkyl, lower alkoxy, fluoro substituted lower alkoxy, lower alkylthio, and fluoro substituted lower alkylthio; provided, however, that the compound is not

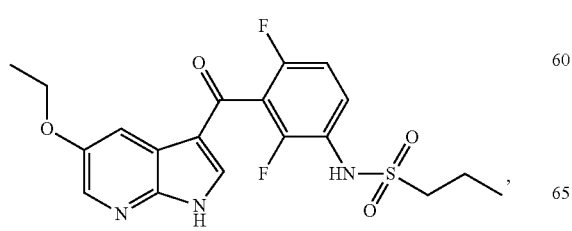

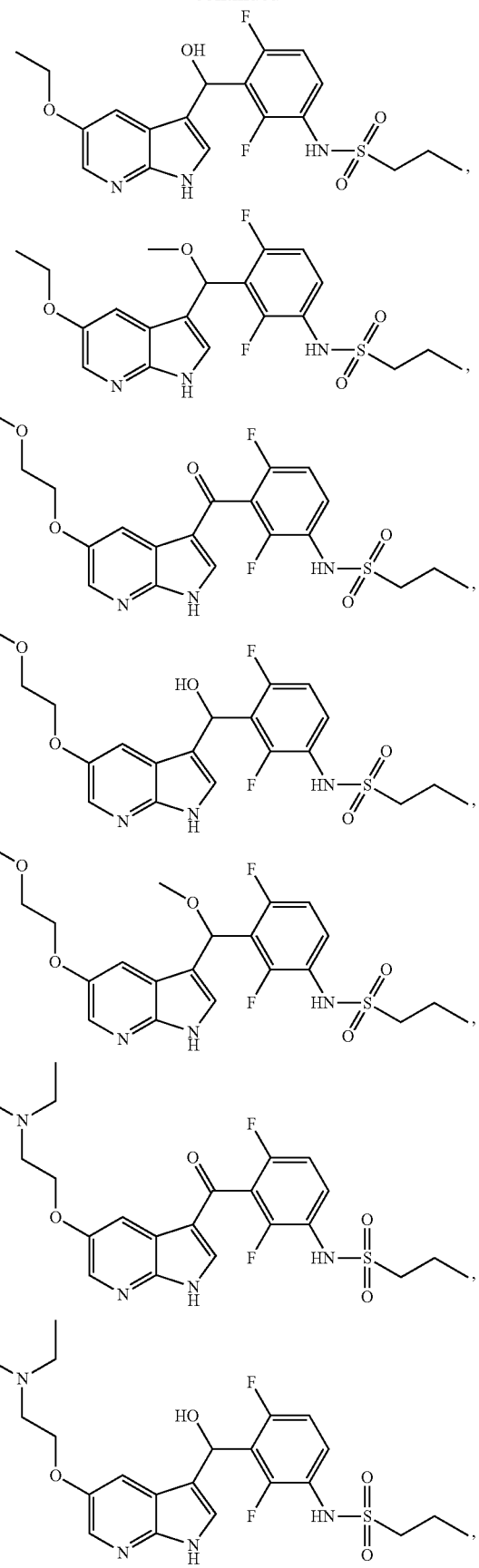

121
-continued
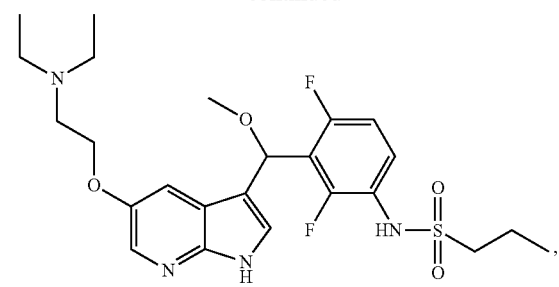
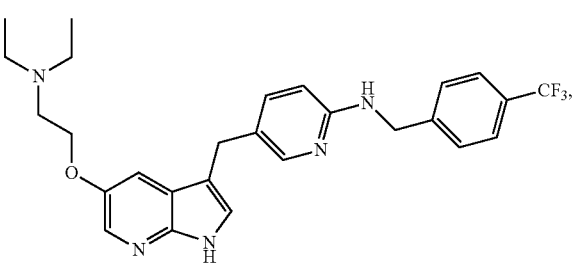
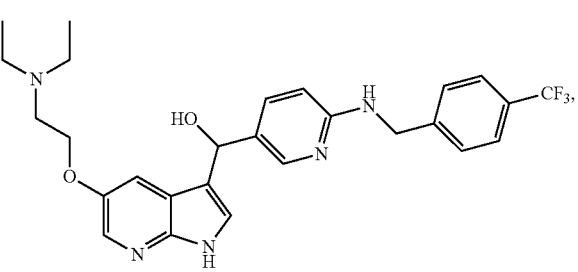
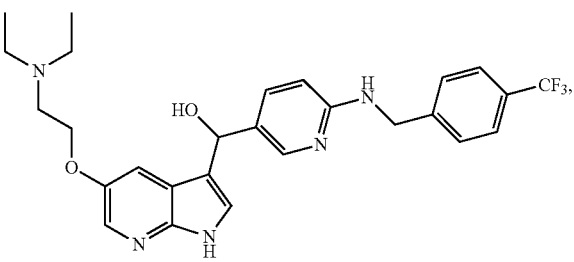
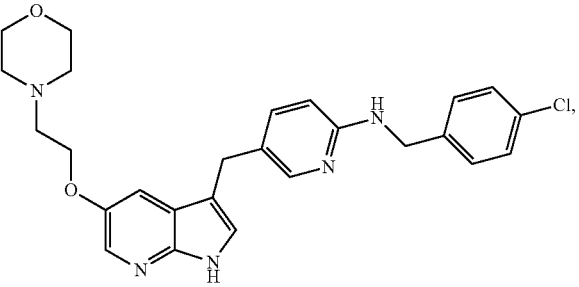
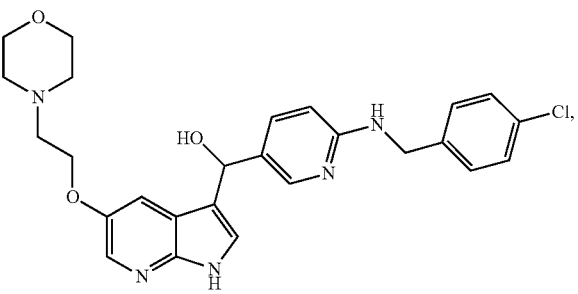
122
-continued
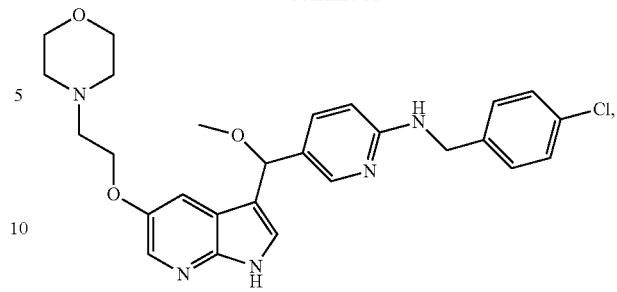
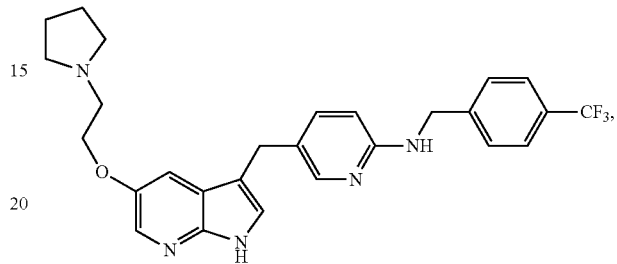
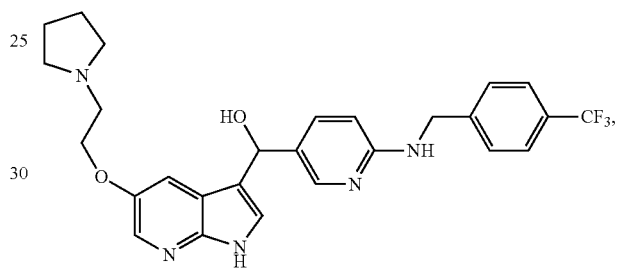
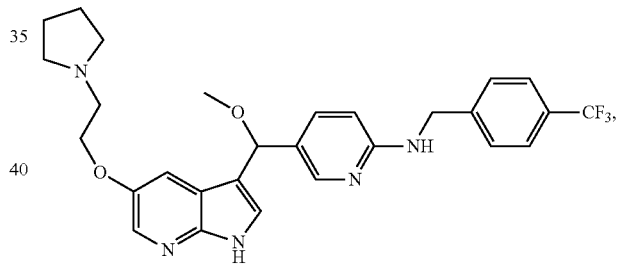
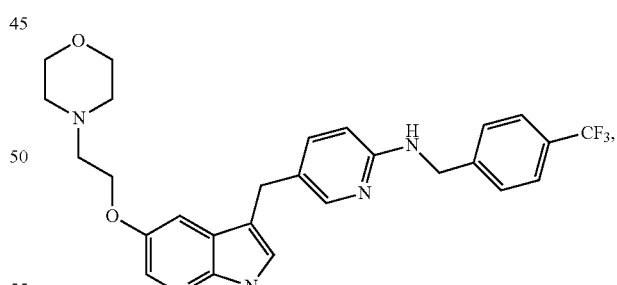
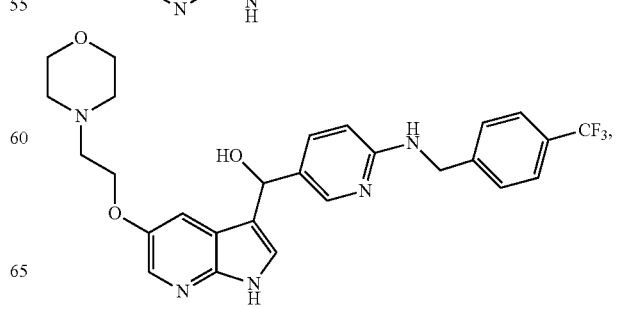

123
-continued
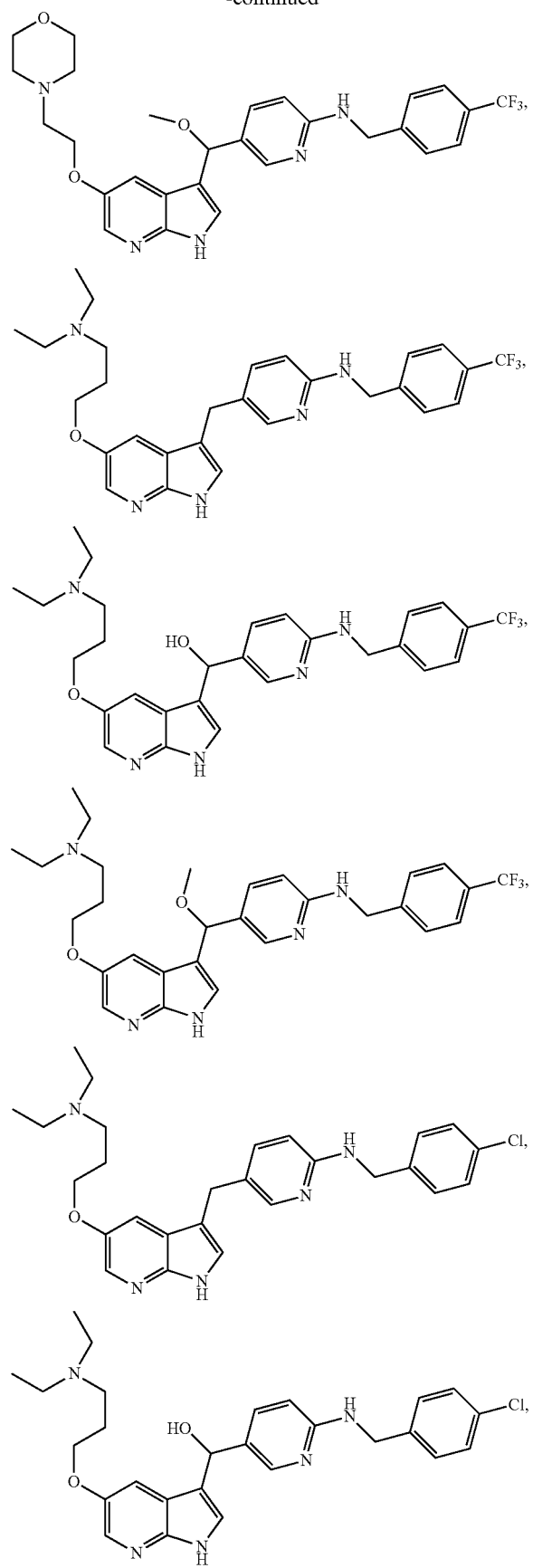
124
-continued
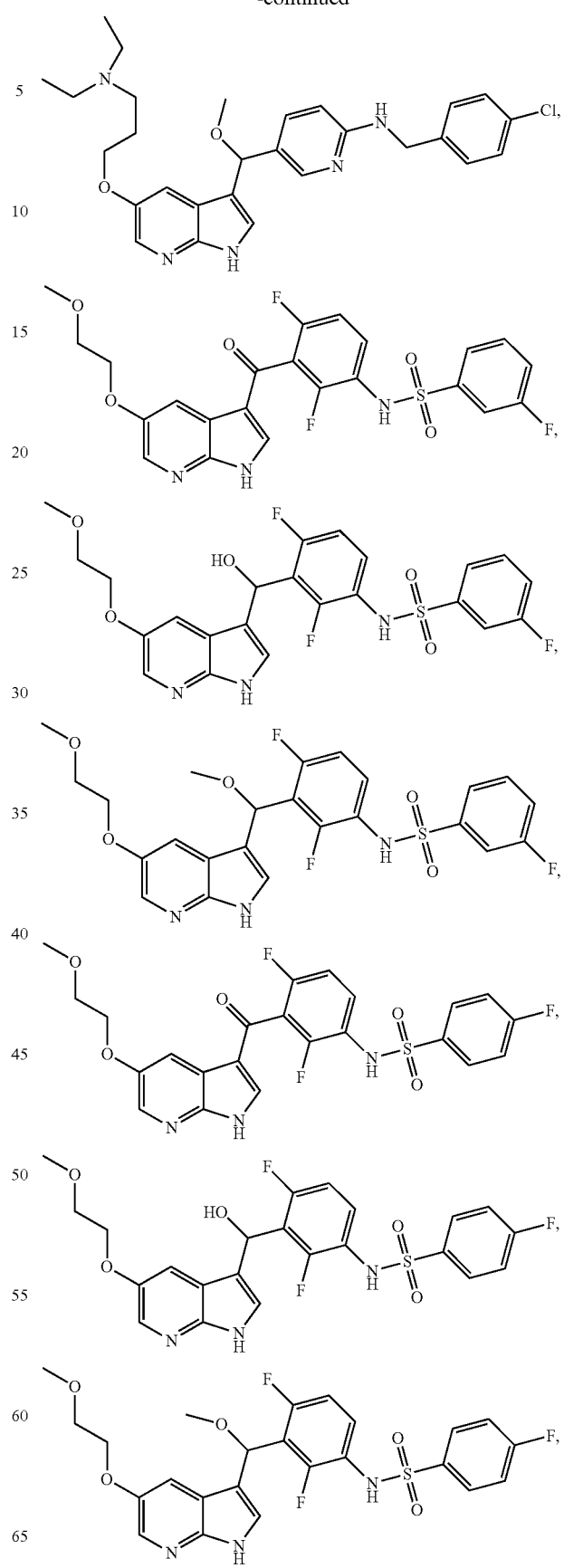

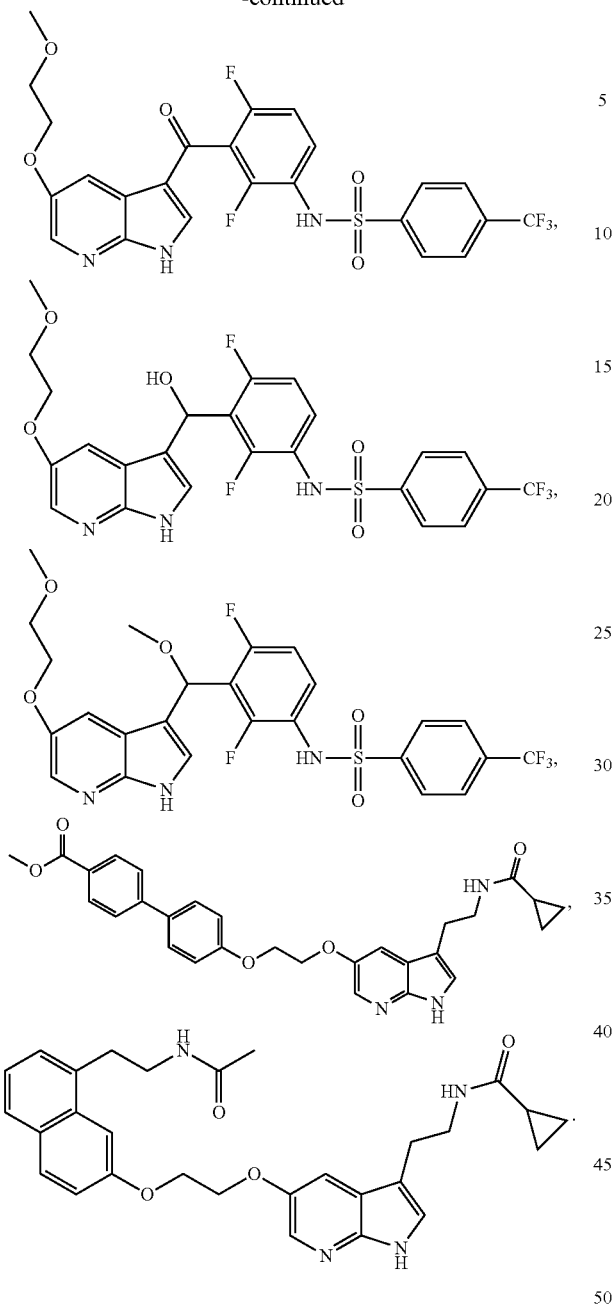

2. The compound of claim 1 having the chemical structure of Formula Ij,

Formula Ij

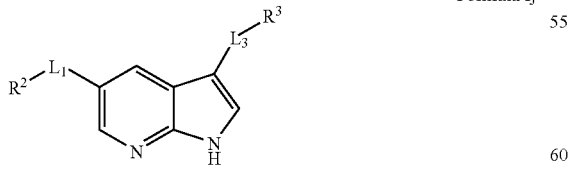

all salts, prodrugs, tautomers stereoisomers or regioisomers thereof,
wherein:
$L_3$ is selected from the group consisting of —O—, —S—, —$CR^aR^b$—, —$NR^4$—, —C(O)—, —C(S)—, —S(O)—, and —$S(O)_2$—; and $R^a$ and $R^b$ at each occurrence are independently selected from the group consisting of hydrogen, fluoro, —OH, —$NH_2$, lower alkyl, lower alkoxy, lower alkylthio, mono-alkylamino, di-alkylamino, and —$NR^5R^6$, wherein the alkyl chain(s) of lower alkyl, lower alkoxy, lower alkylthio, mono-alkylamino, or di-alkylamino are optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl chain carbon bound to O of alkoxy, S of thioalkyl or N of mono- or di-alkylamino is fluoro; or $R^a$ and $R^b$ combine to form a 3-7 membered monocyclic cycloalkyl or 5-7 membered monocyclic heterocycloalkyl, wherein the monocyclic cycloalkyl or monocyclic heterocycloalkyl are optionally substituted with one or more substituents selected from the group consisting of halogen, —OH, —$NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino.

3. The compound of claim 1 having the chemical structure of Formula Ip,

Formula Ip

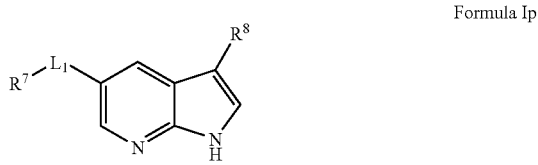

all salts, prodrugs, tautomers, stereoisomers or regioisomers thereof,
wherein:
$R^7$ is selected from the group consisting of -$Cy_1$, -alk-$Cy_1$, -alk-X-(alk)$_b$-$Cy_1$, -alk-$NR^{12}$-(alk)$_b$-$Cy_1$, -alk-C(X)-(alk)$_b$-$Cy_1$, -alk-S(O)-(alk)$_b$-$Cy_1$, alk-$S(O)_2$-(alk)$_b$-$Cy_1$, -alk-OC(X)-(alk)$_b$-$Cy_1$, -alk-C(X)O-(alk)$_b$-$Cy_1$, -alk-C(X)$NR^{12}$-(alk)$_b$-$Cy_1$, -alk-$S(O)_2NR^{12}$-(alk)$_b$-$Cy_1$, -alk-$NR^{12}$C(X)-(alk)$_b$-$Cy_1$, -alk-$NR^{12}S(O)_2$-(alk)$_b$-$Cy_1$, -alk-$NR^{12}$C(X)O-(alk)$_b$-$Cy_1$, -alk-OC(X)$NR^{12}$-(alk)$_b$-$Cy_1$, -alk-$NR^{12}$C(X)$NR^{12}$-(alk)$_b$-$Cy_1$, -alk-$NR^{12}S(O)_2NR^{12}$-(alk)$_b$-$Cy_1$, and $C_{2-4}$ alkyl, wherein $C_{2-4}$ alkyl is optionally substituted with one or more substituents selected from the group consisting of fluoro, —OH, —$NH_2$, lower alkoxy, fluoro substituted lower alkoxy, lower alkylthio, fluoro substituted lower alkylthio, mono-alkylamino, and di-alkylamino;

$R^8$ is selected from the group consisting of —$OR^9$, —$SR^9$, —$CR^{10}R^{11}R^9$, —$NR^{12}R^9$, —$C(O)R^9$, —$C(S)R^9$, —$S(O)R^9$, and —$S(O)_2R^9$;

$R^9$ is selected from the group consisting of lower alkyl, lower alkenyl, lower alkynyl, cycloalkyl, heterocycloalkyl, aryl, and heteroaryl, wherein lower alkyl, lower alkenyl, and lower alkynyl are optionally substituted with one or more substituents selected from the group consisting of fluoro, —OH, —$NH_2$, —C(O)OH, —$C(O)NH_2$, —$OR^{13}$, —$SR^{13}$, —$NR^{12}R^{13}$, —$C(O)OR^{13}$, —$C(O)NR^{12}R^{13}$, cycloalkyl, heterocycloalkyl, aryl, and heteroaryl, and wherein cycloalkyl, heterocycloalkyl, aryl, and heteroaryl as $R^9$, or a substituent of lower alkyl, lower alkenyl, or lower alkynyl are optionally substituted with one or more substituents selected from the group consisting of —OH, —NH$_2$, —CN, —NO$_2$, —C(O)OH, —S(O)$_2$NH$_2$, —C(O)NH$_2$, —C(S)NH$_2$, —NHC(O)NH$_2$, —NHC(S)NH$_2$, —NHS(O)$_2$NH$_2$, —OR$^{13}$, —SR$^{13}$, —NR$^{12}$R$^{13}$, —C(O)R$^{13}$, —C(S)R$^{13}$, —C(O)OR$^{13}$, —C(O)NR$^{12}$R$^{13}$, —C(S)NR$^{12}$R$^{13}$, —S(O)$_2$NR$^{12}$R$^{13}$, —NR$^{12}$C(O)R$^{13}$, —NR$^{12}$C(S)R$^{13}$, —NR$^{12}$S(O)$_2$R$^{13}$, —NR$^{12}$C(O)NR$^{12}$R$^{13}$, —NR$^{12}$C(S)NR$^{12}$R$^{13}$, —NR$^{12}$S(O)$_2$NR$^{12}$R$^{13}$, —S(O)R$^{13}$, —S(O)$_2$R$^{13}$, halogen, lower alkyl, fluoro substituted lower alkyl, and cycloalkylamino;

$Cy_1$ is cycloalkyl, heterocycloalkyl, aryl or heteroaryl, wherein cycloalkyl, heterocycloalkyl, aryl, and heteroaryl are optionally substituted with one or more substituents selected from the group consisting of —OH, —NH$_2$, —CN, —NO$_2$, —C(O)OH, —S(O)$_2$NH$_2$, —C(O)NH$_2$, —C(S)NH$_2$, —NHC(O)NH$_2$, —NHC(S)NH$_2$, —NHS(O)$_2$NH$_2$, —OR$^{13}$, —SR$^{13}$, —NR$^{12}$R$^{13}$, —C(O)R$^{13}$, —C(S)R$^{13}$, —C(O)OR$^{13}$, —C(O)NR$^{12}$R$^{13}$, —C(S)NR$^{12}$R$^{13}$, —S(O)$_2$NR$^{12}$R$^{13}$, —NR$^{12}$C(O)R$^{13}$, —NR$^{12}$C(S)R$^{13}$, —NR$^{12}$S(O)$_2$R$^{13}$, —NR$^{12}$C(O)NR$^{12}$R$^{13}$, —NR$^{12}$C(S)NR$^{12}$R$^{13}$, —NR$^{12}$S(O)$_2$NR$^{12}$R$^{13}$, —S(O)R$^{13}$, —S(O)$_2$R$^{13}$, halogen, lower alkyl, fluoro substituted lower alkyl, and cycloalkylamino;

$R^{10}$ and $R^{11}$ are independently selected from the group consisting of hydrogen, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; or $R^{10}$ and $R^{11}$ combine to form a 3-7 membered monocyclic cycloalkyl or 5-7 membered monocyclic heterocycloalkyl, wherein the monocyclic cycloalkyl or monocyclic heterocycloalkyl is optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^{12}$ at each occurrence is independently hydrogen, lower alkyl or fluoro substituted lower alkyl;

$R^{13}$ at each occurrence is independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, provided, however, that any substitution of the alkyl carbon bound to O, S, or N of —OR$^{13}$, —SR$^{13}$, —NR$^{12}$R$^{13}$, —C(O)OR$^{13}$, —C(O)NR$^{12}$R$^{13}$, or —S(O)$_2$NR$^{12}$R$^{13}$ is fluoro, cycloalkyl, heterocycloalkyl, aryl or heteroaryl, and wherein cycloalkyl, heterocycloalkyl, aryl, and heteroaryl as $R^{13}$ or as substituents of lower alkyl are optionally substituted with one or more substituents selected from the group consisting of —OH, —NH$_2$, —CN, —NO$_2$, —C(O)OH, —S(O)$_2$NH$_2$, —C(O)NH$_2$, —OR$^{14}$, —SR$^{14}$, —NR$^{12}$R$^{14}$, —NR$^{12}$C(O)R$^{14}$, —NR$^{12}$S(O)$_2$R$^{14}$, —S(O)$_2$R$^{14}$, —C(O)R$^{14}$, —C(O)OR$^{14}$, —C(O)NR$^{12}$R$^{14}$, —S(O)$_2$NR$^{12}$R$^{14}$, halogen, lower alkyl, fluoro substituted lower alkyl, and cycloalkylamino; and $R^{14}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl carbon bound to O, S, or N of —OR$^{14}$, —SR$^{14}$, —NR$^{12}$R$^{14}$, —C(O)OR$^{14}$, —C(O)NR$^{12}$R$^{14}$, or —S(O)$_2$NR$^{12}$R$^{14}$ is fluoro, and wherein heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy.

4. The compound of claim 3 wherein:

$R^7$ is selected from the group consisting of -Cy$_1$, -alk-Cy$_1$, -alk-X-(alk)$_b$-Cy$_1$, -alk-NR$^{12}$-(alk)$_b$-Cy$_1$, -alk-C(X)-(alk)$_b$-Cy$_1$, -alk-S(O)-(alk)$_b$-Cy$_1$, -alk-S(O)$_2$-(alk)$_b$-Cy$_1$, -alk-OC(X)-(alk)$_b$-Cy$_1$, -alk-C(X)O-(alk)$_b$-Cy$_1$, -alk-C(X)NR$^{12}$-(alk)$_b$-Cy$_1$, -alk-S(O)$_2$NR$^{12}$-(alk)$_b$-Cy$_1$, -alk-NR$^{12}$C(X)-(alk)$_b$-Cy$_1$, -alk-NR$^{12}$S(O)$_2$-(alk)$_b$-Cy$_1$, -alk-NR$^{12}$C(X)O-(alk)$_b$-Cy$_1$, -alk-OC(X)NR$^{12}$-(alk)$_b$-Cy$_1$, -alk-NR$^{12}$C(X)NR$^{12}$-(alk)$_b$-Cy$_1$, and -alk-NR$^{12}$S(O)$_2$NR$^{12}$-(alk)$_b$-Cy$_1$;

$R^8$ is selected from the group consisting of —OR$^9$, —SR$^9$, —CR$^{10}$R$^{11}$R$^9$, —NR$^{12}$R$^9$, —C(O)R$^9$, —C(S)R$^9$, —S(O)R$^9$, and —S(O)$_2$R$^9$; and $R^9$ is aryl or heteroaryl, wherein aryl or heteroaryl are optionally substituted with one or more substituents selected from the group consisting of —OH, —NH$_2$, —CN, —NO$_2$, —C(O)OH, —S(O)$_2$NH$_2$, —C(O)NH$_2$, —C(S)NH$_2$, —NHC(O)NH$_2$, —NHC(S)NH$_2$, —NHS(O)$_2$NH$_2$, —OR$^{13}$, —SR$^{13}$, —NR$^{12}$R$^{13}$, —C(O)R$^{13}$, —C(S)R$^{13}$, —C(O)OR$^{13}$, —C(O)NR$^{12}$R$^{13}$, —C(S)NR$^{12}$R$^{13}$, —S(O)$_2$NR$^{12}$R$^{13}$, —NR$^{12}$C(O)R$^{13}$, —NR$^{12}$C(S)R$^{13}$, —NR$^{12}$S(O)$_2$R$^{13}$, —NR$^{12}$C(O)NR$^{12}$R$^{13}$, —NR$^{12}$C(S)NR$^{12}$R$^{13}$, —NR$^{12}$S(O)$_2$NR$^{12}$R$^{13}$, —S(O)R$^{13}$, —S(O)$_2$R$^{13}$, halogen, lower alkyl, fluoro substituted lower alkyl, and cycloalkylamino.

5. The compound of claim 4 wherein $R^7$ is -Cy$_1$ or -alk-Cy$_1$.

6. The compound of claim 5 wherein:

$Cy_1$ is cycloalkyl, heterocycloalkyl, aryl or heteroaryl, wherein cycloalkyl, heterocycloalkyl, aryl or heteroaryl are optionally substituted with one or more substituents selected from the group consisting of —OH, —NH$_2$, —CN, —NO$_2$, —S(O)$_2$NH$_2$, —C(O)NH$_2$, —OR$^{13}$, —NR$^{12}$R$^{13}$, —C(O)R$^{13}$, —C(O)NR$^{12}$R$^{13}$, —S(O)$_2$NR$^{12}$R$^{13}$, —NR$^{12}$C(O)R$^{13}$, —NR$^{12}$S(O)$_2$R$^{13}$, —S(O)$_2$R$^{13}$, halogen, lower alkyl, fluoro substituted lower alkyl, and cycloalkylamino; and $R^9$ is aryl or heteroaryl, wherein aryl and heteroaryl are optionally substituted with one or more substituents selected from the group consisting of —OH, —NH$_2$, —CN, —NO$_2$, —S(O)$_2$NH$_2$, —C(O)NH$_2$, —NHC(O)NH$_2$, —NHS(O)$_2$NH$_2$, —OR$^{13}$, —SR$^{13}$, —NR$^{12}$R$^{13}$, —C(O)R$^{13}$, —C(O)NR$^{12}$R$^{13}$, —S(O)$_2$NR$^{12}$R$^{13}$, —NR$^{12}$C(O)R$^{13}$, —NR$^{12}$S(O)$_2$R$^{13}$, —NR$^{12}$C(O)NR$^{12}$R$^{13}$, —NR$^{12}$S(O)$_2$NR$^{12}$R$^{13}$, —S(O)$_2$R$^{13}$, halogen, lower alkyl, fluoro substituted lower alkyl, and cycloalkylamino.

7. A composition comprising: a pharmaceutically acceptable carrier; and a compound according to claim 1.

8. A kit comprising a compound according to claim 1.

9. A compound having the chemical structure of Formula I,

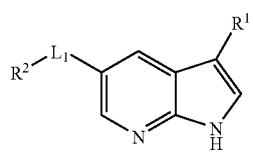

Formula I all salts, prodrugs, tautomers, stereoisomers or regioisomers thereof, wherein:

L$_1$ is —O—, —S(O)—, or —S(O)$_2$—;

R$^1$ is hydrogen;

R$^3$ is selected from the group consisting of hydrogen, provided, however, that hydrogen is not bound to any of S(O), S(O)$_2$, C(O) or C(S) of L, optionally substituted lower alkyl, optionally substituted lower alkenyl, provided, however, that when R$^3$ is optionally substituted lower alkenyl, no alkene carbon thereof is bound to N, S, O, S(O), S(O)$_2$, C(O) or C(S) of L, optionally substituted lower alkynyl, provided, however, that when R$^3$ is optionally substituted lower alkynyl, no alkyne carbon thereof is bound to N, S, O, S(O), S(O)$_2$, C(O) or C(S) of L, optionally substituted cycloalkyl, optionally substituted heterocycloalkyl, optionally substituted aryl, and optionally substituted heteroaryl;

R$^2$ is selected from the group consisting of -Cy, -alk-Cy, -alk-X-(alk)$_b$-Cy, -alk-NR$^4$-(alk)$_b$-Cy, -alk-C(X)-(alk)$_b$-Cy, -alk-S(O)-(alk)$_b$-Cy, -alk-S(O)$_2$-(alk)$_b$-Cy, -alk-OC(X)-(alk)$_b$-Cy, -alk-C(X)O-(alk)$_b$-Cy, -alk-C(X)NR$^4$-(alk)$_b$-Cy, -alk-S(O)$_2$NR$^4$-(alk)$_b$-Cy, -alk-NR$^4$C(X)-(alk)$_b$-Cy, -alk-NR$^4$S(O)$_2$-(alk)$_b$-Cy, -alk-NR$^4$C(X)O-(alk)$_b$-Cy, -alk-OC(X)NR$^4$-(alk)$_b$-Cy, -alk-NR$^4$C(X)NR$^4$-(alk)$_b$-Cy, -alk-NR$^4$S(O)$_2$NR$^4$-(alk)$_b$-Cy, and C$_{2-4}$ alkyl, wherein C$_{2-4}$ alkyl is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, and di-alkylamino;

L at each occurrence is independently selected from the group consisting of optionally substituted methylene, -(alk)$_a$-X-(alk)$_b$-, -(alk)$_a$-NR$^4$-(alk)$_b$-, -(alk)$_a$-C(X)-(alk)$_b$-, -(alk)$_a$-S(O)-(alk)$_b$-, -(alk)$_a$-S(O)$_2$-(alk)$_b$-, -(alk)$_a$-OC(X)-(alk)$_b$-, -(alk)$_a$-C(X)O-(alk)$_b$-, -(alk)$_a$-C(X)NR$^4$-(alk)$_b$-, -(alk)$_a$-S(O)$_2$NR$^4$-(alk)$_b$-, -(alk)$_a$-NR$^4$C(X)-(alk)$_b$-, -(alk)$_a$-NR$^4$S(O)$_2$-(alk)$_b$-, -(alk)$_a$-NR$^4$C(X)O-(alk)$_b$-, -(alk)$_a$-OC(X)NR$^4$-(alk)$_b$-, -(alk)$_a$-NR$^4$C(X)NR$^4$-(alk)$_b$-, and -(alk)$_a$-NR$^4$S(O)$_2$NR$^4$-(alk)$_b$-;

a and b are independently 0 or 1;

alk is C$_{1-3}$ alkylene or C$_{1-3}$ alkylene substituted with one or more substituents selected from the group consisting of fluoro, —OH, —NH$_2$, lower alkyl, lower alkoxy, lower alkylthio, mono-alkylamino, di-alkylamino, and —NR$^5$R$^6$, wherein lower alkyl or the alkyl chain(s) of lower alkoxy, lower alkylthio, mono-alkylamino or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino and cycloalkylamino, provided, however, that any substitution of the alkyl chain carbon bound to O of alkoxy, S of thioalkyl or N of mono- or di-alkylamino is fluoro;

X is O or S;

Cy is optionally substituted cycloalkyl, optionally substituted heterocycloalkyl, substituted aryl, or optionally substituted heteroaryl;

R$^4$ at each occurrence is independently selected from the group consisting of hydrogen, optionally substituted lower alkyl, optionally substituted cycloalkyl, optionally substituted heterocycloalkyl, optionally substituted aryl, and optionally substituted heteroaryl; and R$^5$ and R$^6$ combine with the nitrogen to which they are attached to form a 5-7 membered heterocycloalkyl optionally substituted with one or more substituents selected from the group consisting of fluoro, —OH, —NH$_2$, lower alkyl, fluoro substituted lower alkyl, lower alkoxy, fluoro substituted lower alkoxy, lower alkylthio, and fluoro substituted lower alkylthio; provided, however, that the compound is not

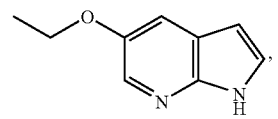
,

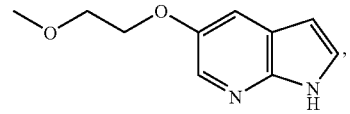
,

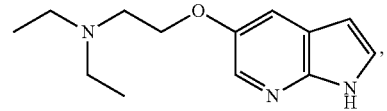
,

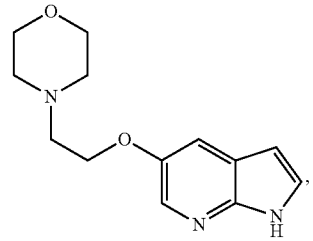
,

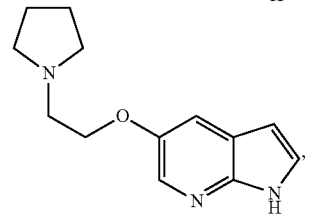
,

131
-continued
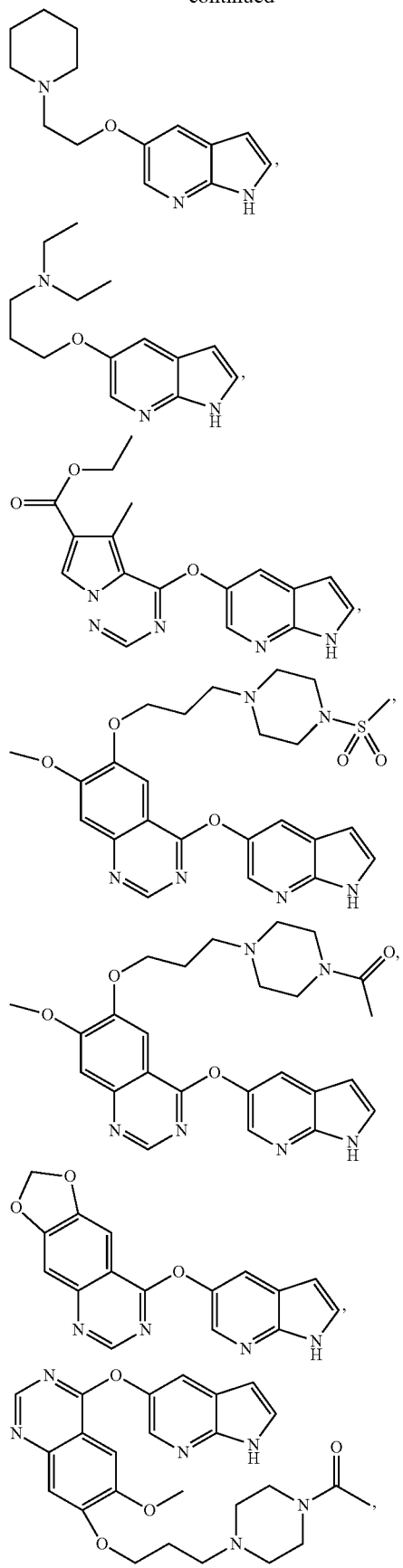
132
-continued
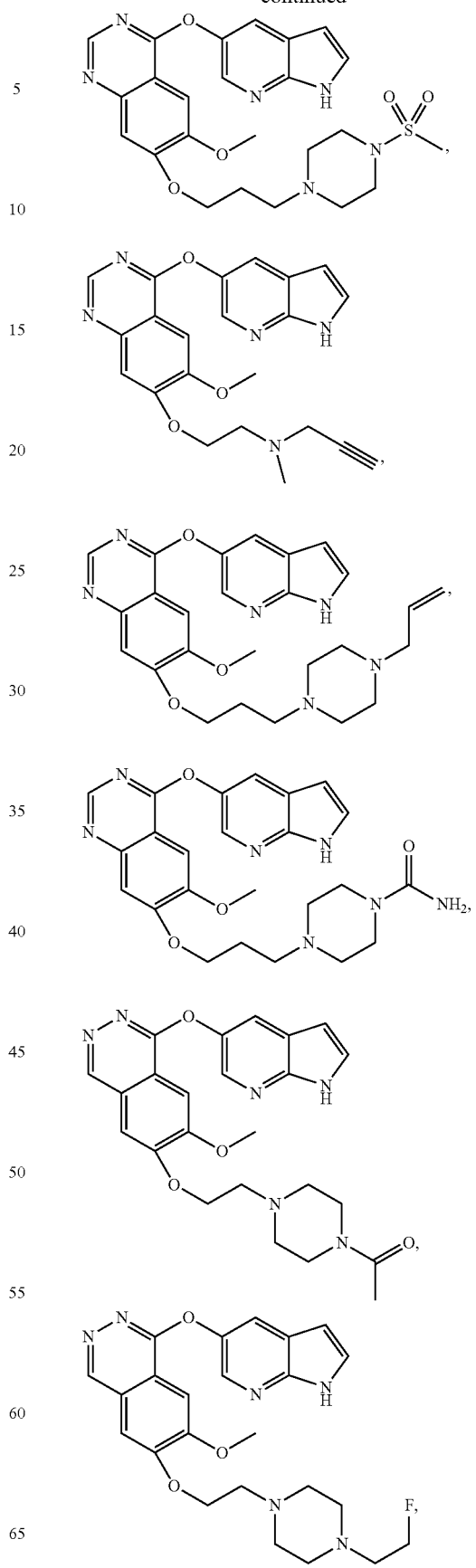

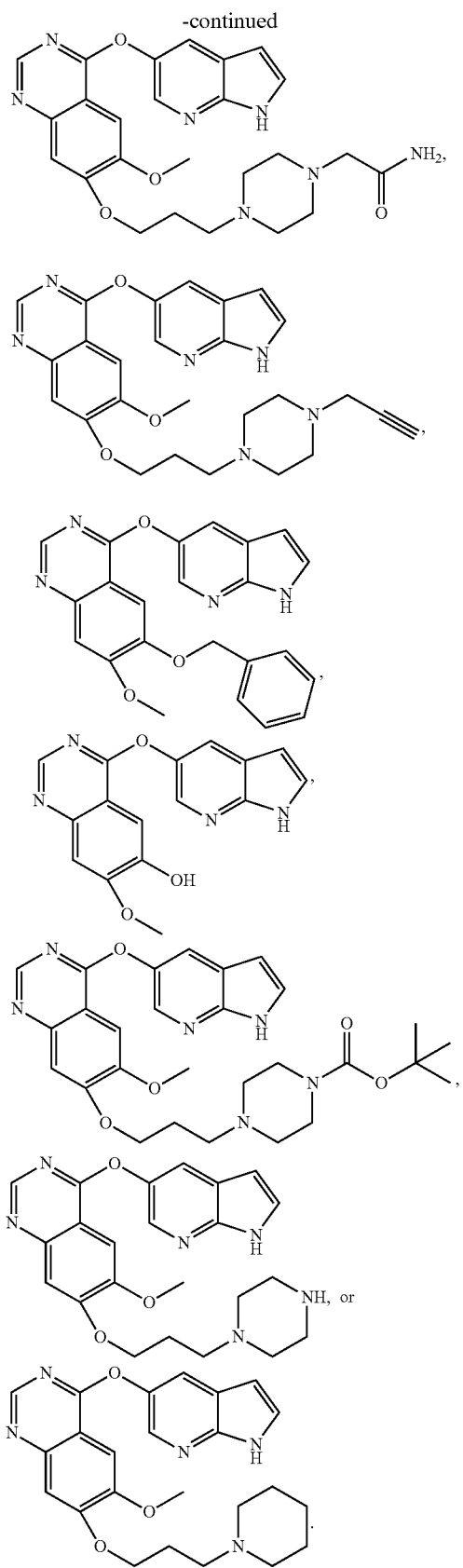

10. The compound of claim 9 having the chemical structure of Formula Ip,

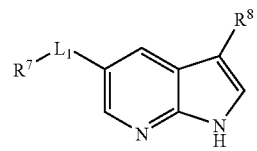

Formula Ip all salts, prodrugs, tautomers, stereoisomers or regioisomers thereof, wherein:

$R^7$ is selected from the group consisting of -Cy$_1$, -alk-Cy$_1$, -alk-X-(alk)$_b$-Cy$_1$, -alk-NR$^{12}$-(alk)$_b$-Cy$_1$, -alk-C(X)-(alk)$_b$-Cy$_1$, -alk-S(O)-(alk)$_b$-Cy$_1$, -alk-S(O)$_2$-(alk)$_b$-Cy$_1$, -alk-OC(X)-(alk)$_b$-Cy$_1$, -alk-C(X)O-(alk)$_b$-Cy$_1$, -alk-C(X)NR$^{12}$-(alk)$_b$-Cy$_1$, -alk-S(O)$_2$NR$^{12}$-(alk)$_b$-Cy$_1$, -alk-NR$^{12}$C(X)-(alk)$_b$-Cy$_1$, -alk-NR$^{12}$S(O)$_2$-(alk)$_b$-Cy$_1$, -alk-NR$^{12}$C(X)O-(alk)$_b$-Cy$_1$, -alk-OC(X)NR$^{12}$-(alk)$_b$-Cy$_1$, -alk-NR$^{12}$C(X)NR$^{12}$-(alk)$_b$-Cy$_1$, -alk-NR$^{12}$S(O)$_2$NR$^{12}$-(alk)$_b$-Cy$_1$, and C$_{2-4}$ alkyl, wherein C$_{2-4}$ alkyl is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, and di-alkylamino;

$R^8$ is selected from the group consisting of hydrogen;

$R^9$ is selected from the group consisting of lower alkyl, lower alkenyl, lower alkynyl, cycloalkyl, heterocycloalkyl, aryl, and heteroaryl, wherein lower alkyl, lower alkenyl, and lower alkynyl are optionally substituted with one or more substituents selected from the group consisting of fluoro, —OH, —NH$_2$, —C(O)OH, —C(O)NH$_2$, —OR$^{13}$, —SR$^{13}$, —NR$^{12}$R$^{13}$, —C(O)OR$^{13}$, —C(O)NR$^{12}$R$^{13}$, cycloalkyl, heterocycloalkyl, aryl, and heteroaryl, and wherein cycloalkyl, heterocycloalkyl, aryl, and heteroaryl as $R^9$, or a substituent of lower alkyl, lower alkenyl, or lower alkynyl are optionally substituted with one or more substituents selected from the group consisting of —OH, —NH$_2$, —CN, —NO$_2$, —C(O)OH, —S(O)$_2$NH$_2$, —C(O)NH$_2$, —C(S)NH$_2$, —NHC(O)NH$_2$, —NHC(S)NH$_2$, —NHS(O)$_2$NH$_2$, —OR$^{13}$, —SR$^{13}$, —NR$^{12}$R$^{13}$, —C(O)R$^{13}$, —C(S)R$^{13}$, —C(O)OR$^{13}$, —C(O)NR$^{12}$R$^{13}$, —C(S)NR$^{12}$R$^{13}$, —S(O)$_2$NR$^{12}$R$^{13}$, —NR$^{12}$C(O)R$^{13}$, —NR$^{12}$C(S)R$^{13}$, —NR$^{12}$S(O)$_2$R$^{13}$, —NR$^{12}$C(O)NR$^{12}$R$^{13}$, —NR$^{12}$C(S)NR$^{12}$R$^{13}$, —NR$^{12}$S(O)$_2$NR$^{12}$R$^{13}$, —S(O)R$^{13}$, —S(O)$_2$R$^{13}$, halogen, lower alkyl, fluoro substituted lower alkyl, and cycloalkylamino;

Cy$_1$ is cycloalkyl, heterocycloalkyl, aryl or heteroaryl, wherein (i) cycloalkyl, heterocycloalkyl, and heteroaryl are optionally substituted with one or more substituents selected from the group consisting of —OH, —NH$_2$, —CN, —NO$_2$, —C(O)OH, —S(O)$_2$NH$_2$, —C(O)NH$_2$, —C(S)NH$_2$, —NHC(O)NH$_2$, —NHC(S)NH$_2$, —NHS(O)$_2$NH$_2$, —OR$^{13}$, —SR$^{13}$, —NR$^{12}$R$^{13}$, —C(O)R$^{13}$, —C(S)R$^{13}$, —C(O)OR$^{13}$, —C(O)NR$^{12}$R$^{13}$, —C(S)NR$^{12}$R$^{13}$, —S(O)$_2$NR$^{12}$R$^{13}$, —NR$^{12}$C(O)R$^{13}$, —NR$^{12}$C(S)R$^{13}$, —NR$^{12}$S(O)$_2$R$^{13}$, —NR$^{12}$C(O)NR$^{12}$R$^{13}$, —NR$^{12}$C(S)NR$^{12}$R$^{13}$, —NR$^{12}$S(O)$_2$NR$^{12}$R$^{13}$, —S(O)R$^{13}$, —S(O)$_2$R$^{13}$, halogen, lower alkyl, fluoro substituted lower alkyl, and cycloalkylamino; and (ii) aryl of Cy$_1$ is substituted with one or more substituents selected from the group consisting of —OH, —NH$_2$, —CN, —$NO_2$, —$C(O)OH$, —$S(O)_2NH_2$, —$C(O)NH_2$, —$C(S)NH_2$, —$NHC(O)NH_2$, —$NHC(S)NH_2$, —$NHS(O)_2NH_2$, —$OR^{13}$, —$SR^{13}$, —$NR^{12}R^{13}$, —$C(O)R^{13}$, —$C(S)R^{13}$, —$C(O)OR^{13}$, —$C(O)NR^{12}R^{13}$, —$C(S)NR^{12}R^{13}$, —$S(O)_2NR^{12}R^{13}$, —$NR^{12}C(O)R^{13}$, —$NR^{12}C(S)R^{13}$, —$NR^{12}S(O)_2R^{13}$, —$NR^{12}C(O)NR^{12}R^{13}$, —$NR^{12}C(S)NR^{12}R^{13}$, —$NR^{12}S(O)_2NR^{12}R^{13}$, —$S(O)R^{13}$, —$S(O)_2R^{13}$, halogen, lower alkyl, fluoro substituted lower alkyl, and cycloalkylamino;

$R^{10}$ and $R^{11}$ are independently selected from the group consisting of hydrogen, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; or $R^{10}$ and $R^{11}$ combine to form a 3-7 membered monocyclic cycloalkyl or 5-7 membered monocyclic heterocycloalkyl, wherein the monocyclic cycloalkyl or monocyclic heterocycloalkyl is optionally substituted with one or more substituents selected from the group consisting of halogen, —OH, —$NH_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^{12}$ at each occurrence is independently hydrogen, lower alkyl or fluoro substituted lower alkyl;

$R^{13}$ at each occurrence is independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, provided, however, that any substitution of the alkyl carbon bound to O, S, or N of —$OR^{13}$, —$SR^{13}$, —$NR^{12}R^{13}$, —$C(O)OR^{13}$, —$C(O)NR^{12}R^{13}$, or —$S(O)_2NR^{12}R^{13}$ is fluoro, cycloalkyl, heterocycloalkyl, aryl or heteroaryl, and wherein cycloalkyl, heterocycloalkyl, aryl, and heteroaryl as $R^{13}$ or as substituents of lower alkyl are optionally substituted with one or more substituents selected from the group consisting of —OH, —$NH_2$, —CN, —$NO_2$, —$C(O)OH$, —$S(O)_2NH_2$, —$C(O)NH_2$, —$OR^{14}$, —$SR^{14}$, —$NR^{12}R^{14}$, —$NR^{12}C(O)R^{14}$, —$NR^{12}S(O)_2R^{14}$, —$S(O)_2R^{14}$, —$C(O)R^{14}$, —$C(O)OR^{14}$, —$C(O)NR^{12}R^{14}$, —$S(O)_2NR^{12}R^{14}$, halogen, lower alkyl, fluoro substituted lower alkyl, and cycloalkylamino; and $R^{14}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, provided, however, that any substitution of the alkyl carbon bound to O, S, or N of —$OR^{14}$, —$SR^{14}$, —$NR^{12}R^{14}$, —$C(O)OR^{14}$, —$C(O)NR^{12}R^{14}$, or —$S(O)_2NR^{12}R^{14}$ is fluoro, and wherein heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy.

11. A composition comprising: a pharmaceutically acceptable carrier; and a compound according to claim 9.

\* \* \* \* \*